United States Patent
Tsuchimura et al.

(10) Patent No.: US 8,808,961 B2
(45) Date of Patent: Aug. 19, 2014

(54) COMPOSITION, RESIST FILM, PATTERN FORMING METHOD, AND INKJET RECORDING METHOD

(75) Inventors: Tomotaka Tsuchimura, Shizuoka (JP); Takeshi Kawabata, Shizuoka (JP); Takayuki Ito, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 736 days.

(21) Appl. No.: 12/914,762

(22) Filed: Oct. 28, 2010

(65) Prior Publication Data

US 2011/0102528 A1   May 5, 2011

(30) Foreign Application Priority Data

Oct. 30, 2009 (JP) ................................. 2009-250886

(51) Int. Cl.
| | | |
|---|---|---|
| *G03F 7/00* | (2006.01) | |
| *C07C 311/48* | (2006.01) | |
| *C07C 311/51* | (2006.01) | |
| *C07C 233/00* | (2006.01) | |
| *B41J 2/01* | (2006.01) | |
| *C07D 317/14* | (2006.01) | |
| *G03F 7/038* | (2006.01) | |
| *C07D 405/12* | (2006.01) | |
| *C07D 317/72* | (2006.01) | |
| *G03F 7/039* | (2006.01) | |
| *G03F 7/004* | (2006.01) | |
| *C07D 317/58* | (2006.01) | |
| *C07D 319/06* | (2006.01) | |
| *G03F 7/20* | (2006.01) | |

(52) U.S. Cl.
CPC ............ *C07D 317/14* (2013.01); *G03F 7/0382* (2013.01); *C07C 311/48* (2013.01); *C07D 405/12* (2013.01); *C07D 317/72* (2013.01); *G03F 7/2041* (2013.01); *G03F 7/0392* (2013.01); *G03F 7/0045* (2013.01); *C07D 317/58* (2013.01); *C07D 319/06* (2013.01)
USPC ............ 430/270.1; 430/322; 564/80; 564/82; 564/123; 347/105

(58) Field of Classification Search
None
See application file for complete search history.

(56) References Cited

U.S. PATENT DOCUMENTS

| | | | | |
|---|---|---|---|---|
| 6,114,082 | A | * | 9/2000 | Hakey et al. ............... 430/270.1 |
| 6,548,221 | B2 | | 4/2003 | Uetani et al. |
| 6,576,392 | B1 | | 6/2003 | Sato et al. |
| 6,680,157 | B1 | | 1/2004 | Fedynshyn |
| 2011/0183258 | A1 | * | 7/2011 | Takahashi et al. ......... 430/270.1 |

FOREIGN PATENT DOCUMENTS

| | | |
|---|---|---|
| EP | 1 480 078 A1 | 11/2004 |
| JP | 09-183928 A | 7/1997 |
| JP | 10-104834 A | 4/1998 |
| JP | 3912761 B2 | 8/2000 |
| JP | 2002-174904 A | 6/2002 |
| JP | 2003-57827 A | 2/2003 |
| JP | 2003057827 A * | 2/2003 |
| JP | 2003-341217 A | 12/2003 |
| WO | 2005/013995 A1 | 2/2005 |
| WO | 2009/022681 A1 | 2/2009 |
| WO | WO 2009022681 A1 * | 2/2009 |

OTHER PUBLICATIONS

Machine translation JP 2003-057827. Feb. 28, 2003.*
Japanese Office Action issued in application No. 2009-250886 dated Aug. 6, 2013.

* cited by examiner

*Primary Examiner* — Cynthia H Kelly
*Assistant Examiner* — Alyssa L Cepluch
(74) *Attorney, Agent, or Firm* — Sughrue Mion, PLLC

(57) ABSTRACT

An embodiment of the composition contains any of compounds of the formula A-LG in which A represents any of residues of general formula (A-1) below and LG represents any of groups that are cleaved to generate acids of the formula A-H when acted on by an acid. The composition further contains at least one of a compound that generates an acid when exposed to actinic rays or radiation and a compound that generates an acid when heated.

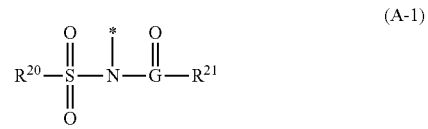

(A-1)

15 Claims, No Drawings

COMPOSITION, RESIST FILM, PATTERN FORMING METHOD, AND INKJET RECORDING METHOD

CROSS-REFERENCE TO RELATED APPLICATIONS

This application is based upon and claims the benefit of priority from prior Japanese Patent Application No. 2009-250886, filed Oct. 30, 2009, the entire contents of which are incorporated herein by reference.

BACKGROUND OF THE INVENTION

1. Field of the Invention

The present invention relates to a composition, a resist film, a method of forming a pattern and a method of inkjet recording. More particularly, the present invention relates to an actinic-ray- or radiation-sensitive resist composition, a resist film formed by the composition, and a method of forming a pattern using the composition. Further, the present invention relates to an actinic-ray- or radiation-sensitive or thermosensitive hardenable composition, a method of inkjet recording using the composition, a print, a process for producing a planographic printing plate, and a planographic printing plate.

2. Description of the Related Art

A chemical amplification photosensitive composition is a pattern forming material that is capable of, upon exposure to far ultraviolet or other radiation, generating an acid at the exposed area and, by a reaction catalyzed by the acid, changing the solubility in a developer between the area having been exposed to actinic radiation and the nonexposed area to thereby attain pattern formation on a substrate.

In the use of a KrF excimer laser as an exposure light source, a resin whose fundamental skeleton consists of a poly(hydroxystyrene) exhibiting a low absorption mainly in the region of 248 nm is employed as a major component. Accordingly, there can be attained a high sensitivity, high resolving power and favorable pattern formation. Thus, a system superior to the conventional naphthoquinone diazide/novolak resin system is realized.

On the other hand, in the use of a light source of a further shorter wavelength, for example, an ArF excimer laser (193 nm) as an exposure light source, as the compounds having an aromatic group inherently exhibit a sharp absorption in the region of 193 nm, the above-mentioned chemical amplification system has not been satisfactory.

Therefore, resists for an ArF excimer laser containing a resin with an alicyclic hydrocarbon structure have been developed.

As for photoacid generator which is a main component of a chemical amplification resist, triphenylsulfonium salt is generally known (see, for example, patent reference 1 below).

However, the known acid generators are unsatisfactory in many respects. Thus, there is a demand in the art for the development of a photosensitive composition that is enhanced in the sensitivity, resolution, pattern configuration, roughness characteristic, etc. through the improvement of such acid generators.

In particular, the roughness characteristic and resolution become serious in accordance with the reduction of pattern dimension. In the field of, for example, the lithography using X-rays, electron beams or EUV, as the formation of a fine pattern of several tens of nanometers is targeted, the demand for especially high resolution and roughness characteristic is strong.

When use is made of a light source emitting electron beams, X-rays, EUV or the like, the exposure is carried out in vacuum. This tends to cause low-boiling-point compounds, such as solvents, and resist materials decomposed by high energy to evaporate to thereby dirty the exposure apparatus. This outgas problem is becoming serious. In recent years, various researches have been made on the reduction of the outgas. Various proposals have been made, which include a proposal to inhibit the evaporation of low-molecular compounds by providing a top coat layer (see, for example, patent reference 2) and a proposal to add a radical trapping agent for the inhibition of polymer decomposition (see, for example, patent reference 3). For acid generators as well, an ingenuity for outgas reduction is demanded.

Furthermore, patent reference 4 proposes a positive photoresist composition for far-ultraviolet exposure which comprises a specified acid-decomposable resin and compound (sulfonic-acid-generating compound) that when acted on by an acid, is decomposed to thereby generate a sulfonic acid for the purpose of solving the problems of development defect, scumming, etc.

In Paragraph 0016 of patent reference 4, there is a description to the effect that as the acid generated by the sulfonic-acid-generating compound, one of high acid strength is preferred. Further, there is a description to the effect that a sulfonic acid containing an alkyl group, a cycloalkyl group, an aryl group or an aralkyl group is preferred as the generated acid. In Paragraphs 0017 and 0018 of the reference, as preferred examples of the generated acids, there are mentioned the compounds of general formulae (1) to (5).

As an image recording system capable of forming an image on a recording medium, such as paper, in accordance with an image data signal, for example, an electrophotographic system, a sublimation or fusion thermal transfer system and an inkjet system are known. The electrophotographic system requires a process for forming an electrostatic latent image on a photoreceptor drum through electrification or exposure to thereby render the system complex with the result that the problem of high production cost or the like arises. In the thermal transfer system, the apparatus cost is low. However, as an ink ribbon is used, the problems of high running cost and waste material output arise. In contrast, in the inkjet system, the apparatus cost is low, and as an ink is jetted to only required image areas so as to carry out direct imaging on a recording medium, the ink can be efficiently used, rendering the running cost low. Further, noise is low. Therefore, the inkjet system is advantageous as an image recording system.

It is required for the ink composition for inkjet recording (radiation-hardenable ink composition) capable of being hardened when exposed to radiation, such as ultraviolet, to have satisfactorily high sensitivity and provide high image quality. Attaining high sensitivity ensures high hardenability upon exposure to radiation and thus realizes many advantages including the reduction of power consumption, the prolongation of life by the reduction of load on a radiation emitter and the prevention of the occurrence of low-molecular substances attributed to unsatisfactory hardening. Further, attaining high sensitivity, especially when the ink composition is used in image areas of a planographic printing plate, increases the strength of image areas hardened, so that an extended plate life can be realized. Such ink compositions per se are being marketed and stored under various conditions. Accordingly, it is required for the ink compositions to have a high storage stability.

An ultraviolet-hardenable resin composition comprising a cationically polymerizable compound and a photoacid is known as an overcoating agent for optical disk (see, for example, patent reference 5). It is reported that this composition realizes a relatively high hardening sensitivity (see the same reference). However, soaking on recycled paper is observed, and the storage stability of the composition is poor. Moreover, coloring is observed at the time of ink hardening, and thus the composition has the drawback that a color difference is brought about between before and after ink hardening.

Still further, it is reported to employ an ink composition in which a basic compound is contained in order to not only improve the discharge stability of ink droplets but also reduce the curling and wrinkling of recording material attributed to ink shrinkage at the time of ink hardening (see, for example, patent reference 6).

[Patent reference 1] U.S. Pat. No. 6,548,221,
[Patent reference 2] European Patent No. 1480078,
[Patent reference 3] U.S. Pat. No. 6,680,157,
[Patent reference 4] Japanese. Patent No. 3912761,
[Patent reference 5] Jpn. Pat. Appln. KOKAI Publication No. (hereinafter referred to as JP-A-) H9-183928, and
[Patent reference 6] JP-A-2003-341217.

BRIEF SUMMARY OF THE INVENTION

It is an object of the present invention to provide a composition excelling in the sensitivity to actinic rays or radiation, or heat; a resist film formed by the composition; and a method of forming a pattern and a method of inkjet recording using the composition. More particularly, it is an object of the present invention to provide an actinic-ray- or radiation-sensitive resin composition excelling in the sensitivity, resolution, roughness characteristics and aging stability, from which a pattern of favorable configuration can be formed; a resist film formed by the composition; and a method of forming a pattern using the composition. Also, it is a particular object of the present invention to provide an actinic-ray- or radiation-sensitive resin composition excelling in the sensitivity, hardenability, adherence and discharge stability; and a method of inkjet recording using the composition. It is another object of the present invention to provide a thermosensitive composition excelling in the hardenability.

Followings are some aspects of the present invention.

[1] A composition comprising: any of compounds of the formula A-LG in which A represents any of residues of general formula (A-1) below and LG represents any of groups that are cleaved to generate acids of the formula A-H when acted on by an acid; and at least one of a compound that generates an acid when exposed to actinic rays or radiation and a compound that generates an acid when heated,

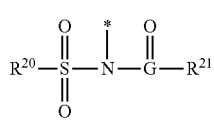

in which
each of $R^{20}$ and $R^{21}$ independently represents an organic group, provided that $R^{20}$ and $R^{21}$ may be bonded to each other to form a ring, and
G represents a carbon atom, a sulfur atom or S=O.

[2] The composition according to [1], wherein A is any of residues of general formula (A-2) below,

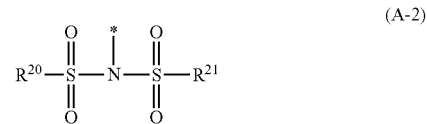

in which
each of $R^{20}$ and $R^{21}$ independently represents an organic group, provided that $R^{20}$ and $R^{21}$ may be bonded to each other to thereby form a ring.

[3] The composition according to [2], wherein A is any of residues of general formula (A-3) below,

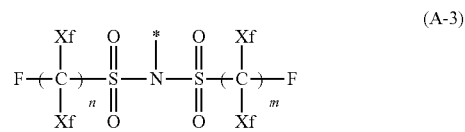

in which
each of Xf's independently represents a fluorine atom or an alkyl group having at least one hydrogen atom thereof substituted with a fluorine atom, and
each of m and n independently is an integer of 1 to 20.

[4] The composition according to [2], wherein A is any of residues of general formula (A-4) below,

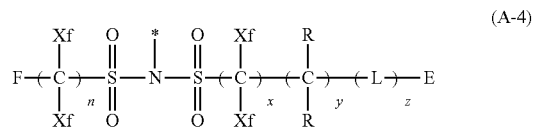

in which
each of Xf's independently represents a fluorine atom or an alkyl group having at least one hydrogen atom thereof substituted with a fluorine atom,
each of R's independently represents a hydrogen atom, a fluorine atom, an alkyl group, or an alkyl group having at least one hydrogen atom thereof substituted with a fluorine atom,
L, or when z≥2 each of L's independently, represents a single bond or a bivalent connecting group,
E represents a group with a cyclic structure,
each of n and x independently is an integer of 1 to 20,
y is an integer of 0 to 10, and
z is an integer of 0 to 10.

[5] The composition according to any of [1] to [4], wherein the formula A-LG is represented by any of general formulae (1) to (5) below,

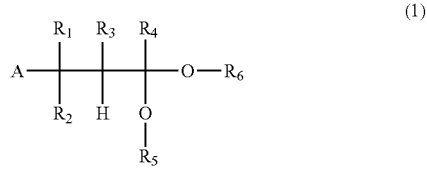

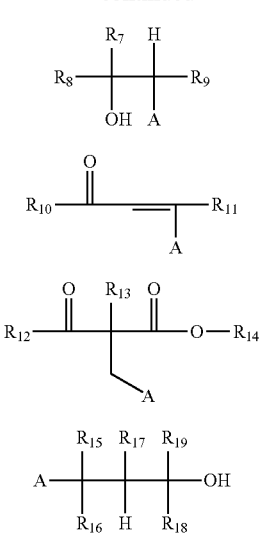

in the formulae, each of $R_1$ to $R_4$, $R_7$ to $R_{13}$ and $R_{15}$ to $R_{19}$ independently represents a hydrogen atom or a monovalent substituent, each of $R_5$, $R_6$ and $R_{14}$ independently represents a monovalent substituent, and A represents any of residues of any of the general formulae (A-1) to (A-4).

[6] The composition according to [5], wherein the formula A-LG is represented by the general formula (1).

[7] The composition according to any of [1] to [6], which contains the compound that generates an acid when exposed to actinic rays or radiation, and further contains a resin that is decomposed to thereby increase its solubility in an alkali developer when acted on by an acid.

[8] The composition according to [7] to be exposed to electron beams, X-rays or EUV light.

[9] A resist film formed by the composition according to [7] or [8].

[10] A method of forming a pattern, comprising: forming the composition of [7] or [8] into a film, exposing the film, and developing the exposed film.

[11] The composition according to any of [1] to [6], further comprising at least one of an acid crosslinking agent and a cationically polymerizable compound.

[12] The composition according to [11], which contains the compound that generates an acid when exposed to actinic rays or radiation.

[13] A method of inkjet recording, comprising: discharging the composition of [12] onto a recording medium, and exposing the discharged composition to actinic rays or radiation to harden the composition.

[14] Compounds of general formula (A1-1) below,

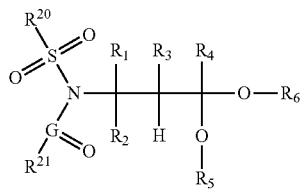

in which each of $R^{20}$ and $R^{21}$ independently represents an organic group, provided that $R^{20}$ and $R^{21}$ may be bonded to each other to thereby form a ring, G represents a carbon atom, a sulfur atom or S=O, each of $R_1$ to $R_4$ independently represents a hydrogen atom or a monovalent substituent, and each of $R_5$ and $R_6$ independently represents a monovalent substituent.

[15] A process for synthesizing the compounds of [14], comprising causing any of amines of general formula (1N-II) below to react with any of acid halides of general formula (1A-II) below or any of acid anhydrides of general formula (1B-II) below in the presence of a base,

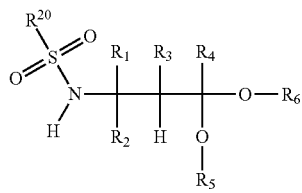

in formula (1N-II), $R^{20}$ represents an organic group, each of $R_1$ to $R_4$ independently represents a hydrogen atom or a monovalent substituent, and each of $R_5$ and $R_6$ independently represents a monovalent substituent,

in formula (1A-II), $R^{21}$ represents an organic group,

G represents a carbon atom, a sulfur atom or S=O, and

X represents a fluorine atom, a chlorine atom, a bromine atom or an iodine atom, and

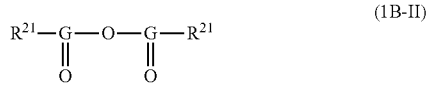

in formula (1B-II), $R^{21}$ represents an organic group, and

G represents a carbon atom, a sulfur atom or S=O.

[16] The process according to [15], further comprising synthesizing the amines of general formula (1N-II) by causing amines of general formula (1N-I) below to react with acid halides of general formula (1A-I) below or acid anhydrides of general formula (1B-I) below in the presence of a base,

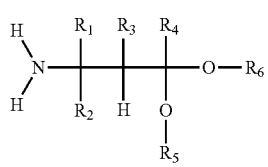

in formula (1N-I), each of $R_1$ to $R_4$ independently represents a hydrogen atom or a monovalent substituent, and each of $R_5$ and $R_6$ independently represents a monovalent substituent,

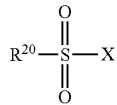  (1A-I)

in formula (1A-I), $R^{20}$ represents an organic group, and

X represents a fluorine atom, a chlorine atom, a bromine atom or an iodine atom, and

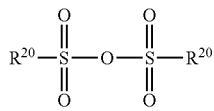  (1B-I)

in formula (1B-I), $R^{20}$ represents an organic group.

DETAILED DESCRIPTION OF THE INVENTION

The present invention will be described below.

Note that, with respect to the expression of a group (or an atomic group) used in this specification, the expression without explicitly referring to whether the group is substituted or unsubstituted encompasses not only groups with no substituents but also groups having one or more substituents. For example, the expression "alkyl group" encompasses not only alkyl groups having no substituents (viz. unsubstituted alkyl groups) but also alkyl groups having one or more substituents (viz. substituted alkyl groups).

In the present invention, the terms "actinic rays" and "radiation" mean, for example, a mercury lamp bright line spectrum, far ultraviolet rays represented by an excimer laser, extreme ultraviolet rays, X-rays, electron beams and the like. In the present invention, the term "light" means actinic rays or radiation.

The expression "exposure" used herein, unless otherwise noted, means not only light irradiation using a mercury lamp, far ultraviolet, X-rays, EUV light, etc. but also lithography using particle beams, such as an electron beam and an ion beam.

The composition according to the present invention comprises [1] a compound that generates an acid by the action of an acid (hereinafter also referred to as an acid amplifier); and [2] a compound that generates an acid when exposed to actinic rays or radiation (hereinafter also referred to as a photoacid generator) and/or [3] a compound that generates an acid by the action of heat (hereinafter also referred to as a thermal acid generator).

[1] Acid Amplifier

The acid amplifier referred to in the present invention is any of the compounds of the formula A-LG. In the formula, A represents any of residues of general formula (A-1) below, and LG represents any of groups that are cleaved to thereby generate acids of the formula A-H when acted on by an acid.

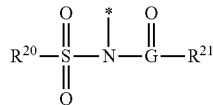  (A-1)

In the formula (A-1), each of $R^{20}$ and $R^{21}$ independently represents an organic group, provided that $R^{20}$ and $R^{21}$ may be bonded to each other to thereby form a ring, and G represents a carbon atom, a sulfur atom or S=O.

The acidity of the acids of the formula A-H is higher than those of sulfonic acids generated by conventional acid amplifiers. Therefore, when the compounds of the formula A-LG are used, for example, the efficiencies of the deprotection reaction of acid-decomposable resins, crosslinking reaction of crosslinking agents and polymerization reaction of cationically polymerizable compounds to be described hereinafter can be enhanced.

In particular, when use is made of an acid-decomposable resin containing a protective group exhibiting a high activation energy of deprotection reaction, the above deprotection reaction occasionally cannot be conducted with satisfactory efficiency by conventional sulfonic acids. Therefore, in such occasions, for example, a compound capable of generating a fluoroalkylsulfonic acid is used. However, it is relatively difficult to simultaneously satisfy the reactivity and stability with the use of such a compound.

In contrast, the compounds of the formula A-LG excel in both of reactivity and stability. Namely, these compounds can be appropriately used even when use is made of an acid-decomposable resin containing a protective group exhibiting a high activation energy of deprotection reaction. Further, these compounds excel in the stability as compared with that of conventional acid amplifiers capable of generating sulfonic acid. Therefore, when these compounds are employed, the aging stability of the composition can be improved over that attained in the use of conventional acid amplifiers capable of generating sulfonic acid.

As the organic group represented by $R^{20}$, there can be mentioned, for example, an alkyl group, a cycloalkyl group, an alkenyl group, a cycloalkenyl group, an alkynyl group, a cycloalkynyl group, an aryl group or a heterocyclic group. $R^{20}$ is preferably an alkyl group or a cycloalkyl group.

As the organic group represented by $R^{21}$, there can be mentioned, for example, an alkyl group, a cycloalkyl group, an alkenyl group, a cycloalkenyl group, an alkynyl group, a cycloalkynyl group, an aryl group or a heterocyclic group. $R^{21}$ is preferably an alkyl group or a cycloalkyl group.

Each of the alkyl groups represented by $R^{20}$ and $R^{21}$ preferably has 1 to 20 carbon atoms, more preferably 1 to 18 carbon atoms and further more preferably 1 to 12 carbon atoms. Further, one or more substituents may be introduced in each of these alkyl groups.

Each of the cycloalkyl groups represented by $R^{20}$ and $R^{21}$ preferably has 3 to 20 carbon atoms, more preferably 3 to 18 carbon atoms and further more preferably 3 to 12 carbon atoms. Further, one or more substituents may be introduced in each of these cycloalkyl groups.

Each of the alkenyl groups represented by $R^{20}$ and $R^{21}$ preferably has 2 to 20 carbon atoms, more preferably 2 to 18 carbon atoms and further more preferably 2 to 12 carbon atoms. Further, one or more substituents may be introduced in each of these alkenyl groups.

Each of the cycloalkenyl groups represented by $R^{20}$ and $R^{21}$ preferably has 3 to 20 carbon atoms, more preferably 3 to 18 carbon atoms and further more preferably 3 to 12 carbon atoms. Further, one or more substituents may be introduced in each of these cycloalkenyl groups.

Each of the alkynyl groups represented by $R^{20}$ and $R^{21}$ preferably has 2 to 20 carbon atoms, more preferably 2 to 18 carbon atoms and further more preferably 2 to 12 carbon atoms. Further, one or more substituents may be introduced in each of these alkynyl groups.

Each of the cycloalkynyl groups represented by $R^{20}$ and $R^{21}$ preferably has 3 to 20 carbon atoms, more preferably 3 to 18 carbon atoms and further more preferably 3 to 12 carbon atoms. Further, one or more substituents may be introduced in each of these cycloalkynyl groups.

Each of the aryl groups represented by $R^{20}$ and $R^{21}$ preferably has 6 to 20 carbon atoms, more preferably 6 to 14 carbon atoms and further more preferably 6 to 10 carbon atoms. Further, one or more substituents may be introduced in each of these aryl groups.

Each of the heterocyclic groups represented by $R^{20}$ and $R^{21}$ contains, for example, a nitrogen atom, an oxygen atom or a sulfur atom as a heteroatom. The number of carbon atoms of each of these heterocyclic groups is preferably in the range of 4 to 20, more preferably 4 to 13.

As the substituents that can be introduced in the above groups, there can be mentioned, for example, the following group of substituents. Of the listed substituents, a fluorine atom is especially preferred. The following substituents may further be introduced in the listed substituents. These substituents if appropriate may be bonded to each other to thereby form a ring.

<Group of Substituents>

A halogen atom (a fluorine atom, a chlorine atom, a bromine atom or an iodine atom), an alkyl group, an alkenyl group, an alkynyl group, an aryl group, an arylalkyl group, an acyl group, an alkoxycarbonyl group, a hydrocarbon ring group, a heterocyclic group, a hydroxyl group, an alkoxy group, an aryloxy group, an N,N-dialkylamino group, an N,N-diarylamino group, an N-alkyl-N-arylamino group, an alkylsulfoxy group, an arylsulfoxy group, an N-alkylacylamino group, an N-arylacylamino group, an alkoxycarbonylamino group, an aryloxycarbonylamino group, an N-alkyl-N-alkoxycarbonylamino group, an N-alkyl-N-aryloxycarbonylamino group, an N-aryl-N-alkoxycarbonylamino group, an N,N-dialkylcarbamoyl group, an N-arylcarbamoyl group, an N,N-diarylcarbamoyl group, an N-alkyl-N-arylcarbamoyl group, an alkylsulfinyl group, an arylsulfinyl group, an alkylsulfonyl group, an arylsulfonyl group, an N,N-dialkylsulfinamoyl group, an N,N-diarylsulfinamoyl group, an N-alkyl-N-arylsulfinamoyl group, an N,N-dialkylsulfamoyl group, an N,N-diarylsulfamoyl group, an N-alkyl-N-arylsulfamoyl group, a cyano group, an alkylthioxy group and an arylthioxy group.

It is especially preferred for each of $R^{20}$ and $R^{21}$ to be independently an alkyl group having at least one hydrogen atom thereof substituted with a fluorine atom.

As mentioned above, G represents a carbon atom, a sulfur atom or S=O. Preferably, G is S=O. Namely, preferably, the residual A is any of those of general formula (A-2) below. If so, the acid strength can be increased by the intensification of electron withdrawing properties, so that the efficiencies of deprotection reaction of acid-decomposable resins, crosslinking reaction of crosslinking agents and polymerization reaction of cationically polymerizable compounds can be enhanced.

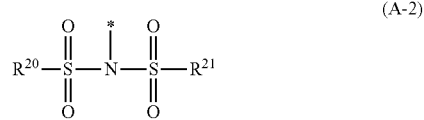

In general formula (A-2), $R^{20}$ and $R^{21}$ are as defined above in connection with general formula (A-1).

It is preferred for the residue A to be any of those of general formula (A-2') below. If so, the strength of the acid of the formula A-H can be enhanced.

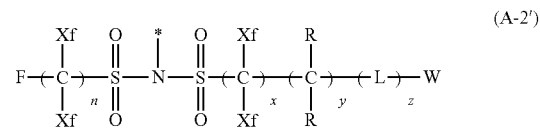

In the formula, each of Xf's independently represents a fluorine atom or an alkyl group having at least one hydrogen atom thereof substituted with a fluorine atom.

Each of R's independently represents a hydrogen atom, a fluorine atom, an alkyl group or an alkyl group having at least one hydrogen atom thereof substituted with a fluorine atom.

L, or when z≥2 each of L's independently, represents a single bond or a bivalent connecting group.

W represents a hydrogen atom or a monovalent substituent.

Each of n and x independently is an integer of 1 to 20;
y is an integer of 0 to 10, and
z is an integer of 0 to 10.

Preferred examples of Xf, R, L, n, x, y and z are the same as to be mentioned hereinbelow in connection with general formulae (A-3) and (A-4) below.

W represents, for example, a hydrogen atom, a fluorine atom, an alkyl group, an aryl group or a group with a cyclic structure (for example, a cycloaliphatic group, an aryl group or a heterocyclic group). It is preferred for W to represent a fluorine atom or a group with a cyclic structure.

The residue A is preferably any of those of general formulae (A-3) and (A-4) below. If so, the strength of the acid of the formula A-H can be enhanced.

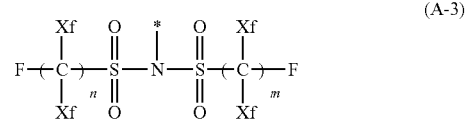

In the formula (A-3),
each of Xf's independently represents a fluorine atom or an alkyl group having at least one hydrogen atom thereof substituted with a fluorine atom, and
each of m and n independently is an integer of 1 to 20.

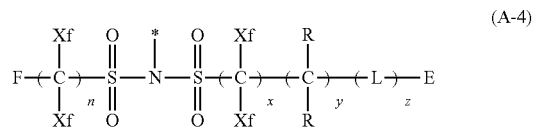

In the formula (A-4),
each of Xf's independently represents a fluorine atom or an alkyl group having at least one hydrogen atom thereof substituted with a fluorine atom, each of R's independently represents a hydrogen atom, a fluorine atom, an alkyl group or an alkyl group having at least one hydrogen atom thereof substituted with a fluorine atom, L, or when z≥2 each of L's independently, represents a single bond or a bivalent connecting group, E represents a group with a cyclic structure, each of n and x independently is an integer of 1 to 20, y is an integer of 0 to 10, and z is an integer of 0 to 10.

In general formulae (A-3) and (A-4), Xf is a fluorine atom or an alkyl group having at least one hydrogen atom thereof substituted with a fluorine atom. This alkyl group preferably has 1 to 10 carbon atoms, more preferably 1 to 4 carbon atoms. It is preferred for the alkyl group substituted with a fluorine atom to be a perfluoroalkyl group.

Xf is preferably a fluorine atom or a perfluoroalkyl group having 1 to 4 carbon atoms. In particular, Xf is preferably a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$. Of these, a fluorine atom and $CF_3$ are preferred. A fluorine atom is most preferred.

As mentioned above, each of m and n is an integer of 1 to 20. Each of m and n independently is preferably in the range of 1 to 10, more preferably 1 to 7 and further more preferably 1 to 4.

R, as mentioned above, represents a hydrogen atom, a fluorine atom, an alkyl group or an alkyl group having at least one hydrogen atom thereof substituted with a fluorine atom. The alkyl group optionally substituted with a fluorine atom preferably has 1 to 4 carbon atoms. The alkyl group substituted with a fluorine atom is most preferably a perfluoroalkyl group having 1 to 4 carbon atoms. In particular, there can be mentioned $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$. Of these, $CF_3$ is preferred.

L, as mentioned above, represents a single bond or a bivalent connecting group. As the bivalent connecting group, there can be mentioned, for example, —COO—, —OCO—, —CO—, —O—, —S—, —SO—, —SO$_2$—, an alkylene group, a cycloalkylene group or an alkenylene group. Of these, —COO—, —COO—, —CO—, —O—, —S—, —SO— and —SO$_2$— are preferred. —COO—, —COO— and —SO$_2$— are more preferred.

E represents a group with a cyclic structure. As the group with a cyclic structure, there can be mentioned, for example, a cycloaliphatic group, an aryl group or a heterocyclic group.

The cycloaliphatic group represented by E may be monocyclic or polycyclic. The monocycloaliphatic group is preferably a monocycloalkyl group, such as a cyclopentyl group, a cyclohexyl group or a cyclooctyl group. The polycycloaliphatic group is preferably a polycycloalkyl group, such as a norbornyl group, a tricyclodecanyl group, a tetracyclodecanyl group, a tetracyclododecanyl group or an adamantyl group. In particular, when a cycloaliphatic group with a bulky structure having a 6- or more-membered ring is employed as E, not only can any in-film diffusion of acid be inhibited in the step of post-exposure bake (PEB) but also the resolving power and exposure latitude (EL) can be enhanced.

The aryl group represented by E is, for example, a phenyl group, a naphthyl group, a phenanthryl group or an anthryl group.

The heterocyclic group represented by E may have aromaticity or no aromaticity. The heteroatom contained therein is preferably a nitrogen atom or an oxygen atom. As particular examples of the heterocycles, there can be mentioned a furan ring, a thiophene ring, a benzofuran ring, a benzothiophene ring, a dibenzofuran ring, a dibenzothiophene ring, a pyridine ring, a piperidine ring, a morpholine ring and the like. Of these, a furan ring, a thiophene ring, a pyridine ring, a piperidine ring and a morpholine ring are preferred.

One or more substituents may be introduced in the group of E. As the substituent, there can be mentioned, for example, an alkyl group (may be linear, branched or cyclic, preferably having 1 to 12 carbon atoms), an aryl group (preferably having 6 to 30 carbon atoms), a hydroxyl group, an alkoxy group, an ester group, an amido group, a urethane group, a ureido group, a thioether group, a sulfonamido group or a sulfonic ester group.

In the formula, x is preferably 1 to 8, more preferably 1 to 4; y is preferably 0 to 4, more preferably 0; and z is preferably 0 to 8, more preferably 0 to 4.

Particular examples of the residues A's are shown below.

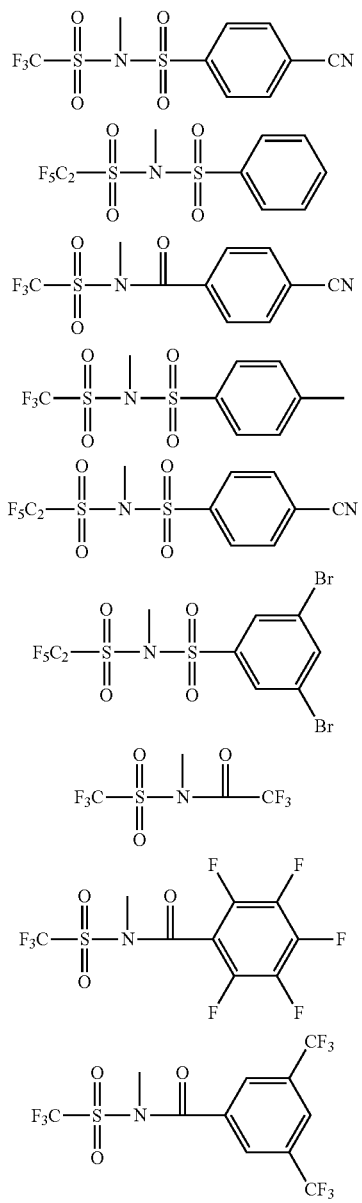

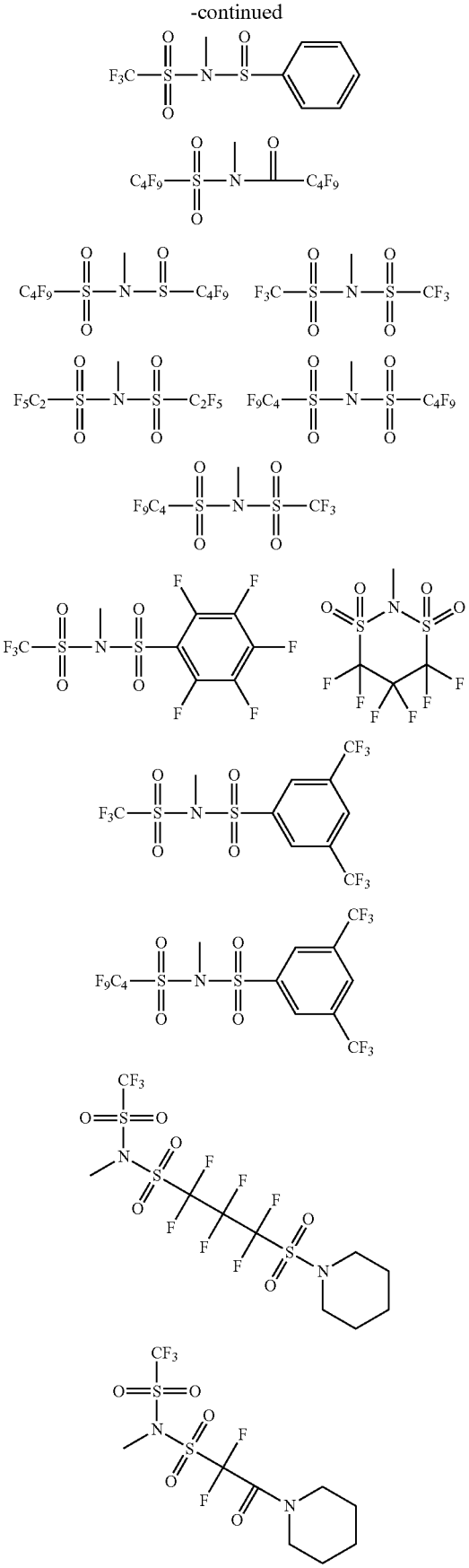
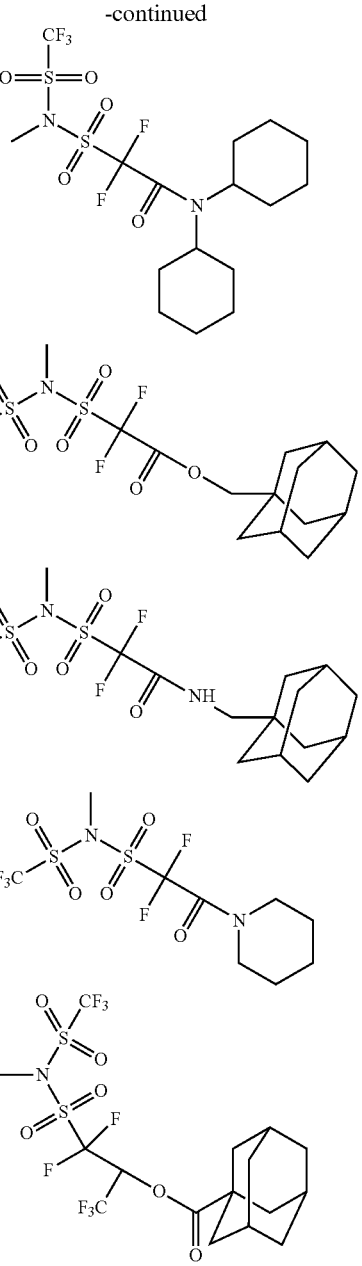

Now, examples of the groups of the formula LG will be described. LG are, as mentioned above, groups that when acted on by an acid, are cleaved to thereby generate acids of the formula A-H.

The compounds of the formula A-LG are, for example, the compounds of any of general formulae (1) to (5) below. It is most preferred for the compounds of the formula A-LG to be the compounds of general formula (1) below.

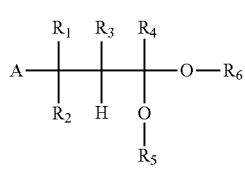
(1)

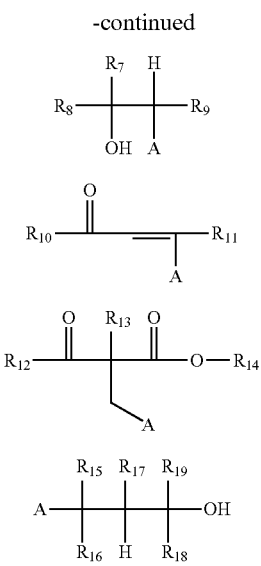

In the formulae, each of $R_1$ to $R_4$, $R_7$ to $R_{13}$ and $R_{15}$ to $R_{19}$ independently represents a hydrogen atom or a monovalent substituent, each of $R_5$, $R_6$ and $R_{14}$ independently represents a monovalent substituent, and A represents any of residues of any of general formulae (A-1) to (A-4) above.

Each of these compounds of general formulae (1) to (5) may have a plurality of residues (A). Namely, each of these compounds of general formulae (1) to (5) may have in the same molecule a plurality of structures capable of generating the acids of the formula A-H.

The compounds of general formula (1) will be described in detail below.

First, $R_1$ to $R_4$ will be described.

In formula (1), each of $R_1$ to $R_4$ represents a hydrogen atom or a monovalent substituent.

As the monovalent substituent, there can be mentioned, for example, an alkyl group, a cycloalkyl group, an alkenyl group, an alkynyl group, an aryl group, a halogen atom, an alkoxy group, an aryloxy group, an alkanoyl group, an alkoxycarbonyl group, an aryloxycarbonyl group, an alkylsulfonyloxy group, an arylsulfonyloxy group, an alkylsulfonyl group, an arylsulfonyl group, a cyano group, an alkylthioxy group, an arylthioxy group or a heterocyclic group. One or more substituents may be introduced in, among them, an alkyl group, a cycloalkyl group, an alkenyl group, an alkynyl group, an aryl group, an alkoxy group, an aryloxy group, an alkanoyl group, an alkoxycarbonyl group, an aryloxycarbonyl group, an alkylsulfonyloxy group, an arylsulfonyloxy group, an alkylsulfonyl group, an arylsulfonyl group, a cyano group, an alkylthioxy group, an arylthioxy group and a heterocyclic group.

The alkyl group is preferably an alkyl group having 1 to 30 carbon atoms. As such, there can be mentioned, for example, a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group, a trifluoromethyl group, a 2-ethylhexyl group, a phenacyl group, a 1-naphthoylmethyl group, a 2-naphthoylmethyl group, a 4-methylsulfanylphenacyl group, a 4-phenylsulfanylphenacyl group, a 4-dimethylaminophenacyl group, a 4-cyanophenacyl group, a 4-methylphenacyl group, a 2-methylphenacyl group, a 3-fluorophenacyl group, a 3-trifluoromethylphenacyl group or a 3-nitrophenacyl group.

The cycloalkyl group may have a monocyclic structure or polycyclic structure. The cycloalkyl group with a monocyclic structure is preferably a cyclopentyl group, a cyclohexyl group, a cyclooctyl group or the like. The cycloalkyl group with a polycyclic structure is preferably a norbornyl group, a tricyclodecanyl group, a tetracyclodecanyl group, a tetracyclododecanyl group, an adamantyl group or the like. Cycloalkyl groups each having 3 to 8 carbon atoms are preferred. For example, a cyclopentyl group and a cyclohexyl group are more preferred.

The alkenyl group is preferably one having 2 to 10 carbon atoms. As such, there can be mentioned, for example, a vinyl group, an allyl group, a styryl group or the like.

The alkynyl group is preferably one having 2 to 10 carbon atoms. As such, there can be mentioned, for example, an ethynyl group, a propynyl group, a propargyl group or the like.

The aryl group is preferably one having 6 to 30 carbon atoms. As such, there can be mentioned, for example, a phenyl group, a biphenyl group, a 1-naphthyl group, a 2-naphthyl group, a 9-anthryl group, a 9-phenanthryl group, a 1-pyrenyl group, a 5-naphthacenyl group, a 1-indenyl group, a 2-azulenyl group, a 9-fluorenyl group, a terphenyl group, a quaterphenyl group, an o-, m- or p-tolyl group, a xylyl group, an o-, m- or p-cumenyl group, a mesityl group, a pentalenyl group, a binaphthalenyl group, a ternaphthalenyl group, a quaternaphthalenyl group, a heptalenyl group, a biphenylenyl group, an indacenyl group, a fluoranthenyl group, an acenaphthylenyl group, an aceanthrylenyl group, a phenalenyl group, a fluorenyl group, an anthryl group, a bianthracenyl group, a teranthracenyl group, a quateranthracenyl group, an anthraquinolyl group, a phenanthryl group, a triphenylenyl group, a pyrenyl group, a chrysenyl group, a naphthacenyl group, a pleiadenyl group, a picenyl group, a perylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group or an ovalenyl group.

As the halogen atom, there can be mentioned a fluorine atom, a chlorine atom, a bromine atom or an iodine atom.

As the alkoxy group, there can be mentioned, for example, a methoxy group, an ethoxy group, a propoxy group, an n-butoxy group, a trifluoromethoxy group, a hexyloxy group, a t-butoxy group, a 2-ethylhexyloxy group, a cyclohexyloxy group, a decyloxy group or a dodecyloxy group.

As the aryloxy group, there can be mentioned, for example, a phenyloxy group, a 1-naphthyloxy group, a 2-naphthyloxy group, a tolyloxy group, a methoxyphenyloxy group, a naphthyloxy group, a chlorophenyloxy group, a trifluoromethylphenyloxy group, a cyanophenyloxy group or a nitrophenyloxy group.

The alkanoyl group is preferably one having 2 to 20 carbon atoms. As such, there can be mentioned, for example, an acetyl group, a propanoyl group, a butanoyl group, a trifluoromethylcarbonyl group, a pentanoyl group, a benzoyl group, a 1-naphthoyl group, a 2-naphthoyl group, a 4-methylsulfanylbenzoyl group, a 4-phenylsulfanylbenzoyl group, a 4-dimethylaminobenzoyl group, a 4-diethylaminobenzoyl group, a 2-chlorobenzoyl group, a 2-methylbenzoyl group, a 2-methoxybenzoyl group, a 2-butoxybenzoyl group, a 3-chlorobenzoyl group, a 3-trifluoromethylbenzoyl group a 3-cyanobenzoyl group, a 3-nitrobenzoyl group, a 4-fluorobenzoyl group, a 4-cyanobenzoyl group or a 4-methoxybenzoyl group.

The alkoxycarbonyl group is preferably one having 2 to 20 carbon atoms. As such, there can be mentioned, for example, a methoxycarbonyl group, an ethoxycarbonyl group, a propoxycarbonyl group, a butoxycarbonyl group, a hexyloxycarbonyl group, an octyloxycarbonyl group, a decyloxycarbonyl group, an octadecyloxycarbonyl group or a trifluoromethyloxycarbonyl group.

As the aryloxycarbonyl group, there can be mentioned, for example, a phenoxycarbonyl group, a 1-naphthyloxycarbonyl group, a 2-naphthyloxycarbonyl group, a 4-methylsulfanylphenyloxycarbonyl group, a 4-phenylsulfanylphenyloxycarbonyl group, a 4-dimethylaminophenyloxycarbonyl group, a 4-diethylaminophenyloxycarbonyl group, a 2-chlorophenyloxycarbonyl group, a 2-methylphenyloxycarbonyl group, a 2-methoxyphenyloxycarbonyl group, a 2-butoxyphenyloxycarbonyl group, a 3-chlorophenyloxycarbonyl group, a 3-trifluoromethylphenyloxycarbonyl group, a 3-cyanophenyloxycarbonyl group, a 3-nitrophenyloxycarbonyl group, a 4-fluorophenyloxycarbonyl group, a 4-cyanophenyloxycarbonyl group or a 4-methoxyphenyloxycarbonyl group.

The alkylsulfonyloxy group is preferably one having 1 to 20 carbon atoms. As such, there can be mentioned, for example, a methylsulfonyloxy group, an ethylsulfonyloxy group, a propylsulfonyloxy group, an isopropylsulfonyloxy group, a butylsulfonyloxy group, a hexylsulfonyloxy group, a cyclohexylsulfonyloxy group, an octylsulfonyloxy group, a 2-ethylhexylsulfonyloxy group, a decanoylsulfonyloxy group, a dodecanoylsulfonyloxy group, an octadecanoylsulfonyloxy group, a cyanomethylsulfonyloxy group, a methoxymethylsulfonyloxy group or a perfluoroalkylsulfonyloxy group.

The arylsulfonyloxy group is preferably one having 6 to 30 carbon atoms. As such, there can be mentioned, for example, a phenylsulfonyloxy group, a 1-naphthylsulfonyloxy group, a 2-naphthylsulfonyloxy group, a 2-chlorophenylsulfonyloxy group, a 2-methylphenylsulfonyloxy group, a 2-methoxyphenylsulfonyloxy group, a 2-butoxyphenylsulfonyloxy group, a 3-chlorophenylsulfonyloxy group, a 3-trifluoromethylphenylsulfonyloxy group, a 3-cyanophenylsulfonyloxy group, a 3-nitrophenylsulfonyloxy group, a 4-fluorophenylsulfonyloxy group, a 4-cyanophenylsulfonyloxy group, a 4-methoxyphenylsulfonyloxy group, a 4-methylsulfanylphenylsulfonyloxy group, a 4-phenylsulfanylphenylsulfonyloxy group or a 4-dimethylaminophenylsulfonyloxy group.

The alkylsulfonyl group is preferably one having 1 to 20 carbon atoms. As such, there can be mentioned, for example, a methylsulfonyl group, an ethylsulfonyl group, a propylsulfonyl group, an isopropylsulfonyl group, a butylsulfonyl group, a hexylsulfonyl group, a cyclohexylsulfonyl group, an octylsulfonyl group, a 2-ethylhexylsulfonyl group, a decanoylsulfonyl group, a dodecanoylsulfonyl group, an octadecanoylsulfonyl group, a cyanomethylsulfonyl group, a methoxymethylsulfonyl group or a perfluoroalkylsulfonyl group.

The arylsulfonyl group is preferably one having 6 to 30 carbon atoms. As such, there can be mentioned, for example, a phenylsulfonyl group, a 1-naphthylsulfonyl group, a 2-naphthylsulfonyl group, a 2-chlorophenylsulfonyl group, a 2-methylphenylsulfonyl group, a 2-methoxyphenylsulfonyl group, a 2-butoxyphenylsulfonyl group, a 3-chlorophenylsulfonyl group, a 3-trifluoromethylphenylsulfonyl group, a 3-cyanophenylsulfonyl group, a 3-nitrophenylsulfonyl group, a 4-fluorophenylsulfonyl group, a 4-cyanophenylsulfonyl group, a 4-methoxyphenylsulfonyl group, a 4-methylsulfanylphenylsulfonyl group, a 4-phenylsulfanylphenylsulfonyl group or a 4-dimethylaminophenylsulfonyl group.

As the alkylthioxy group, there can be mentioned, for example, a methylthioxy group, an ethylthioxy group, a propylthioxy group, an n-butylthioxy group, a trifluoromethylthioxy group, a hexylthioxy group, a t-butylthioxy group, a 2-ethylhexylthioxy group, a cyclohexylthioxy group, a decylthioxy group or a dodecylthioxy group.

As the arylthioxy group, there can be mentioned, for example, a phenylthioxy group, a 1-naphthylthioxy group, a 2-naphthylthioxy group, a tolylthioxy group, a methoxyphenylthioxy group, a naphthylthioxy group, a chlorophenylthioxy group, a trifluoromethylphenylthioxy group, a cyanophenylthioxy group or a nitrophenylthioxy group.

The heterocyclic group is preferably an aromatic or aliphatic heterocycle containing a nitrogen atom, an oxygen atom, a sulfur atom or a phosphorus atom. As the heterocyclic group, there can be mentioned, for example, a thienyl group, a benzo[b]thienyl group, a naphtho[2,3-b]thienyl group, a thianthrenyl group, a furyl group, a pyranyl group, an isobenzofuranyl group, a chromenyl group, a xanthenyl group, a phenoxathiyl group, a 2H-pyrrolyl group, a pyrrolyl group, an imidazolyl group, a pyrazolyl group, a pyridyl group, a pyrazinyl group, a pyrimidinyl group, a pyridazinyl group, an indolizinyl group, an isoindolyl group, a 3H-indolyl group, an indolyl group, a 1H-indazolyl group, a purinyl group, a 4H-quinolizinyl group, an isoquinolyl group, a quinolyl group, a phthalazinyl group, a naphthyridinyl group, a quinoxalinyl group, a quinazolinyl group, a cinnolinyl group, a puteridinyl group, a 4aH-carbazolyl group, a carbazolyl group, a β-carbolinyl group, a phenanthridinyl group, an acridinyl group, a perimidinyl group, a phenanthrolinyl group, a phenazinyl group, a phenarsazinyl group, an isothiazolyl group, a phenothiazinyl group, an isoxazolyl group, a furazanyl group, a phenoxadinyl group, an isochromanyl group, a chromanyl group, a pyrrolidinyl group, a pyrrolinyl group, an imidazolidinyl group, an imidazolinyl group, a pyrazolidinyl group, a pyrazolinyl group, a piperidyl group, a piperazinyl group, an indolinyl group, an isoindolinyl group, a quinucridinyl group, a morpholinyl or a thioxanthryl group.

As the substituents that can be introduced in any of $R_1$ to $R_4$, there can be mentioned, for example, a halogen atom such as a fluorine atom, a chlorine atom, a bromine atom or an iodine atom; an alkoxy group such as a methoxy group, an ethoxy group or a tert-butoxy group; an aryloxy group such as a phenoxy group or a p-tolyloxy group; an alkoxycarbonyl group such as a methoxycarbonyl group, a butoxycarbonyl group or a phenoxycarbonyl group; an acyloxy group such as an acetoxy group, a propionyloxy group or a benzoyloxy group; an acyl group such as an acetyl group, a benzoyl group, a isobutyryl group, an acryloyl group, a methacryloyl group or a methoxalyl group; an alkylsulfanyl group such as a methylsulfanyl group or a tert-butylsulfanyl group; an arylsulfanyl group such as a phenylsulfanyl group or a p-tolylsulfanyl group; an alkylamino group such as a methylamino group or a cyclohexylamino group; a dialkylamino group such as a dimethylamino group, a diethylamino group, a morpholino group or a piperidino group; an arylamino group such as a phenylamino group or a p-tolylamino group; an alkyl group such as a methyl group, an ethyl group, a tert-butyl group or a dodecyl group; an aryl group such as a phenyl group, a p-tolyl group, a xylyl group, a cumenyl group, a naphthyl group, an anthryl group or a phenanthryl group; a hydroxyl group; a carboxyl group; a formyl group; a mercapto group; a sulfo group; a mesyl group; a p-toluenesulfonyl group; an amino group; a nitro group; a cyano group; a trifluoromethyl group; a trichloromethyl group; a trimethylsilyl group; a phosphinico group; a phosphono group; a trimethylammoniumyl group; a dimethylsulfoniumyl group; and a triphenylphenancylphosphoniumyl group.

Two or more of $R_1$ to $R_4$ may be bonded to each other to thereby form a cyclic structure. This cyclic structure may be an aliphatic or aromatic hydrocarbon ring, or a heterocycle containing a heteroatom. These $R_1$ to $R_4$ may also form a polycondensed ring.

As the aliphatic or aromatic hydrocarbon ring, there can be mentioned, for example, one with a 6-membered, 5-membered or 7-membered ring structure. As the hydrocarbon ring, one with a 6-membered or 5-membered ring structure is preferred. One with a 5-membered ring structure is most preferred.

As the heterocycle, there can be mentioned, for example, one containing a sulfur atom, an oxygen atom or a nitrogen atom as a heteroatom. It is preferred for the heterocycle to be one containing a sulfur atom as a heteroatom.

As the polycondensed ring, there can be mentioned, for example, a condensed ring composed only of a hydrocarbon ring. As such a polycondensed ring, there can be mentioned, for example, one resulting from the condensation of 2 to 4 benzene rings or one resulting from the condensation of a benzene ring with a 5-membered unsaturated ring.

The polycondensed ring may be a condensed ring containing at least one heterocycle. As such a polycondensed ring, there can be mentioned, for example, one resulting from the condensation of a benzene ring with a 5-membered heterocycle or one resulting from the condensation of a benzene ring with a 6-membered heterocycle.

As the cyclic structure that can be formed by $R_1$ to $R_4$, there can be mentioned, for example, a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, a dithiorane ring, an oxirane ring, a dioxirane ring, a thiirane ring, a pyrrolidine ring, a piperidine ring, an imidazole ring, an isooxazole ring, a benzothiazole ring, an oxazole ring, a thiazole ring, a benzothiazole ring, a benzimidazole ring, a benzoxazole ring, a pyridine ring, a pyrazine ring, a pyrimidine ring, a pyridazine ring, an indolizine ring, an indole ring, a benzofuran ring, a benzothiophene ring, a benzodithiol ring, an isobenzofuran ring, a quinolizine ring, a quinoline ring, a phthalazine ring, a naphthyridine ring, a quinoxaline ring, a quinazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring or a phenazine ring. Of these, a dithiorane ring, a benzothiol ring, a benzothiazole ring, a benzimidazole ring and a benzoxazole ring are especially preferred.

The groups $R_1$ to $R_4$ used in general formula (1) mean, for example, those groups appearing in the following chemical formulae.

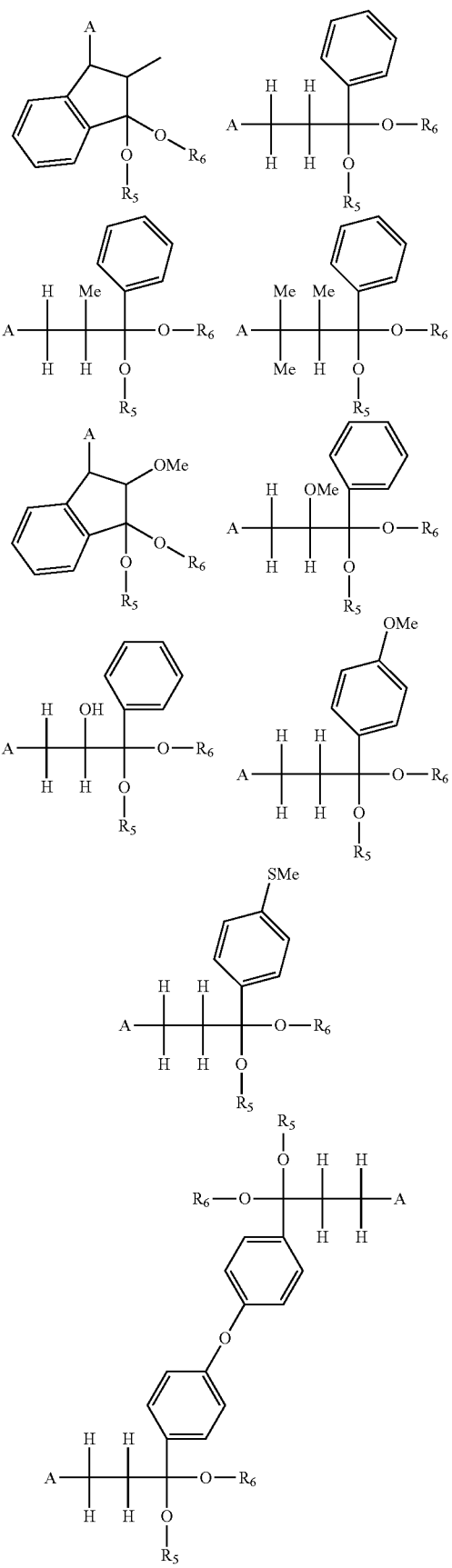

-continued

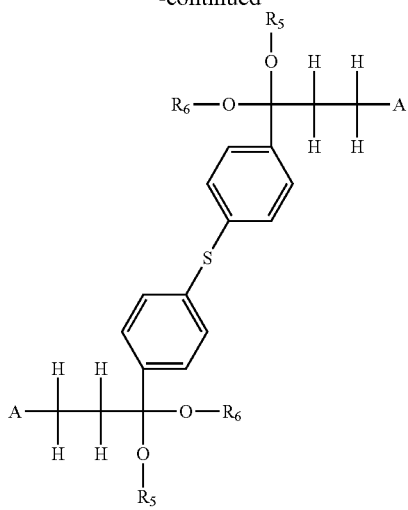

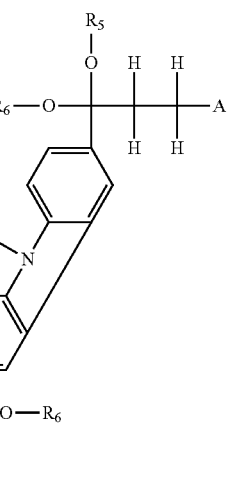

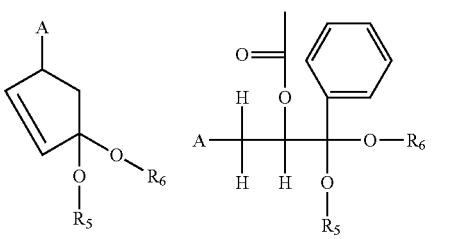

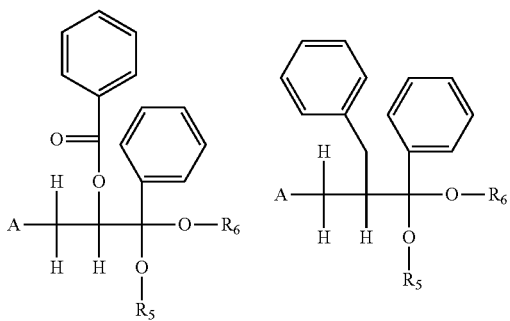

-continued

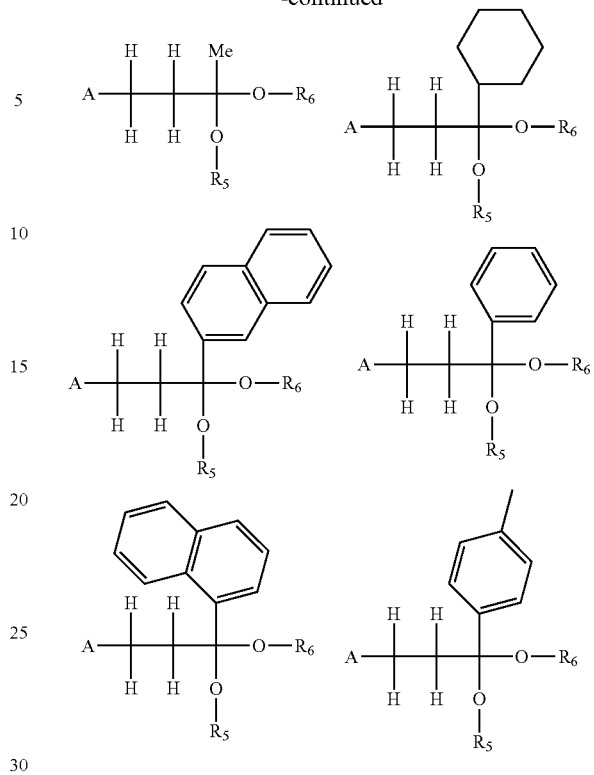

Now, $R_5$ and $R_6$ will be described.

In formula (1), each of $R_5$ and $R_6$ represents a monovalent substituent. As the monovalent substituent, there can be mentioned, for example, a monovalent organic group or a silyl group. As the monovalent organic group, there can be mentioned, for example, an alkyl group, a cycloalkyl group, an alkenyl group, an alkynyl group, an aryl group, an alkanoyl group, an alkoxycarbonyl group, an aryloxycarbonyl group, an alkylsulfonyl group, an arylsulfonyl group, an alkylthiocarbonyl group, an arylthiocarbonyl group or a dialkylaminocarbonyl group. One or more substituents may be introduced in each of these monovalent organic groups.

As the alkyl group, cycloalkyl group, alkenyl group, alkynyl group, aryl group, alkanoyl group, alkoxycarbonyl group, aryloxycarbonyl group, alkylsulfonyl group, arylsulfonyl group, alkylthiocarbonyl group and arylthiocarbonyl group, there can be mentioned, for example, those set forth above in connection with $R_1$ to $R_4$.

As the optionally substituted dialkylaminocarbonyl group, there can be mentioned, for example, a dimethylaminocarbonyl group, a diethylaminocarbonyl group, a dipropylaminocarbonyl group or a dibutylaminocarbonyl group.

It is preferred for $R_5$ and $R_6$ to be bonded to each other to thereby form a cycloacetal structure. An aliphatic or aromatic hydrocarbon ring or a heterocycle containing a heteroatom may be introduced as a substituent in this cycloacetal structure. The above hydrocarbon ring and/or heterocycle may form a condensed ring in cooperation with the cycloacetal. As the hydrocarbon ring and heterocycle, there can be mentioned, for example, those set forth above in connection with $R_1$ to $R_4$.

The groups $R_5$ and $R_6$ used in general formula (1) mean, for example, those groups appearing in the following chemical formulae.

-continued
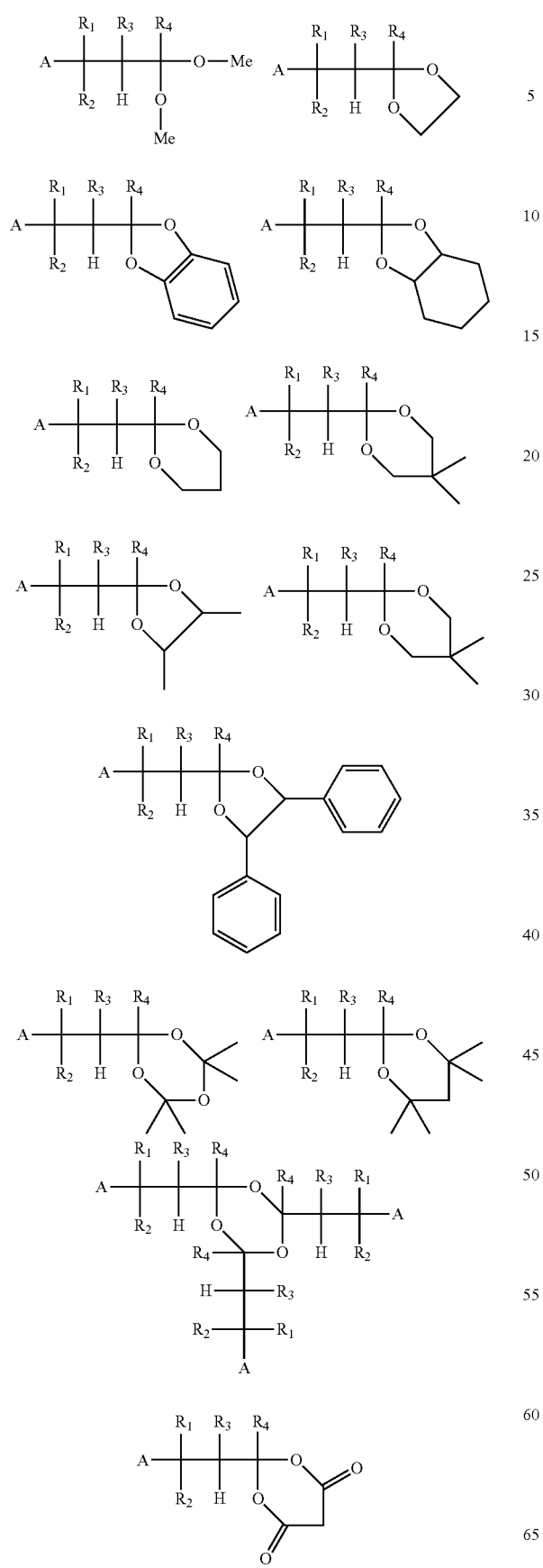
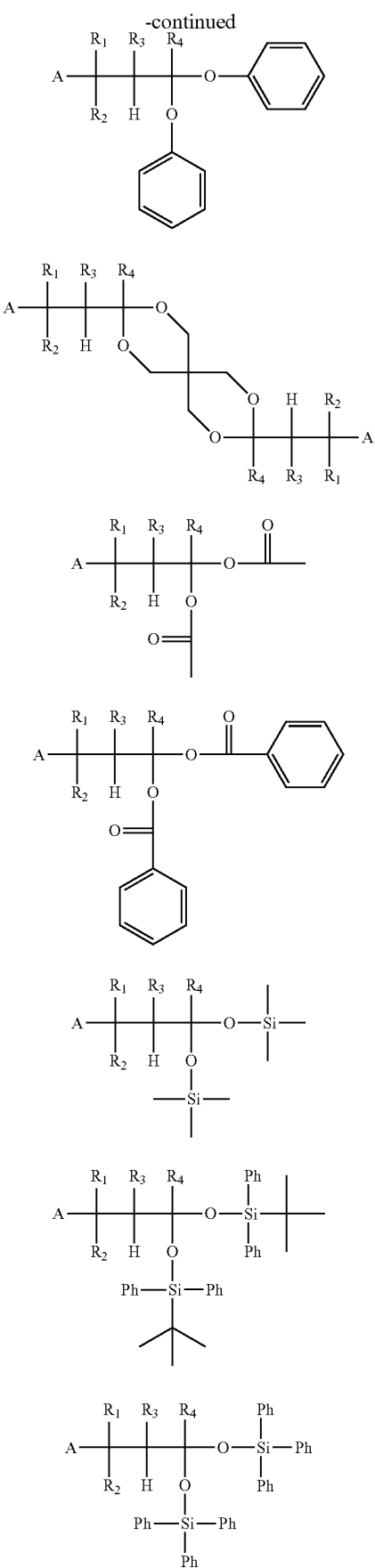

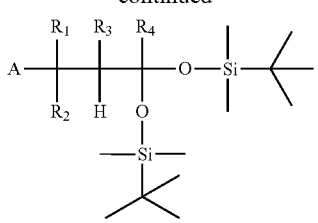

As the compounds of general formula (1), there can be mentioned, for example, those of the following chemical formulae.

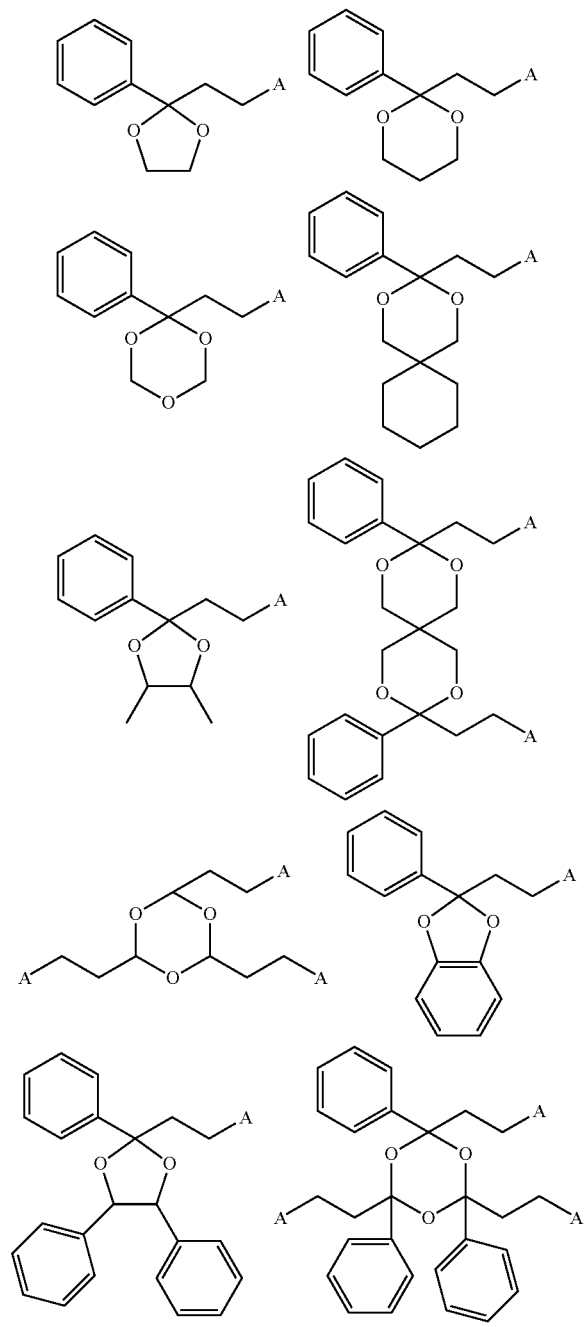

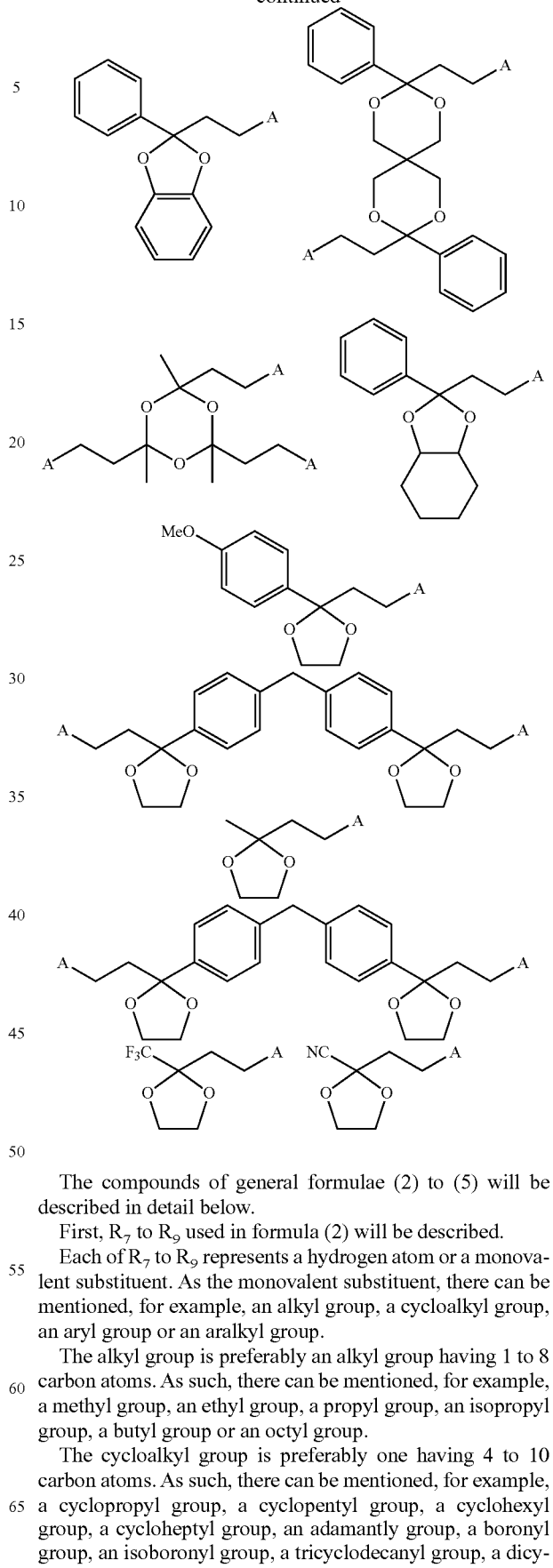

The compounds of general formulae (2) to (5) will be described in detail below.

First, $R_7$ to $R_9$ used in formula (2) will be described.

Each of $R_7$ to $R_9$ represents a hydrogen atom or a monovalent substituent. As the monovalent substituent, there can be mentioned, for example, an alkyl group, a cycloalkyl group, an aryl group or an aralkyl group.

The alkyl group is preferably an alkyl group having 1 to 8 carbon atoms. As such, there can be mentioned, for example, a methyl group, an ethyl group, a propyl group, an isopropyl group, a butyl group or an octyl group.

The cycloalkyl group is preferably one having 4 to 10 carbon atoms. As such, there can be mentioned, for example, a cyclopropyl group, a cyclopentyl group, a cyclohexyl group, a cycloheptyl group, an adamantly group, a boronyl group, an isoboronyl group, a tricyclodecanyl group, a dicyclopentenyl group, a norbornaneepoxy group, a menthyl group, an isomenthyl group, a neomenthyl group and a tetracyclododecanyl group.

The aryl group is preferably one having 6 to 14 carbon atoms. As such, there can be mentioned, for example, a phenyl group, a naphthyl group or a tolyl group.

As the aralkyl group, there can be mentioned an aralkyl group having 7 to 20 carbon atoms, for example, a benzyl group, a phenethyl group, a naphthylethyl group or the like.

One or more substituents may be introduced in these alkyl group, cycloalkyl group, aryl group and aralkyl group. As such substituents, there can be mentioned, for example, a halogen atom such as Cl, Br or F, a —CN group, an —OH group, an alkyl group having 1 to 4 carbon atoms, a cycloalkyl group having 3 to 8 carbon atoms, an alkoxy group having 1 to 4 carbon atoms, an acylamino group such as an acetylamino group, an aralkyl group such as a benzyl group or a phenethyl group, an aryloxyalkyl group such as a phenoxyethyl group, an alkoxycarbonyl group having 2 to 5 carbon atoms and an acyloxy group having 2 to 5 carbon atoms.

$R_7$ is preferably, for example, a hydrogen atom, a methyl group, an ethyl group, a propyl group, a butyl group, a pentyl group, a cyclopropyl group, a cyclopentyl group, a cyclohexyl group, a phenyl group, a naphthyl group, a benzyl group or a phenethyl group.

$R_8$ is preferably, for example, a methyl group, an ethyl group, an isopropyl group, a t-butyl group, a neopentyl group, a cyclohexyl group, a phenyl group, a benzyl group or a hydrogen atom.

$R_9$ is preferably, for example, a hydrogen atom, a methyl group, an ethyl group, a propyl group, a butyl group, a pentyl group, a cyclopropyl group, a cyclopentyl group, a cyclohexyl group, a phenyl group, a naphthyl group, a benzyl group or a phenethyl group.

It is preferred for $R_7$ and $R_9$ to be bonded to each other to thereby form a ring structure. The ring structure is most preferably a cyclopentyl ring or a cyclohexyl ring.

Below, $R_{10}$ and $R_{11}$ appearing in formula (3) will be described.

Each of $R_{10}$ and $R_{11}$ represents a hydrogen atom or a monovalent substituent.

$R_{10}$ is, for example, an alkyl group, a cycloalkyl group, an aryl group, an aralkyl group, an alkoxy group, an aryloxy group, an alkenyloxy group or a hydrogen atom.

$R_{11}$ is, for example, an alkyl group, a cycloalkyl group, an aryl group, an aralkyl group, an alkoxy group, an aryloxy group, an alkenyl group or a hydrogen atom.

As the alkyl group, cycloalkyl group, aryl group and aralkyl group, there can be mentioned, for example, those set forth above in connection with general formula (2).

The alkoxy group is preferably one having 1 to 8 carbon atoms. As such, there can be mentioned, for example, a methoxy group, an ethoxy group, a propoxy group, a cyclohexyloxy group or a butoxy group.

The aryloxy group is preferably one having 6 to 14 carbon atoms. As such, there can be mentioned, for example, a phenoxy group or a naphthoxy group.

The alkenyl group is preferably one having 2 to 6 carbon atoms. For example, there can be mentioned a vinyl group, a propenyl group, an allyl group, a butenyl group, a pentenyl group, a hexenyl group or a cyclohexenyl group.

The alkenyloxy group is preferably one having 2 to 8 carbon atoms. For example, there can be mentioned a vinyloxy group or an allyloxy group.

One or more substituents may be introduced in each of these alkyl group, cycloalkyl group, aryl group, aralkyl group, alkoxy group, aryloxy group, alkenyl group and alkenyloxy group. As such substituents, there can be mentioned, for example, those set forth above in connection with general formula (2).

$R_{10}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyloxy group or a methylvinyloxy group.

$R_{11}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyl group or an allyl group.

It is preferred for $R_{10}$ and $R_{11}$ to be bonded to each other to thereby form a ring structure. The ring structure is most preferably a 3-oxocyclohexenyl ring or a 3-oxoindenyl ring. These 3-oxocyclohexenyl ring or a 3-oxoindenyl ring may contain an oxygen atom in the ring thereof.

Further, $R_{12}$ to $R_{14}$ appearing in formula (4) will be described.

Each of $R_{12}$ and $R_{13}$ represents a hydrogen atom or a monovalent substituent. $R_{14}$ represents a monovalent substituent.

$R_{12}$ is, for example, an alkyl group, a cycloalkyl group, an aryl group, an aralkyl group, an alkoxy group, an aryloxy group or a hydrogen atom.

$R_{13}$ is, for example, an alkyl group, an alkoxy group, a halogen atom, an aralkyl group or a hydrogen atom.

$R_{14}$ is, for example, a group that when acted on by an acid, is cleaved.

As the group that is cleaved by the action of an acid, there can be mentioned, for example, —C($R_{36}$)($R_{37}$)($R_{38}$), —C(=O)—O—C($R_{36}$)($R_{37}$)($R_{38}$), —C($R_{01}$)($R_{02}$)(O$R_{39}$), —C($R_{01}$)($R_{02}$)—C(=O)—O—C($R_{36}$)($R_{37}$)($R_{38}$), —CH($R_{36}$)(Ar) or the like.

In the formulae, each of $R_{36}$ to $R_{39}$ independently represents an alkyl group, a cycloalkyl group, an aryl group, an aralkyl group, or an alkenyl group. $R_{36}$ and $R_{37}$ may be bonded to each other to form a ring.

Each of $R_{01}$ and $R_{02}$ independently represents a hydrogen atom, an alkyl group, a cycloalkyl group, an aryl group, an aralkyl group, or an alkenyl group.

Ar represents an aryl group.

As the alkyl group, cycloalkyl group, aryl group, aralkyl group, alkoxy group and aryloxy group, there can be mentioned, for example, those set forth above in connection with general formulae (2) and (3). One or more substituents may be introduced in each of these groups. As such substituents, there can be mentioned, for example, those set forth above in connection with general formula (2).

As the halogen atom, there can be mentioned, for example, a fluorine atom, a chlorine atom, a bromine atom or an iodine atom.

$R_{12}$ is preferably, for example, a methyl group, an ethyl group, a propyl group, a cyclopropyl group, a cyclopentyl group, a cyclohexyl group, a phenyl group, a naphthyl group, a benzyl group, a phenethyl group, a naphthylmethyl group or a hydrogen atom.

$R_{13}$ is preferably, for example, a methyl group, an ethyl group, a propyl group, a butyl group, a benzyl group or a hydrogen atom.

$R_{14}$ is preferably, for example, a tertiary alkyl group such as a t-butyl group, an alkoxyalkyl group such as a methoxymethyl group, an ethoxymethyl group or a 1-ethoxyethyl group, or a tetrahydropyranyl group.

Now, $R_{15}$ to $R_{19}$ appearing in formula (5) will be described.

Each of $R_{15}$ to $R_{19}$ represents a hydrogen atom or a monovalent substituent.

$R_{15}$ is, for example, an alkyl group, a cycloalkyl group, an aryl group, an aralkyl group, an alkoxy group, an aryloxy group, an alkenyloxy group or a hydrogen atom.

$R_{16}$ is, for example, an alkyl group, a cycloalkyl group, an aryl group, an aralkyl group, an alkoxy group, an aryloxy group, an alkenyl group or a hydrogen atom.

$R_{17}$ is, for example, an alkyl group, a cycloalkyl group, an aryl group, an aralkyl group, an alkoxy group, an aryloxy group, an alkenyl group or a hydrogen atom.

$R_{18}$ is, for example, an alkyl group, a cycloalkyl group, an aryl group, an aralkyl group, an alkoxy group, an aryloxy group, an alkenyl group or a hydrogen atom.

$R_{19}$ is, for example, an alkyl group, a cycloalkyl group, an aryl group, an aralkyl group, an alkoxy group, an aryloxy group, an alkenyl group or a hydrogen atom.

As the alkyl group, cycloalkyl group, aryl group, aralkyl group, alkoxy group, aryloxy group, alkenyl group and alkenyloxy group, there can be mentioned, for example, those set forth above in connection with general formulae (2) and (3).

One or more substituents may be introduced in each of these alkyl group, cycloalkyl group, aryl group, aralkyl group, alkoxy group, aryloxy group, alkenyl group and alkenyloxy group. As such substituents, there can be mentioned, for example, those set forth above in connection with general formula (2).

$R_{15}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyloxy group or a methylvinyloxy group.

$R_{16}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyl group or an allyl group.

$R_{17}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyl group or an allyl group.

$R_{18}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyl group or an allyl group.

$R_{19}$ is preferably, for example, a hydrogen atom, a methyl group, an ethyl group, a propyl group, an isopropyl group, a butyl group, an isobutyl group, a cyclopropyl group, a cyclopentyl group, a cyclohexyl group, a methoxy group, an ethoxy group, a phenyl group, a naphthyl group, a benzyl group, a phenoxy group, a naphthoxy group, a vinyl group or an allyl group.

At least two of $R_{15}$ to $R_{19}$ may be bonded to each other to thereby form a ring structure.

The characters $R_7$ to $R_{19}$ used in general formulae (2) to (5) mean, for example, those groups appearing in the following chemical formulae.

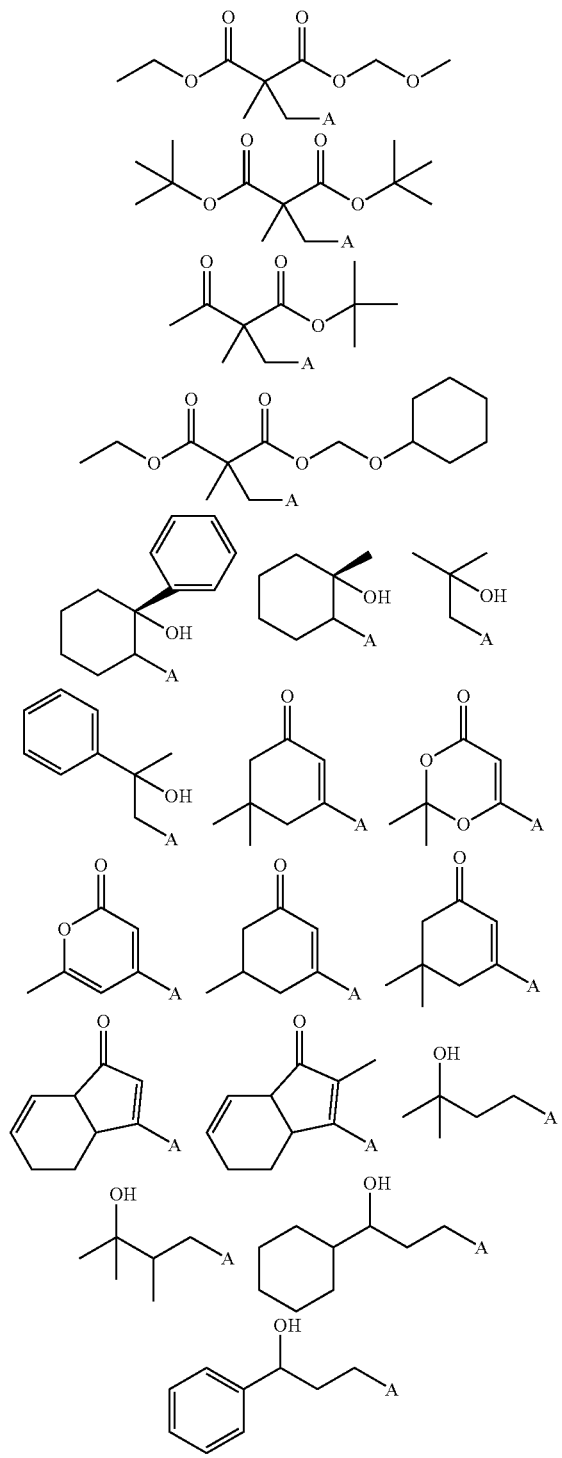

As the compounds of any of general formulae (1) to (5), there can be mentioned, for example, those of the following chemical formulae.

31
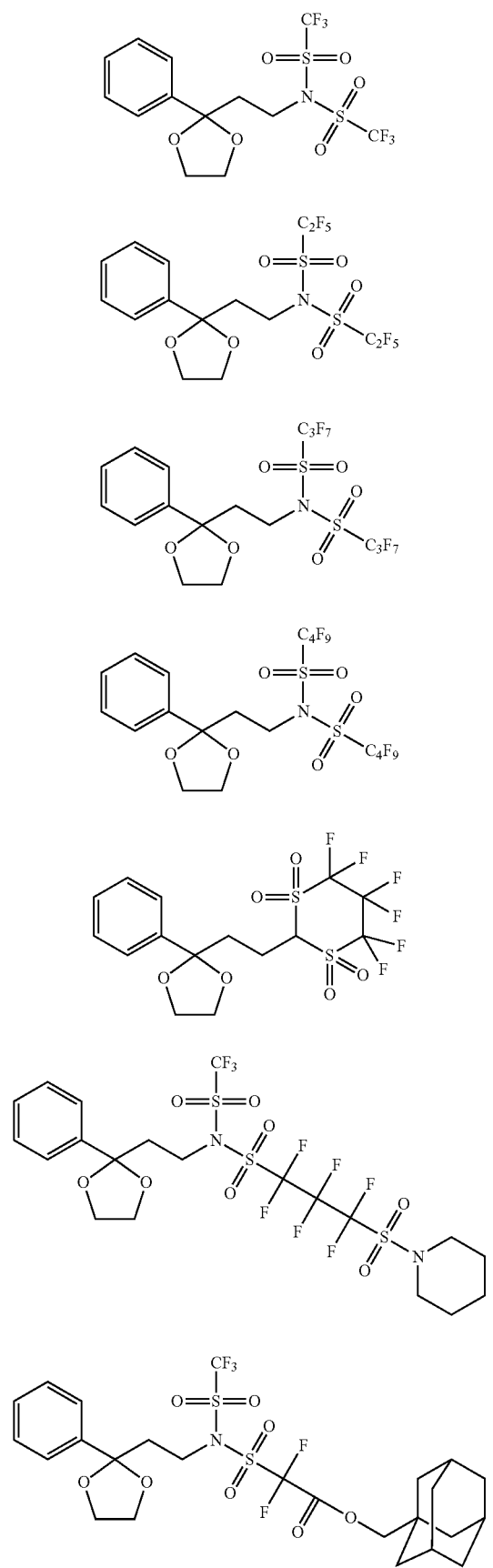
32
-continued
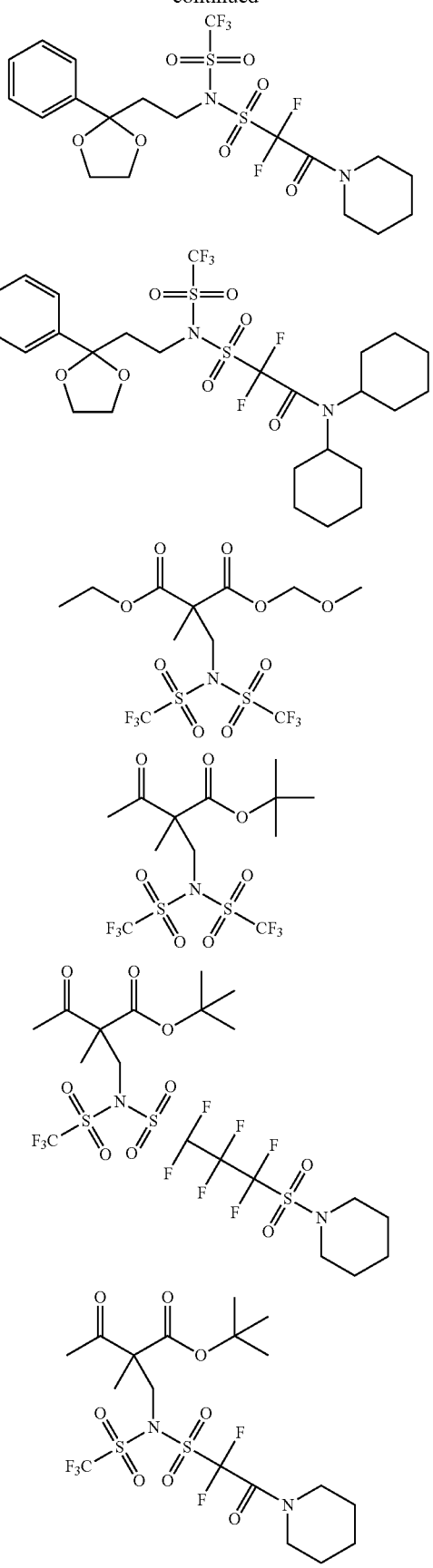

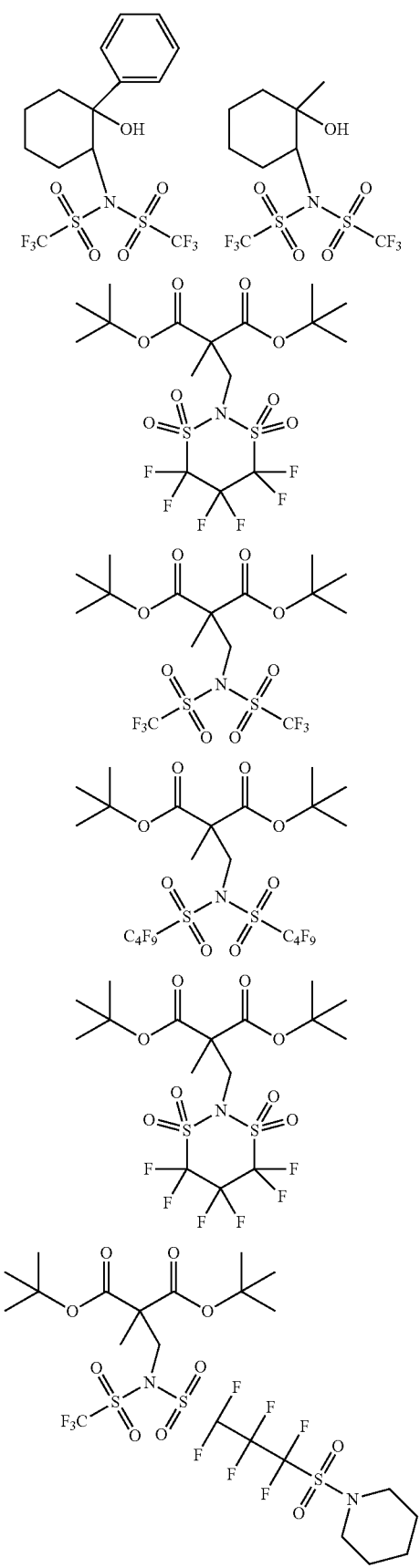
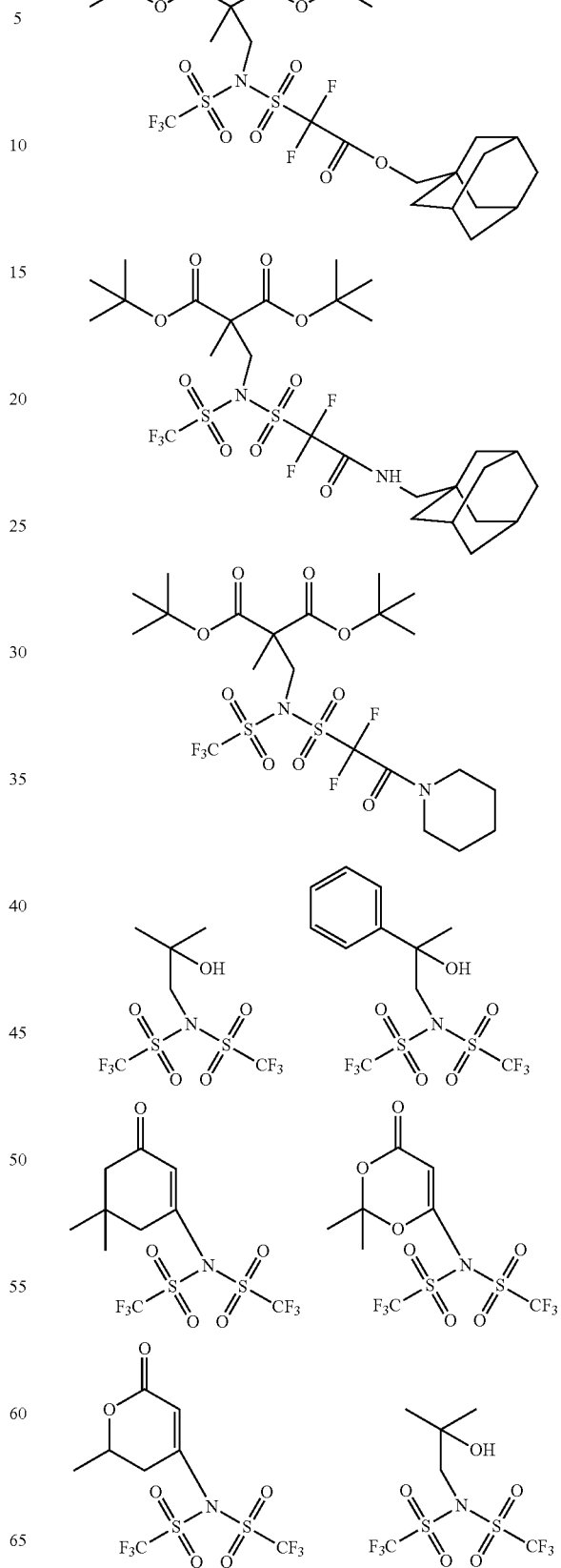

35
-continued
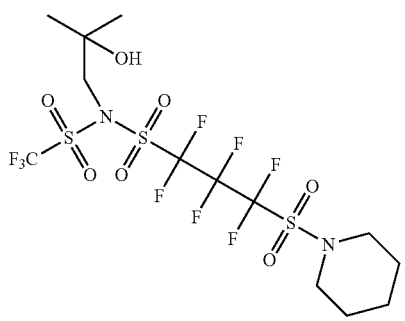
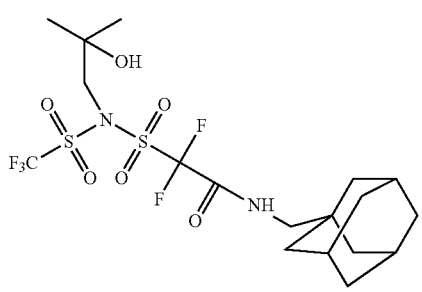
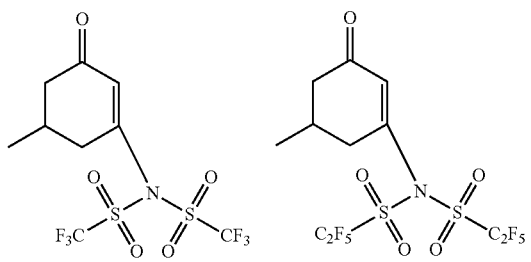
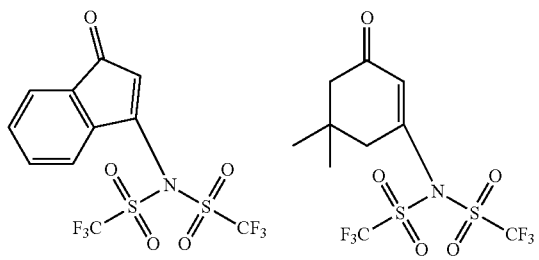
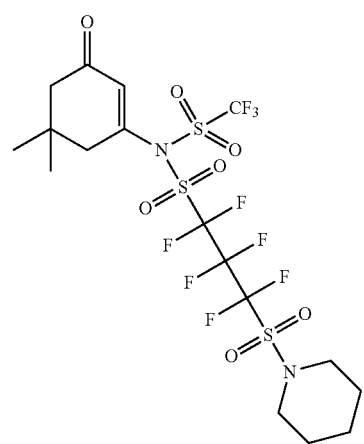
36
-continued
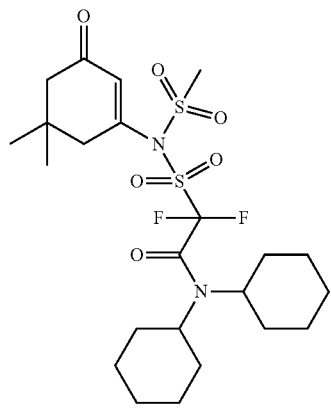
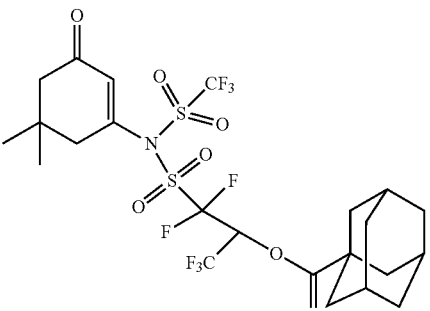
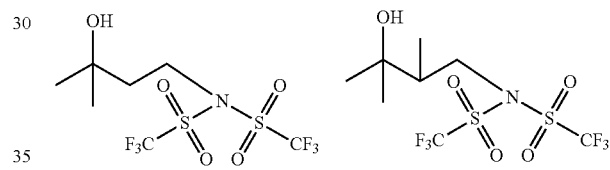
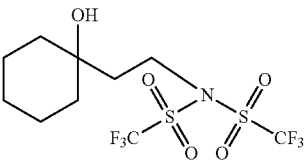
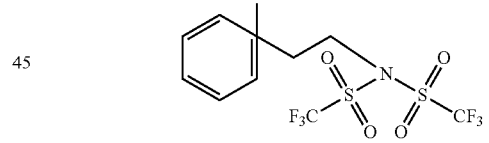
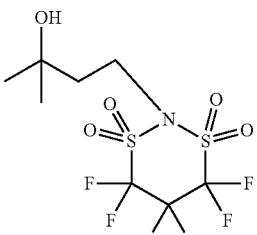
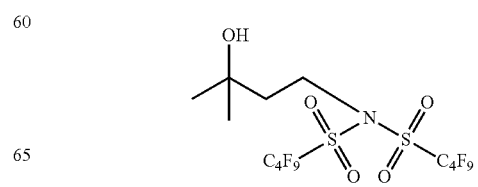

37
-continued
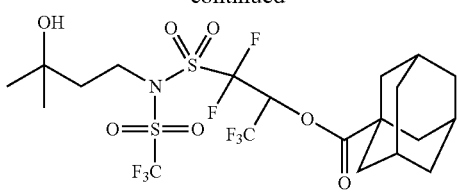
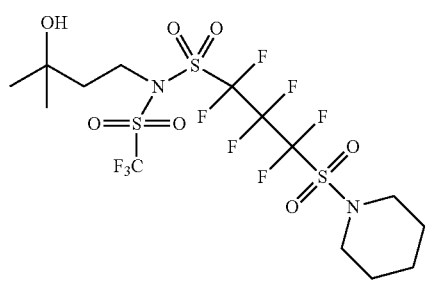
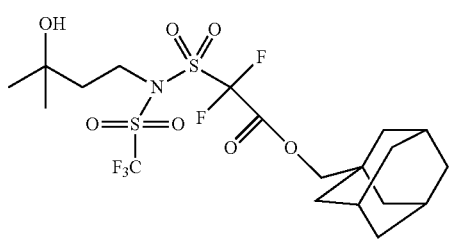
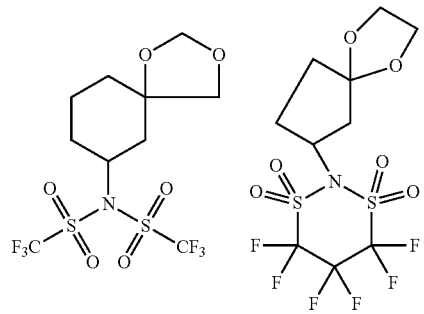
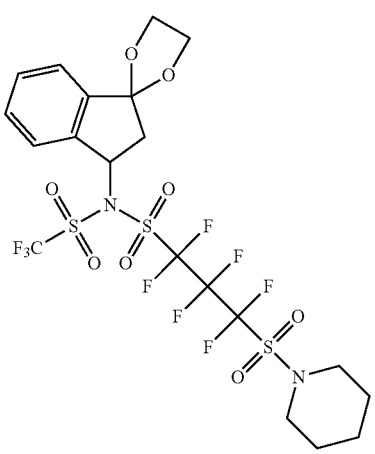
38
-continued
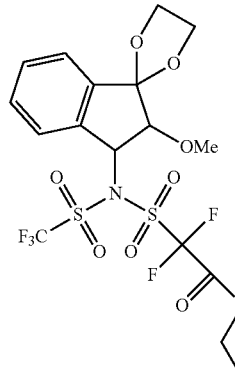
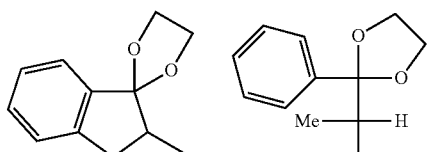
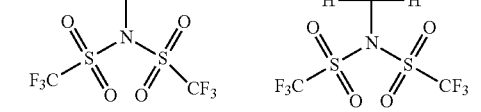
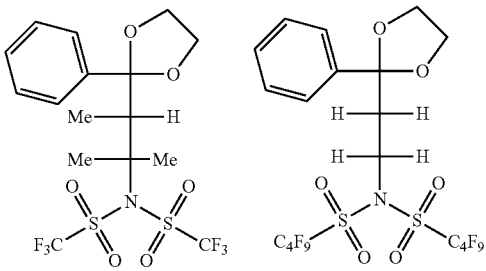
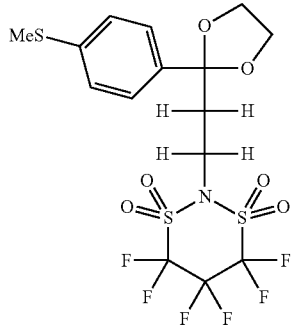
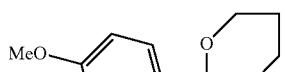
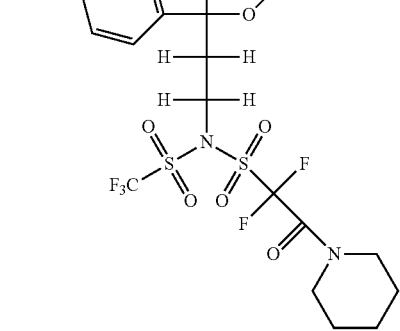

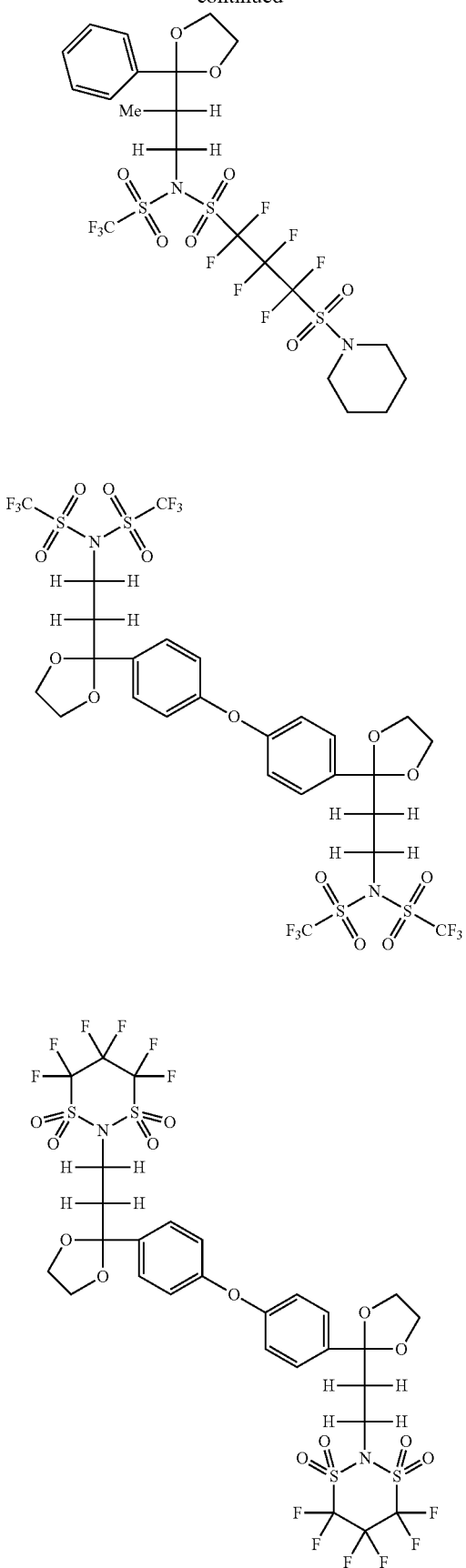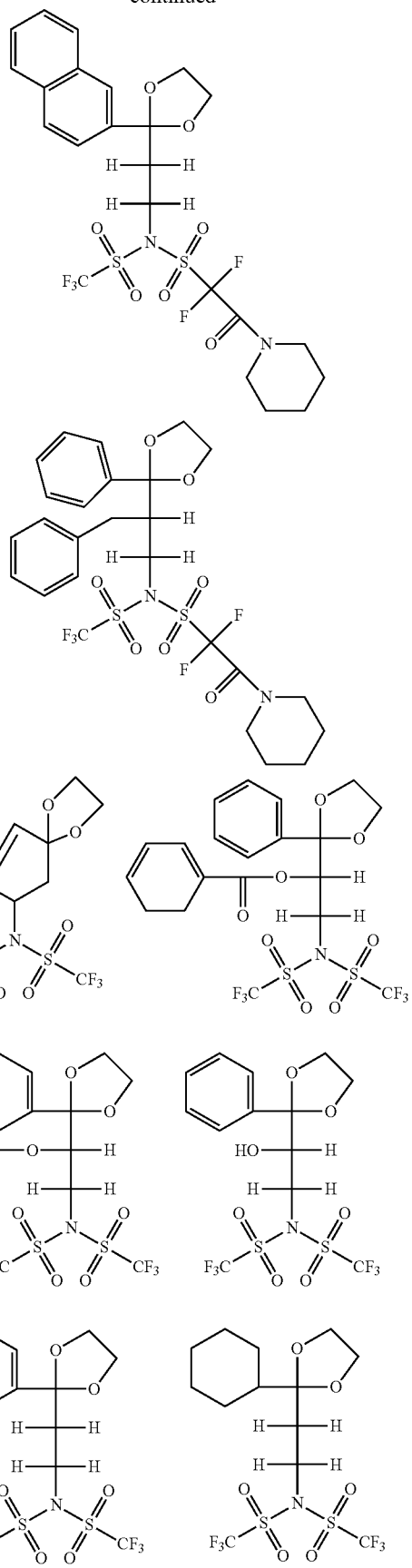

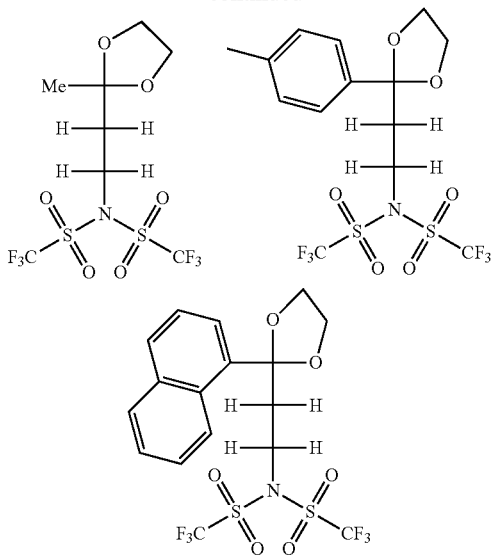

It is most preferred for the compounds of the formula A-LG to be those of general formula (A1-1) below.

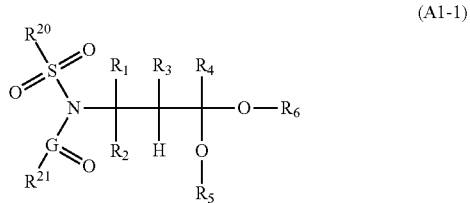

In formula (A1-1), $R^{20}$, $R^{21}$ and G are as defined above in connection with general formula (A-1). $R_1$ to $R_6$ are as defined above in connection with general formula (1).

The compounds of general formula (A1-1) are synthesized in, for example, the following manner.

First, an amine expressed by general formula (1N-I) below is caused to react with an acid halide expressed by general formula (1A-I) below or an acid anhydride expressed by general formula (1B-I) below in the presence of a base. Thus, an amine expressed by general formula (1N-II) below is synthesized.

The molar ratio of acid halide or acid anhydride to amine expressed by general formula (1N-I) is in the range of, for example, 0.9 to 2.0, typically 1.0 to 1.1.

The reaction is preferably performed by dropping the acid halide or acid anhydride at low temperatures. Various types of reaction solvents can be used as long as the reaction is not inhibited thereby. Among the reaction solvents, for example, n-hexane, n-pentane, benzene, toluene and xylene can be used as hydrocarbon solvents. As an ether solvent, there can be mentioned, for example, diethyl ether, diisopropyl ether, methyl t-butyl ether, tetrahydrofuran, dimethoxyethane or 1,4-dioxane. As an amide solvent, there can be mentioned, for example, N,N-dimethylformamide, N,N-dimethylacetamide or N-methylpyrrolidine. As a halogenated hydrocarbon solvent, there can be mentioned, for example, chloroform, methylene chloride or 1,2-dichloroethane. Other solvents include water, acetonitrile, dimethyl sulfoxide, acetic esters, acetone and the like. A single solvent may be used alone, or a plurality of solvents may be used in combination. Among these solvents, the ether solvents and halogenated hydrocarbon solvents are preferred. The halogenated hydrocarbon solvents are more preferred.

Preferred reaction temperature depends on the type of base and employed solvent. However, it is in the range of −78° C. to the boiling point of employed solvent, most preferably −20 to −15° C. The reaction time is in the range of, for example, 10 minutes to 48 hours, preferably 30 minutes to 6 hours.

Both an organic solvent and an inorganic solvent can be used as the base in this reaction. For example, use can be made of a hydroxide, carbonate or hydrogen carbonate of alkali metal or alkaline earth metal, such as sodium, potassium, lithium or calcium; a phosphate, such as trisodium phosphate or tripotassium phosphate; an alkali metal alkoxide, such as potassium t-butoxide; a metal hydride, such as sodium hydride, potassium hydride or lithium hydride; an alkyllithium reagent, such as n-butyllithium, methyllithium or lithium diisopropylamide; or an organic base, such as pyridine, triethylamine, N,N-diisopropylethylamine, 1,8-diazabicyclo[5.4.0]undec-7-ene (DBU), 1,8-diazabicyclo[4.3.0]non-5-ene (DBN), dimethylaniline, N-methylmorpholine, 2,6-lutidine or dimethylaminopyridine. Using an organic base is most preferred.

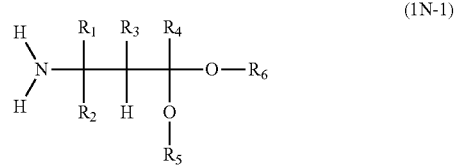

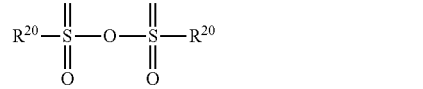

In formula (1N-I), $R_1$ to $R_6$ are as defined above in connection with general formula (1).

In formula (1A-I), $R^{20}$ is as defined above in connection with general formula (A-1). X represents a fluorine atom, a chlorine atom, a bromine atom or an iodine atom.

In formula (1B-I), $R^{20}$ is as defined above in connection with general formula (A-1).

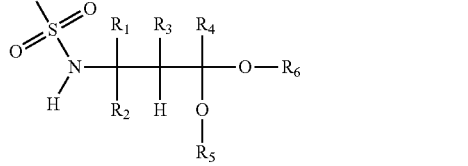

In formula (1N-II), $R^{20}$ is as defined above in connection with general formula (A-1). $R_1$ to $R_6$ are as defined above in connection with general formula (1).

Next, an amine expressed by general formula (1N-II) above is caused to react with an acid halide expressed by general formula (1A-II) below or an acid anhydride expressed by general formula (1B-II) below in the presence of a base. As a result, a compound expressed by general formula (A1-1) is obtained.

The molar ratio of acid halide or acid anhydride to amine expressed by general formula (1N-II) is in the range of, for example, 0.9 to 2.0, typically 1.0 to 1.5.

The reaction is preferably performed by dropping the acid halide or acid anhydride at low temperatures. Various types of reaction solvents can be used as long as the reaction is not inhibited thereby. Among the reaction solvents, for example, n-hexane, n-pentane, benzene, toluene and xylene can be used as hydrocarbon solvents. As an ether solvent, there can be mentioned, for example, diethyl ether, diisopropyl ether, methyl t-butyl ether, tetrahydrofuran, dimethoxyethane or 1,4-dioxane. As an amide solvent, there can be mentioned, for example, N,N-dimethylformamide, N,N-dimethylacetamide or N-methylpyrrolidine. As a halogenated hydrocarbon solvent, there can be mentioned, for example, chloroform, methylene chloride or 1,2-dichloroethane. Other solvents include water, acetonitrile, dimethyl sulfoxide, acetic esters, acetone and the like. A single solvent may be used alone, or a plurality of solvents may be used in combination. Using the ether solvent among these solvents is most preferred.

Preferred reaction temperature depends on the type of base and employed solvent. However, it is in the range of −78° C. to the boiling point of employed solvent, most preferably −20 to −15° C. The reaction time is in the range of, for example, 10 minutes to 48 hours, preferably 30 minutes to 6 hours.

Both an organic solvent and an inorganic solvent can be used as the base in this reaction. For example, use can be made of a hydroxide, carbonate or hydrogen carbonate of alkali metal or alkaline earth metal, such as sodium, potassium, lithium or calcium; a phosphate, such as trisodium phosphate or tripotassium phosphate; an alkali metal alkoxide, such as potassium t-butoxide; a metal hydride, such as sodium hydride, potassium hydride or lithium hydride; an alkyllithium reagent, such as n-butyllithium, methyllithium or lithium diisopropylamide; or an organic base, such as pyridine, triethylamine, N,N-diisopropylethylamine, 1,8-diazabicyclo[5.4.0]undec-7-ene (DBU), 1,8-diazabicyclo[4.3.0]non-5-ene (DBN), dimethylaniline, N-methylmorpholine, 2,6-lutidine or dimethylaminopyridine. As the base, a metal hydride is preferred. Sodium hydride is most preferred.

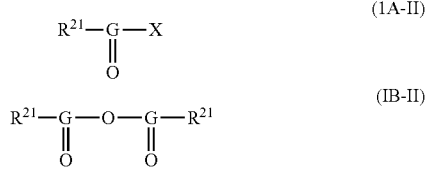

In formula (1A-II), $R^{21}$ and G are as defined above in connection with general formula (A-1). X represents a fluorine atom, a chlorine atom, a bromine atom or an iodine atom.

In formula (1B-II), $R^{21}$ and G are as defined above in connection with general formula (A-1).

The above description illustrates the method of synthesis through substitution of the hydrogen atom of a secondary amine provided with a $R^{20}$-containing group with a $R^{21}$-containing group. However, the method of synthesizing the compounds of general formula (A1-1) is not limited to the above method. For example, the compounds may be synthesized by a method involving substitution of the hydrogen atom of a secondary amine provided with a $R^{21}$-containing group with a $R^{20}$-containing group.

The other compounds of the formula A-LG can be synthesized by, for example, the same methods as described above with respect to the compounds of general formula (A1-1).

The above acid amplifiers may be used individually or in combination. The content of acid amplifier based on the total solids of the composition is preferably in the range of 0.1 to 40 mass %, more preferably 0.5 to 30 mass % and further more preferably 1 to 20 mass %. It is preferred for the content of acid amplifier to be 0.5 to two times that of photoacid generator to be described hereinbelow.

[2] Photoacid Generator

As such a photoacid generator, use can be made of, for example, a member appropriately selected from among a photoinitiator for photocationic polymerization, a photoinitiator for photoradical polymerization, a photo-achromatic agent and photo-discoloring agent for dyes, any of heretofore known compounds that when exposed to actinic rays or radiation, generate an acid, employed in microresists, etc., and mixtures thereof. As examples of the photoacid generators, there can be mentioned an onium salt, such as a sulfonium salt or an iodonium salt, and a diazodisulfone compound, such as a bis(alkylsulfonyldiazomethane).

As preferred compounds among the acid generators, those represented by the following general formulae (ZI), (ZII) and (ZIII) can be exemplified.

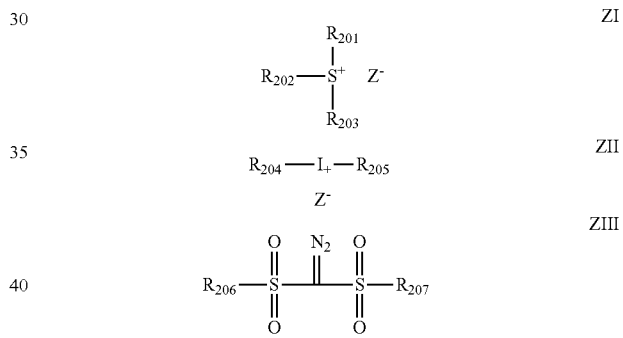

In the above general formula (ZI), each of $R_{201}$, $R_{202}$ and $R_{203}$ independently represents an organic group.

The number of carbon atoms in the organic group represented by $R_{201}$, $R_{202}$ and $R_{203}$ is generally in the range of 1 to 30, preferably 1 to 20.

Two of $R_{201}$ to $R_{203}$ may be bonded to each other through single bond or connecting group to form a ring. As the connecting group, for example, an ether bond, a thioether bond, an ester bond, an amido bond, a carbonyl group, a methylene group, and an ethylene group can be exemplified. As the group formed by bonding of two of $R_{201}$ to $R_{203}$, for example, an alkylene group such as a butylene group or a pentylene group can be exemplified.

As the specific examples of $R_{201}$, $R_{202}$, and $R_{203}$, corresponding groups in the compounds (ZI-1), (ZI-2), or (ZI-3) described below can be exemplified.

X⁻ represents a normucleophilic anion. As X⁻, for example, a sulfonate anion, a bis(alkylsulfonyl)imido anion, a tris(alkylsulfonyl)methyl anion, $BF_4^-$, $PF_6^-$, and $SbF_6^-$ can be exemplified. X⁻ preferably is an organic anion containing one or more carbon atoms. As the preferred organic anions, any of those represented by the following AN1 to AN3 can be exemplified.

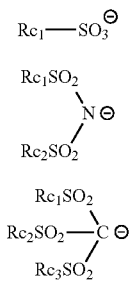

In the formulae AN1 to AN3, $Rc_1$ to $Rc_3$ each independently represents an organic group. As the organic group, those having 1 to 30 carbon atoms can be exemplified. Preferably, an alkyl group, an aryl group, or a group in which these groups are connected through a single bond or a connecting group. As the connecting group, for example, —O—, —$CO_2$—, —S—, —$SO_3$— and —$SO_2N(Rd_1)$- can be exemplified. Here, $Rd_1$ represents a hydrogen atom or an alkyl group, and may form a ring together with a binding alkyl or aryl group.

An organic group represented by $Rc_1$ to $Rc_3$ may be an alkyl group whose 1-position is substituted with a fluorine atom or a fluoroalkyl group; or a phenyl group substituted with a fluorine atom or a fluoroalkyl group. Presence of a fluorine atom or a fluoroalkyl group can make an acidity of the acid generated by irradiating light become higher. This can enhance the sensitivity of the composition. $Rc_1$ to $Rc_3$ may bond to other alkyl groups, aryl groups, and the like, to thereby form a ring.

[200] As preferred $X^−$, a sulfonate anion represented by any of the following general formula (SA1) and (SA2) can be exemplified.

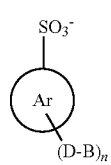

In the formula (SA1),

Ar represents an aryl group, and may further contain one or more substituents other than groups represented by -(D-B).

n is an integer of 1 or greater. n is preferably 1 to 4, more preferably 2 or 3, and most preferably 3.

D represents a single bond or a bivalent connecting group. The bivalent connecting group is, for example, an ether group, a thioether group, a carbonyl group, a sulfoxide group, a sulfone group, a sulfonic ester group, or an ester group.

B represents a hydrocarbon atom.

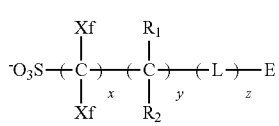

In the formula (SA2), each of Xfs independently represents a fluorine atom or an alkyl group substituted with at least one fluorine atom.

Each of $R_1$ and $R_2$ independently represents a member selected from among a hydrogen atom, a fluorine atom, an alkyl group and an alkyl group substituted with at least one fluorine atom. When two or more $R_1$s or $R_2$s are contained, the two or more may be identical to or different from each other.

L represents a single bond or a bivalent connecting group. When two or more Ls are contained, they may be identical to or different from each other.

E represents a group with a cyclic structure.

In the formula, x is an integer of 1 to 20, y an integer of 0 to 10 and z an integer of 0 to 10.

First, a sulfonate anion represented by the formula (SA1) will be described.

In the formula (SA1), Ar is preferably an aromatic ring having 6 to 30 carbon atoms. As the aromatic ring, there can be mentioned, for example, a benzene ring, a naphthalene ring, a pentalene ring, an indene ring, an azulene ring, a heptalene ring, an indecene ring, a perylene ring, a pentacene ring, an acenaphthalene ring, a phenanthrene ring, an anthracene ring, a naphthacene ring, a chrysene ring, a triphenylene ring, a fluorene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an iodolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring, a phenazine ring or the like. Of these, a benzene ring, a naphthalene ring and an anthracene ring are preferred from the viewpoint of the simultaneous attainment of roughness improvement and sensitivity enhancement. A benzene ring is more preferred.

The aromatic ring may have one or more substituents other than the -(D-B) groups. As the substituent, there can be mentioned, for example, a halogen group such as a fluorine atom, a chlorine atom, a bromine atom or an iodine atom, an alkoxy group such as a methoxy group, an ethoxy group or a tert-butoxy group, an aryloxy group such as a phenoxy group or a p-tolyloxy group, an alkylthioxy group such as a methylthioxy group, an ethylthioxy group or a tert-butylthioxy group, an arylthioxy group such as a phenylthioxy group or a p-tolylthioxy group, an alkoxycarbonyl group such as a methoxycarbonyl group or a butoxycarbonyl group, a phenoxycarbonyl group, an acetoxy group, a linear or branched alkyl group such as a methyl group, an ethyl group, a propyl group, a butyl group, a heptyl group, a hexyl group, a dodecyl group or a 2-ethylhexyl group, an alkenyl group such as a vinyl group, a propenyl group or a hexenyl group, an alkynyl group such as an acetylene group, a propynyl group or a hexynyl group, an aryl group such as a phenyl group or a tolyl group, an acyl group such as a benzoyl group, an acetyl group or a toluoyl group, a hydroxyl group, a carboxyl group, a sulfonate group or the like. Of these, a linear or branched alkyl group is preferred from the viewpoint of roughness improvement.

In the formula (SA1), D preferably is a single bond, an ether bond, or an ester bond. A single bond is especially preferred.

In the formula (SA1), B preferably is an alkyl group, an alkenyl group, an alkynyl group, an aryl group, or a cycloalkyl group. B preferably is an alkyl group or a cycloalkyl group. an alkyl group, an alkenyl group, an alkynyl group, an aryl group, or a cycloalkyl group represented by B may have one or more substituents.

An alkyl group represented by B preferably is a branched alkyl group. As the branched alkyl group, an isopropyl group, a tert-butyl group, a tert-pentyl group, a neopentyl group, a sec-butyl group, an isobutyl group, an isohexyl group, a 3,3-dimethylpentyl group, and a 2-ethylhexyl group can be exemplified.

A cycloalkyl group represented by B may either be monocyclic or polycyclic. As the monocyclic cycloalkyl group, for example, a cyclopropyl group, a cyclobutyl group, a cyclopentyl group, a cyclohexyl group, a cycloheptyl group, and a cyclooctyl group can be exemplified. As the polycyclic cycloalkyl group, for example, an adamantyl group, a norbornyl group, a bornyl group, a campheryl group, a decahydronaphthyl group, a tricyclodecanyl group, a tetracyclodecanyl group, a camphoroyl group, a dicyclohexyl group, and a pinenyl group can be exemplified.

When an alkyl group, an alkenyl group, an alkynyl group, an aryl group, or a cycloalkyl group represented by B have one or more substituents, the followings can be exemplified as the substituents. That is, as the substituents, a halogen atom such as a fluorine atom, a chlorine atom, a bromine atom, or an iodine atom; an alkoxy group such as a methoxy group, an ethoxy group, or a tert-butyl group; an aryloxy group such as phenoxy group or a p-tolyloxy group; an alkylthioxy group such as a methylthioxy group, an ethylthioxy group, or a tert-butylthioxy group; an arylthioxy group such as a phenylthioxy group or a p-tolylthioxy group; an alkoxycarbonyl group such as a methoxycarbonyl group, a butoxycarbonyl group, or a phenoxycarbonyl group; an acetoxy group; a linear alkyl group such as a methyl group, an ethyl group, a propyl group, a butyl group, a heptyl group, a hexyl group, or a dodecyl group; a branched alkyl group such as a 2-ethylhexyl group; a cycloalkyl group such as a cycloalkyl group; an alkenyl group such as a vinyl group, a propenyl group, or a hexenyl group; an aryl group such as a phenyl group or a tolyl group; a hydroxy group; a carboxy group; a sulfonic group; and a carbonyl group can be exemplified. A linear alkyl group and a branched alkyl group are preferred for simultaneously achieving roughness improvement and high sensitivity.

Now a sulfonate anion represented by the formula (SA2) will be described in details.

In the formula (SA2), Xf is a fluorine atom or an alkyl group at least one hydrogen atom of which is substituted by a fluorine atom. As the alkyl group, those having 1 to 10 carbon atoms are preferred, and those having 1 to 4 carbon atoms are more preferred. The alkyl group substituted with one or more fluorine atoms preferably is a perfluoroalkyl group.

Xf is preferably a fluorine atom or a perfluoroalkyl group having 1 to 4 carbon atoms. In particular, a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$ can be exemplified. Of these, a fluorine atom and $CF_3$ are preferred, and a fluorine atom are particularly preferred.

In the formula (SA2), each of R1 and R2 is a group selected from a hydrogen atom, a fluorine atom, an alkyl group, and an alkyl group at least one hydrogen atom of which is substituted by a fluorine atom. As the alkyl group which may be substituted with one or more fluorine atoms, those having 1 to 4 carbon atoms are preferred. Further, as the alkyl group substituted with one or more fluorine atoms, a perfluoroalkyl group having 1 to 4 carbon atoms are particularly preferred. In particular, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$ can be exemplified. Of these, $CF_3$ is preferred.

In the formula (SA2), x is preferably 1 to 8, more preferably 1 to 4. y is preferably 0 to 4, more preferably 0. z is preferably 0 to 8, more preferably 0 to 4.

In the formula (SA2), L represents a single bond or a bivalent connecting group. As the a bivalent connecting group, —COO—, —COO—, —CO—, —O—, —S—, —SO—, —SO$_2$—, an alkylene group, a cycloalkylene group, and an alkenylene group can be exemplified. Of these, —COO—, —COO—, —CO—, —O—, —S—, —SO—, or —SO$_2$— is more preferred. —COO—, —COO—, or —SO$_2$— is particularly preferred.

In the formula (SA2), E represents a group with a cyclic structure. As the group, an alicyclic group, an aryl group, and a group with any of heterocyclic structures can be exemplified.

The alicyclic group represented by E may either be monocyclic or polycyclic. As the alicyclic group of a single ring, a monocyclic cycloalkyl group such as a cyclopentyl group, a cyclohexyl group, or a cyclooctyl group is preferred. As the alicyclic group of multiple rings, a polycyclic cycloalkyl group such as a norbornyl group, a tricyclodecanyl group, a tetracyclodecanyl group, a tetracyclododecanyl group or an adamantyl group is preferred. In particular, employing a bulky alicyclic group which has a ring having 6 or more carbon atoms as the group E can reduce in-film diffusion in the PEB (post-exposure bake) stage, thereby enhancing a resolving power and EL (Exposure Latitude).

The aryl group represented by is, for example, a phenyl group, a naphthyl group, a phenanthryl group, or an anthryl group.

The group with a heterocyclic structure represented by E may either be aromatic or non-aromatic. As a heteroatom contained in the group, a nitrogen atom or a sulfur atom is preferred. As the specific example of the heterocyclic structure, a furan ring, a thiophene ring, a benzofuran ring, a benzothiophene ring, a dibenzofuran ring, a dibenzothiophene ring, a pyridine ring, pyperidine ring, and a morpholine ring can be exemplified. Of these, a furan ring, a thiophene ring, a pyridine ring, pyperidine ring, and a morpholine ring are particularly preferred.

E may have one or more substituents. As the substituent, an alkyl group (may be linear, branched or cyclic, preferably having 1 to 12 carbon atoms), an aryl group (preferably having 6 to 14 carbon atoms), a hydroxyl group, an alkoxy group, an ester group, an amido group, a urethane group, a ureido group, a thioether group, a sulfonamido group, and a sulfonic ester group can be exemplified.

Appropriate use may be made of compounds with two or more of the structures represented by the general formula (ZI). For example, use may be made of compounds having a structure wherein at least one of $R_{201}$ to $R_{203}$ of a compound represented by the general formula (ZI) is bonded to at least one of $R_{201}$ to $R_{203}$ of another compound represented by the general formula (ZI).

As preferred (ZI) components, the following compounds (ZI-1) to (ZI-4) can be exemplified.

The compounds (ZI-1) are arylsulfonium compounds of the general formula (ZI) wherein at least one of $R_{201}$ to $R_{203}$ is an aryl group, namely, compounds containing an arylsulfonium as a cation.

In the arylsulfonium compounds, all of the $R_{201}$ to $R_{203}$ may be aryl groups. It is also appropriate that the $R_{201}$ to $R_{203}$ are partially an aryl group and the remainder is an alkyl group or a cycloalkyl group. When the compound (ZI) contains two or more aryl groups, these may either be identical to or different from each other.

As the compound (ZI), there can be mentioned, for example, a triarylsulfonium compound, a diarylalkylsulfonium compound, an aryldialkylsulfonium compound, a diarylcycloalkylsulfonium compound and an aryldicycloalkylsulfonium compound.

As an aryl group in the compound (ZI-1), a phenyl group, a naphthyl group, or a heteroaryl group such as an indole group and a pyrrole group. Of these, a phenyl group, a naphthyl group, or an indole group is particularly preferred.

The alkyl group or cycloalkyl group contained in the arylsulfonium compound according to necessity is preferably a linear or branched alkyl group having 1 to 15 carbon atoms or a cycloalkyl group having 3 to 15 carbon atoms. As such, there can be mentioned, for example, a methyl group, an ethyl group, a propyl group, an n-butyl group, a sec-butyl group, a t-butyl group, a cyclopropyl group, a cyclobutyl group, a cyclohexyl group or the like.

The aryl group, alkyl group or cycloalkyl group represented by $R_{201}$ to $R_{203}$ may have one or more substituents. As the substituent, an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxy group, and a phenylthio group can be exemplified.

Preferred substituents are a linear or branched alkyl group having 1 to 12 carbon atoms, a cycloalkyl group having 3 to 12 carbon atoms and a linear, branched or cyclic alkoxy group having 1 to 12 carbon atoms. More preferred substituents are an alkyl group having 1 to 6 carbon atoms and an alkoxy group having 1 to 6 carbon atoms. The substituents may be contained in any one of the three $R_{201}$ to $R_{203}$, or alternatively may be contained in all three of $R_{201}$ to $R_{203}$. When $R_{201}$ to $R_{203}$ represent a phenyl group, the substituent preferably lies at the p-position of the phenyl group.

Further, an embodiment that one or two or the $R_{201}$ to $R_{203}$ is an optionally-substituted aryl group and the remainder is an alkyl group or a cycloalkyl group is also preferred. As the specific example of the structure, those represented in [0141] to [0153] of JP-A-2004-210670.

In this case, the aryl group is the same as the one described above, and preferably is a phenyl group or a naphthyl group. The aryl group preferably contain one or more hydroxy groups, alkoxy groups, or alkyl groups as substituent. The substituent is more preferably an alkoxy group having 1 to 12 carbon atoms, and further preferably an alkyl group having 1 to 6 carbon atoms.

The alkyl group or cycloalkyl group as the remainder is preferably the one having 1 to 6 carbon atoms. These groups may contain one or more substituents. Further, when two groups are present as the remainder, these may be bonded to each other to thereby form a ring.

The compound (ZI-1) is, for example, the one represented by the following formula (ZI-1A).

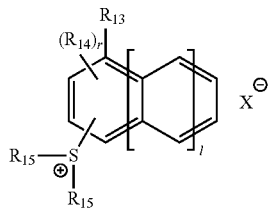

(ZI-1A)

In the general formula (ZI-1A), $R_{13}$ represents a hydrogen atom, a fluorine atom, a hydroxyl group, an alkyl group, a cycloalkyl group, an alkoxy group, or an alkoxycarbonyl group.

$R_{14}$, each independently when r≥2, represents an alkyl group, a cycloalkyl group, an alkoxy group, an alkoxycarbonyl group, an alkylcarbonyl group, an alkylsulfonyl group, or a cycloalkylsulfonyl group.

$R_{15}$ each independently represents an alkyl group or a cycloalkyl group, provided that the two $R_{15}$s may be bonded to each other to thereby form a ring.

l is an integer of 0 to 2.

r is an integer of 0 to 8.

$X^-$ represents a normucleophilic anion. As such, there can be mentioned any of the same normucleophilic anions as mentioned with respect to the $X^-$ of the general formula (ZI).

In general formula (ZI-4), the alkyl groups represented by $R_{13}$, $R_{14}$ and $R_{15}$ may be linear or branched and preferably each have 1 to 10 carbon atoms. As such, there can be mentioned a methyl group, an ethyl group, an n-propyl group, an i-propyl group, an n-butyl group, a 2-methylpropyl group, a 1-methylpropyl group, a t-butyl group, an n-pentyl group, a neopentyl group, an n-hexyl group, an n-heptyl group, an n-octyl group, a 2-ethylhexyl group, an n-nonyl group, an n-decyl group and the like. Of these alkyl groups, a methyl group, an ethyl group, an n-butyl group, and a t-butyl group are particularly preferred.

As the cycloalkyl groups represented by $R_{13}$, $R_{14}$ and $R_{15}$, there can be mentioned cyclopropyl group, cyclobutyl group, cyclopentyl group, cyclohexyl group, cycloheptyl group, cyclooctyl group, cyclododecanyl group, cyclopentenyl group, cyclohexenyl group, cyclooctadienyl group and the like. Cyclopropyl group, cyclopentyl group, cyclohexyl group and cyclooctyl group are especially preferred.

As the alkyl moieties in the alkoxy groups represented by $R_{13}$ and $R_{14}$, those explained for the alkyl groups represented by $R_{13}$, $R_{14}$ and $R_{15}$ can be exemplified. As the alkoxy group, a methoxy group, an ethoxy group, an n-propoxy group, and an n-butoxy group are especially preferred.

As the cycloalkyl moieties in the cycloalkoxy groups represented by $R_{13}$ and $R_{14}$, those explained for the cycloalkyl groups represented by $R_{13}$, $R_{14}$ and $R_{15}$ can be exemplified. As the cycloalkoxy group, a cyclopentyloxy group and a cyclohexyloxy group are especially preferred.

As the alkyl moieties in the alkoxycarbonyl groups represented by $R_{13}$, those explained for the alkyl groups represented by $R_{13}$, $R_{14}$ and $R_{15}$ can be exemplified. As the alkoxycarbonyl group, a methoxycarbonyl group, an ethoxycarbonyl group, and an n-butoxycarbonyl group are especially preferred.

As the alkyl moieties in the alkylsulfonyl groups represented by $R_{14}$, those explained for the alkyl groups represented by $R_{13}$, $R_{14}$ and $R_{15}$ can be exemplified. As the alkyl moieties in the cycloalkylsulfonyl groups represented by $R_{14}$, those explained for the cycloalkyl groups represented by $R_{13}$, $R_{14}$ and $R_{15}$ can be exemplified. As the alkylsulfonyl group and the cycloalkylsulfonyl group, a methylsulfonyl group, an ethylsulfonyl group, an n-propylsulfonyl group, an n-butylsulfonyl group, a cyclopentylsulfonyl group, and a cyclohexyl sulfonyl group are especially preferred.

l preferably is 0 or 1, and more preferably is 1. r preferably is an integer of 0 to 2.

Each of the groups may have one or more substituents. As such substituent, there can be mentioned, for example, a halogen atom (e.g., a fluorine atom), a hydroxyl group, a carboxyl group, a cyano group, a nitro group, an alkoxy group, a cycloalkyloxy group, an alkoxyalkyl group, a cycloalkoxyalkyl group, an alkoxycarbonyl group, a cycloalkoxycarbonyl group, an alkoxycarbonyloxy group, a cycloalkoxycarbonyloxy group, or the like.

As the alkoxy group, there can be mentioned, for example, a linear or branched alkoxy group having 1 to 20 carbon atoms, such as a methoxy group, an ethoxy group, an n-propoxy group, an i-propoxy group, an n-butoxy group, a 2-methylpropoxy group, a 1-methylpropoxy group, and a t-butoxy group.

As the cycloalkoxy group, there can be mentioned, for example, those having 3 to 20 carbon atoms, such as a cyclopentyloxy group and a cyclohexyloxy group.

As the alkoxyalkyl group, there can be mentioned, for example, a linear or branched alkoxyalkyl group having 2 to 21 carbon atoms, such as a methoxymethyl group, an ethoxymethyl group, a 1-methoxyethyl group, a 2-methoxyethyl group, a 1-ethoxyethyl group, and a 2-ethoxyethyl group.

As the cycloalkoxyalkyl group, there can be mentioned, for example, those having 4 to 21 carbon atoms, such as a cyclopentyloxymethyl group and a cyclohexyloxyethyl group.

As the alkoxycarbonyl group, there can be mentioned, for example, a linear or branched alkoxycarbonyl group having 2 to 21 carbon atoms, such as a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, and a t-butoxycarbonyl group.

As the cycloalkoxycarbonyl group, there can be mentioned, for example, those having 4 to 21 carbon atoms, such as a cyclopentyloxycarbonyl group and a cyclohexyloxycarbonyl group.

As the alkoxycarbonyloxy group, there can be mentioned, for example, a linear or branched alkoxycarbonyloxy group having 2 to 21 carbon atoms, such as a methoxycarbonyloxy group, an ethoxycarbonyloxy group, an n-propoxycarbonyloxy group, an i-propoxycarbonyloxy group, an n-butoxycarbonyloxy group, and a t-butoxycarbonyloxy group.

As the cycloalkoxycarbonyloxy group, there can be mentioned, for example, those having 4 to 21 carbon atoms, such as a cyclopentyloxycarbonyloxy group and a cyclohexyloxycarbonyloxy group.

The cyclic structure that may be formed by the bonding of the two $R_{15}$s to each other is preferably a 5- or 6-membered ring, especially a 5-membered ring (namely, a tetrahydrothiophene ring) formed by two bivalent $R_{15}$s in cooperation with the sulfur atom of general formula (ZI-1A).

The bivalent $R_{15}$s may have substituents. As such substituents, there can be mentioned, for example, a hydroxyl group, a carboxyl group, a cyano group, a nitro group, an alkoxy group, an alkoxyalkyl group, an alkoxycarbonyl group, an alkoxycarbonyloxy group and the like as mentioned above.

It is especially preferred for the $R_{15}$ of general formula (ZI-1A) to be a methyl group, an ethyl group, or the bivalent group allowing two $R_{15}$s to be bonded to each other so as to form a tetrahydrothiophene ring structure in cooperation with the sulfur atom of the general formula (ZI-1A)

Each of $R_{13}$ and $R_{14}$ may have one or more substituents. As such a substituent, there can be mentioned, for example, a hydroxyl group, an alkoxy group, an alkoxycarbonyl group, a halogen atom (especially, a fluorine atom) or the like.

Specific examples of the cation moieties in the compounds represented by the general formula (ZI-1A) will be given below.

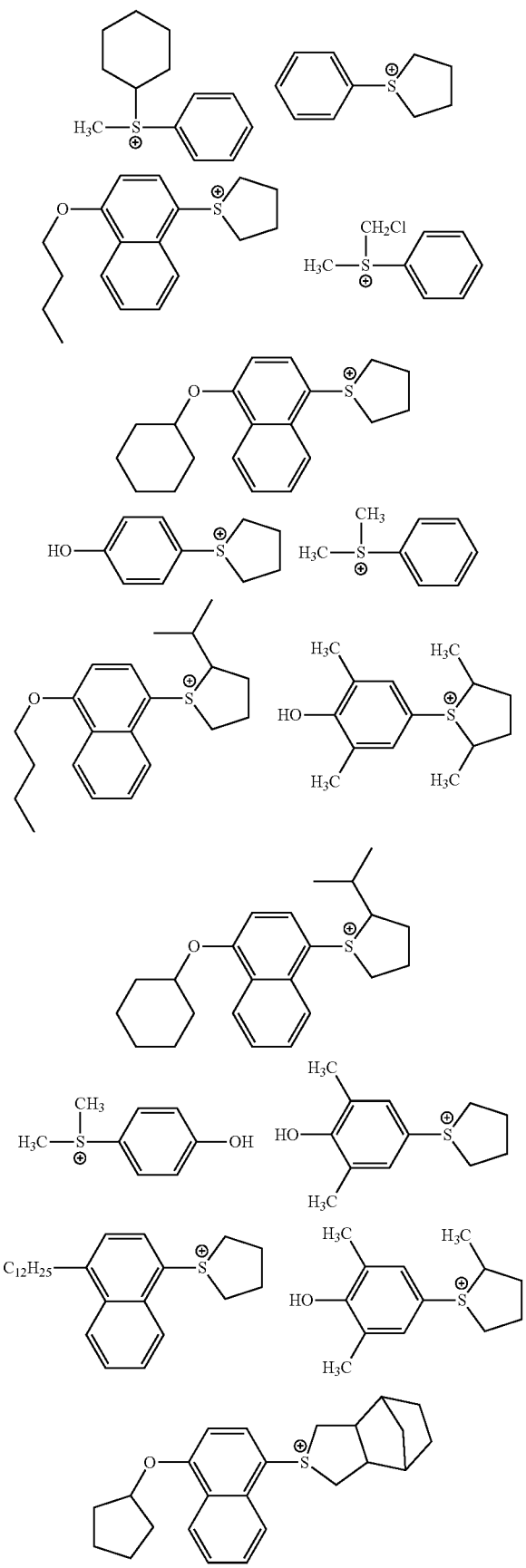

-continued

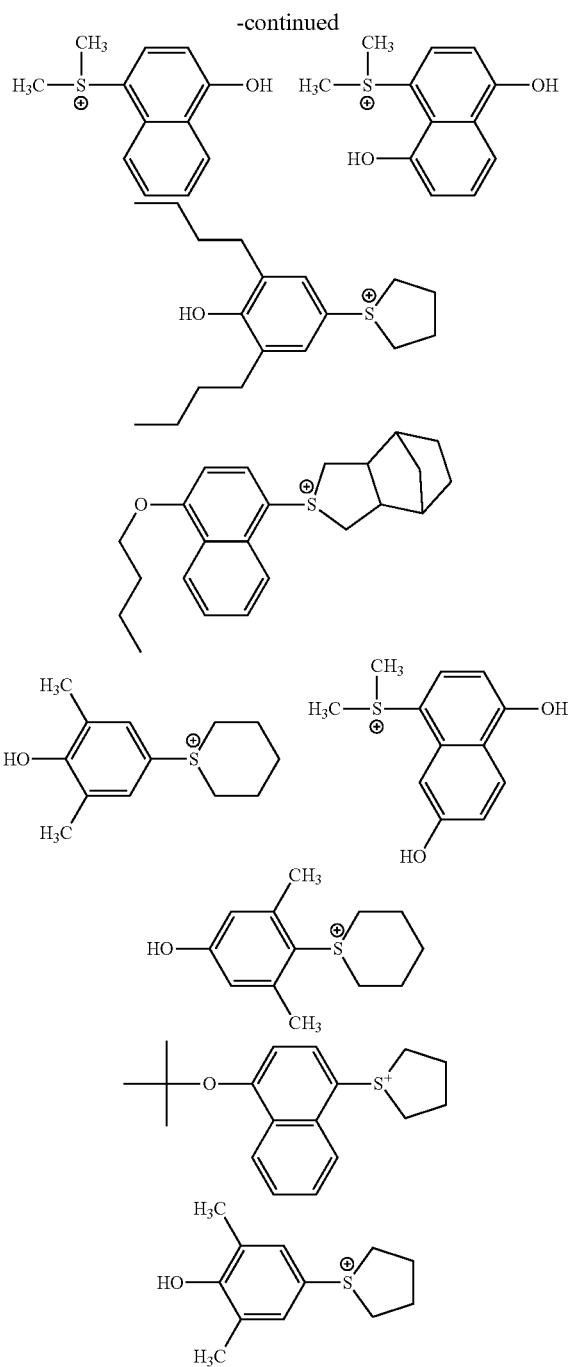

Now, the compounds (ZI-2) will be described.

The compounds (ZI-2) are compounds of formula (ZI) wherein each of $R_{201}$ to $R_{203}$ independently represents an organic group having no aromatic ring. The aromatic rings include an aromatic ring having a heteroatom.

The organic group having no aromatic ring represented by $R_{201}$ to $R_{203}$ generally has 1 to 30 carbon atoms, preferably 1 to 20 carbon atoms.

Preferably, each of $R_{201}$ to $R_{203}$ independently represents an alkyl group, a cycloalkyl group, an allyl group or a vinyl group. More preferred groups are a linear or branched 2-oxoalkyl group, a 2-oxocycloalkyl group and an alkoxycarbonylmethyl group. Especially preferred is a linear or branched 2-oxoalkyl group.

As preferred alkyl groups and cycloalkyl groups represented by $R_{201}$ to $R_{203}$, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group).

The 2-oxoalkyl group may be linear or branched. A group having >C=O at the 2-position of the alkyl group is preferred. The 2-oxocycloalkyl group is preferably a group having >C=O at the 2-position of the cycloalkyl group.

As preferred alkoxy moieties in the alkoxycarbonylmethyl group, there can be mentioned alkoxy groups having 1 to 5 carbon atoms (a methoxy group, an ethoxy group, a propoxy group, a butoxy group and a pentoxy group).

The $R_{201}$ to $R_{203}$ may be further substituted with a halogen atom, an alkoxy group (for example, 1 to 5 carbon atoms), a hydroxyl group, a cyano group and/or a nitro group.

Two of $R_{201}$ to $R_{203}$ may be bonded to each other to thereby form a ring structure, and the ring within the same may contain an oxygen atom, a sulfur atom, an ester bond, an amido bond or a carbonyl group. As the group formed by the ring formation, an alkylene group such as a butylene group and a pentylene group can be exemplified.

The explanation on the compounds (ZI-3) follows.

The compounds (ZI-3) are those represented by the following general formula (ZI-3) which have a phenacylsulfonium salt structure.

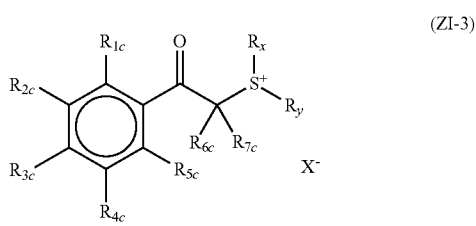

(ZI-3)

In the formula, each of $R_{1c}$ to $R_{5c}$ independently represents a hydrogen atom, an alkyl group, an alkoxy group, or a halogen atom. The alkyl group and the alkoxy group preferably have 1 to 6 carbon atoms.

Each of $R_{6c}$ and $R_{7c}$ independently represents a hydrogen atom or an alkyl group. The alkyl group preferably has 1 to 6 carbon atoms.

Each of $R_x$ and $R_y$ independently represents an alkyl group, a 2-oxoalkyl group, an alkoxycarbonylalkyl group, an allyl group, or a vinyl group. These groups preferably have 1 to 6 carbon atoms.

Any two or more of $R_{1c}$ to $R_{5c}$, and $R_{6c}$ and $R_{7c}$, and $R_x$ and $R_y$ may be bonded with each other to thereby form a ring structure. This ring structure may contain an oxygen atom, a sulfur atom, an ester bond, and/or an amido bond.

$X^-$ in compounds (ZI3) represents the same as mentioned with respect to the $X^-$ in the general formula (ZI).

As the specific examples of the compounds (ZI-3), those described in [0046] and [0047] of JP-A-2004-233661 and in [0040]-[0046] of JP-A-2003-35948 can be exemplified.

Now the compounds (ZI-4) will be described.

The compounds (ZI-4) are those having a cation structure represented by the general formula (ZI-4) below. The compounds (ZI-4) are effective for suppressing outgas.

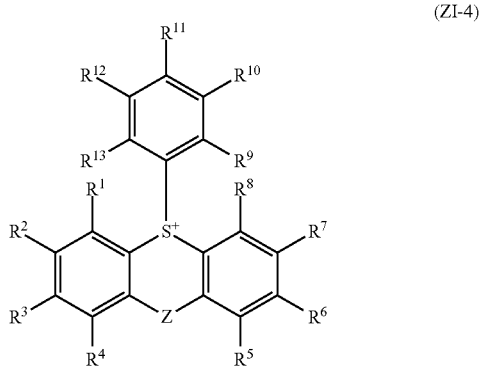

(ZI-4)

In the formula (ZI-4), $R^1$ to $R^{13}$ each independently represents a hydrogen atom or a substituent. Preferably, at least one of $R^1$ to $R^{13}$ is a substituent containing one or more alcoholic hydroxy groups. Here, the term "alcoholic hydroxy group" means a hydroxy group bonded to a carbon atom in an alkyl group.

Z is a single bond or a bivalent connecting group.

When $R^1$ to $R^{13}$ is a substituent containing one or more alcoholic hydroxy groups, $R^1$ to $R^{13}$ preferably is a group represented by —(W—Y). Here, Y represents an alkyl group substituted with one or more hydroxy group, and W represents a single bond or a bivalent connecting group.

As preferred alkyl groups represented by Y, an ethyl group, a propyl group, and an isopropyl group can be exemplified. Y preferably contains a structure represented by —$CH_2CH_2OH$.

As preferred bivalent connecting group represented by Z, there can be mentioned a bivalent group formed by substituting an arbitrary hydrogen atom with a single bond in an alkoxy group, an acyloxy group, an acylamino group, an alkyl and aryl sulfonylamino group, an alkylthio group, an alkylsulfonyl group, an acyl group, an alkoxycarbonyl group, or a carbamoyl group. More preferably, W represents a single bond, or a bivalent group formed by substituting an arbitrary hydrogen atom with a single bond in an acyloxy group, a alkylsulfonyl group, an acyl group, or an alkoxycarbonyl group.

When $R^1$ to $R^{13}$ is a substituent containing one or more alcoholic hydroxy groups, they each preferably contains 2 to 10 carbon atoms, more preferably contains 2 to 6 carbon atoms, and further preferably 2 to 4 carbon atoms.

Each of $R^1$ to $R^{13}$ may contains two or more alcoholic hydroxy group. The number of alcoholic hydroxy groups in each of $R^1$ to $R^{13}$ preferably 1 to 6, more preferably 1 to 3, and most preferably 1.

The number of alcoholic hydroxy groups in a compound (ZI-4) is preferably 1 to 10, more preferably 1 to 6, and most preferably 1 to 3.

In a case each of $R^1$ to $R^{13}$ does not contain alcoholic hydroxy groups, the substituent represented by them is, for example, a halogen atom, an alkyl group, a cycloalkyl group, an alkenyl group, a cycloalkenyl group, an alkynyl group, an aryl group, a heterocyclic group, a cyano group, a nitro group, a carboxy group, an alkoxy group, an aryloxy group, a silyloxy group, a heterocyclic-oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl and aryl sulfonylamino group, a mercapto group, an alkylthio group, an arylthio group, a heterocyclic-thio group, a sulfamoyl group, a sulfo group, an alkyl and aryl sulfynyl group, an alkyl and aryl sulfonyl group, an acyl group, an aryloxycarbonyl group, an alkoxycarbonyl group, a carbamoyl group, an aryl and heterocyclic azo group, an imido group, a phosphino group, a phosphynyl group, a phosphynyloxy group, a phosphynylamino group, an phosphono group, a silyl group, a hydrazino group, a ureido group, a boronic acid group [—$B(OH)_2$], a phosphato group [—$OPO(OH)_2$], a sulfato group [—$OSO_3H$], or other known substituents.

In a case each of $R^1$ to $R^{13}$ does not contain alcoholic hydroxy groups, each of them preferably is a hydrogen atom, a halogen atom, an alkyl group, a cycloalkyl group, an alkenyl group, a cycloalkenyl group, an alkynyl group, an aryl group, a cyano group, a carboxy group, an alkoxy group, an aryloxy group, an acyloxy group, a carbamoyloxy group, an acylamino group, an aminocarbonylamino group, an alkoxycarbonylamino group, an aryloxycarbonylamino group, a sulfamoylamino group, an alkyl and aryl sulfonylamino group, an alkylthio group, an arylthio group, a sulfamoyl group, an alkyl and aryl sulfonyl group, an aryloxycarbonyl group, an alkoxycarbonyl group, a carbamoyl group, an imido group, a silyl group, or a ureido group.

In a case each of $R^1$ to $R^{13}$ does not contain alcoholic hydroxy groups, each of them more preferably is a hydrogen atom, a halogen atom, an alkyl group, a cycloalkyl group, a cyano group, an alkoxy group, an acyloxy group, an acylamino group, an aminocarbonylamino group, an alkoxycarbonylamino group, an alkyl and aryl sulfonylamino group, an alkylthio group, a sulfamoyl group, an alkyl and aryl sulfonyl group, an alkoxycarbonyl group, or a carbamoyl group.

In a case each of $R^1$ to $R^{13}$ does not contain alcoholic hydroxy groups, each of them particularly preferably is a hydrogen atom, an alkyl group, a cycloalkyl group, a halogen atom, or an alkoxy group.

The neighboring two of $R^1$ to $R^{13}$ may bond to each other to form a ring. Examples of the ring include an aromatic and nonaromatic hydrocarbon rings, and an aromatic and nonaromatic heterocycles. There rings may combined together to form a condensed ring.

The compounds (ZI-4) preferably have a structure in which at least one of $R^1$ to $R^{13}$ contains one or more alcoholic hydroxy group. More preferably, The compounds (ZI-4) preferably have a structure in which at least one of $R^9$ to $R^{13}$ contains one or more alcoholic hydroxy group.

As stated, Z represents a single bond or a bivalent connecting group. As the connecting group, for example, an alkylene group, an arylene group, a carbonyl group, a sulfonyl group, a carbonyloxy group, a carbonylamino group, a sulfonylamido group, an ether group, a thioether group, an amino group, a disulfide group, an acyl group, an alkylsulfonyl group The bivalent connecting group may contain one or more substituents. As such, those explained for $R^1$ to $R^{13}$ can be exemplified.

Z preferably is a single bond or a connecting group having no electron-withdrawing properties. As the connecting group, an alkylene group, an arylene group, an ether group, a thioether group, an amino group, —CH=CH—, an aminocarbonylamino group, and an aminosulfonylamino group can be exemplified. Z more preferably is a single bond, an ether group, or a thioether group. Of these, a single bond is especially preferred.

Explanations on general formula (ZII) and (ZIII) will follow.

In the general formulae (ZII) and each of $R_{204}$ to $R_{207}$ independently represents an aryl group, an alkyl group or a cycloalkyl group. These groups can contain one or more substituents.

As preferred aryl group represented by $R_{204}$ to $R_{207}$, those explained for $R_{201}$ to $R_{203}$ in the compounds (ZI-1) can be exemplified.

As preferred alkyl group and cycloalkyl group, those explained for $R_{201}$ to $R_{203}$ in the compounds (ZI-2) can be exemplified.

$X^-$ in the general formulae (ZII) and (ZIII) is the same as in the general formula (ZI).

As other examples of photoacid generator, compounds represented by the following general formula (ZIV), (ZV) or (ZVI) can be exemplified.

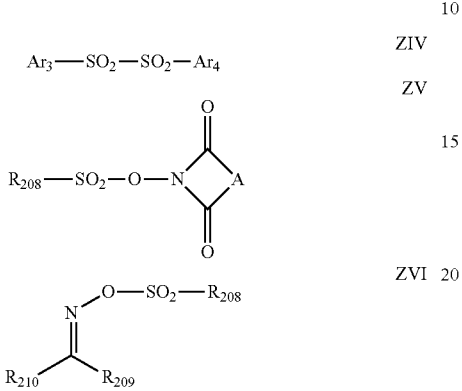

In the general formulae (ZIV) to (ZVI), each of $Ar_3$ and $Ar_4$ independently represents an aryl group.

Each of $R_{208}$ independently represents an alkyl group, a cycloalkyl group or an aryl group. These groups may either be substituted or unsubstituted.

It is preferable for these groups to be substituted with one or more fluorine atoms. This leads to higher acidity of an acid generated by the photoacid generator.

Each of $R_{209}$ and $R_{210}$ independently represents an alkyl group, a cycloalkyl group, an aryl group, or an electron-withdrawing group. These groups may either be ubstituted or unsubstituted.

As preferred $R_{209}$, substituted or unsubstituted aryl groups can be exemplified.

As preferred $R_{210}$, electron-withdrawing groups can be exemplified. As such, a cyano group and a fluoroalkyl group is preferable.

A represents an alkylene group, an alkenylene group, or an arylene group. These groups may contain one or more substituents.

As a photoacid generator, compounds containing two or more structures represented by the general formula (ZVI) are also preferable. As such, compounds in which two or more structures represented by the general formula (ZVI) are combined to at the positions of $R_{209}$s or $R_{210}$s.

As photoacid generators, compounds represented by the general formula (ZI) to (ZIII) is more preferable. Of these, compounds represented by the general formula (ZI) is especially preferred. Particularly, compounds (ZI-1) to (ZI-3) is most preferable.

Specific examples of the photoacid generator will be shown below.

(z1)

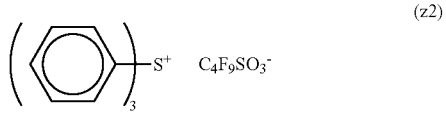
(z2)

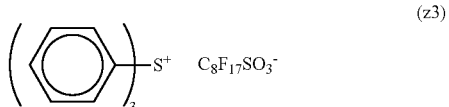
(z3)

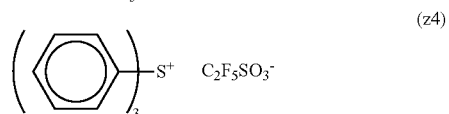
(z4)

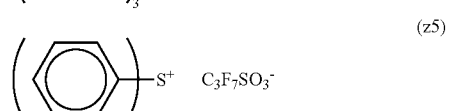
(z5)

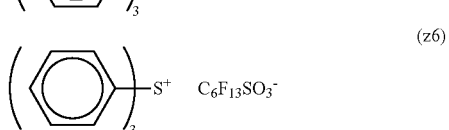
(z6)

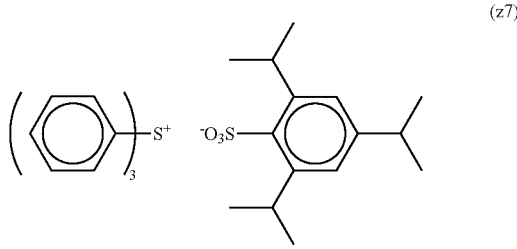
(z7)

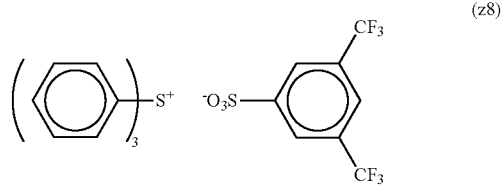
(z8)

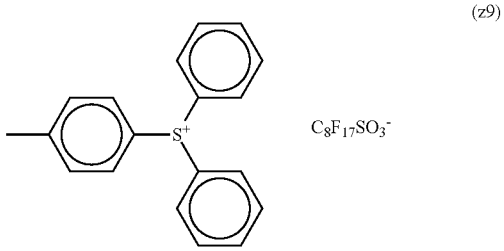
(z9)

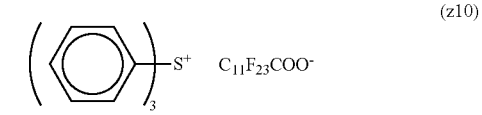
(z10)

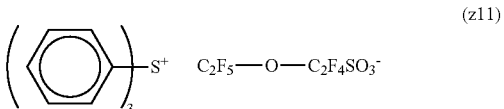
(z11)

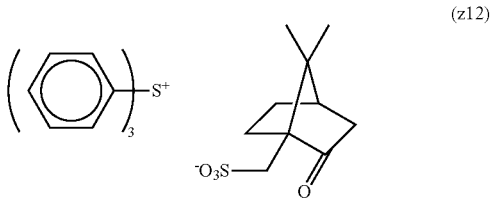
(z12)

(z13)
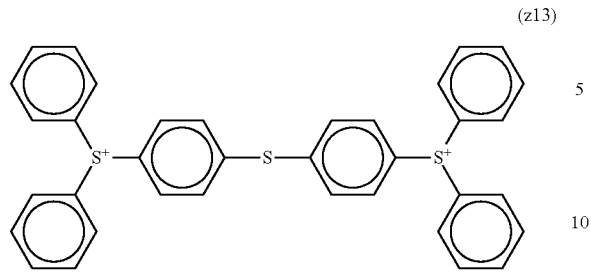
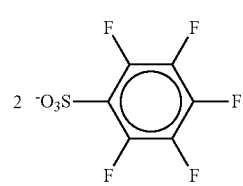
(z14)
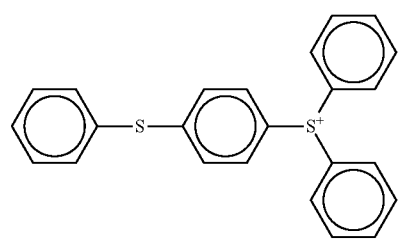
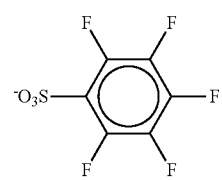
(z15)
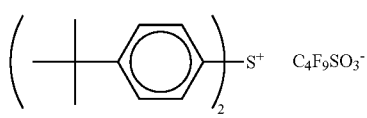
(z16)
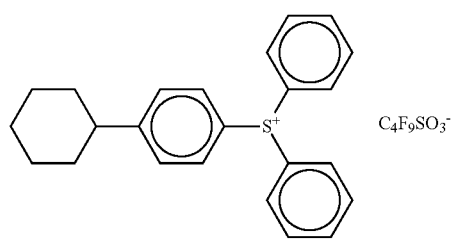
(z17)
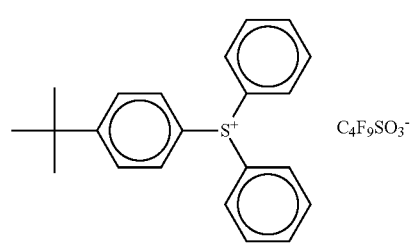
(z18)
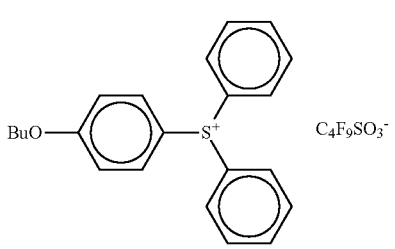
(z19)
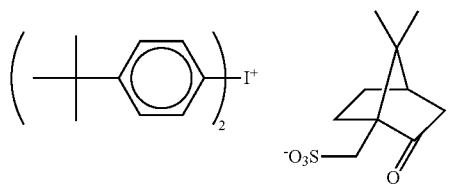
(z20)
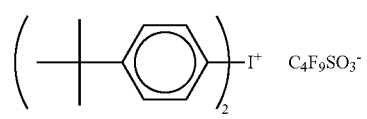
(z21)
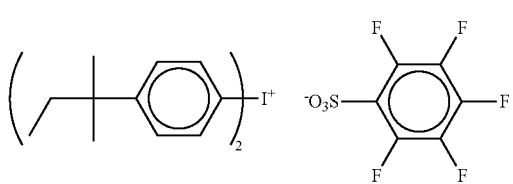
(z22)
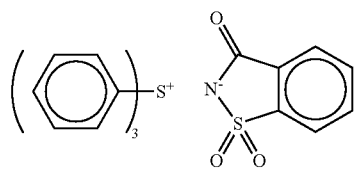
(z23)
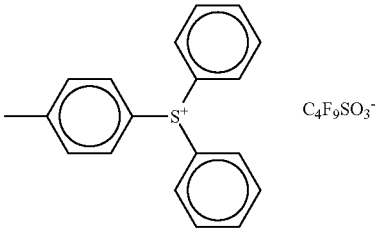
(z24)
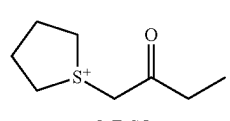
(z25)
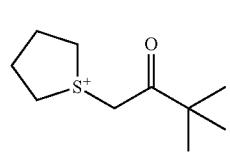
(z26)
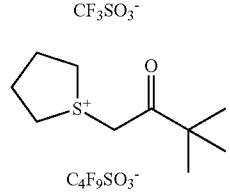

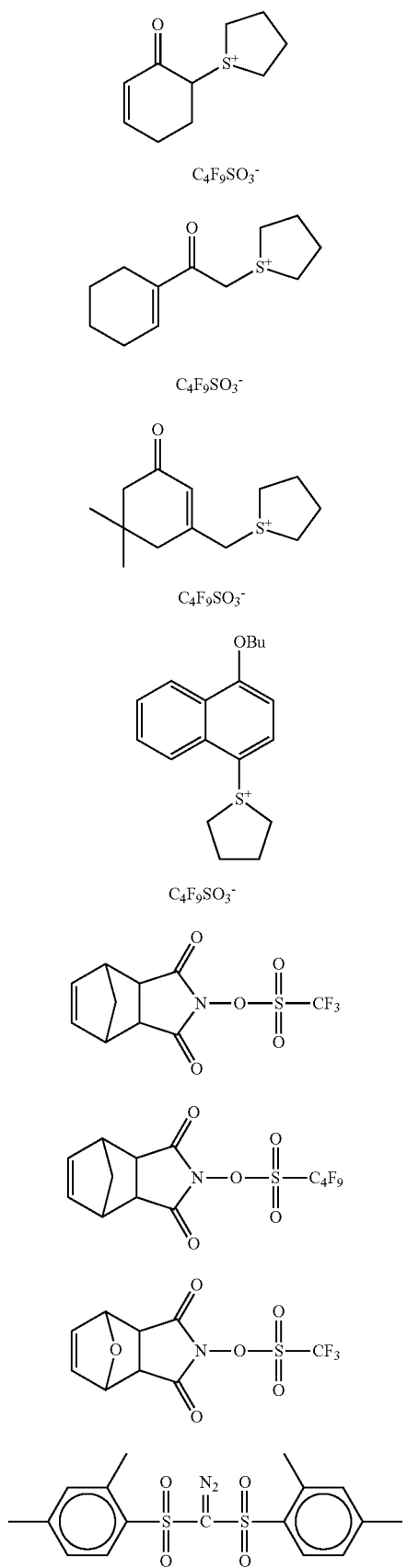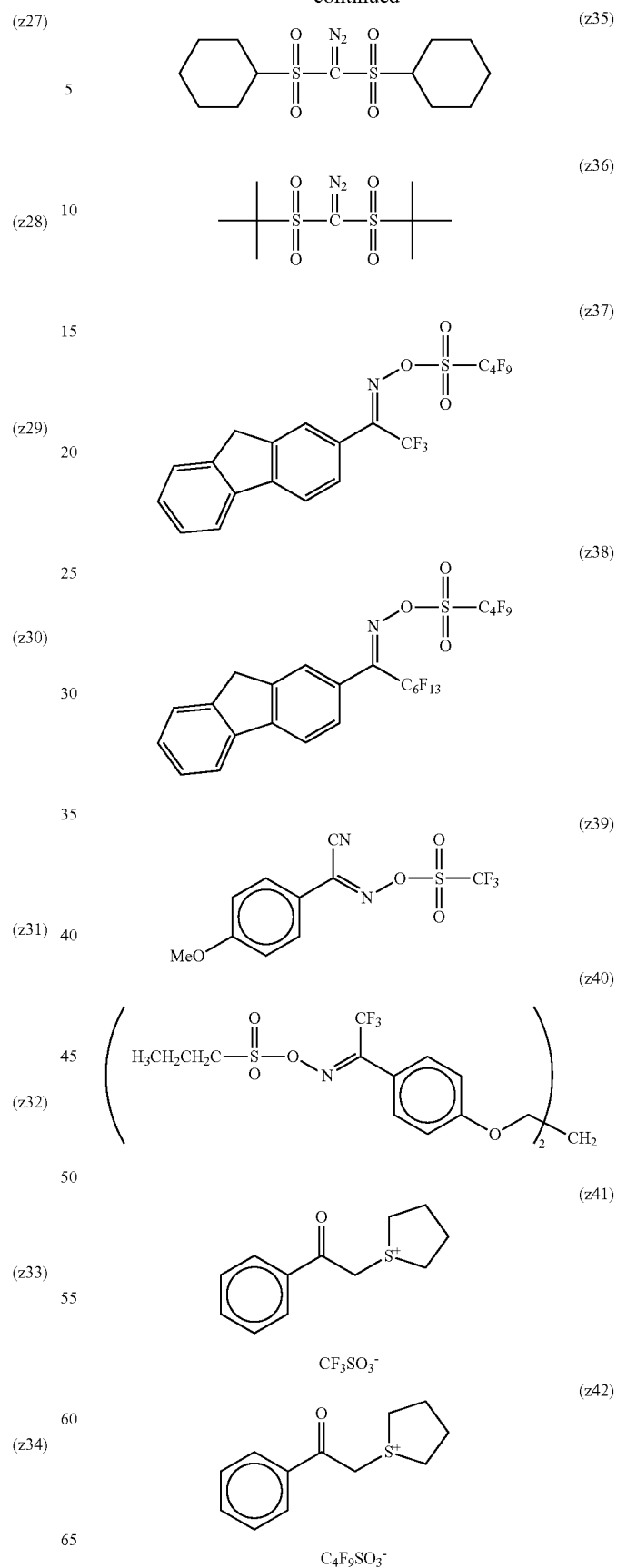

(z43)
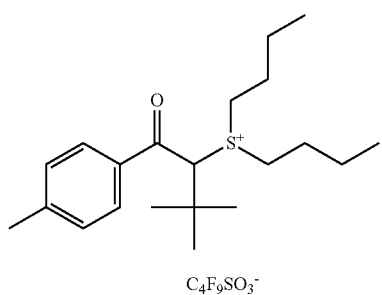
C₄F₉SO₃⁻
(z44)
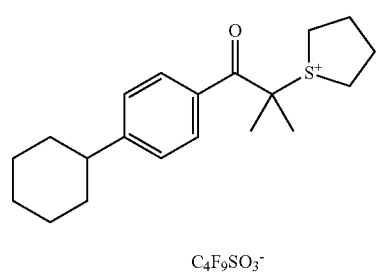
C₄F₉SO₃⁻
(z45)
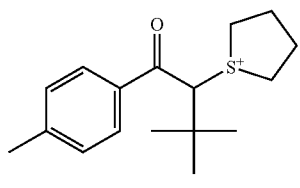
C₄F₉SO₃⁻
(z46)
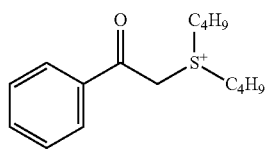
C₄F₉SO₃⁻
(z47)
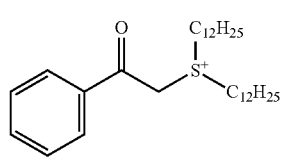
C₄F₉SO₃⁻
(z48)
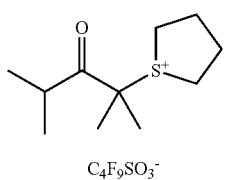
C₄F₉SO₃⁻
(z49)
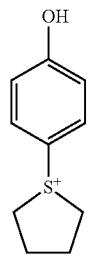
C₄F₉SO₃⁻
(z50)
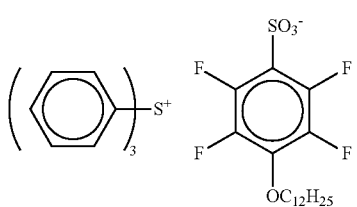
(z51)
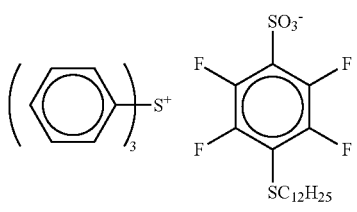
(z52)
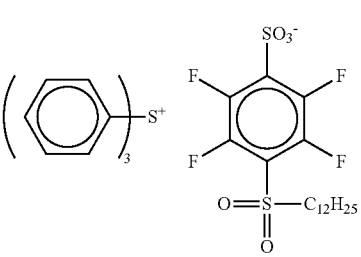
(z53)
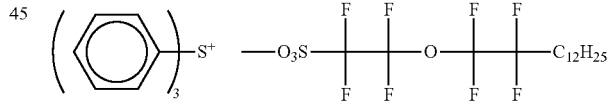
(z54)
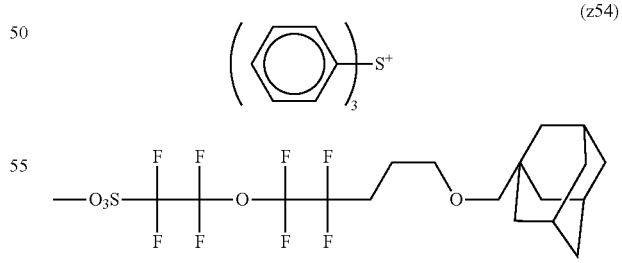
(z55)
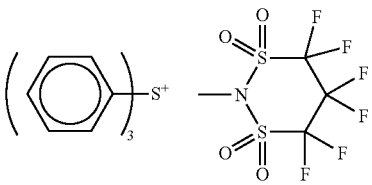

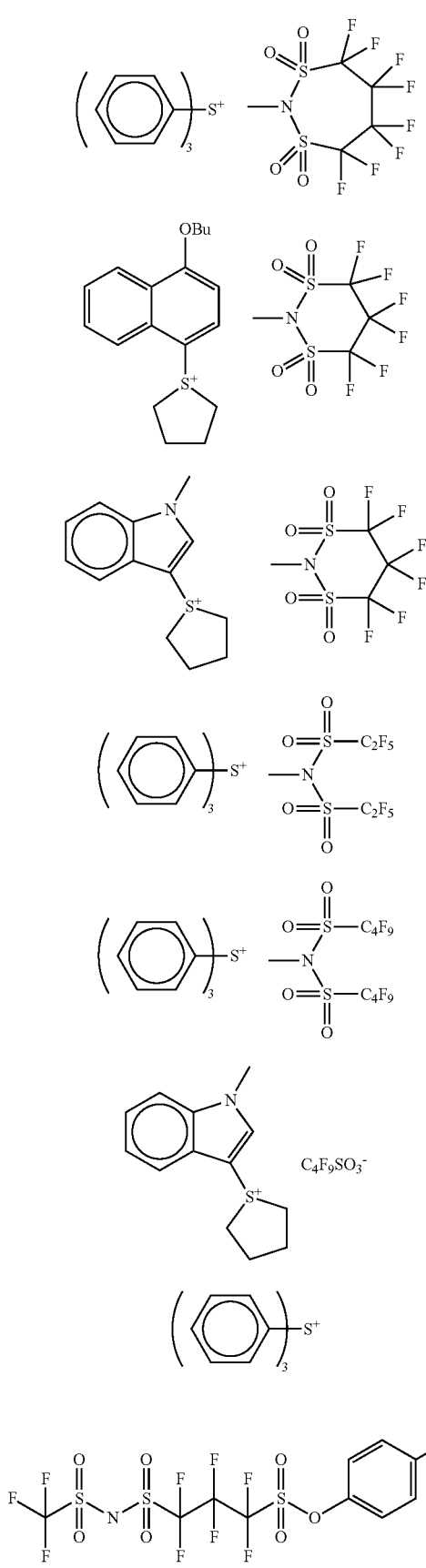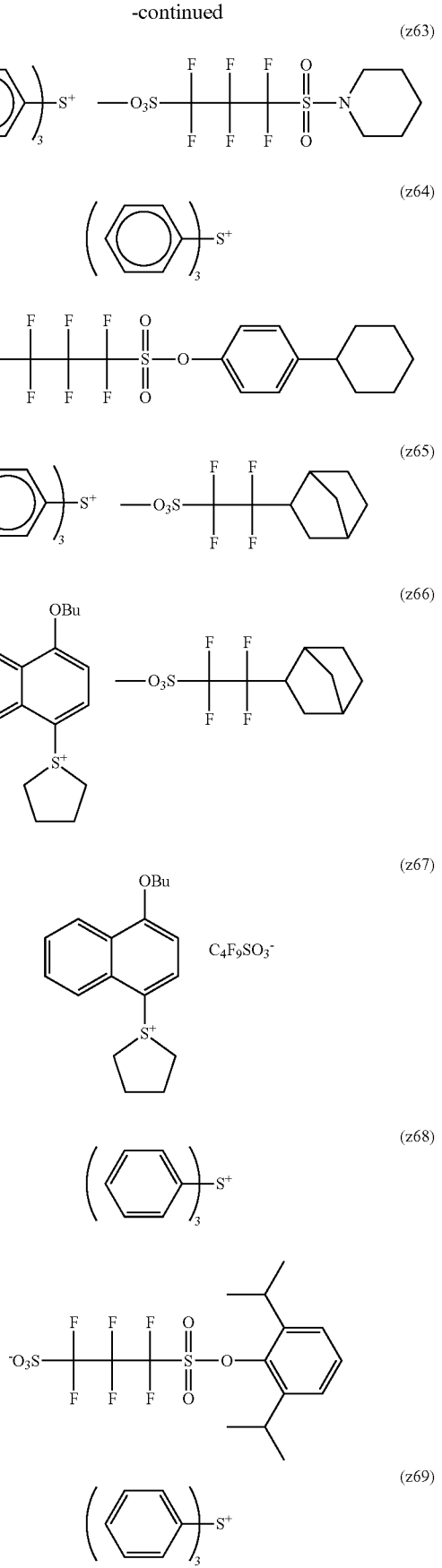

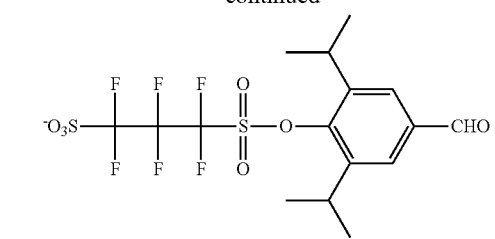
(z70)
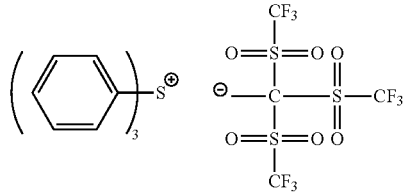
(z71)
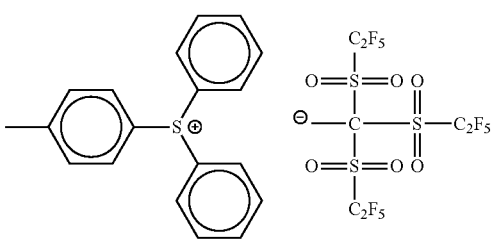
(z72)
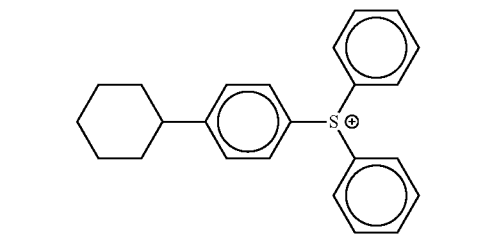
(z73)
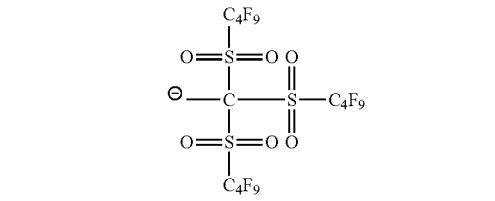
(z74)
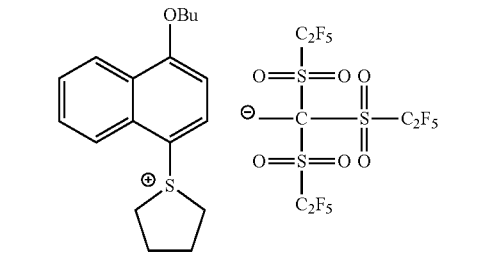
(z75)
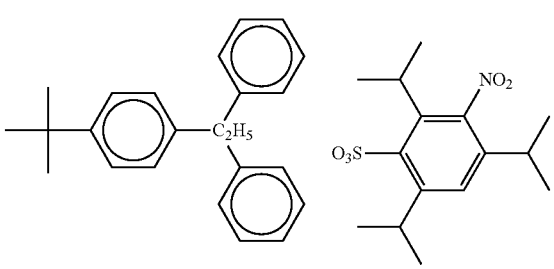
(z76)
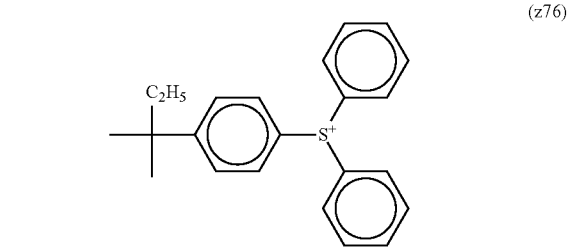
(z77)
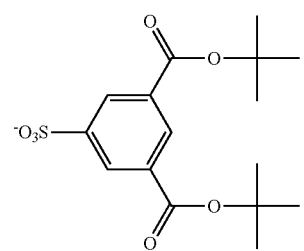
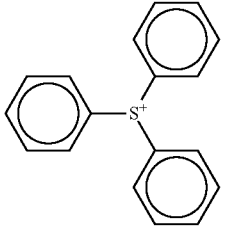
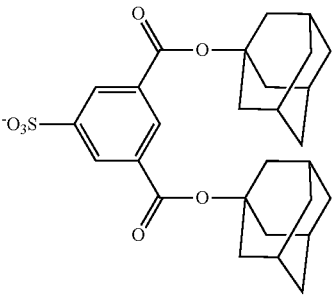
(z78)
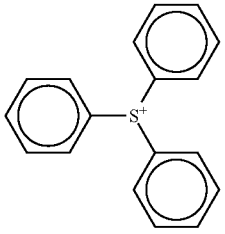

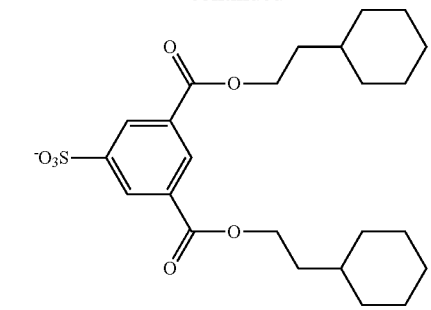
(z79)
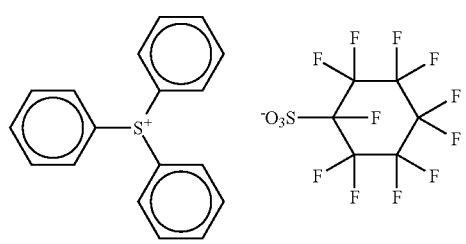
(z80)
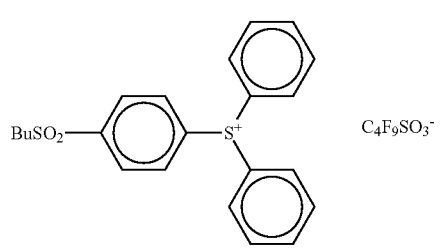
(z81)
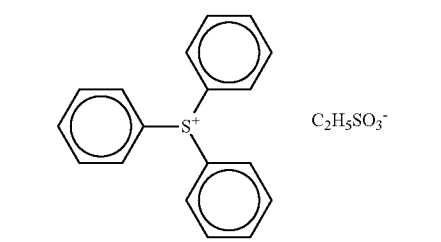
(z82)
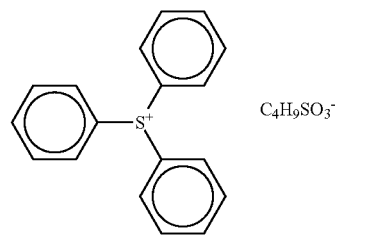
(z83)
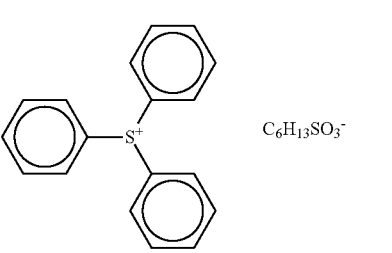
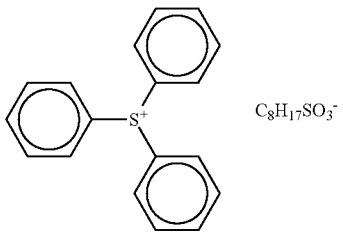
(z84)
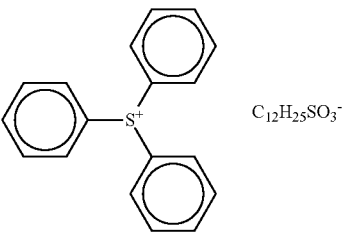
(z85)
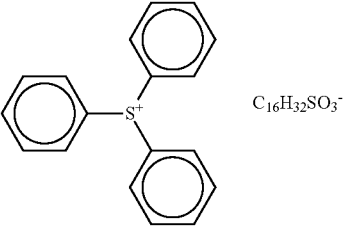
(z86)
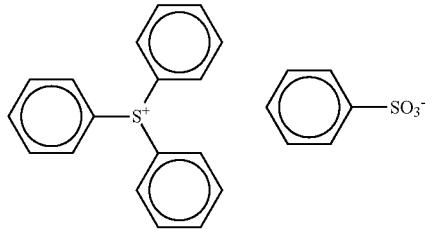
(z87)
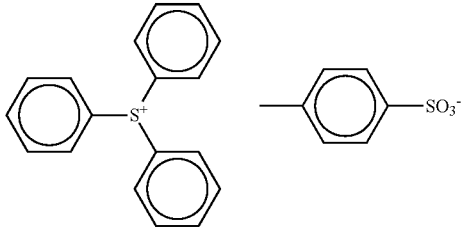
(z88)
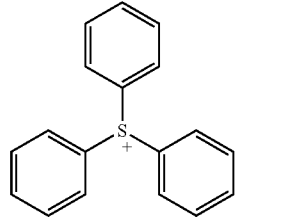
(z89)
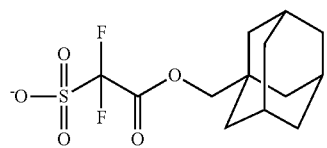

-continued
(z90)
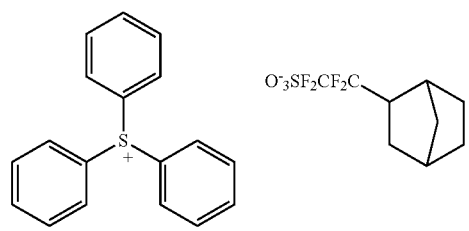
(z91)
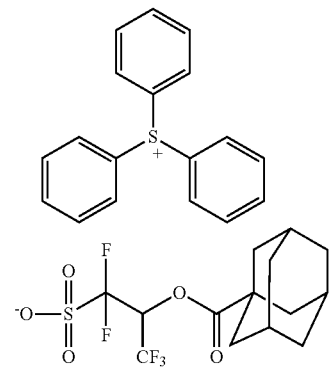
(z92)
(z93)
(z94)
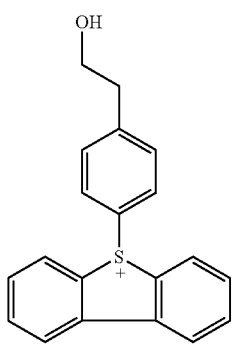
-continued
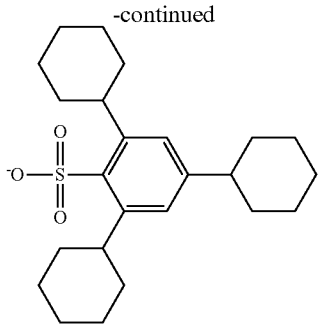
(z95)
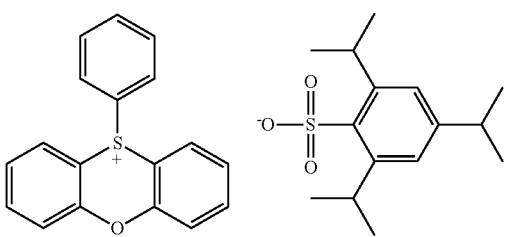
(z96)
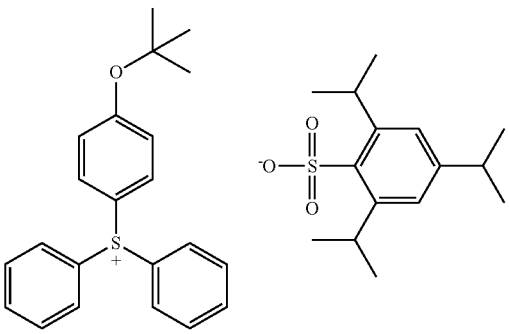
(z97)
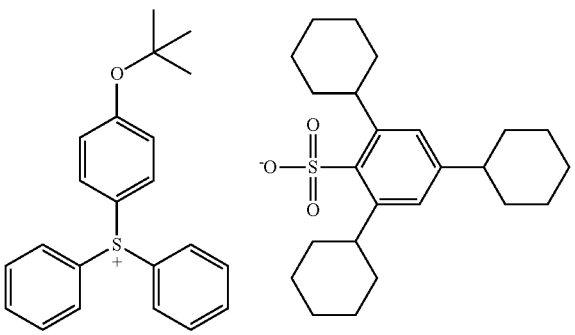
(z98)

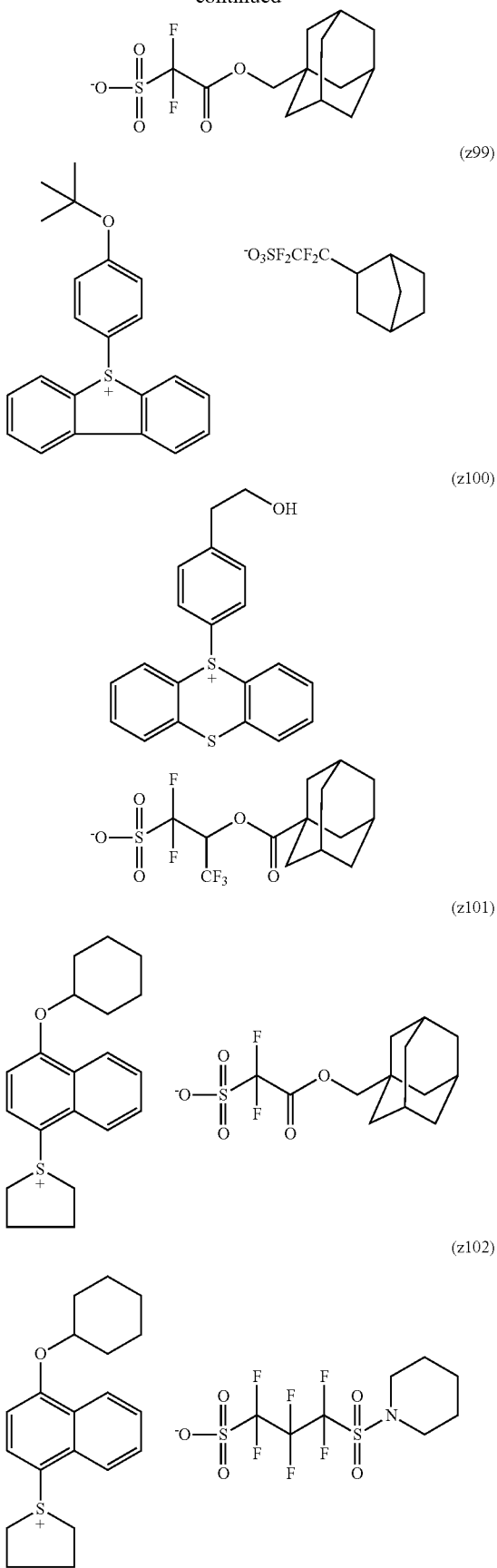

The acid generators can be used either individually or in combination of two or more kinds. When used in combination, compounds generating two kinds of organic acids that the number of atoms other than hydrogen atoms are different from each other and the difference of which is two or more.

The content of the photoacid generator based on the total solids of the composition is preferably in the range of 0.1 to 40 mass %, more preferably 0.5 to 30 mass % and further more preferably 1 to 20 mass %.

[3] Thermal Acid Generator

The thermal acid generator is a compound that generates an acid when heated usually at 50 to 450° C., preferably 200 to 350° C. As the thermal acid generator; use can be made of an onium salt, such as a sulfonium salt, a benzothiazolium salt, an ammonium salt or a phosphonium salt.

As the sulfonium salt, there can be mentioned, for example, an alkylsulfonium salt such as 4-acetophenyldimethylsulfonium hexafluoroantimonate, 4-acetoxyphenyldimethylsulfonium hexafluoroarsenate, dimethyl-4-(benzyloxycarbonyloxy)phenylsulfonium hexafluoroantimonate, dimethyl-4-(benzoyloxy)phenylsulfonium hexafluoroantimonate, dimethyl-4-(benzoyloxy)phenylsulfonium hexafluoroarsenate or dimethyl-3-chloro-4-acetoxyphenylsulfonium hexafluoroantimonate; a benzylsulfonium salt such as benzyl-4-hydroxyphenylmethylsulfonium hexafluoroantimonate, benzyl-4-hydroxyphenylmethylsulfonium hexafluorophosphate, 4-acetoxyphenylbenzylmethylsulfonium hexafluoroantimonate, benzyl-4-methoxyphenylmethylsulfonium hexafluoroantimonate, benzyl-2-methyl-4-hydroxyphenylmethylsulfonium hexafluoroantimonate, benzyl-3-chloro-4-hydroxyphenylmethylsulfonium hexafluoroarsenate, 4-methoxybenzyl-4-hydroxyphenylmethylsulfonium hexafluorophosphate, benzoin tosylate or 2-nitrobenzyl tosylate; a dibenzylsulfonium salt such as dibenzyl-4-hydroxyphenylsulfonium hexafluoroantimonate, dibenzyl-4-hydroxyphenylsulfonium hexafluorophosphate, 4-acetoxyphenyldibenzylsulfonium hexafluoroantimonate, dibenzyl-4-methoxyphenylsulfonium hexafluoroantimonate, dibenzyl-3-chloro-4-hydroxyphenylsulfonium hexafluoroarsenate, dibenzyl-3-methyl-4-hydroxy-5-tert-butylphenylsulfonium hexafluoroantimonate or benzyl-4-methoxybenzyl-4-hydroxyphenylsulfonium hexafluorophosphate; or a substituted benzylsulfonium salt such as p-chlorobenzyl-4-hydroxyphenylmethylsulfonium hexafluoroantimonate, p-nitrobenzyl-4-hydroxyphenylmethylsulfonium hexafluoroantimonate, p-chlorobenzyl-4-hydroxyphenylmethylsulfonium hexafluorophosphate, p-nitrobenzyl-3-methyl-4-hydroxyphenylmethylsulfonium hexafluoroantimonate, 3,5-dichlorobenzyl-4-hydroxyphenylmethylsulfonium hexafluoroantimonate or o-chlorobenzyl-3-chloro-4-hydroxyphenylmethylsulfonium hexafluoroantimonate.

As the benzothiazonium salt, there can be mentioned, for example, a benzylbenzothiazolium salt such as 3-benzylbenzothiazolium hexafluoroantimonate, 3-benzylbenzothiazolium hexafluorophosphate, 3-benzylbenzothiazolium tetrafluoroborate, 3-(p-methoxybenzyl)benzothiazolium hexafluoroantimonate, 3-benzyl-2-methylthiobenzothiazolium hexafluoroantimonate or 3-benzyl-5-chlorobenzo[h]azolium hexafluoroantimonate.

As an example of thermal acid generators other than those mentioned above, there can be mentioned 2,4,4,6-tetrabromocyclohexadienone. Among the above compounds, 4-acetoxyphenyldimethylsulfonium hexafluoroarsenate, benzyl-4-hydroxyphenylmethylsulfonium hexafluoroantimonate, 4-acetoxyphenylbenzylmethylsulfonium hexafluoroantimonate, dibenzyl-4-hydroxyphenylsulfonium hexafluoroantimonate, 4-acetoxyphenylbenzylsulfonium hexafluoroantimonate and 3-benzylbenzothiazolium hexafluoroantimonate are especially preferred. As commercially available products of these compounds, there can be mentioned, for example, Sanaid SI-L85, SI-L110, SI-L145, SI-L150 and SI-L160 (produced by Sanshin Chemical Industry Co., Ltd.).

These compounds may be used individually or in combination.

The content of thermal acid generator based on the total solids of the composition is preferably in the range of 0.1 to 30 mass %, more preferably 1 to 25 mass % and further more preferably 2 to 20 mass %.

<Resist Composition>

When the composition according to the present invention is used in resists, the composition contains the above photoacid generator [2]. The composition may further contain the thermal acid generator [3]. This composition may be used as a positive composition or a negative composition.

In the use as a positive composition, the composition according to the present invention typically further contains a resin [A1] that when acted on by an acid, is decomposed to thereby increase its solubility in an alkali developer (hereinafter also referred to as an acid-decomposable resin). This composition may still further contain a compound of 3000 or less molecular weight [A3] that when acted on by an acid, is decomposed to thereby increase its solubility in an alkali developer (hereinafter also referred to as a dissolution-inhibiting compound).

In the use as a negative composition, the composition according to the present invention may further contain a resin [A2] soluble in an alkali developer (hereinafter also referred to as an "alkali-soluble resin") and an acid crosslinking agent [A4] capable of crosslinking with the above alkali-soluble resin under the action of an acid.

Moreover, the composition according to the present invention may still further contain a basic compound [A5], a fluorinated and/or siliconized surfactant [A6], a hydrophobic resin [A7], an organic solvent [A8] and/or other additives [A9].

[A1] Acid-Decomposable Resin

The acid-decomposable resin typically contain one or more groups that is decomposed by the action of an acid to thereby generate an alkali-soluble group (hereinafter also referred to as acid-decomposable groups). The resin may contain the acid-decomposable group in its principal chain, in its side chain, or in both thereof. Among them, a resin having an acid-decomposable group in its side chain is preferred.

The acid-decomposable group is preferably a group resulting from substitution of the hydrogen atom of an alkali-soluble group, such as a —COOH group or an —OH group, with an acid-eliminable group. The acid-decomposable group is preferably an acetal group or a tertiary ester group.

The matrix resin for bonding of the acid-decomposable group as a side chain is an alkali-soluble resin having, in its side chain, an —OH or —COOH group. For example, there can be mentioned the alkali-soluble resins to be described hereinafter.

The alkali dissolution rate of the alkali-soluble resin as measured in a 0.261 N tetramethylammonium hydroxide (TMAH) (23° C.) is preferably 17 nm/sec or greater. The alkali dissolution rate is especially preferably 33 nm/sec or greater.

The alkali-soluble resins especially preferred from this viewpoint include alkali-soluble resins having hydroxystyrene structural units, such as o-, m- or p-poly(hydroxystyrene) and copolymers thereof, hydrogenated poly(hydroxystyrene), halogenated or alkylated poly(hydroxystyrene), poly(hydroxystyrene) having its part O-alkylated or O-acylated, styrene-hydroxystyrene copolymer, α-methylstyrene-hydroxystyrene copolymer and hydrogenated novolak resin and include alkali-soluble resins having carboxylated repeating units, such as those of (meth)acrylic acid and norbornene carboxylic acid.

As repeating units having an acid-decomposable group preferred in the present invention, there can be mentioned, for example, repeating units derived from t-butoxycarbonyloxystyrene, a 1-alkoxyethoxystyrene and a (meth)acrylic acid tertiary alkyl ester. Repeating units derived from a 2-alkyl-2-adamantyl(meth)acrylate and a dialkyl(1-adamantyl)methyl (meth)acrylate are more preferred.

The resin for use in the present invention can be obtained by reaction of a precursor of acid-decomposable group with an alkali-soluble resin or by copolymerization of an alkali-soluble resin monomer having an acid-decomposable group bonded thereto with various monomers, as disclosed in, for example, EP 254853 and JP-A's 2-25850, 3-223860 and 4-251259.

When the positive photosensitive composition according to the present invention is exposed to KrF excimer laser beams, electron beams, X-rays or high-energy light rays of 50 nm or less wavelength (EUV, etc.), it is preferred for the resin to have hydroxystyrene repeating units. More preferably, the resin is a copolymer of hydroxystyrene/hydroxystyrene protected by an acid-decomposable group or a copolymer of hydroxystyrene/(meth)acrylic acid tertiary alkyl ester.

In particular, the resin is preferably, for example, the one having any of the repeating units of general formula (A) below.

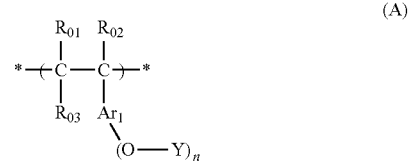

(A)

In the formula, each of $R_{01}$, $R_{02}$ and $R_{03}$ independently represents a hydrogen atom, an alkyl group, a cycloalkyl group, a halogen atom, a cyano group or an alkoxycarbonyl group. $Ar_1$ represents, for example, an aromatic ring group. Alternatively, $R_{03}$ and $Ar_1$ may be simultaneously alkylene groups and bonded to each other so as to form a 5-membered or 6-membered ring in cooperation with —C—C—.

Each of n Y's independently represents a hydrogen atom or a group that is eliminated by the action of an acid, provided that at least one of the Y's is a group that is eliminated by the action of an acid.

In the formula, n is an integer of 1 to 4, preferably 1 or 2 and more preferably 1.

As preferred alkyl groups represented by $R_{01}$ to $R_{03}$ in the general formula, there can be mentioned alkyl groups having up to 20 carbon atoms, such as a methyl group, an ethyl group, a propyl group, an isopropyl group, an n-butyl group, a sec-butyl group, a hexyl group, a 2-ethylhexyl group, an octyl group and a dodecyl group. Alkyl groups having up to 8 carbon atoms are more preferred. These alkyl group may contain one or more substituents.

The alkyl groups contained in the alkoxycarbonyl groups are preferably the same as the above-mentioned alkyl groups represented by $R_{01}$ to $R_{03}$.

The cycloalkyl groups may be monocyclic or polycyclic. As preferred examples thereof, there can be mentioned monocyclic alkyl groups having 3 to 8 carbon atoms, such as a cyclopropyl group, a cyclopentyl group and a cyclohexyl group. These cycloalkyl groups may contain one or more substituents.

As the halogen atom, there can be mentioned a fluorine atom, a chlorine atom, a bromine atom or an iodine atom. A fluorine atom is preferred.

As preferred alkylene groups represented by $R_{03}$, there can be mentioned those having 1 to 8 carbon atoms, such as a methylene group, an ethylene group, a propylene group, a butylene group, a hexylene group and an octylene group.

The aromatic ring group represented by $Ar_1$ is preferably an aromatic ring group having 6 to 14 carbon atoms. In particular, there can be mentioned a benzene ring, a toluene ring, a naphthalene ring or the like. These aromatic ring groups may contain one or more substituents.

As the group Y that is eliminated by the action of an acid, there can be mentioned, for example, —C($R_{36}$)($R_{37}$)($R_{38}$), —C(=O)—O—C($R_{36}$)($R_{37}$)($R_{38}$), —C($R_{01}$)($R_{02}$)(O$R_{39}$), —C($R_{01}$)($R_{02}$)—C(=O)—O—C($R_{36}$)($R_{37}$)($R_{38}$), —CH($R_{36}$)(Ar) or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded with each other to thereby form a ring structure.

Each of $R_{01}$ and $R_{02}$ independently represents a hydrogen atom, an alkyl group, a cycloalkyl group, an aryl group, an aralkyl group or an alkenyl group.

Ar represents an aryl group.

The alkyl groups represented by $R_{36}$ to $R_{39}$ and $R_{01}$ and $R_{02}$ each preferably have 1 to 8 carbon atoms. For example, there can be mentioned a methyl group, an ethyl group, a propyl group, an n-butyl group, a sec-butyl group, a hexyl group, an octyl group and the like.

The cycloalkyl groups represented by $R_{36}$ to $R_{39}$ and $R_{01}$ and $R_{02}$ may be monocyclic or polycyclic. The monocyclic alkyl groups are preferably cycloalkyl groups having 3 to 8 carbon atoms. As such, there can be mentioned, for example, a cyclopropyl group, a cyclobutyl group, a cyclopentyl group, a cyclohexyl group, a cyclooctyl group and the like. The polycyclic alkyl groups are preferably cycloalkyl groups having 6 to 20 carbon atoms. As such, there can be mentioned, for example, an adamantyl group, a norbornyl group, an isobornyl group, a camphonyl group, a dicyclopentyl group, an α-pinel group, a tricyclodecanyl group, a tetracyclododecyl group, an androstanyl group and the like. With respect to these, the carbon atoms of each of the cycloalkyl groups may be partially substituted with a heteroatom, such as an oxygen atom.

The aryl groups represented by $R_{36}$ to $R_{39}$, $R_{01}$ and $R_{02}$ and Ar each preferably have 6 to 10 carbon atoms. For example, there can be mentioned a phenyl group, a naphthyl group, an anthryl group and the like.

The aralkyl groups represented by $R_{36}$ to $R_{39}$, $R_{01}$ and $R_{02}$ each preferably have 7 to 12 carbon atoms. For example, there can be mentioned a benzyl group, a phenethyl group, a naphthylmethyl group and the like.

The alkenyl groups represented by $R_{36}$ to $R_{39}$, $R_{01}$ and $R_{02}$ each preferably have 2 to 8 carbon atoms. For example, there can be mentioned a vinyl group, an allyl group, a butenyl group, a cyclohexenyl group and the like.

The ring formed by mutual bonding of $R_{36}$ and $R_{37}$ may be monocyclic or polycyclic. The monocyclic structure is preferably a cycloalkane structure having 3 to 8 carbon atoms. As such, there can be mentioned, for example, a cyclopropane structure, a cyclobutane structure, a cyclopentane structure, a cyclohexane structure, a cycloheptane structure, a cyclooctane structure or the like. The polycyclic structure is preferably a cycloalkane structure having 6 to 20 carbon atoms. As such, there can be mentioned, for example, an adamantane structure, a norbornane structure, a dicyclopentane structure, a tricyclodecane structure, a tetracyclododecane structure or the like. With respect to these, the carbon atoms of each of the cycloalkane structure may be partially substituted with a heteroatom, such as an oxygen atom.

Each of the groups represented by $R_{36}$ to $R_{39}$, $R_{01}$, $R_{02}$, $R_{03}$, Ar and $Ar_1$ may have one or more substituents. As the substituent, there can be mentioned, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, a nitro group or the like. Preferably, the number of carbon atoms of each of the substituents is up to 8.

The group Y that is eliminated by the action of an acid more preferably has any of the structures of general formula (B) below.

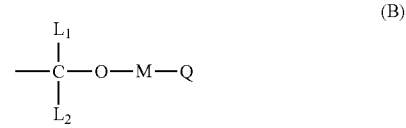

(B)

In the formula, each of $L_1$ and $L_2$ independently represents a hydrogen atom, an alkyl group, a cycloalkyl group, an aryl group or an aralkyl group.

M represents a single bond or a bivalent connecting group.

Q represents an alkyl group, a cycloalkyl group, an alicyclic group, an aromatic ring group, an amino group, an ammonium group, a mercapto group, a cyano group or an aldehyde group. Note that the alicyclic group or the aromatic ring group may contain one or more hetero-atoms.

At least two of Q, M and $L_1$ may be bonded to each other to thereby form a 5-membered or 6-membered ring.

The alkyl groups represented by $L_1$ and $L_2$ are, for example, alkyl groups having 1 to 8 carbon atoms. As preferred examples thereof, there can be mentioned a methyl group, an ethyl group, a propyl group, an n-butyl group, a sec-butyl group, a hexyl group and an octyl group.

The cycloalkyl groups represented by $L_1$ and $L_2$ are, for example, cycloalkyl groups having 3 to 15 carbon atoms. As preferred examples thereof, there can be mentioned a cyclopentyl group, a cyclohexyl group, a norbornyl group and an adamantyl group.

The aryl groups represented by $L_1$ and $L_2$ are, for example, aryl groups having 6 to 15 carbon atoms. As preferred examples thereof, there can be mentioned a phenyl group, a tolyl group, a naphthyl group, an anthryl group and the like.

The aralkyl groups represented by L1 and L2 are, for example, those having 6 to 20 carbon atoms. There can be mentioned a benzyl group, a phenethyl group and the like.

The bivalent connecting group represented by M is, for example, an alkylene group (e.g., a methylene group, an ethylene group, a propylene group, a butylene group, a hexylene group, an octylene group, etc.), a cycloalkylene group (e.g., a cyclopentylene group, a cyclohexylene group, etc.), an alkenylene group (e.g., an ethylene group, a propenylene group, a butenylene group, etc.), an arylene group (e.g., a phenylene group, a tolylene group, a naphthylene group, etc.), —S—, —O—, —CO—, —$SO_2$—, —N($R_0$)— or a bivalent connecting group resulting from combination of these groups. $R_0$ represents a hydrogen atom or an alkyl group. The alkyl group is, for example, an alkyl group having 1 to 8 carbon atoms such as a methyl group, an ethyl group, a propyl group, an n-butyl group, a sec-butyl group, a hexyl group, an octyl group or the like.

The alkyl group and cycloalkyl group represented by Q are the same as those mentioned above as $L_1$ and $L_2$.

As the alicyclic group and aromatic ring group contained in the alicyclic group optionally containing a heteroatom and aromatic ring group optionally containing a heteroatom represented by Q, there can be mentioned, for example, the cycloalkyl group and aryl group mentioned above as $L_1$ and $L_2$. Preferably, each of the alicyclic group and aromatic ring group has 3 to 15 carbon atoms.

As the alicyclic group containing a heteroatom and aromatic ring group containing a heteroatom, there can be mentioned, for example, groups having a heterocyclic structure, such as thiirane, cyclothiorane, thiophene, furan, pyrrole, benzothiophene, benzofuran, benzopyrrole, triazine, imidazole, benzimidazole, triazole, thiadiazole, thiazole and pyrrolidone. However, the alicyclic groups and aromatic ring groups are not limited to these as long as the ring is formed by carbon and a heteroatom or by heteroatoms.

As the 5-membered or 6-membered ring that may be formed by mutual bonding of at least two of Q, M and $L_1$, there can be mentioned the 5-membered or 6-membered ring resulting from mutual bonding of at least two of Q, M and $L_1$ so as to form, for example, a propylene group or a butylene group and subsequent formation of a ring containing an oxygen atom.

In the general formula (2), each of the groups represented by $L_1$, $L_2$, M and Q may have one or more substituents. As the substituent, there can be mentioned, for example, an alkyl group, a cycloalkyl group, an aryl group, an amino group, an amido group, an ureido group, an urethane group, a hydroxy group, a carboxy group, a halogen atom, an alkoxy group, a thioether group, an acyl group, an acyloxy group, an alkoxycarbonyl group, a cyano group, and a nitro group. Preferably, the number of carbon atoms of each of the substituents is up to 8.

The groups of the formula -(M-Q) are preferably groups having 1 to 30 carbon atoms, more preferably groups having 5 to 20 carbon atoms. From the viewpoint of outgas suppression, it is especially preferred for the number of carbon atoms to be 6 or greater.

As other preferable resin, those containing repeating units represented by the following general formula (X) can be exemplified.

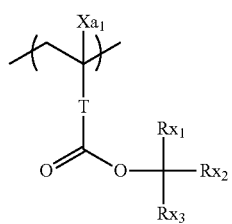

(X)

In general formula (X), $Xa_1$ represents a hydrogen atom, a methyl group, a trifluoromethyl group or a hydroxymethyl group, T represents a single bond or a bivalent connecting group, and each of $Rx_1$ to $Rx_3$ independently represents an alkyl group (linear or branched) or a cycloalkyl group (monocyclic or polycyclic), wherein at least two of $Rx_1$ to $Rx_3$ may be bonded to each other to form a monocyclic or polycyclic alkyl group.

As the bivalent connecting group represented by T, an alkylene group, a group of the formula —COO-Rt-, and a group of the formula —O-Rt- can be exemplified. In the formulae, Rt represents an alkylene group or a cycloalkylene group.

T is preferably a single bond or a group of the formula —COO-Rt-. Rt is preferably an alkylene group having 1 to 5 carbon atoms, more preferably a —$CH_2$— group or —$(CH_2)_3$— group.

The alkyl group represented by each of $Rx_1$ to $Rx_3$ is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of $Rx_1$ to $Rx_3$ is preferably a monocyclic alkyl group such as a cyclopentyl group or a cyclohexyl group, or a polycyclic alkyl group such as a norbornyl group, a tetracyclodecanyl group, a tetracyclododecanyl group or an adamantyl group.

The cycloalkyl group formed by bonding of at least two of $Rx_1$ to $Rx_3$ is preferably a monocyclic alkyl group such as a cyclopentyl group or a cyclohexyl group, or a polycyclic alkyl group such as a norbornyl group, a tetracyclodecanyl group, a tetracyclododecanyl group or an adamantyl group.

Particularly preferred is an embodiment in which $Rx_1$ is a methyl group or an ethyl group, and $Rx_2$ and $Rx_3$ are bonded to each other to form the above-mentioned cycloalkyl group.

Specific examples of the repeating units represented by the general formula (X) will be shown below, which however in no way limit the scope of the present invention.

In the formulae, Rx represents H, $CH_3$, $CF_3$, or $CH_2OH$. Each of Rxa and Rxb independently represents an alkyl group having 1 to 4 carbon atoms.

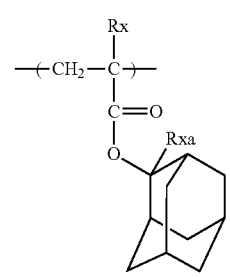

1

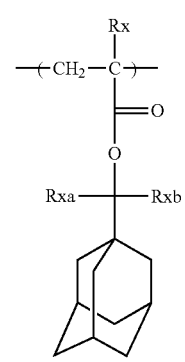

2

-continued

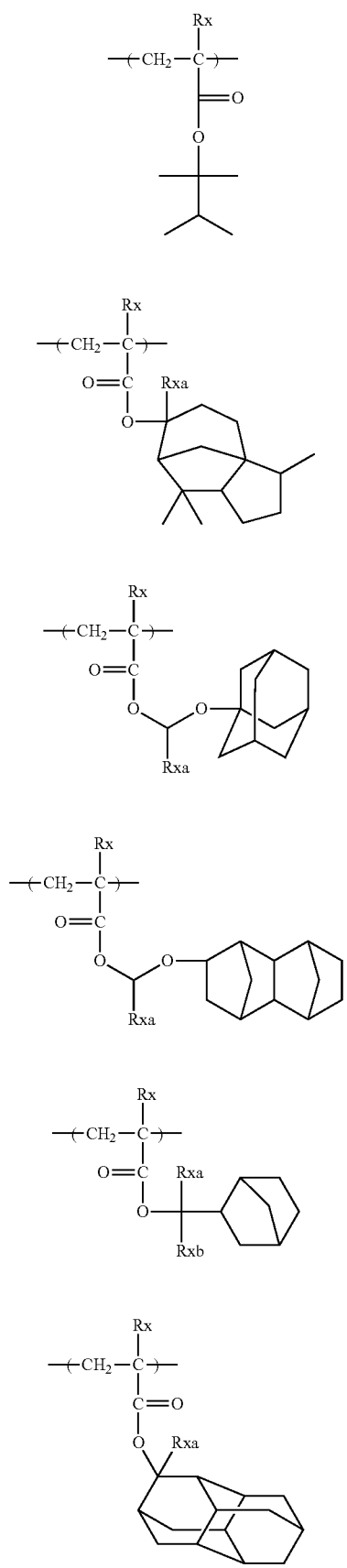
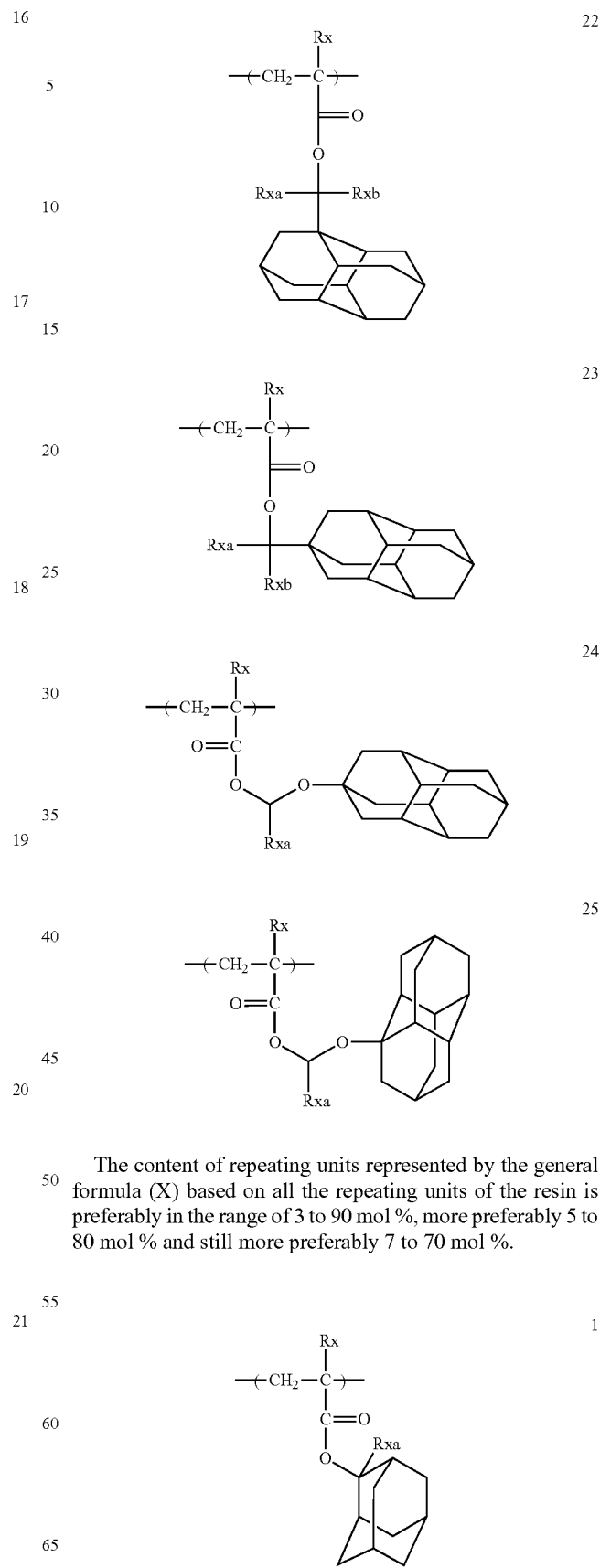
The content of repeating units represented by the general formula (X) based on all the repeating units of the resin is preferably in the range of 3 to 90 mol %, more preferably 5 to 80 mol % and still more preferably 7 to 70 mol %.

2
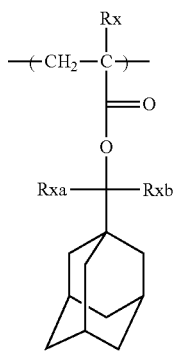
3
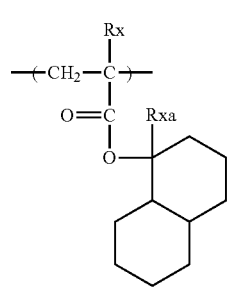
4
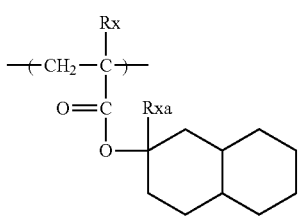
5
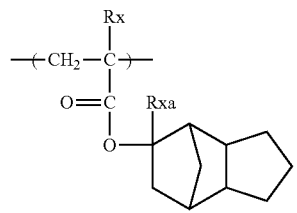
6
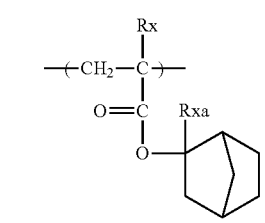
7
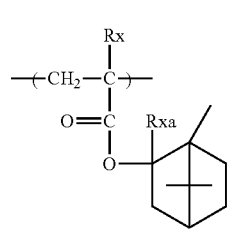
8
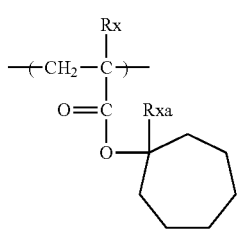
9
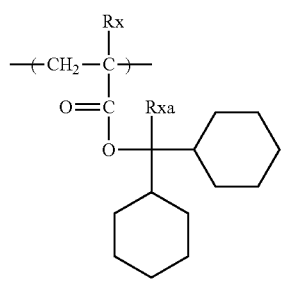
10
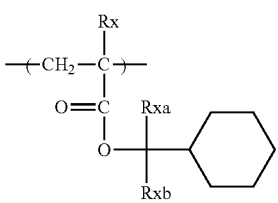
11
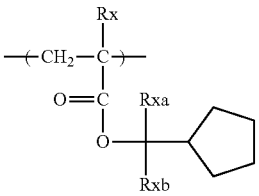
12
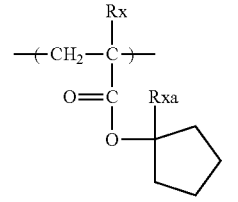
13
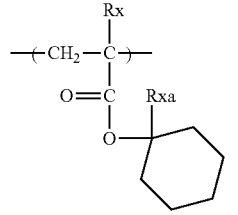
14
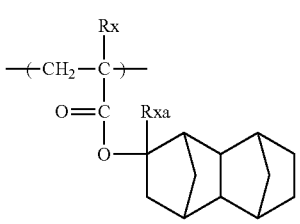

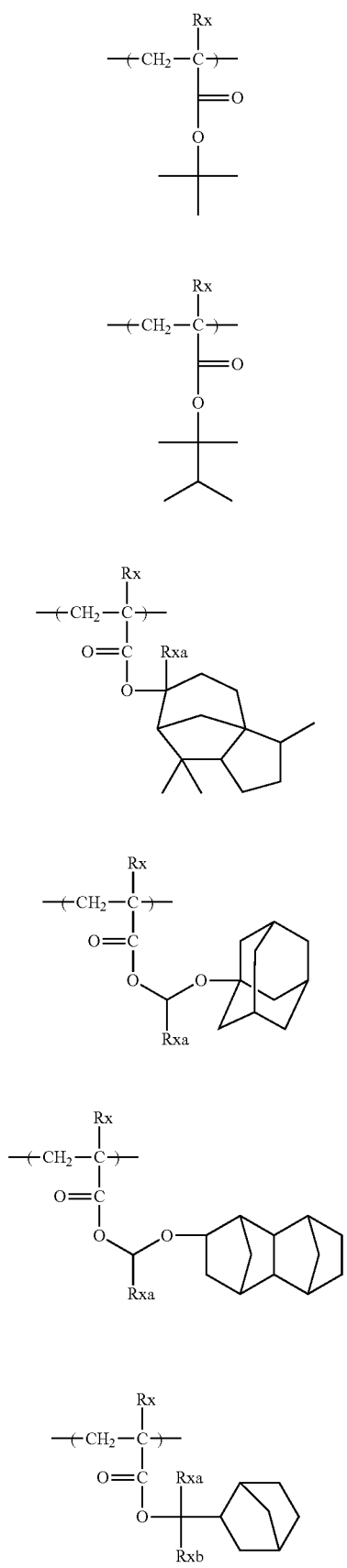
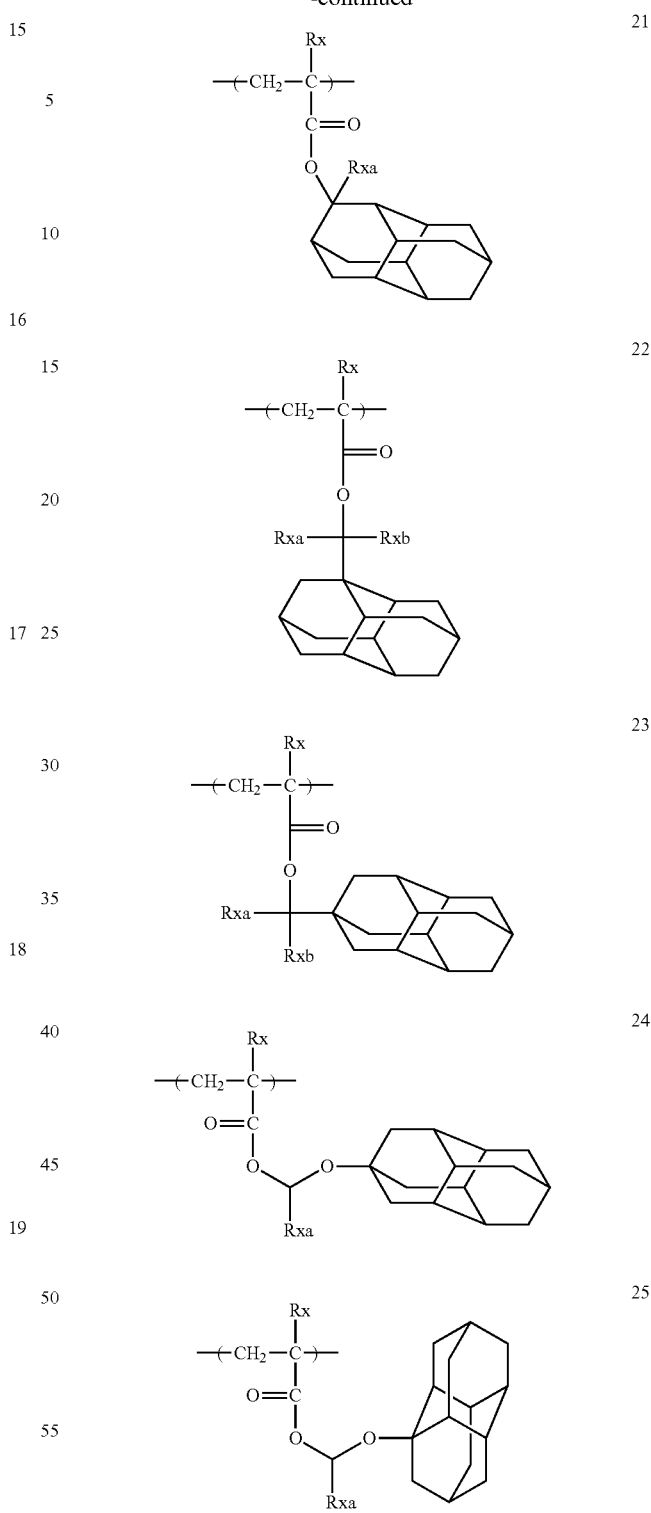
The content of repeating units represented by the general formula (X) based on all the repeating units of the resin is preferably in the range of 3 to 90 mol %, more preferably 5 to 80 mol % and still more preferably 7 to 70 mol %.
Specific examples of the resin explained above will be shown below, which however in no way limit the scope of the present invention.

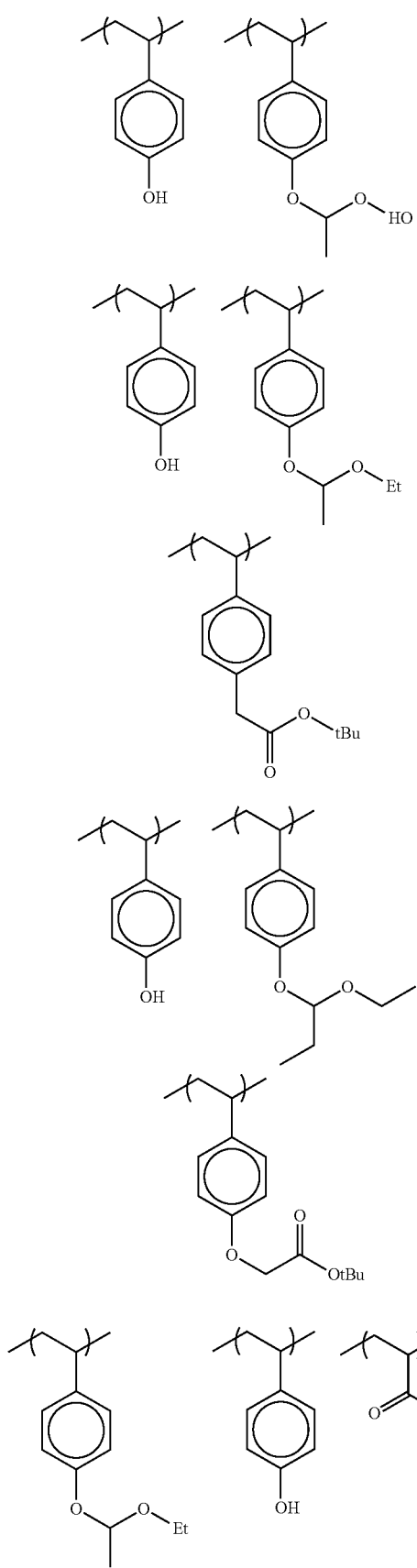

(R-9)
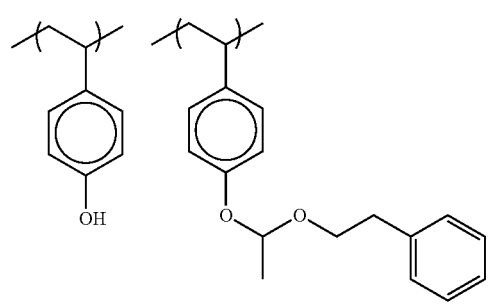
(R-10)
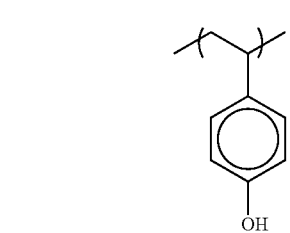
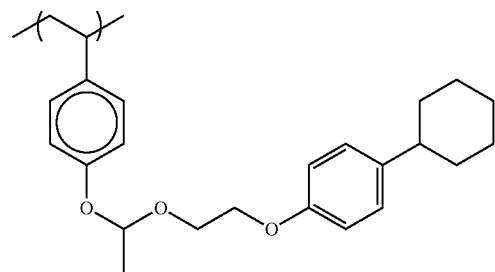
(R-11)
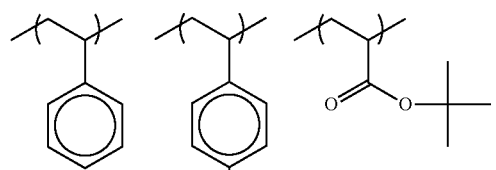
(R-12)
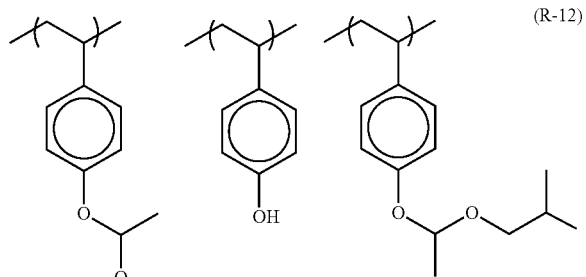
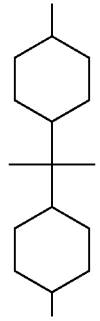
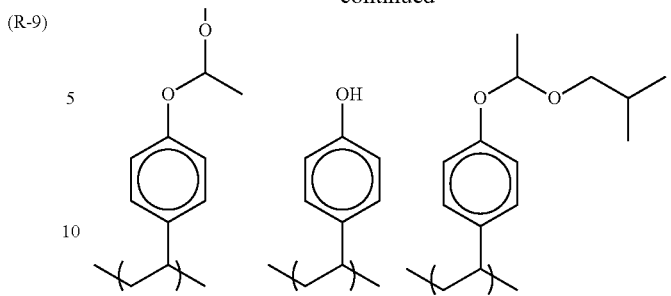
(R13)
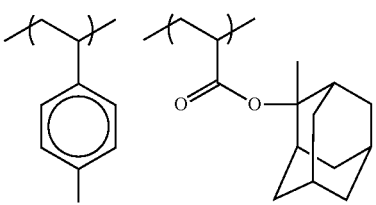
(R-14)
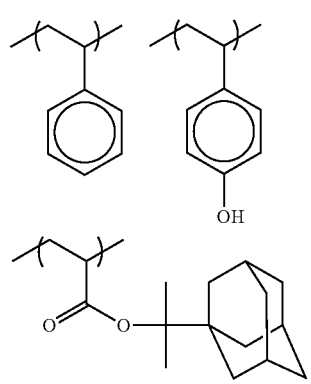
(R-15)
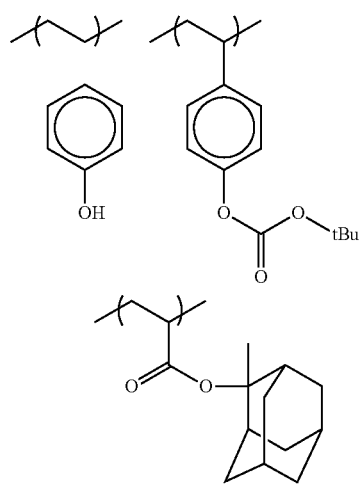
(R-16)
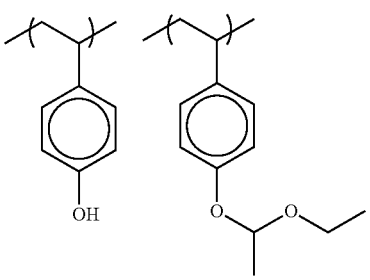

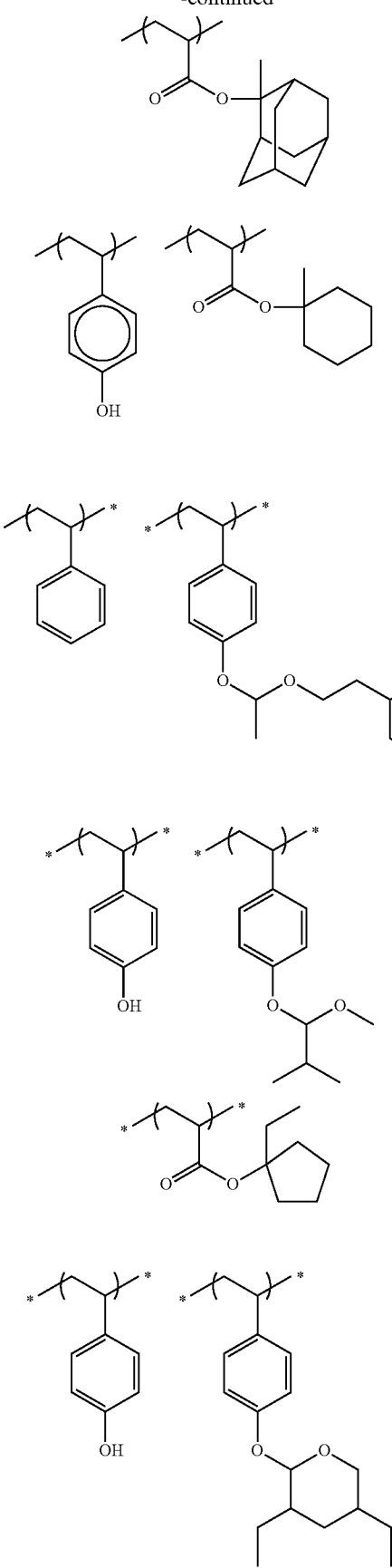
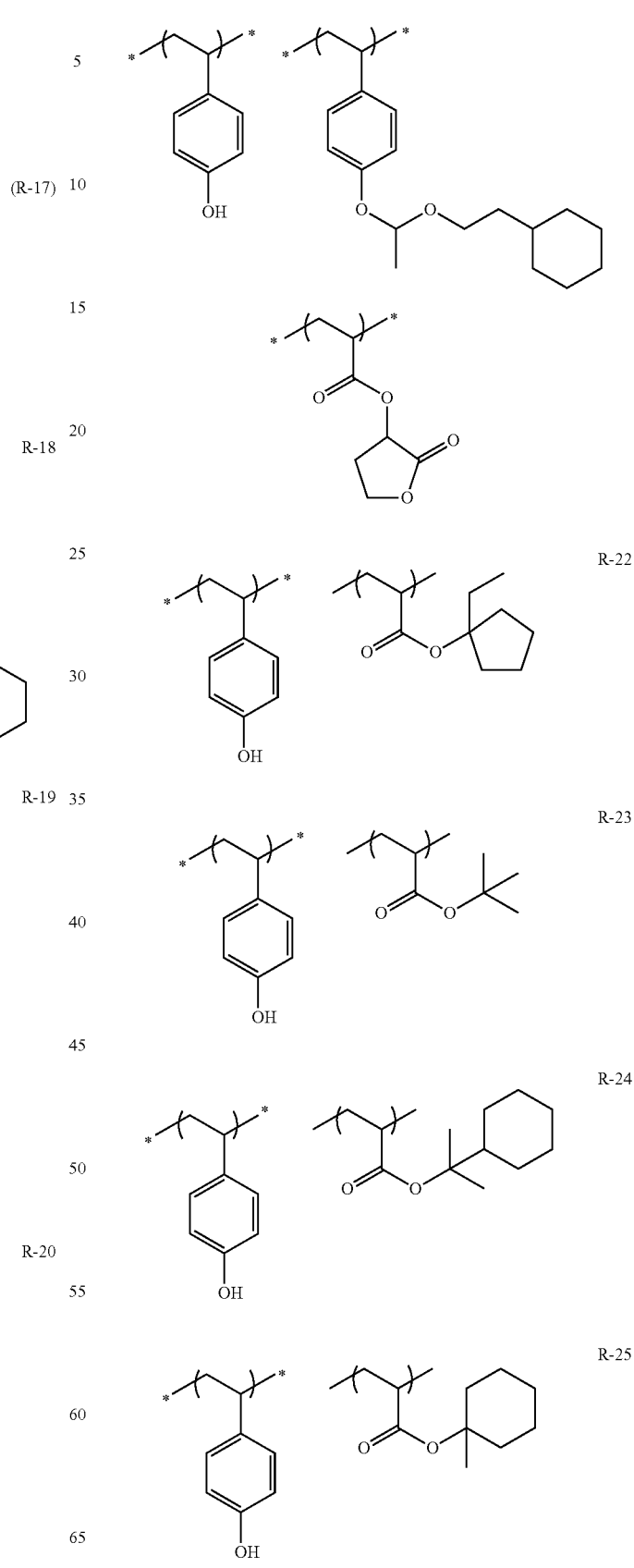

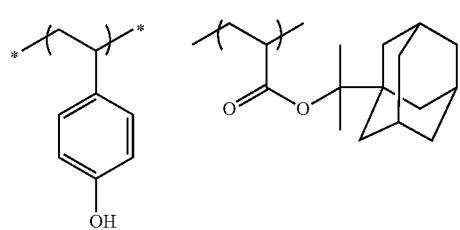
R-26

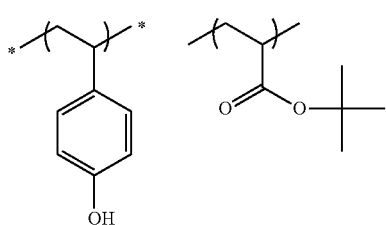
R-27

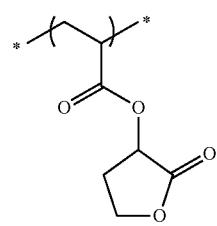

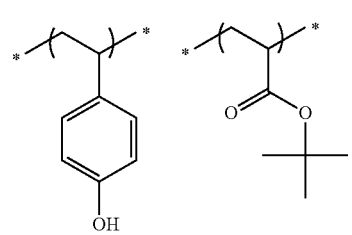
R-28

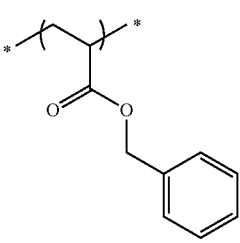

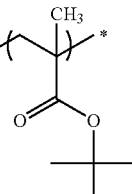 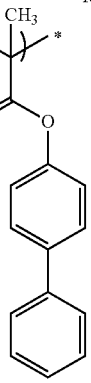 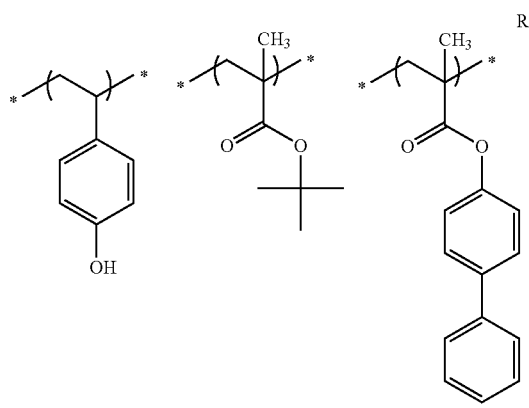
R-29

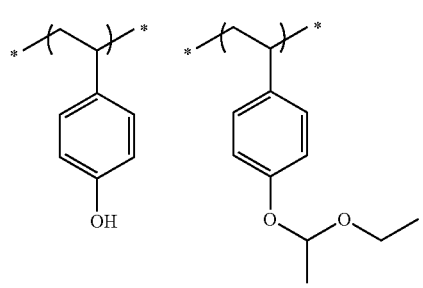
R-30

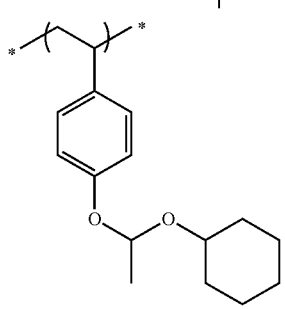

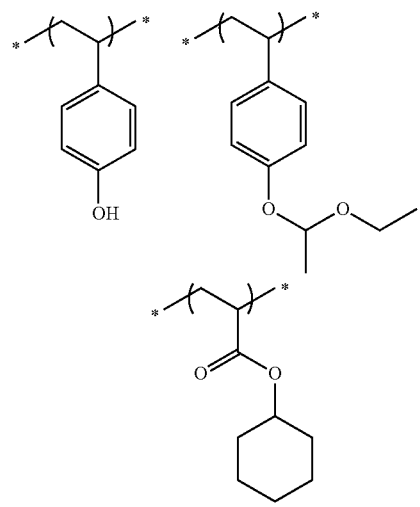
R-31

In the specific examples above, tBu represents a t-butyl group.

The content of acid-decomposable group is expressed by the formula B/(B+S) wherein B refers to the number of acid-decomposable groups contained in the resin and S refers to the number of alkali-soluble groups not protected by any acid-eliminable group. The content is preferably in the range of 0.01 to 0.7, more preferably 0.05 to 0.50 and further preferably 0.05 to 0.40.

When the composition according to the present invention is exposed to ArF excimer laser beams, it is preferred for the resin to contain an alicyclic hydrocarbon structure of a single ring or multiple rings. Such resins will be referred to as "alicyclic hydrocarbon based acid-decomposable resin" hereinbelow.

Preferably, the alicyclic hydrocarbon based acid-decomposable resin contains at least one member selected from the group consisting of the repeating units having partial structures containing the alicyclic hydrocarbons of general formulae (pI) to (pV) below and the repeating units of general formula (II-AB) below.

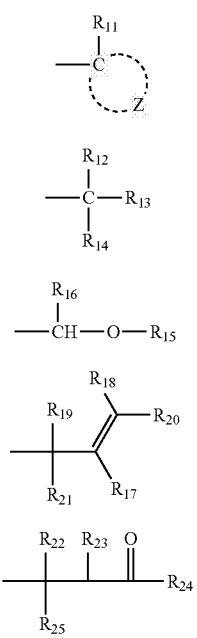

(pI)

(pII)

(pIII)

(pIV)

(pV)

In the general formulae (pI) to (pV), $R_{11}$ represents a methyl group, an ethyl group, an n-propyl group, an isopropyl group, an n-butyl group, an isobutyl group or a sec-butyl group, and Z represents an atomic group required for formation of a cycloalkyl group in cooperation with a carbon atom.

Each of $R_{12}$ to $R_{16}$ independently represents a cycloalkyl group or a linear or branched alkyl group having 1 to 4 carbon atoms, provided that at least one of $R_{12}$ to $R_{14}$ and either $R_{15}$ or $R_{16}$ represents a cycloalkyl group.

Each of $R_{17}$ to $R_{21}$ independently represents a hydrogen atom or a cycloalkyl group or a linear or branched alkyl group having 1 to 4 carbon atoms, provided that at least one of $R_{17}$ to $R_{21}$ represents a cycloalkyl group. Either $R_{19}$ or $R_{21}$ represents a cycloalkyl group or a linear or branched alkyl group having 1 to 4 carbon atoms.

Each of $R_{22}$ to $R_{25}$ independently represents a hydrogen atom or a cycloalkyl group or a linear or branched alkyl group having 1 to 4 carbon atoms, provided that at least one of $R_{22}$ to $R_{25}$ represents a cycloalkyl group. $R_{23}$ and $R_{24}$ may be bonded to each other to thereby form a ring.

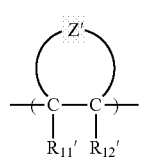

(II-AB)

In the general formula (II-AB), each of $R_{11}'$ and $R_{12}'$ independently represents a hydrogen atom, a cyano group, a halogen atom or an alkyl group.

Z' represents an atomic group for formation of an alicyclic structure wherein two bonded carbon atoms (C—C) are contained.

Further preferably, the general formula (II-AB) is either general formula (II-AB1) or general formula (II-AB2) below.

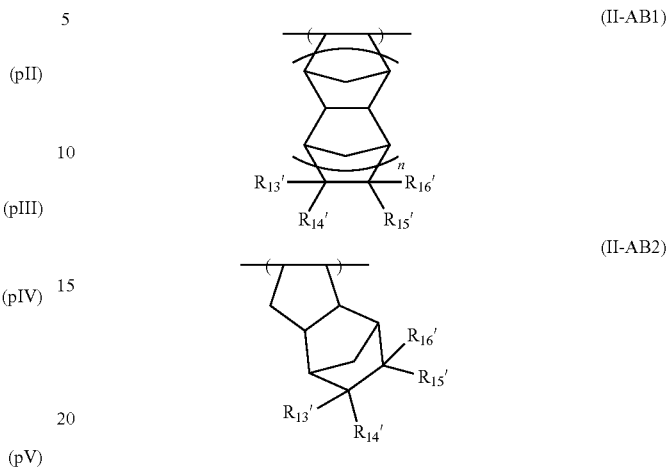

In the general formulae (II-AB1) and (II-AB2), each of $R_{13}'$ to $R_{16}'$ independently represents a hydrogen atom, a halogen atom, a cyano group, a hydroxyl group, —COOH, —COOR$_5$, a group that is decomposed by the action of an acid, —C(=O)—X-A'—$R_{17}'$, an alkyl group or a cycloalkyl group. In the above formula, $R_5$ represents an alkyl group, a cycloalkyl group or a group with a lactone structure. X represents an oxygen atom, a sulfur atom, —NH—, —NHSO$_2$— or —NHSO$_2$NH—. A' represents a single bond or a bivalent connecting group. $R_{17}'$ represents —COOH, —COOR$_5$, —CN, a hydroxyl group, an alkoxy group, —CO—NH—$R_6$, —CO—NH—SO$_2$—$R_6$ or a group with a lactone structure. $R_6$ represents an alkyl group or a cycloalkyl group. At least two of $R_{13}'$ to $R_{16}'$ may be bonded to each other to thereby form a ring.

n represents 0 or 1.

In the general formulae (pI) to (pV), each of the alkyl groups represented by $R_{12}$ to $R_{25}$ is a linear or branched alkyl group having 1 to 4 carbon atoms. As such, there can be mentioned, for example, a methyl group, an ethyl group, a propyl group, an n-butyl group, a sec-butyl group, a t-butyl group or the like.

The cycloalkyl groups represented by $R_{11}$ to $R_{25}$ and the cycloalkyl group formed by Z and a carbon atom may be monocyclic or polycyclic. In particular, there can be mentioned groups of a monocyclo, bicyclo, tricyclo or tetracyclo structure or the like having 5 or more carbon atoms. The number of carbon atoms thereof is preferably in the range of 6 to 30, especially preferably 7 to 25.

As preferred cycloalkyl groups, there can be mentioned an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group and a cyclododecanyl group. As more preferred cycloalkyl groups, there can be mentioned an adamantyl group, a norbornyl group, a cyclohexyl group, a cyclopentyl group, a tetracyclododecanyl group and a tricyclodecanyl group.

These alkyl groups and cycloalkyl groups may further have substituents. As substituents that can be introduced in the alkyl groups and cycloalkyl groups, there can be mentioned an alkyl group (1 to 4 carbon atoms), a halogen atom, a hydroxyl group, an alkoxy group (1 to 4 carbon atoms), a carboxyl group and an alkoxycarbonyl group (2 to 6 carbon atoms). These alkyl groups, alkoxy groups, alkoxycarbonyl groups, etc. may further have substituents. As substituents that can be further introduced in the alkyl groups, alkoxy groups, alkoxycarbonyl groups, etc., there can be mentioned a hydroxyl group, a halogen atom and an alkoxy group.

The structures of the general formulae (pI) to (pV) employed in the above resin can be used for the protection of the alkali-soluble groups. As the alkali-soluble groups, there can be mentioned various groups generally known in this technical field.

In particular, there can be mentioned, for example, structures resulting from replacement of a hydrogen atom of a carboxylic acid group, sulfonic acid group, phenol group or thiol group with any of the structures of the general formulae (pI) to (pV). Structures resulting from replacement of a hydrogen atom of a carboxylic acid group or sulfonic acid group with any of the structures of the general formulae (pI) to (pV) are preferred.

As preferred repeating units having any of the alkali-soluble groups protected by the structures of the general formulae (pI) to (pV), there can be mentioned those of general formula (pA) below.

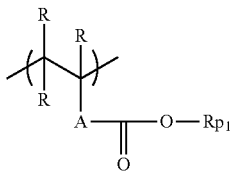

(pA)

In the general formula (pA), R represents a hydrogen atom, a halogen atom or a linear or branched alkyl group having 1 to 4 carbon atoms. Two or more R's may be identical to or different from each other.

A represents any one or a combination of two or more groups selected from the group consisting of a single bond, an alkylene group, an ether group, a thioether group, a carbonyl group, an ester group, an amido group, a sulfonamido group, a urethane group and a urea group. A single bond is preferred.

Rp1 represents any of the groups of the above general formulae (pI) to (pV).

The repeating units of the general formula (pA) are most preferably those derived from a 2-alkyl-2-adamantyl(meth) acrylate and a dialkyl(1-adamantyl)methyl(meth)acrylate.

Specific examples of the repeating units of the general formula (pA) will be shown below.

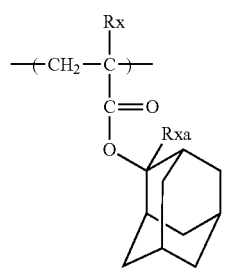

1

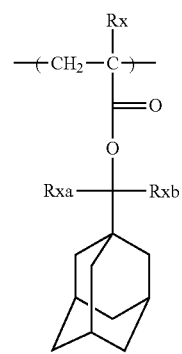

2

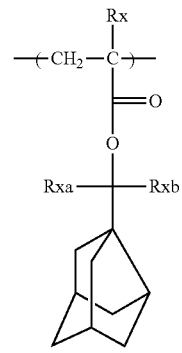

3

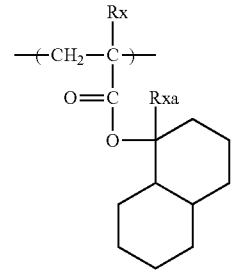

4

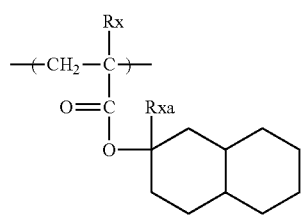

5

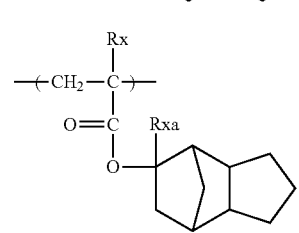

6

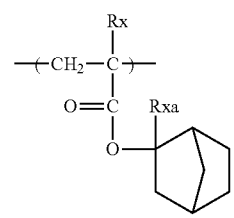

7

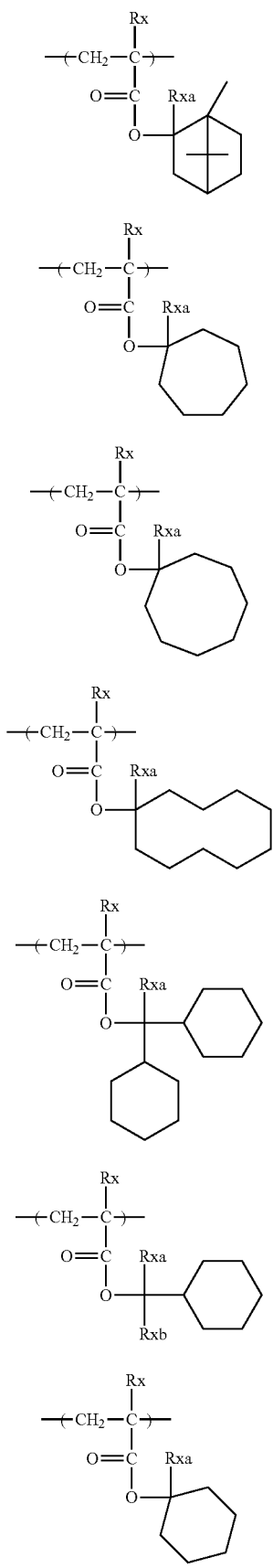
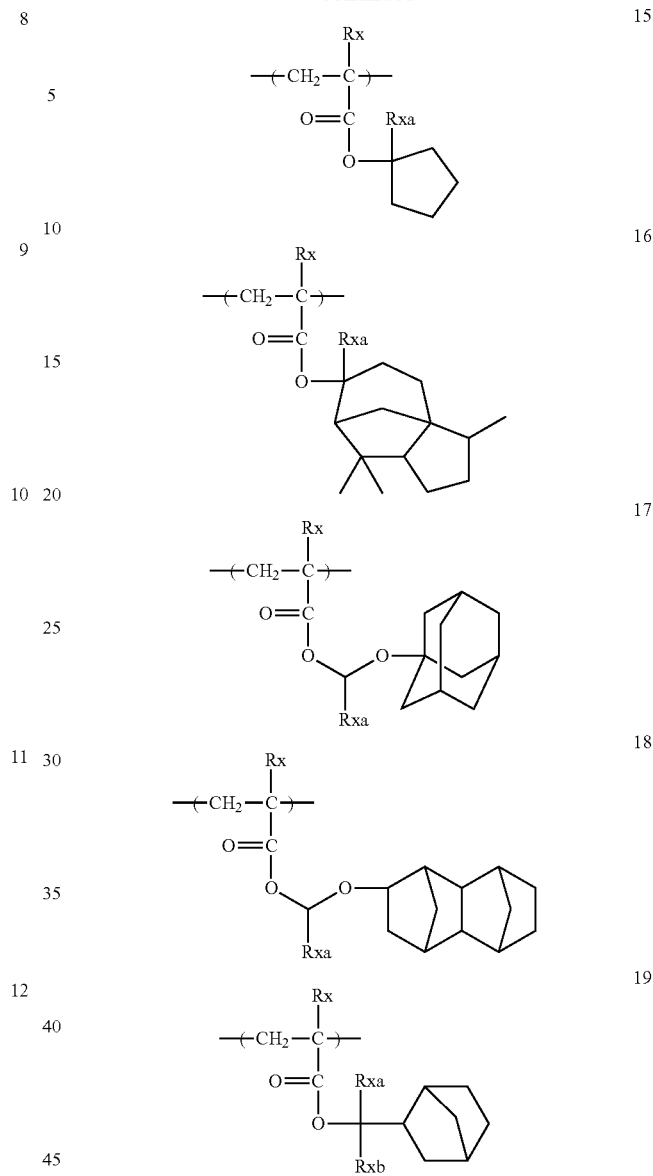

In the above structural formulae, Rx represents H, CH$_3$, CF$_3$ or CH$_2$OH. Each of Rxa and Rxb independently represents an alkyl group having 1 to 4 carbon atoms.

In the general formula (II-AB), the halogen atoms represented by R$_{11}$' and R$_{12}$' include a chlorine atom, a bromine atom, a fluorine atom, an iodine atom, etc.

The alkyl groups represented by R$_{11}$' and R$_{12}$' are preferably linear or branched alkyl groups each having 1 to 10 carbon atoms. For example, there can be mentioned a methyl group, an ethyl group, an n-propyl group, an isopropyl group, a linear or branched butyl, pentyl, hexyl or heptyl group, and the like.

The atomic group for formation of the alicyclic structure represented by Z' is an atomic group capable of providing the resin with a repeating unit of optionally substituted alicyclic hydrocarbon. The atomic group is especially preferably one capable of providing a bridged alicyclic structure for formation of a bridged alicyclic hydrocarbon repeating unit.

The provided alicyclic hydrocarbon skeleton can be the same as that of the cycloalkyl groups represented by R$_{12}$ to R$_{25}$ in the general formulae (pI) to (pV).

The alicyclic hydrocarbon skeleton may have one or more substituents. As the substituent, there can be mentioned any of the atoms or groups represented by $R_{13}'$ to $R_{16}'$ in the general formulae (II-AB1) and (II-AB2).

In the alicyclic hydrocarbon based acid-decomposable resin, the group that is decomposed by the action of an acid can be contained in at least one repeating unit selected from among the repeating units having partial structures containing the alicyclic hydrocarbons of the general formulae (pI) to (pV), the repeating units of general formula (II-AB) and the repeating units of copolymer components to be described below.

Any of the various substituents that can be introduced in $R_{13}'$ to $R_{16}'$ in the general formulae (II-AB1) and (II-AB2) can be a substituent for the atomic groups for formation of the alicyclic structures of the general formula (II-AB) or the atomic groups Z for formation of the bridged alicyclic structures.

Specific examples of the repeating units of the above general formulae (II-AB1) and (II-AB2) will be shown below, which however in no way limit the scope of the present invention.

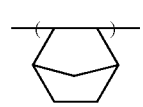
[II-1]

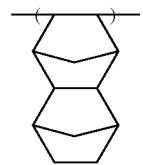
[II-2]

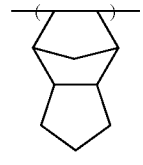
[II-3]

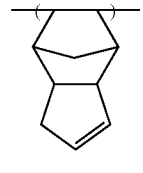
[II-4]

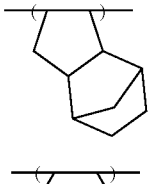
[II-5]

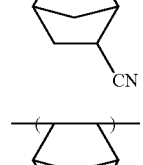
[II-6]

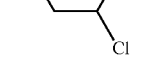
[II-7]

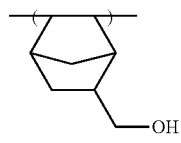
[II-8]

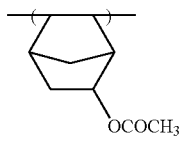
[II-9]

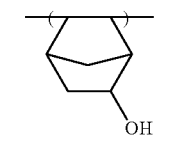
[II-10]

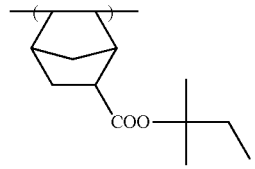
[II-11]

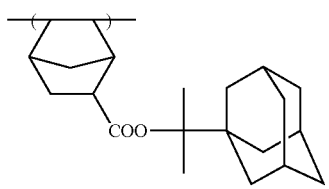
[II-12]

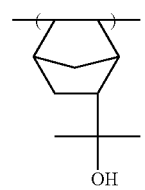
[II-13]

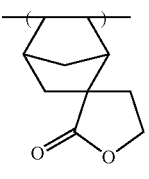
[II-14]

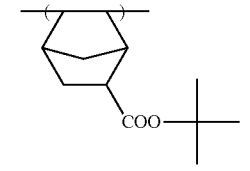
[II-15]

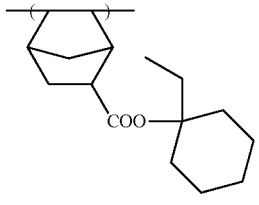
[II-16]

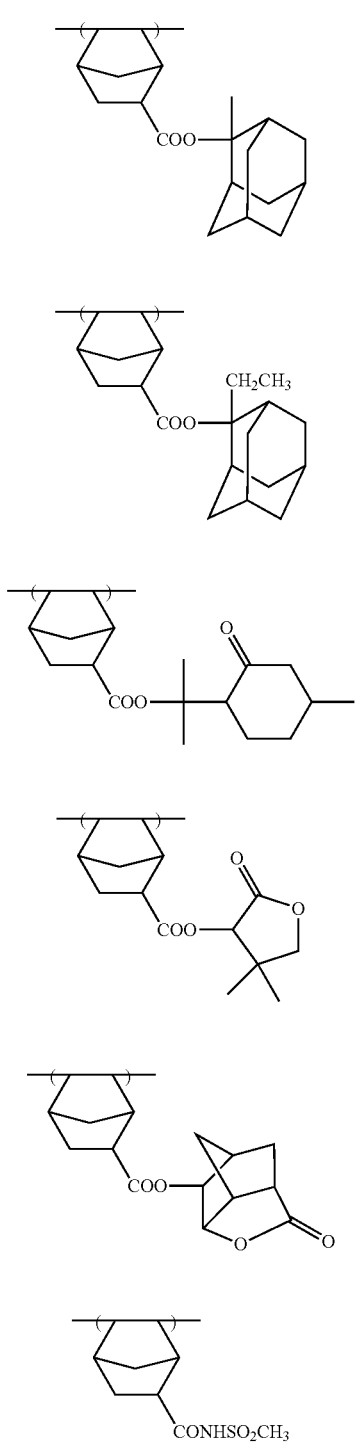
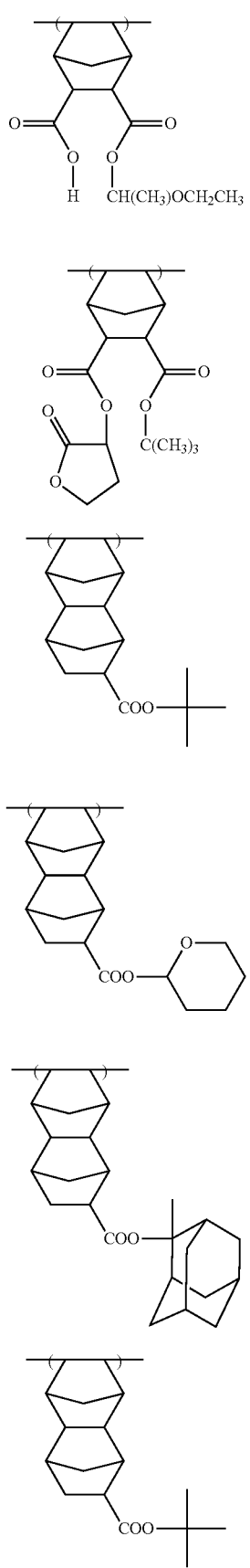

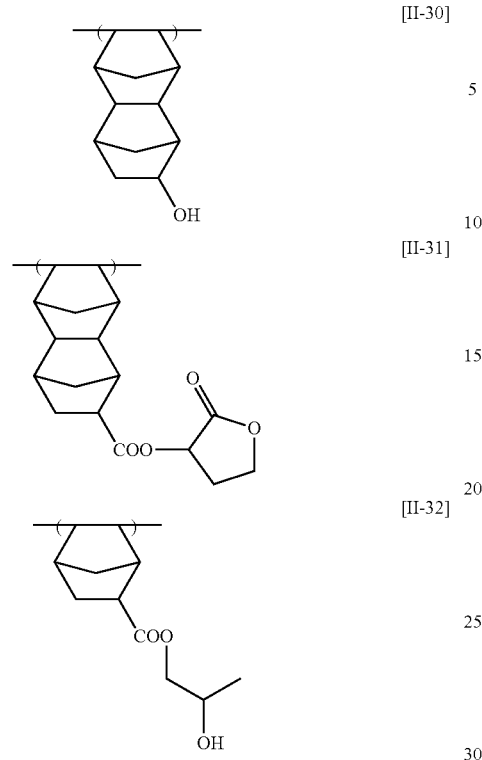

It is preferred for the alicyclic hydrocarbon based acid-decomposable resin to have a repeating unit having a lactone group. Any lactone groups can be employed as long as a lactone structure is possessed therein. However, groups with a 5 to 7-membered ring lactone structure are preferred, and those resulting from condensation of lactone structures of a 5 to 7-membered ring with other cyclic structures effected in a fashion to form a bicyclo structure or spiro structure are especially preferred.

More preferably, the alicyclic hydrocarbon based acid-decomposable resin has a repeating unit having a lactone structure represented by any of general formulae (LC1-1) to (LC1-17) below. The groups with lactone structures may be directly bonded to the principal chain of the resin. Preferred lactone structures are those of the formulae (LC1-1), (LC1-4), (LC1-5), (LC1-6), (LC1-13), (LC1-14), and (LC1-17). The use of these specified lactone structures would realize improvement in the line edge roughness and development defect.

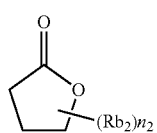

LC1-1

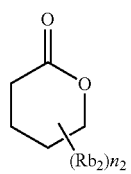

LC1-2

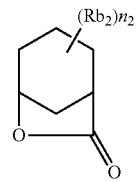

LC1-3

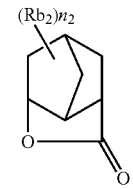

LC1-4

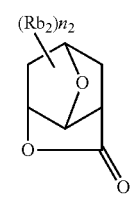

LC1-5

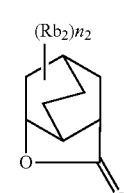

LC1-6

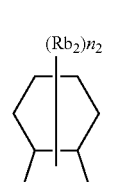

LC1-7

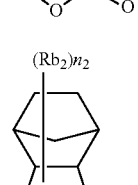

LC1-8

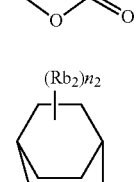

LC1-9

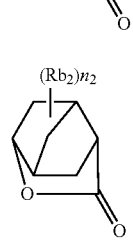

LC1-10

LC1-11
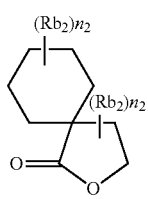

LC1-12
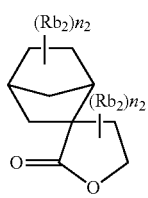

LC1-13
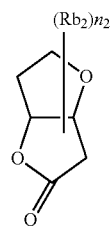

LC1-14
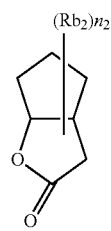

LC1-15
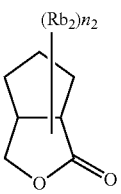

LC1-16
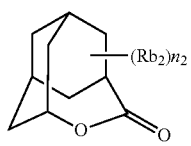

LC1-17
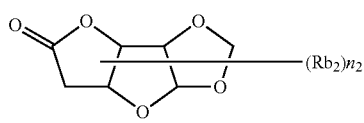

The presence of a substituent ($Rb_2$) on the portion of the lactone structure is optional. As preferred substituents ($Rb_2$), there can be mentioned an alkyl group having 1 to 8 carbon atoms, a cycloalkyl group having 3 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, an acid-decomposable group and the like.

In the formulae, $n_2$ is an integer of 0 to 4. When $n_2$ is an integer of 2 or greater, the plurality of present substituents ($Rb_2$) may be identical to or different from each other. Further, the plurality of present substituents ($Rb_2$) may be bonded to each other to thereby form a ring.

As the repeating units having the groups with lactone structures of any of the general formulae (LC1-1) to (LC1-17), there can be mentioned the repeating units of the general formulae (II-AB1) and (II-AB2) wherein at least one of $R13'$ to $R16'$ has any of the groups of the general formulae (LC1-1) to (LC1-17) as well as the repeating units of general formula (AI) below. Examples of the former include a structure in which the $R_5$ of —$COOR_5$ represents any of the groups of the general formulae (LC1-1) to (LC1-17).

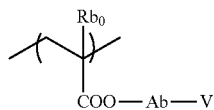

(AI)

In the general formula (AI), $Rb_0$ represents a hydrogen atom, a halogen atom or an alkyl group having 1 to 4 carbon atoms.

As the alkyl group represented by $Rb_0$, there can be mentioned, for example, a methyl group, an ethyl group, a propyl group, an n-butyl group, a sec-butyl group, a t-butyl group or the like. The alkyl group represented by $Rb_0$ may have one or more substituents. As preferred substituents that may be introduced in the alkyl group represented by $Rb_0$, there can be mentioned, for example, a hydroxyl group and a halogen atom.

As the halogen atom represented by $Rb_0$, there can be mentioned a fluorine atom, a chlorine atom, a bromine atom or an iodine atom.

The $Rb_0$ is preferably a hydrogen atom or a methyl group.

Ab represents an alkylene group, a bivalent connecting group with an alicyclic hydrocarbon structure of a single ring or multiple rings, a single bond, an ether group, an ester group, a carbonyl group, a carboxyl group or a bivalent connecting group resulting from combination of these. A single bond and a connecting group of the formula -$Ab_1$-$CO_2$— are preferred.

$Ab_1$ is a linear or branched alkylene group or a cycloalkylene group of a single ring or multiple rings, being preferably a methylene group, an ethylene group, a cyclohexylene group, an adamantylene group or a norbornylene group.

V represents any of the groups of the general formulae (LC1-1) to (LC1-17).

The repeating unit having a lactone structure is generally present in the form of optical isomers. Any of the optical isomers may be used. It is both appropriate to use a single type of optical isomer alone and to use a plurality of optical isomers in the form of a mixture. When a single type of optical isomer is mainly used, the optical purity thereof is preferably 90% ee or higher, more preferably 95% ee or higher.

Especially preferred repeating units containing lactone group, the followings can be exemplified. Selecting the best lactone group can improve a pattern profile and iso-dense dependense. In the formulae below, each of Rx and R independently represents H, $CH_3$, $CH_2OH$, or $CF_3$.

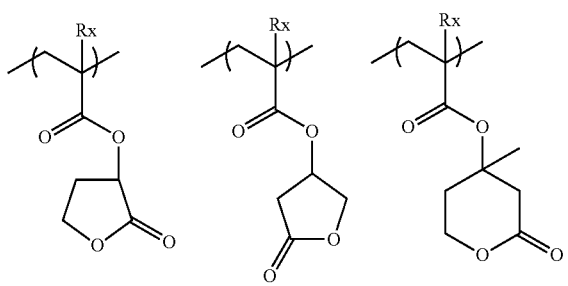
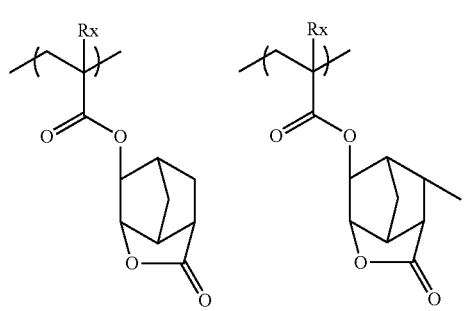
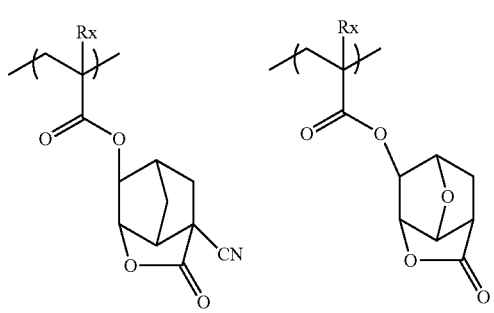
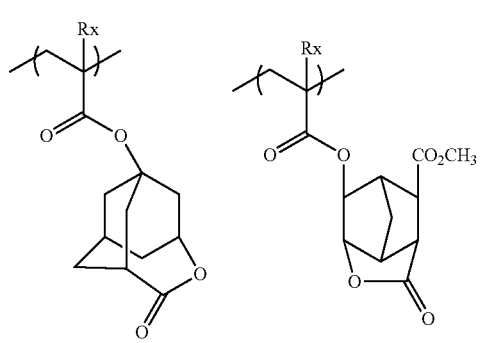
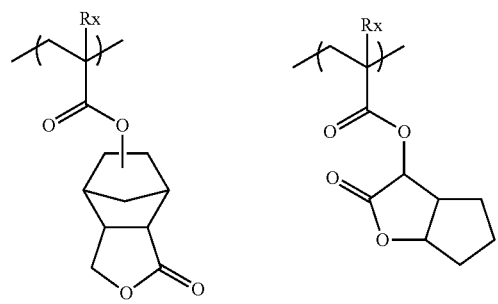
-continued
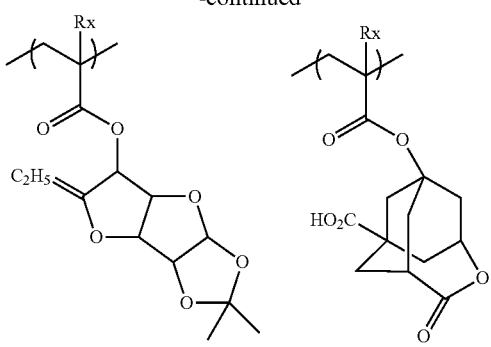
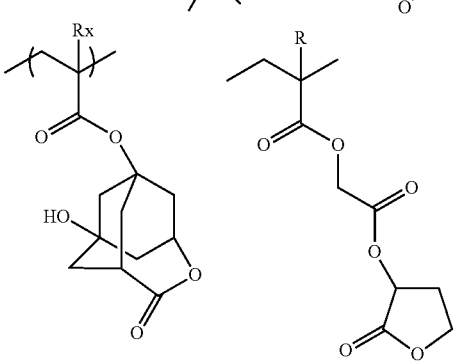
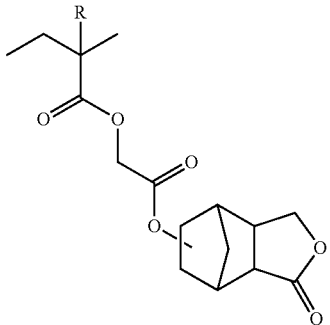
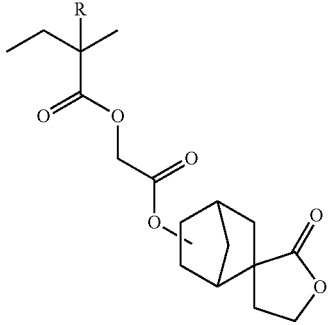
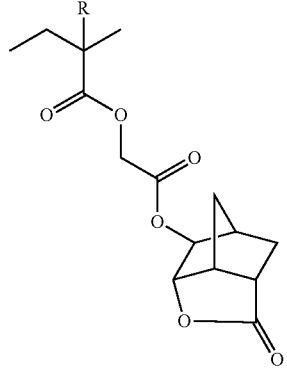

113
-continued
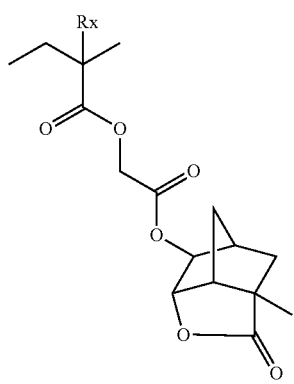
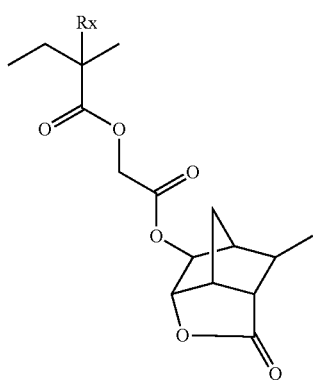
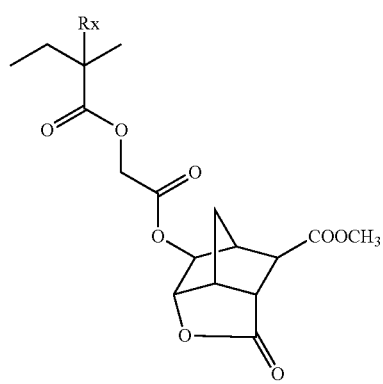
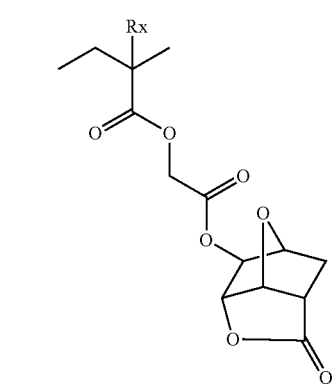
114
-continued
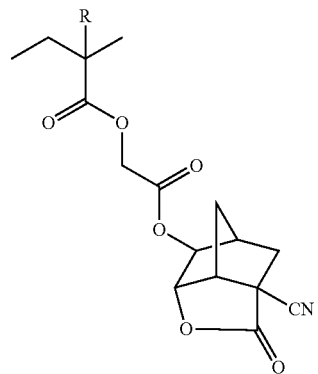
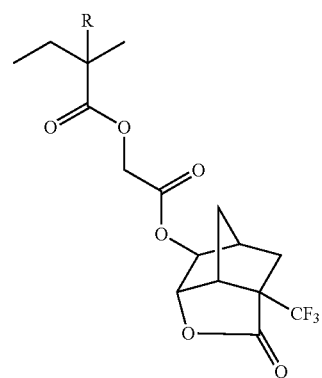
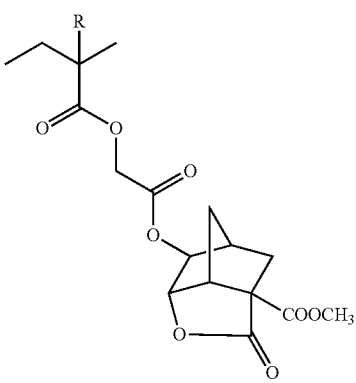
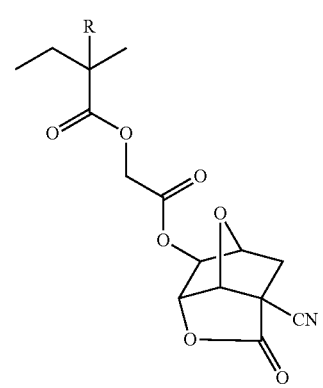

115
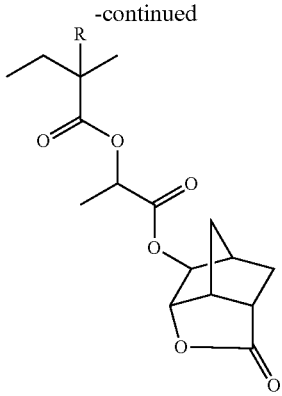
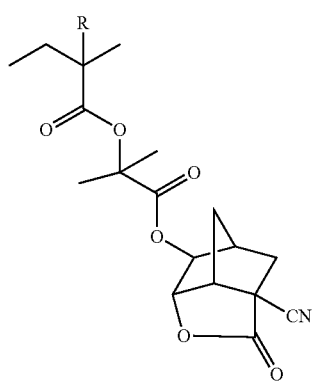
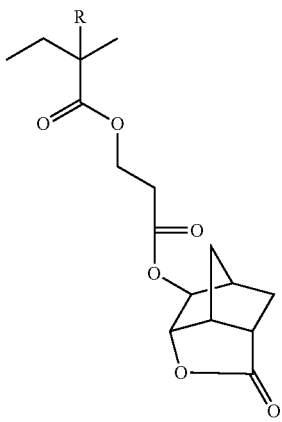
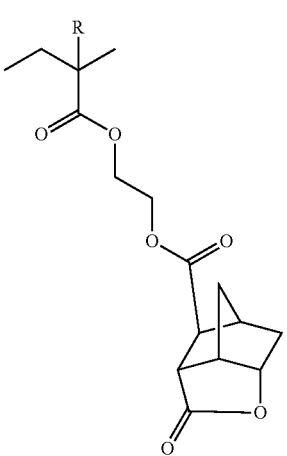
116
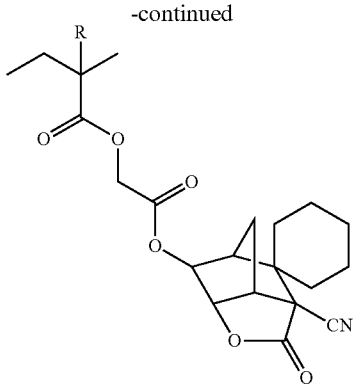
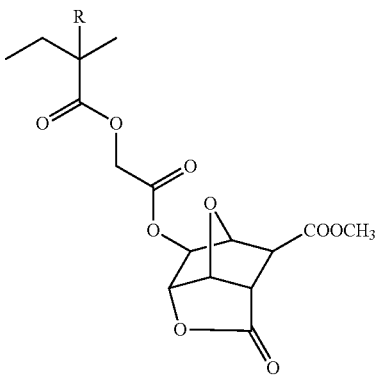
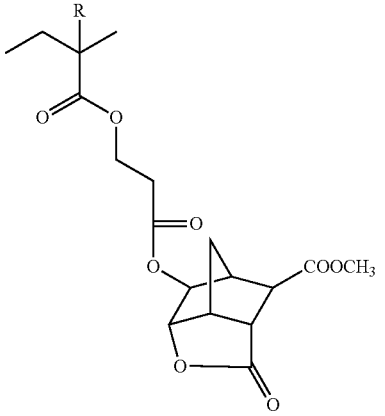
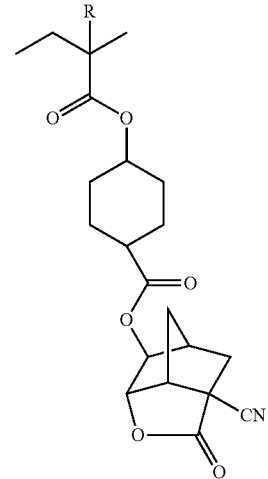

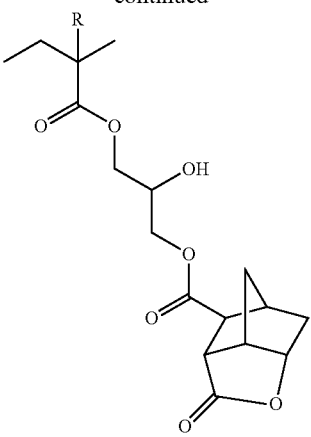

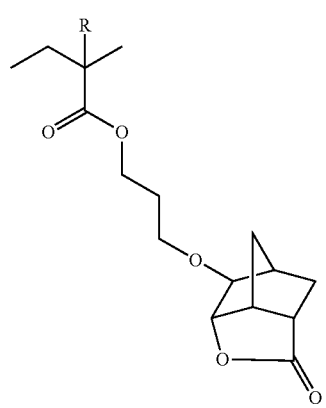

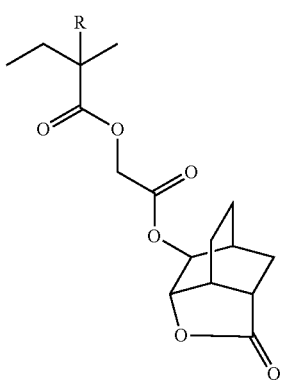

It is preferred for the alicyclic hydrocarbon based acid-decomposable resin to have a repeating unit having an alicyclic hydrocarbon structure substituted with a polar group. The containment of this repeating unit would realize enhancements of adhesion to substrate and developer affinity. The polar group is preferably a hydroxyl group or a cyano group. The hydroxyl group as the polar group constitutes an alcoholic hydroxyl group.

As the alicyclic hydrocarbon structure substituted with a polar group, there can be mentioned, for example, any of the structures of general formulae (VIIa) and (VIIb) below.

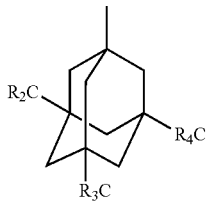

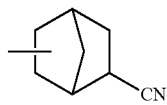

In the general formula (VIIa), each of $R_2c$ to $R_4c$ independently represents a hydrogen atom, a hydroxyl group or a cyano group, provided that at least one of the $R_2c$ to $R_4c$ represents a hydroxyl group or a cyano group. Preferably, one or two of the $R_2c$ to $R_4c$ are hydroxyl groups and the remainder is a hydrogen atom. More preferably, two of the $R_2c$ to $R_4c$ are hydroxyl groups and the remainder is a hydrogen atom.

The groups of the general formula (VIIa) preferably have a dihydroxy form or monohydroxy form, more preferably a dihydroxy form.

As the repeating units having the groups of the general formula (VIIa) or (VIIb), there can be mentioned the repeating units of the general formulae (II-AB1) and (II-AB2) wherein at least one of R13' to R16' has any of the groups of the general formula (VIIa) or (VIIb) as well as the repeating units of general formula (AIIa) or (AIIb) below. Examples of the former include a structure in which the $R_5$ of —COOR$_5$ represents any of the groups of the general formula (VIIa) or (VIIb)

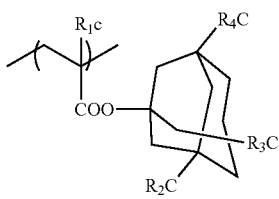

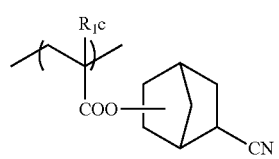

In the general formulae (AIIa) and (AIIb), $R_1c$ represents a hydrogen atom, a methyl group, a trifluoromethyl group or a hydroxymethyl group.

$R_2c$ to $R_4c$ have the same meaning as those of the general formula (VIIa).

Specific examples of the repeating units represented by the general formula (AIIa) or (AIIb) will be shown below, which however in no way limit the scope of the present invention.

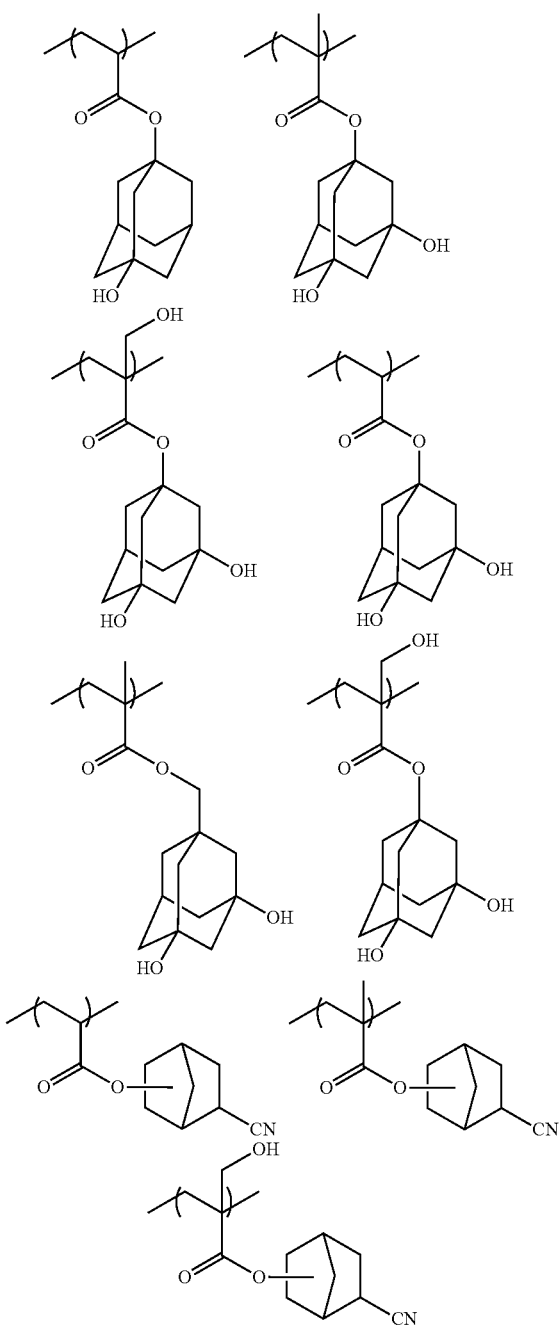

The alicyclic hydrocarbon based acid-decomposable resin according to the present invention may have any of the repeating units of general formula (VIII) below.

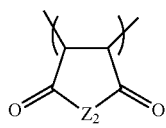
(VIII)

In the general formula (VIII), $Z_2$ represents —O— or —N($R_{41}$)—. $R_{41}$ represents a hydrogen atom, a hydroxyl group, an alkyl group or —$OSO_2$—$R_{42}$. $R_{42}$ represents an alkyl group, a cycloalkyl group or a camphor residue. The alkyl groups represented by $R_{41}$ and $R_{42}$ may be substituted with, for example, a halogen atom. As the halogen atom, a fluorine atom is preferable.

Specific examples of the repeating units of the general formula (VIII) will be shown below, which however in no way limit the scope of the present invention.

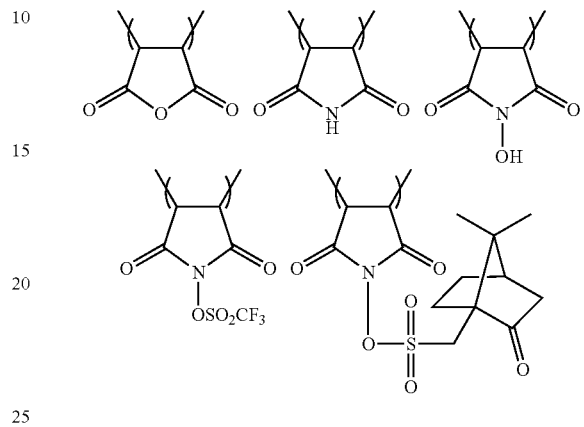

It is preferred for the alicyclic hydrocarbon based acid-decomposable resin to contain a repeating unit having an alkali-soluble group, especially a repeating unit having a carboxyl group. The introduction of the repeating unit having an alkali-soluble group would increase the resolving power in contact hole usage.

The repeating unit having a carboxyl group is preferably either a repeating unit wherein the carboxyl group is directly bonded to the principal chain of a resin or a repeating unit wherein the carboxyl group is bonded via a connecting group to the principal chain of a resin.

Examples of the former case include a repeating unit formed by acrylic acid or methacrylic acid. In the latter case, the connecting group may have a cyclohydrocarbon structure of a single ring or multiple rings.

As the repeating units having a carboxyl group, those formed by acrylic acid or methacrylic acid is most preferred.

The resin may further contain a repeating unit that has an alicyclic hydrocarbon structure having no polar group and does not exhibit any acid decomposability. As such, any of the repeating units represented by general formula (IV) below can be exemplified.

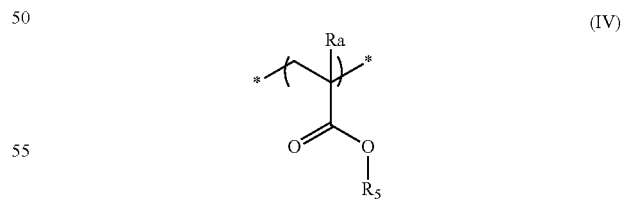
(IV)

In the general formula (IV), $R_5$ represents a hydrocarbon group having at least one cyclic structure in which neither a hydroxyl group nor a cyano group is contained.

Ra represents a hydrogen atom, an alkyl group or a group of the formula —$CH_2$—O—$Ra_2$ in which $Ra_2$ represents a hydrogen atom, an alkyl group or an acyl group. Ra is preferably a hydrogen atom, a methyl group, a hydroxymethyl group or a trifluoromethyl group, further preferably a hydrogen atom or a methyl group.

The cyclic structures contained in $R_5$ include a monocyclic hydrocarbon group and a polycyclic hydrocarbon group. As the monocyclic hydrocarbon group, a cycloalkyl group having 3 to 12 carbon atoms and a cycloalkenyl group having 3 to 12 carbon atoms can be exemplified. Preferably, the monocyclic hydrocarbon group is a monocyclic hydrocarbon group having 3 to 7 carbon atoms. As such, a cyclopentyl group and a cyclohexyl group can be exemplified.

The polycyclic hydrocarbon groups include ring-assembly hydrocarbon groups and crosslinked-ring hydrocarbon groups.

As the ring-assembly hydrocarbon groups, for example, a bicyclohexyl group and a perhydronaphthalenyl group can be exemplified.

As the crosslinked-ring hydrocarbon rings, there can be mentioned, for example, bicyclic hydrocarbon rings, such as pinane, bornane, norpinane, norbornane and bicyclooctane rings (e.g., bicyclo[2.2.2]octane ring or bicyclo[3.2.1]octane ring); tricyclic hydrocarbon rings, such as homobledane, adamantane, tricyclo[5.2.1.0$^{2,6}$]decane and tricyclo[4.3.1.1$^{2,5}$] undecane rings; and tetracyclic hydrocarbon rings, such as tetracyclo[4.4.0.1$^{2,5}$.1$^{7,10}$]dodecane and perhydro-1,4-methano-5,8-methanonaphthalene rings.

Further, the crosslinked-ring hydrocarbon rings include condensed-ring hydrocarbon rings, for example, condensed rings resulting from condensation of multiple 5- to 8-membered cycloalkane rings, such as perhydronaphthalene (decalin), perhydroanthracene, perhydrophenanthrene, perhydroacenaphthene, perhydrofluorene, perhydroindene and perhydrophenalene rings.

As preferred crosslinked-ring hydrocarbon rings, there can be mentioned a norbornyl group, an adamantyl group, a bicyclooctanyl group, a tricyclo[5.2.1.0$^{2,6}$]decanyl group and the like. As more preferred crosslinked-ring hydrocarbon rings, there can be mentioned a norbornyl group and an adamantyl group.

These alicyclic hydrocarbon groups may have one or more substituents. As preferred substituents, a halogen atom, an alkyl group, a hydroxyl group protected by a protective group, and an amino group protected by a protective group can be exemplified.

The halogen atom is preferably a bromine, chlorine or fluorine atom.

The alkyl group is preferably a methyl, ethyl, butyl or t-butyl group. The alkyl group may further have one or more substituents. As the optional substituent, a halogen atom, an alkyl group, a hydroxyl group protected by a protective group, and an amino group protected by a protective group can be exemplified.

As the protective group, an alkyl group, a cycloalkyl group, an aralkyl group, a substituted methyl group, a substituted ethyl group, an alkoxycarbonyl group and an aralkyloxycarbonyl group can be exemplified. Preferred alkyl groups include alkyl groups having 1 to 4 carbon atoms. Preferred substituted methyl groups include methoxymethyl, methoxythiomethyl, benzyloxymethyl, t-butoxymethyl and 2-methoxyethoxymethyl groups. Preferred substituted ethyl groups include 1-ethoxyethyl and 1-methyl-1-methoxyethyl groups. Preferred acyl groups include aliphatic acyl groups having 1 to 6 carbon atoms, such as formyl, acetyl, propionyl, butyryl, isobutyryl, valeryl and pivaloyl groups. Preferred alkoxycarbonyl groups include alkoxycarbonyl groups having 1 to 4 carbon atoms and the like.

Specific examples of the repeating units that have an alicyclic hydrocarbon structure having no polar group and do not exhibit any acid decomposability will be shown below, which however in no way limit the scope of the present invention. In the formulae, Ra represents H, $CH_3$, $CH_2OH$ or $CF_3$

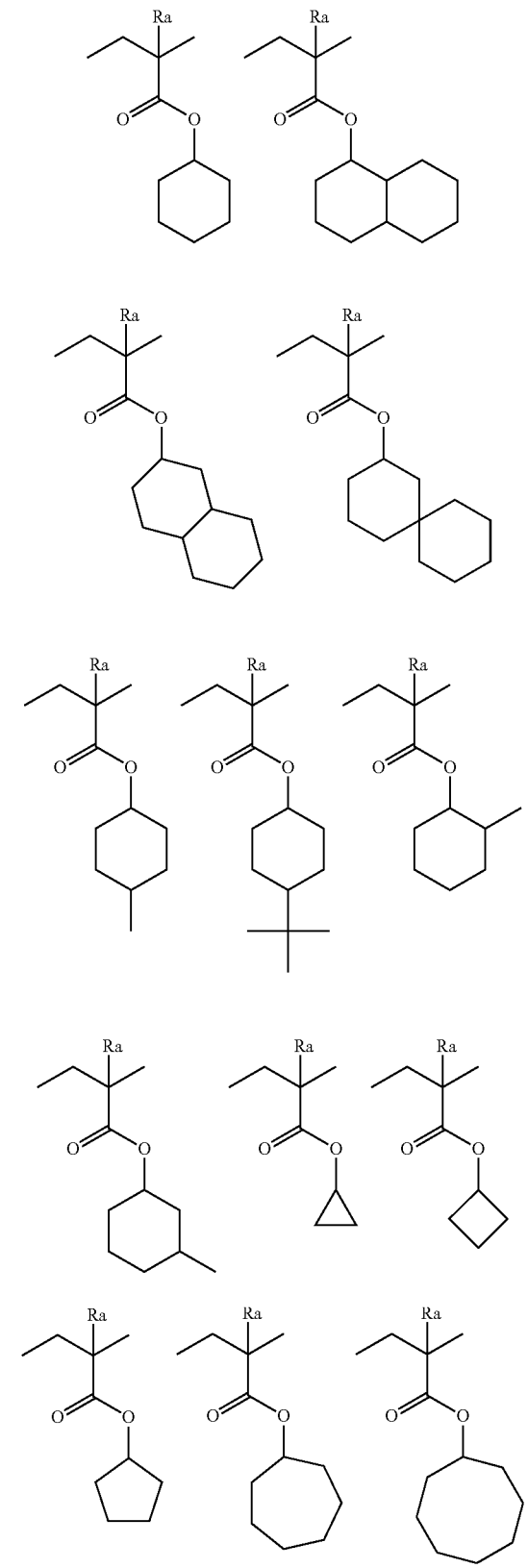

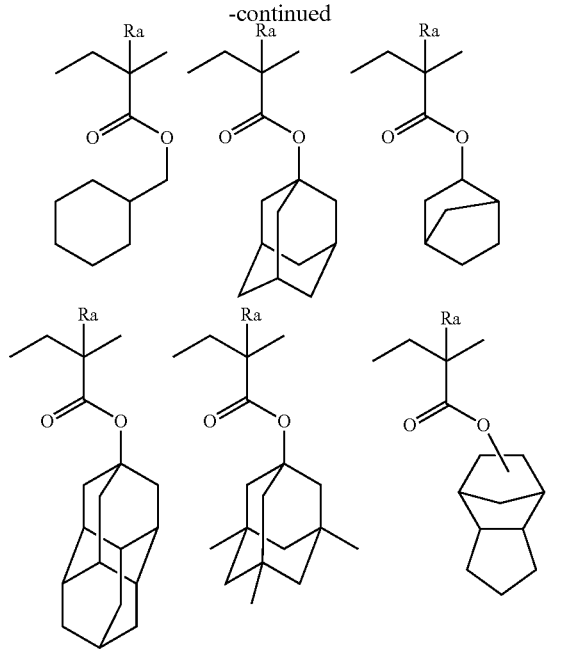

The content of the repeating unit that has an alicyclic hydrocarbon structure having no polar group and does not exhibit any acid decomposability based on all the repeating units of the resin is preferably in the range of 0 to 40 mol %, more preferably 5 to 20 mol %.

The resin may further contain repeating units other than those described above, especially when the composition is used for KrF, EB, or EUV exposure. As such, repeating units that is stable against the action of an acid can be exemplified.

As repeating units that is stable against the action of an acid, for example, repeating units in which the side chain of acrylic structure contains aryl or cycloalkyl structure which does not shown acid decomposability, such as those represented by the general formula (IV), can be exemplified. In the repeating units represented by the general formula (IV), $R_5$ preferably is a hydrocarbon group containing a cyclic structure therein. As the specific examples of the case, there can be mentioned, for example, a monocyclic or polycyclic cycloalkyl group (having preferably 3 to 12, more preferably 3 to 7 carbon atoms; a cyclohexyl group is especially preferred), a monocyclic or polycyclic cycloalkenyl group (having preferably 3 to 12 carbon atoms), an aryl group (having preferably 6 to 20, more preferably 6 to 12 carbon atoms; a phenyl group and a naphthyl group is especially preferred), and an aralkyl group (having preferably 7 to 20, more preferably 7 to 12 carbon atoms; a benzyl group is especially preferred). Incorporating such structures can lead to an adjustment of contrast and an enhancement of etching resistance.

The content of the repeating units that is stable against the action of an acid based on all the repeating units in the resin is preferably in the range of 0 to 40 mol %, and more preferably in the range of 1 to 20 mol %.

As the specific examples of the repeating units that is stable against the action of an acid, the followings can be exemplified in addition to the ones described for the repeating units represented by the general formula (IV). In the formulae, Ra represents H, $CH_3$, $CH_2OH$, or $CF_3$.

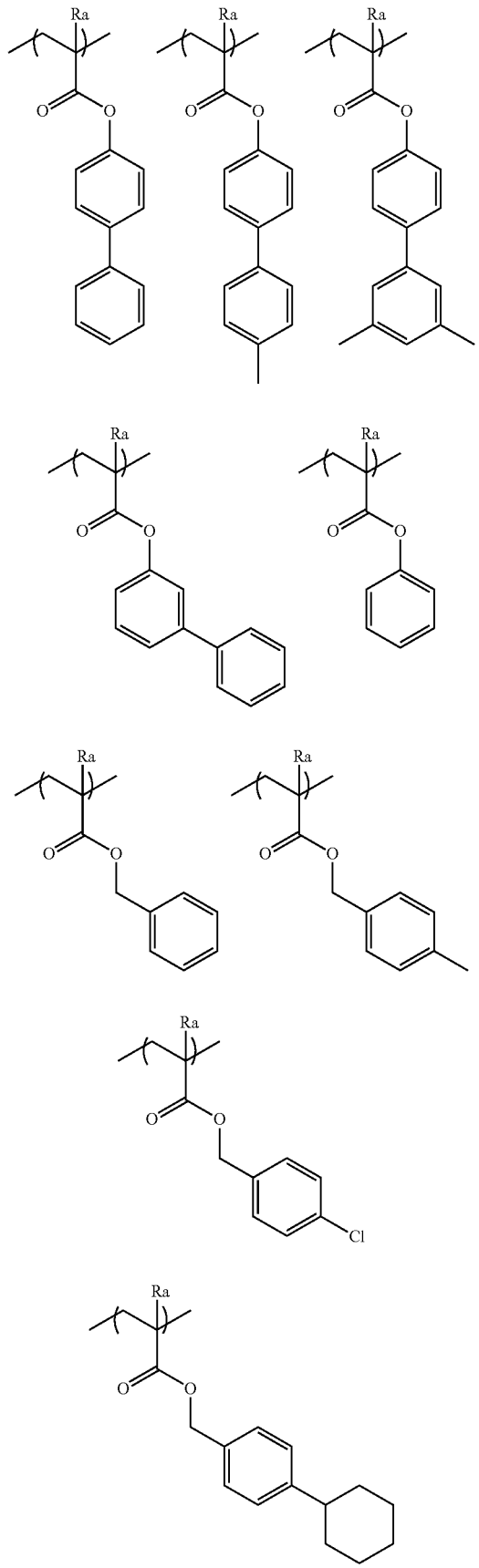

-continued

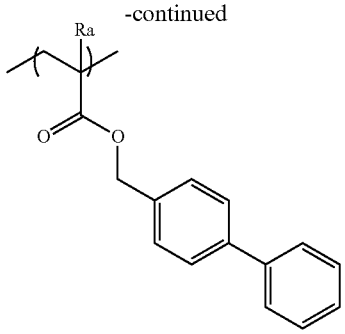

The molecular weight in terms of polystyrene molecular weight measured by GPC of the resin is not particularly limited. Preferably, the weight average molecular weight (Mw) thereof is in the range of 2000 to 200,000. By making Mw higher than 2,000, the heat resistance and dry etching resistance can be enhanced. By making Mw lower than 200,000, developability can be enhanced, and the viscosity of the composition can be decreased leading to better film forming property.

More preferable Mw falls in between 2,500 to 50,000, and further more preferable Mw in between 3,000 to 25,000. In cases for pattern formation using an electron beam, X-ray, or high-energy beam whose wavelength is 50 nm or lower (for example, EUV), it is particularly preferable for Mw to fall within the range of 3,000 to 10,000. By adjusting the Mw, increase in the heat resistance, enhancement of the resolving power, and decrease of the development defect can simultaneously be realized.

The dispersity (Mw/Mn) of the resin is preferably in the range of 1.0 to 3.0, more preferably 1.2 to 2.5, and further preferably 1.2 to 1.6. By adjusting the dispersity, for example, line edge roughness characteristics can be enhanced.

The resin may be used alone, or two or more types thereof may be used in combination. The content of the resinis preferably in the range of 0 to 99.9 mass %, more preferably 50 to 95 mass %, and further preferably 60 to 93 mass % based on the total solids of the composition.

[A2] Alkali-Soluble Resin

The alkali dissolution rate of the alkali-soluble resin as measured in a 0.261 N tetramethylammonium hydroxide (TMAH) (23° C.) is preferably 2 nm/sec or higher, especially preferably 20 nm/sec or higher.

As the alkali-soluble resin for use in the present invention, there can be mentioned, for example, a novolak resin, a hydrogenated novolak resin, an acetone-pyrogallol resin, an o-polyhydroxystyrene, a m-polyhydroxystyrene, a p-polyhydroxystyrene, a hydrogenated polyhydroxystyrene, a halogenated or alkylated polyhydroxystyrene, a hydroxystyrene-N-substituted maleimide copolymer, an o/p- and m/p-hydroxystyrene copolymer, a partial O-alkylation product of hydroxyl of polyhydroxystyrene (for example, a 5 to 30 mol % O-methylation product, O-(1-methoxy)ethylation product, O-(1-ethoxy)ethylation product, O-2-tetrahydropyranylation product, O-(t-butoxycarbonyl)methylation product, etc.), an O-acylation product thereof (for example, a 5 to 30 mol % O-acetylation product, O-(t-butoxy)carbonylation product, etc.), a styrene-maleic anhydride copolymer, a styrene-hydroxystyrene copolymer, an α-methylstyrene-hydroxystyrene copolymer, a carboxylated methacrylic resin or its derivative, or a polyvinyl alcohol derivative. However, the alkali-soluble resins are not limited to these.

Especially preferred alkali-soluble resins are a novolak resin, an o-polyhydroxystyrene, a m-polyhydroxystyrene, a p-polyhydroxystyrene, a copolymer of these polyhydroxystyrenes, an alkylated polyhydroxystyrene, a partial O-alkylation product or O-acylation product of polyhydroxystyrene, a styrene-hydroxystyrene copolymer and an α-methylstyrene-hydroxystyrene copolymer.

The resins containing one or more hydroxystyrene structures are particularly preferred. Of these, those containing one or more m-hydroxystyrene structures are especially preferred.

The above novolak resin can be obtained by addition condensation of a given monomer as a main component with an aldehyde conducted in the presence of an acid catalyst.

The weight average molecular weight of the alkali-soluble resin is 2000 or greater, preferably from 5000 to 200,000 and more preferably 5000 to 100,000. Herein, the weight average molecular weight is in terms of polystyrene molecular weight measured by gel permeation chromatography.

The alkali-soluble resins can be used individually or in combination.

The amount of alkali-soluble resin added, based on the solid contents of the whole composition, is preferably in the range of 40 to 97 mass %, and more preferably in the range of 60 to 90 mass %.

[A3] Dissolution-Inhibiting Compound

From the viewpoint of preventing any lowering of 220 nm or shorter transmission, the dissolution inhibiting compound is preferably an alicyclic or aliphatic compound containing an acid-decomposable group. As such, for example, cholic acid derivatives having an acid-decomposable group described in Proceeding of SPIE, 2724, 355 (1996) can be exemplified. The acid-decomposable group and alicyclic structure are the same as described above with respect to the alicyclic hydrocarbon based acid-decomposable resin.

When the composition according to the present invention is exposed to a KrF excimer laser or irradiated with electron beams, preferred use is made of a compound containing a structure resulting from substitution of the phenolic hydroxyl group of a phenol compound with an acid-decomposable group. The phenol compound preferably contains 1 to 9 phenol skeletons, more preferably 2 to 6 phenol skeletons.

Molecular weight of the dissolution-inhibiting compound is 3000 or less. The molecular weight is preferably in the range of 300 to 3000, and more preferably in the range of 500 to 2500.

The amount of dissolution inhibiting compound added is preferably in the range of 3 to 50 mass %, more preferably 5 to 40 mass % based on the solid contents of the composition.

Specific examples of the dissolution inhibiting compounds will be shown below, which however in no way limit the scope of the present invention.

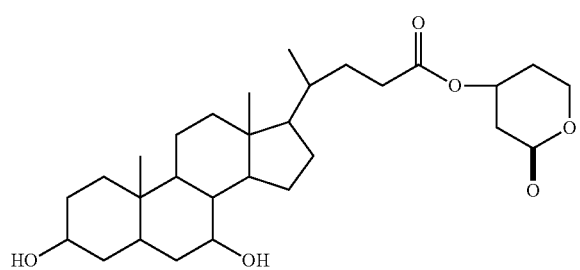

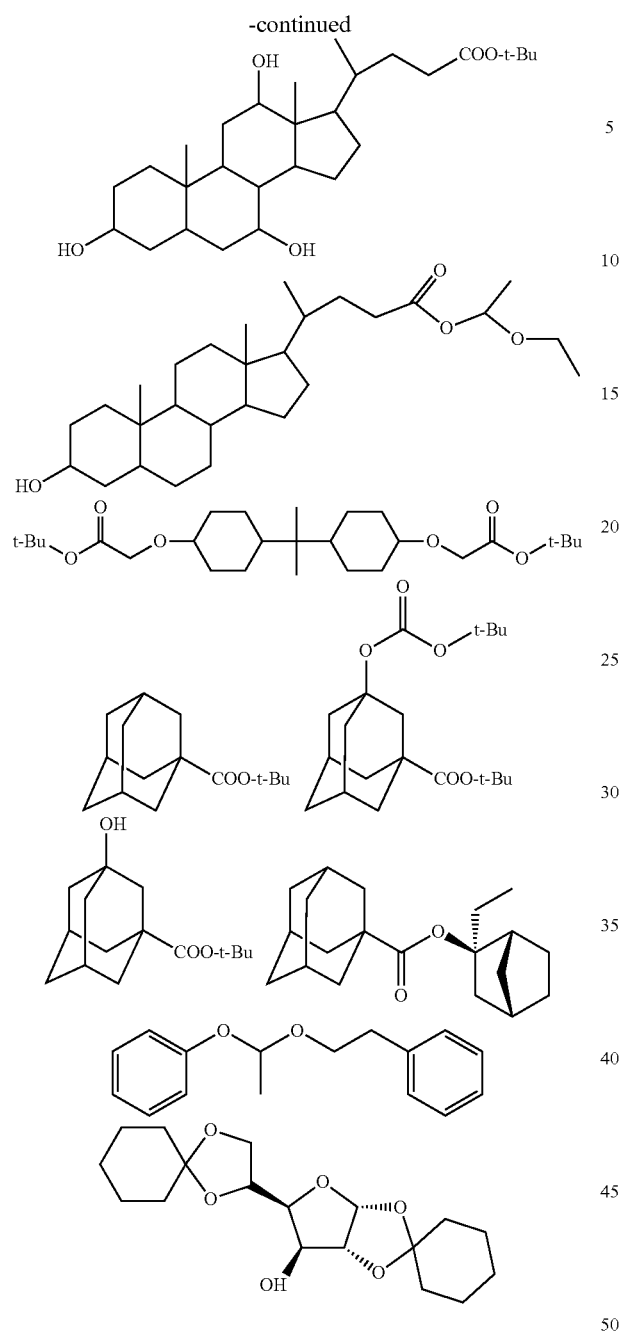

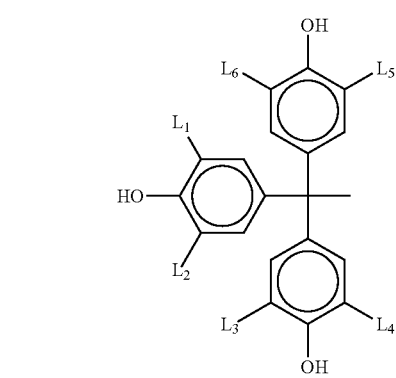

[A4] Acid Crosslinking Agent

Any crosslinking agent can be used as long as it is a compound capable of crosslinking with the resin soluble in an alkali developer by the action of an acid. However, compounds (1) to (3) below are preferred.

(1) A hydroxymethylated form, alkoxymethylated or acyloxymethylated form of phenol derivative.

(2) A compound having an N-hydroxymethyl group, an N-alkoxymethyl group or an N-acyloxymethyl group.

(3) A compound having an epoxy group.

The alkoxymethyl group preferably has 6 or less carbon atoms, and the acyloxymethyl group preferably has 6 or less carbon atoms.

Those especially preferred among these crosslinking agents will be shown below.

-continued

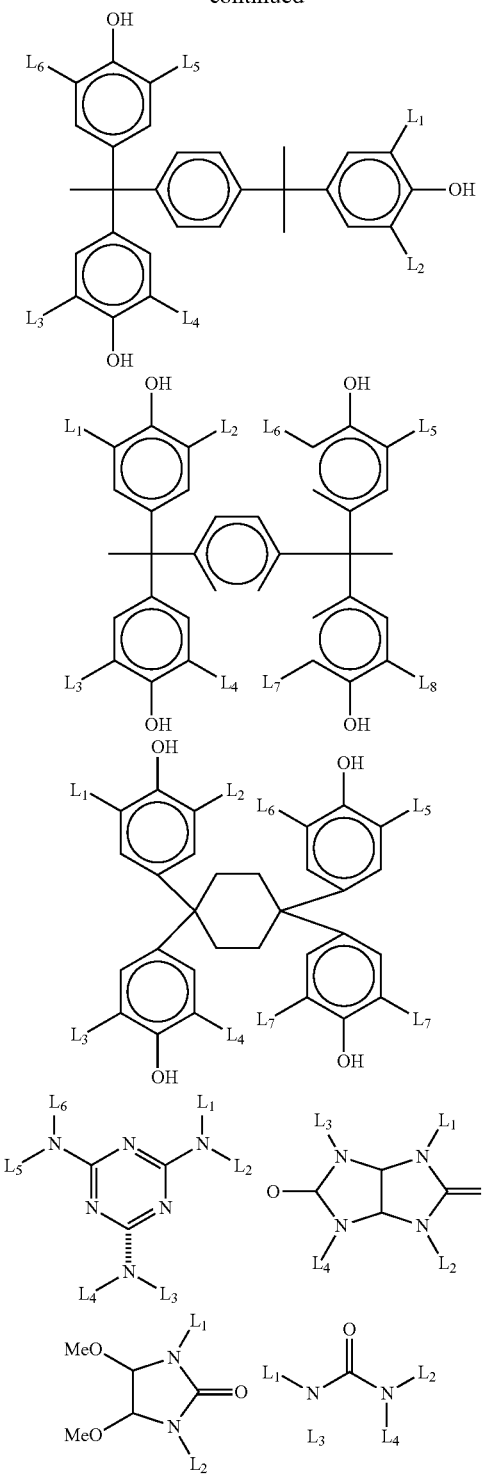

In the formulae, $L_1$ to $L_8$ may be identical to or different from each other, and each thereof represents a hydrogen atom, a hydroxymethyl group, a methoxymethyl group, an ethoxymethyl group or an alkyl group having 1 to 6 carbon atoms.

The crosslinking agent is generally added in an amount of 3 to 70 mass %, preferably 5 to 50 mass %, based on the solid content of the composition.

[A5] Basic Compound

The resist composition of the present invention preferably contains a basic compound in order to reduce any performance change over time from exposure to bake. The role of the basic compound is to quench any deprotection reaction by the acid generated by exposure, and the diffusivity and basicity thereof would influence the substantial diffusivity of the acid.

As preferred structures, there can be mentioned basic compounds with the structures of formulae (A) to (E) below and ammonium salts.

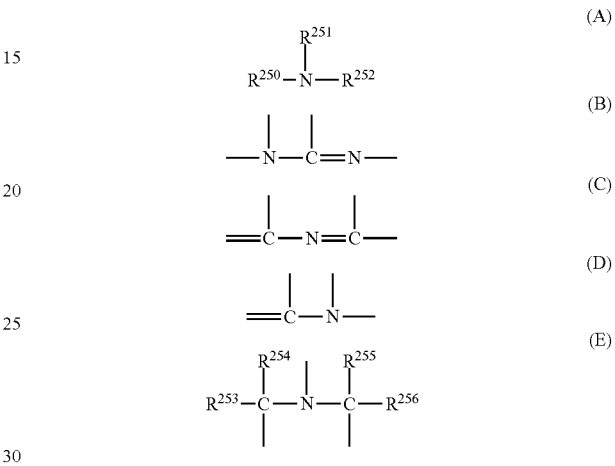

In the formula (A), each of $R^{250}$, $R^{251}$ and $R^{252}$ independently represents a hydrogen atom, an alkyl group (preferably having 1 to 20 carbon atoms), a cycloalkyl group (preferably having 3 to 20 carbon atoms) or an aryl group (preferably having 6 to 20 carbon atoms). $R^{250}$ and $R^{251}$ may be bonded to each other to thereby form a ring. These groups may contain one or more substituents.

The alkyl group and cycloalkyl group having substituents are preferably an aminoalkyl group having 1 to 20 carbon atoms, an aminocycloalkyl group having 3 to 20 carbon atoms, a hydroxyalkyl group having 1 to 20 carbon atoms and a hydroxycycloalkyl group having 3 to 20 carbon atoms.

These groups may contain an oxygen atom, a sulfur atom or a nitrogen atom in the alkyl chain thereof.

In the formula (E), each of $R^{253}$, $R^{254}$, $R^{255}$ and $R^{256}$ independently represents an alkyl group (preferably having 1 to 6 carbon atoms) or a cycloalkyl group (preferably having 3 to 6 carbon atoms). These groups may contain one or more substituents.

As preferred compounds, there can be mentioned guanidine, aminopyrrolidine, pyrazole, pyrazoline, piperazine, aminomorpholine, aminoalkylmorpholines, piperidine and the like. These may have substituents.

As further preferred compounds, there can be mentioned compounds with an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, aniline derivatives having a hydroxyl group and/or an ether bond and the like.

As the compounds with an imidazole structure, there can be mentioned imidazole, 2,4,5-triphenylimidazole, benzimidazole and the like.

As the compounds with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like.

As the compounds with an onium hydroxide structure, there can be mentioned triarylsulfonium hydroxides, phenacylsulfonium hydroxide, and sulfonium hydroxides having a 2-oxoalkyl group such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like.

As the compounds with an onium carboxylate structure, there can be mentioned those having a carboxylate at the anion moiety of the compounds with an onium hydroxide structure, for example, acetate, adamantane-1-carboxylate, perfluoroalkyl carboxylates and the like.

As the compounds with a trialkylamine structure, there can be mentioned tri(n-butyl)amine, tri(n-octyl)amine and the like.

As the aniline compounds, there can be mentioned 2,6-diisopropylaniline, N,N-dimethylaniline and the like.

As the alkylamine derivatives having a hydroxyl group and/or an ether bond, there can be mentioned ethanolamine, diethanolamine, triethanolamine, tris(methoxyethoxyethyl)amine and the like.

As the aniline derivatives having a hydroxyl group and/or an ether bond, there can be mentioned N,N-bis(hydroxyethyl)aniline and the like.

Further, as basic compounds, there can be mentioned at least one nitrogenous compound selected from among an amine compound having a phenoxy group, and an ammonium salt compound having a phenoxy group.

As the amine compound, use can be made of primary, secondary and tertiary amine compounds. An amine compound having at least one alkyl group bonded to the nitrogen atom thereof is preferred. Among the amine compounds, a tertiary amine compound is more preferred. In the amine compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom.

In the amine compounds, it is preferred for the alkyl chain thereof to contain an oxygen atom, thereby forming an oxyalkylene group. The number of oxyalkylene groups in each molecule is one or more, preferably 3 to 9, and more preferably 4 to 6. The oxyalkylene group is preferably an oxyethylene group (—CH$_2$CH$_2$O—) or an oxypropylene group (—CH(CH$_3$)CH$_2$O— or —CH$_2$CH$_2$CH$_2$O—), more preferably an oxyethylene group.

In the ammonium salt compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom.

In the ammonium salt compounds, it is preferred for the alkyl chain thereof to contain an oxygen atom, thereby forming an oxyalkylene group. The number of oxyalkylene groups in each molecule is one or more, preferably 3 to 9 and more preferably 4 to 6. The oxyalkylene group is preferably an oxyethylene group (—CH$_2$CH$_2$O—) or an oxypropylene group (—CH(CH$_3$)CH$_2$O— or —CH$_2$CH$_2$CH$_2$O—), more preferably an oxyethylene group.

As the anion of the ammonium salt compounds, there can be mentioned a halide, a sulfonate, a borate, a phosphate, a hydroxide or the like. Of these, a hydroxide is preferred.

Among halides, a chloride, a bromide and an iodide are especially preferred.

The amine compound having a phenoxy group can be obtained by first heating a primary or secondary amine having a phenoxy group and a haloalkyl ether so as to effect a reaction therebetween, subsequently adding an aqueous solution of a strong base, such as sodium hydroxide, potassium hydroxide or a tetraalkylammonium, and thereafter carrying out an extraction with an organic solvent, such as ethyl acetate or chloroform. Alternatively, the amine compound having a phenoxy group can be obtained by first heating a primary or secondary amine and a haloalkyl ether having a phenoxy group at its terminus so as to effect a reaction therebetween, subsequently adding an aqueous solution of a strong base, such as sodium hydroxide, potassium hydroxide or a tetraalkylammonium, and thereafter carrying out an extraction with an organic solvent, such as ethyl acetate or chloroform.

From the viewpoint of sensitivity, roughness and stability, an ammonium salt compound is preferred among the various basic compounds. A quaternary ammonium salt compound, in its hydroxide form is most preferred.

These basic compounds may be used either individually or in combination.

The molecular weight of the basic compounds is preferably in the range of 250 to 1000, more preferably 250 to 800 and further preferably 400 to 800.

The amount of basic compound contained in the composition, based on the total solid content of the composition, is preferably in the range of 1.0 to 8.0 mass %, more preferably 1.5 to 5.0 mass % and further preferably 2.0 to 4.0 mass %.

[A6] Fluorinated and/or Siliconized Surfactant

The composition according to the present invention may further contain one or more fluorinated and/or siliconized surfactants. As the fluorinated and/or siliconized surfactant, a fluorinated surfactant, a siliconized surfactant, a surfactant containing both fluorine and silicon atoms, and a mixture thereof can be exemplified.

The composition according to the present invention when containing the fluorinated and/or siliconized surfactant would, in the use of an exposure light source of 250 nm or below, especially 220 nm or below, realize favorable sensitivity and resolving power and produce a resist pattern of less adhesion and development defects.

As useful commercially available surfactants, there can be mentioned, for example, fluorinated or siliconized surfactants, such as Eftop EF301 and EF303 (produced by Shin-Akita Kasei Co., Ltd.), Florad FC 430 and 431 (produced by Sumitomo 3M Ltd.), Megafac F171, F173, F176, F189 and R08 (produced by Dainippon Ink & Chemicals, Inc.), Surflon S-382, SC101, 102, 103, 104, 105 and 106 (produced by Asahi Glass Co., Ltd.) and Troy Sol S-366 (produced by Troy Chemical Co., Ltd.). Further, polysiloxane polymer KP-341 (produced by Shin-Etsu Chemical Co., Ltd.) can be employed as the siliconized surfactant.

As the surfactants, besides the above publicly known surfactants, use can be made of a surfactant based on a polymer having a fluorinated aliphatic group derived from a fluorinated aliphatic compound produced by a telomerization technique (also called a telomer process) or an oligomerization technique (also called an oligomer process). The fluorinated aliphatic compound can be synthesized by the process described in JP-A-2002-90991.

The polymer having a fluorinated aliphatic group is preferably a copolymer from a monomer having a fluorinated aliphatic group and a poly(oxyalkylene) acrylate and/or poly(oxyalkylene)methacrylate, which copolymer may have an irregular distribution or may result from block copolymerization.

As the poly(oxyalkylene) group, there can be mentioned a poly(oxyethylene) group, a poly(oxypropylene) group, a poly(oxybutylene) group or the like. Further, use can be made of a unit having alkylene groups of different chain lengths in a single chain, such as poly(oxyethylene-oxypropylene-oxyethylene block concatenation) or poly(oxyethylene-oxypropylene block concatenation).

Moreover, the copolymer from a monomer having a fluorinated aliphatic group and a poly(oxyalkylene) acrylate (or methacrylate) is not limited to two-monomer copolymers and may be a three or more monomer copolymer obtained by simultaneous copolymerization of two or more different monomers having a fluorinated aliphatic group, two or more different poly(oxyalkylene)acrylates (or methacrylates), etc.

For example, as a commercially available surfactant, there can be mentioned Megafac F178, F-470, F-473, F-475, F-476 or F-472 (produced by Dainippon Ink & Chemicals, Inc.). Further, there can be mentioned a copolymer from an acrylate (or methacrylate) having a $C_6F_{13}$ group and a poly(oxyalkylene)acrylate (or methacrylate), a copolymer from an acrylate (or methacrylate) having a $C_6F_{13}$ group, poly(oxyethylene) acrylate (or methacrylate) and poly(oxypropylene) acrylate (or methacrylate), a copolymer from an acrylate (or methacrylate) having a $C_8F_{17}$ group and a poly(oxyalkylene)acrylate (or methacrylate), a copolymer from an acrylate (or methacrylate) having a $C_8F_{17}$ group, poly(oxyethylene)acrylate (or methacrylate) and poly(oxypropylene)acrylate (or methacrylate), or the like.

The amount of fluorinated and/or siliconized surfactant used is preferably in the range of 0.0001 to 2 mass %, more preferably 0.001 to 1 mass % based on the total solids of the composition.

[A7] Hydrophobic Resin

As mentioned above, the composition according to the present invention may further contain a hydrophobic resin. When a hydrophobic resin is further contained, the hydrophobic resin is unevenly localized in the surface layer of the film formed from the composition. Thus, when water is used as a liquid for liquid immersion, the receding contact angle of the film with reference to the liquid for liquid immersion can be increased. Accordingly, the liquid-immersion liquid tracking property of the film can be enhanced.

The hydrophobic resin typically contains fluorine atom and/or silicone atom. The fluorine atom and/or silicon atom in the hydrophobic resin may be present in the principal chain of the resin or may be a substituent on the side chain thereof.

When the hydrophobic resin contains fluorine atom, the resin preferably has, as a partial structure containing one or more fluorine atoms, an alkyl group containing one or more fluorine atoms, a cycloalkyl group containing one or more fluorine atoms, or an aryl group containing one or more fluorine atoms.

The alkyl group containing one or more fluorine atoms is a linear or branched alkyl group having at least one hydrogen atom thereof substituted with one or more fluorine atoms. The group preferably has 1 to 10 carbon atoms, more preferably 1 to 4 carbon atoms. Further, other substituents than fluorine atom may also be contained.

The cycloalkyl group containing one or more fluorine atoms is a monocyclic or polycyclic alkyl group having at least one hydrogen atom thereof substituted with one or more fluorine atoms. Further, other substituents than fluorine atom may also be contained.

The aryl group containing one or more fluorine atoms is an aryl group having at least one hydrogen atom of an aryl group substituted with one or more fluorine atoms. As the aryl group, a phenyl or a naphthyl group can be exemplified. Further, other substituents than fluorine atom may also be contained.

As preferred alkyl groups containing one or more fluorine atoms, cycloalkyl groups containing one or more fluorine atoms and aryl groups containing one or more fluorine atoms, groups of the following general formulae (F2) to (F4) can be exemplified.

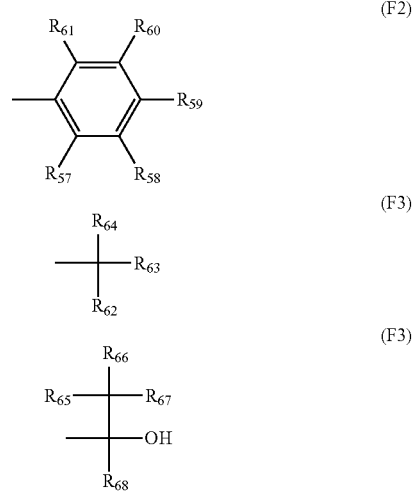

In the general formulae (F2) to (F4), each of $R_{57}$ to $R_{68}$ independently represents a hydrogen atom, a fluorine atom or an alkyl group in condition that: at least one of $R_{57}$-$R_{61}$ represents a fluorine atom or an alkyl group having at least one hydrogen atom thereof substituted with one or more fluorine atoms; at least one of $R_{62}$-$R_{64}$ represents a fluorine atom or an alkyl group having at least one hydrogen atom thereof substituted with one or more fluorine atoms; and at least one of $R_{65}$-$R_{68}$ represents a fluorine atom or an alkyl group having at least one hydrogen atom thereof substituted with one or more fluorine atoms. These alkyl groups preferably are those having 1 to 4 carbon atoms.

It is preferred that all of $R_{57}$-$R_{61}$ and $R_{65}$-$R_{67}$ represent fluorine atoms.

Each of $R_{62}$, $R_{63}$ and $R_{68}$ preferably represents an alkyl group having at least one hydrogen atom thereof substituted with one or more fluorine atoms, more preferably a perfluoroalkyl group having 1 to 4 carbon atoms. $R_{62}$ and $R_{63}$ may be bonded to each other to form a ring.

Specific examples of the groups represented by the general formula (F2) include a p-fluorophenyl group, a pentafluorophenyl group, and a 3,5-di(trifluoromethyl)phenyl group.

Specific examples of the groups represented by the general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, and a perfluorocyclohexyl group. Of these, a hexafluoroisopropyl group, a heptafluoroisopropyl group, a hexafluoro(2-methyl)isopropyl group, an octafluoroisobutyl group, a nonafluoro-t-butyl group and a perfluoroisopentyl group are preferred. A hexafluoroisopropyl group and a heptafluoroisopropyl group are more preferred.

Specific examples of the groups represented by the general formula (F4) include —C(CF$_3$)$_2$OH, —C(C$_2$F$_5$)$_2$OH, —C(CF$_3$)(CH$_3$)OH, —CH(CF$_3$)OH and the like. Of these, —C(CF$_3$)$_2$OH is particularly preferred.
Specific examples of the repeating units having a fluorine atom will be shown below.
In the specific examples, X$_1$ represents a hydrogen atom, —CH$_3$, —F or —CF$_3$. X$_2$ represents —F or —CF$_3$.
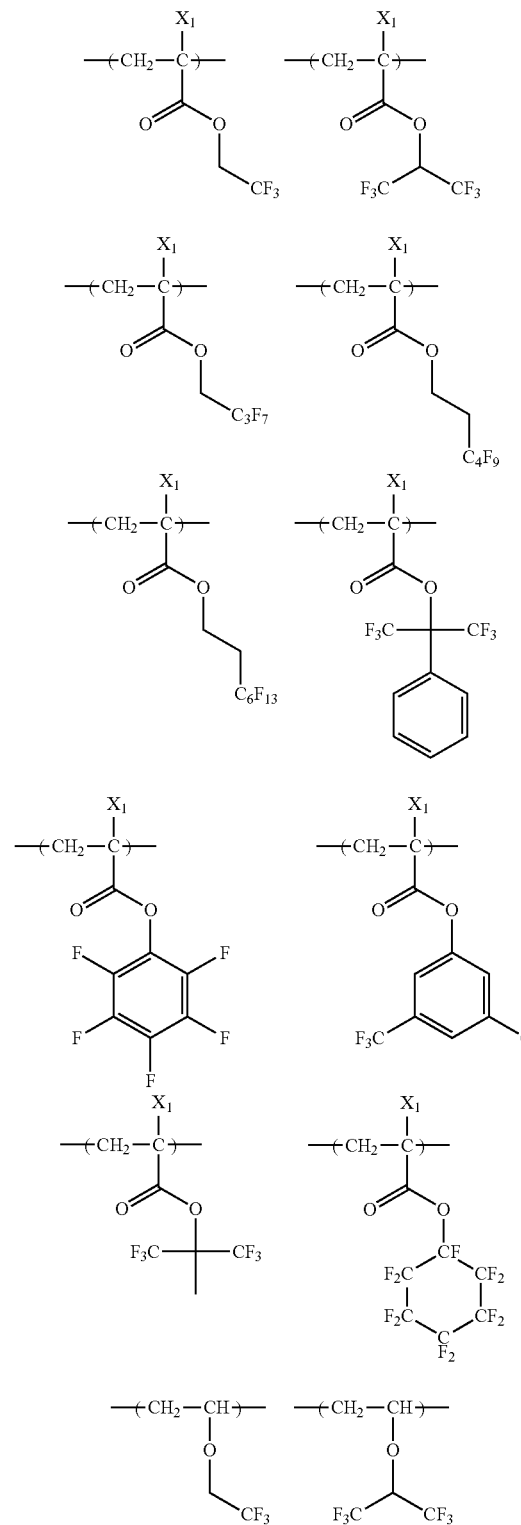
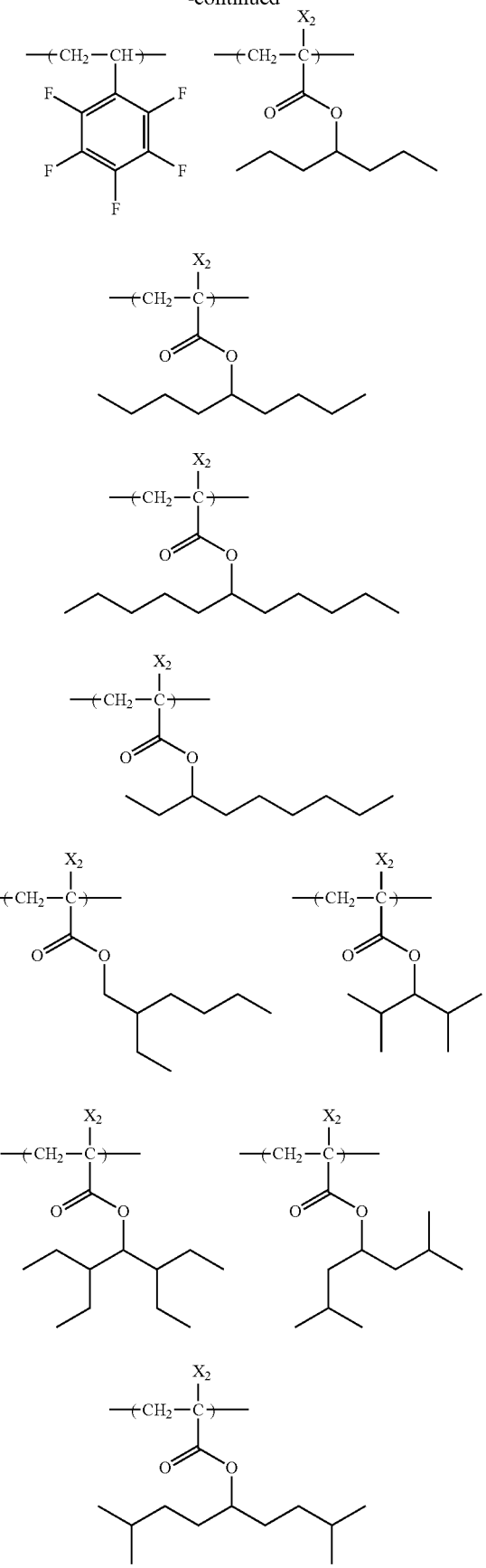

-continued

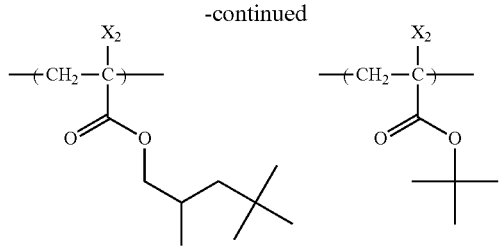

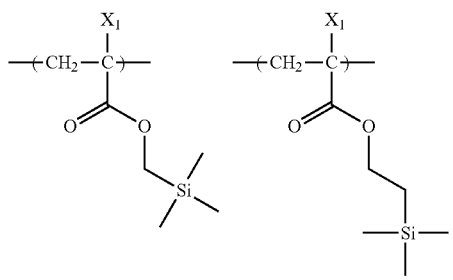

When the hydrophobic resin contains one or more silicon atoms, the resin preferably contains, as partial structure containing the silicon atom, an alkylsilyl structure or a cyclosiloxane structure. Preferred alkylsilyl structure is that containing one or more trialkylsilyl groups.

As the alkylsilyl structure and cyclosiloxane structure, any of the groups represented by the following general formulae (CS-1) to (CS-3) can be exemplified.

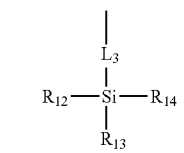
(CS-1)

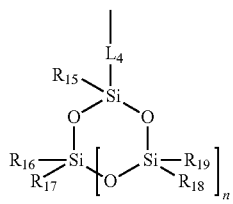
(CS-2)

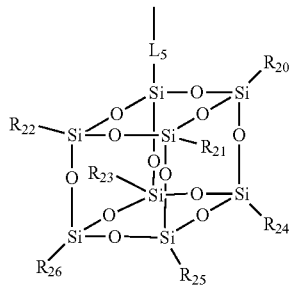
(CS-3)

In the general formulae (CS-1) to (CS-3), each of $R_{12}$ to $R_{26}$ independently represents a linear or branched alkyl group or a cycloalkyl group. The alkyl group preferably has 1 to 20 carbon atoms. The cycloalkyl group preferably has 3 to 20 carbon atoms.

Each of $L_3$ to $L_5$ represents a single bond or a bivalent connecting group. As the bivalent connecting group, any one or a combination of two or more groups selected from the group consisting of an alkylene group, a phenylene group, an ether group, a thioether group, a carbonyl group, an ester group, an amido group, a urethane group and a urea group can be exemplified.

In the formulae, n is an integer of 1 to 5, and preferably an integer of 2 to 4.

Specific examples of the repeating units having the groups represented by the general formulae (CS-1) to (CS-3) will be shown below. In the specific examples, $X_1$ represents a hydrogen atom, —$CH_3$, —F or —$CF_3$.

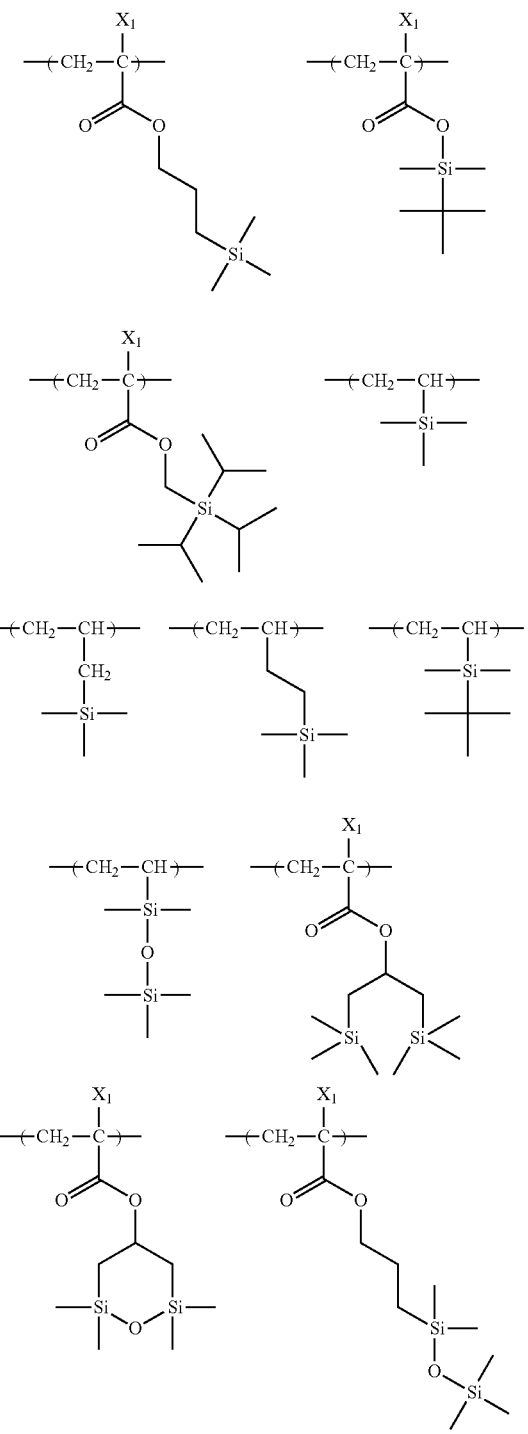

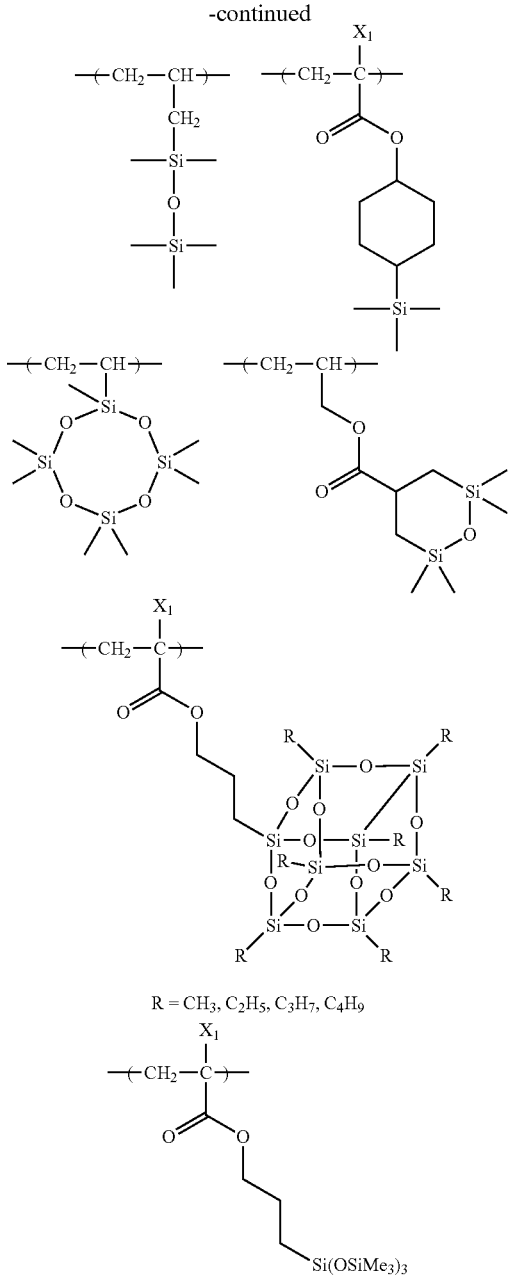

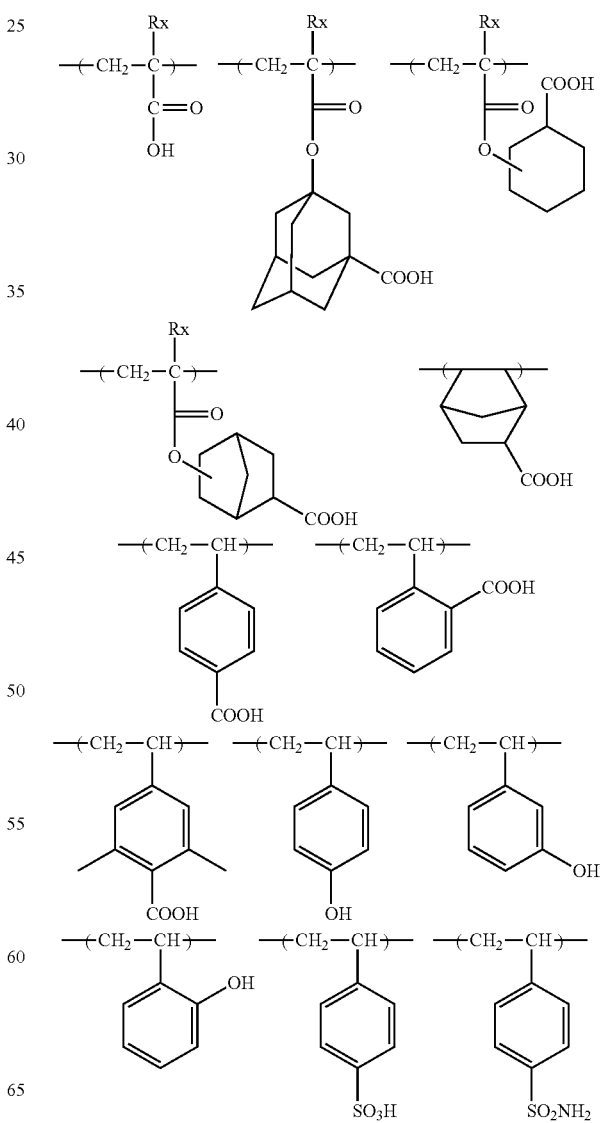

and a bis(carbonyl)methylene group can be exemplified. As preferred fluoroalcohol group, a hexafluoroisopropanol group can be exemplified.

As the repeating unit having an alkali soluble group (x), use can be made of any of a repeating unit resulting from direct bonding of an alkali soluble group to the principal chain of a resin like a repeating unit of acrylic acid or methacrylic acid; a repeating unit resulting from bonding, via a connecting group, of an alkali soluble group to the principal chain of a resin; and a repeating unit resulting from polymerization with the use of a chain transfer agent or polymerization initiator having an alkali soluble group to introduce the same in a polymer chain terminal.

The content of repeating units having an alkali soluble group based on all the repeating units of the polymer is preferably in the range of 1 to 50 mol %, more preferably 3 to 35 mol %, and still more preferably 5 to 20 mol %.

Specific examples of the repeating units having an alkali soluble group will be shown below. In the formulae, Rx represents H, $CH_3$, $CF_3$, or $CH_2OH$.

The hydrophobic resin may further contain at least one group selected from among the following groups (x) to (z):

(x) an alkali soluble group, (y) a group that is decomposed by the action of an alkali developer, resulting in an increase of solubility in the alkali developer, and (z) a group that is decomposed by the action of an acid.

As the alkali soluble group (x), a phenolic hydroxy group, a carboxylate group, a fluoroalcohol group, a sulfonate group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group can be exemplified. As preferred alkali soluble groups, a fluoroalcohol group, a sulfonimido group, -continued

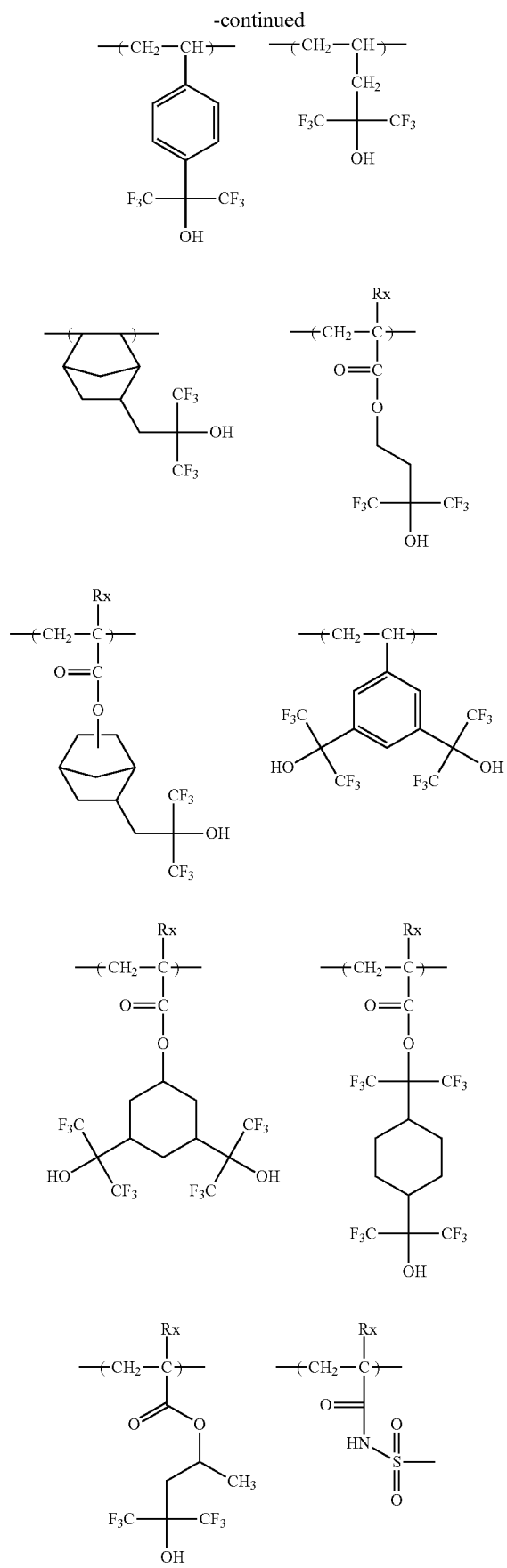

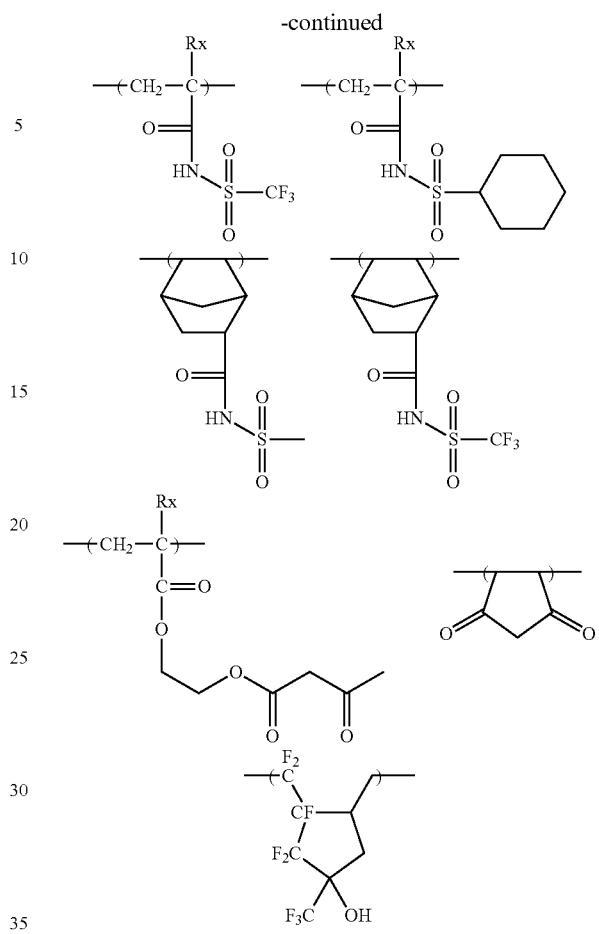

As the group (y) that is decomposed by the action of an alkali developer resulting in an increase of solubility in the alkali developer, a group having a lactone structure, an acid anhydride group, and an acid imide group can be exemplified. Of these, a group having a lactone structure is particularly preferred.

As the repeating unit having a group that is decomposed by the action of an alkali developer resulting in an increase of solubility in the alkali developer, use can be made of both of a repeating unit resulting from bonding of a group that is decomposed by the action of an alkali developer resulting in an increase of solubility in the alkali developer to the principal chain of a resin such as a repeating unit of acrylic ester or methacrylic ester, and a repeating unit resulting from polymerization with the use of a chain transfer agent or polymerization initiator having a group resulting in an increase of solubility in an alkali developer to introduce the same in a polymer chain terminal.

As the repeating unit having a group that is decomposed by the action of an alkali developer resulting in an increase of solubility in the alkali developer, for example, those explained in connection with [1] Resin can be exemplified.

The content of repeating units having a group resulting in an increase of solubility in an alkali developer based on all the repeating units of the polymer is preferably in the range of 1 to 40 mol %, more preferably 3 to 30 mol %, and still more preferably 5 to 15 mol %.

As the repeating unit (z) having a group that is decomposed by the action of an acid, those explained in connection with [1] Resin can be exemplified.

The content of repeating units having a group that is decomposed by the action of an acid in the hydrophobic resin based on all the repeating units of the polymer is preferably in the range of 1 to 80 mol %, more preferably 10 to 80 mol %, and still more preferably 20 to 60 mol %.

The hydrophobic resin may further have any of the repeating units represented by the following general formula (III).

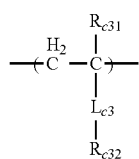
(III)

In the general formula (III), $R_{c31}$ represents a hydrogen atom, an alkyl group, an alkyl group optionally substituted with one or more fluorine atoms, a cyano group or a group of the formula —$CH_2$—O—$R_{ac2}$ in which $R_{ac2}$ represents a hydrogen atom, an alkyl group or an acyl group.

$R_{c31}$ is preferably a hydrogen atom, a methyl group, a hydroxymethyl group, or a trifluoromethyl group, more preferably a hydrogen atom or a methyl group.

$R_{c32}$ represents a group containing an alkyl group, a cycloalkyl group, an alkenyl group, a cycloalkenyl group, or an aryl group. These groups may be substituted with fluorine atom and/or silicon atom.

The alkyl group represented by $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably an aryl group having 6 to 20 carbon atoms, such as a phenyl group or a naphthyl group. These groups may have one or more substituents.

Preferably, $R_{c32}$ represents an unsubstituted alkyl group or an alkyl group substituted with one or more fluorine atoms.

$L_{c3}$ represents a single bond or a bivalent connecting group. As the bivalent connecting group represented by $L_{c3}$, an ester group, an alkylene group (preferably having 1 to 5 carbon atoms), an oxy group, a phenylene group, and an ester bond (a group represented by —COO—) can be exemplified.

The hydrophobic resin may further have any of the repeating units represented by general formula (CII-AB) below.

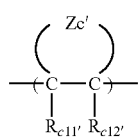
(CII-AB)

In the formula (CII-AB), each of $R_{c11}'$ and $R_{c12}'$ independently represents a hydrogen atom, a cyano group, a halogen atom or an alkyl group. Zc' represents an atomic group required for forming an alicyclic structure in cooperation with two carbon atoms (C—C) to which $R_{c11}'$ and $R_{c12}'$ are respectively bonded.

Specific examples of the repeating units represented by the general formula (III) and general formula (CII-AB) will be shown below. In the specific examples, Ra represents H, $CH_3$, $CH_2OH$, $CF_3$ or CN.

Specific examples of the hydrophobic resins will be shown below. The following Table 1 shows the molar ratio of individual repeating units (corresponding to individual repeating units in order from the left), weight average molecular weight, and degree of dispersal with respect to each of the resins.

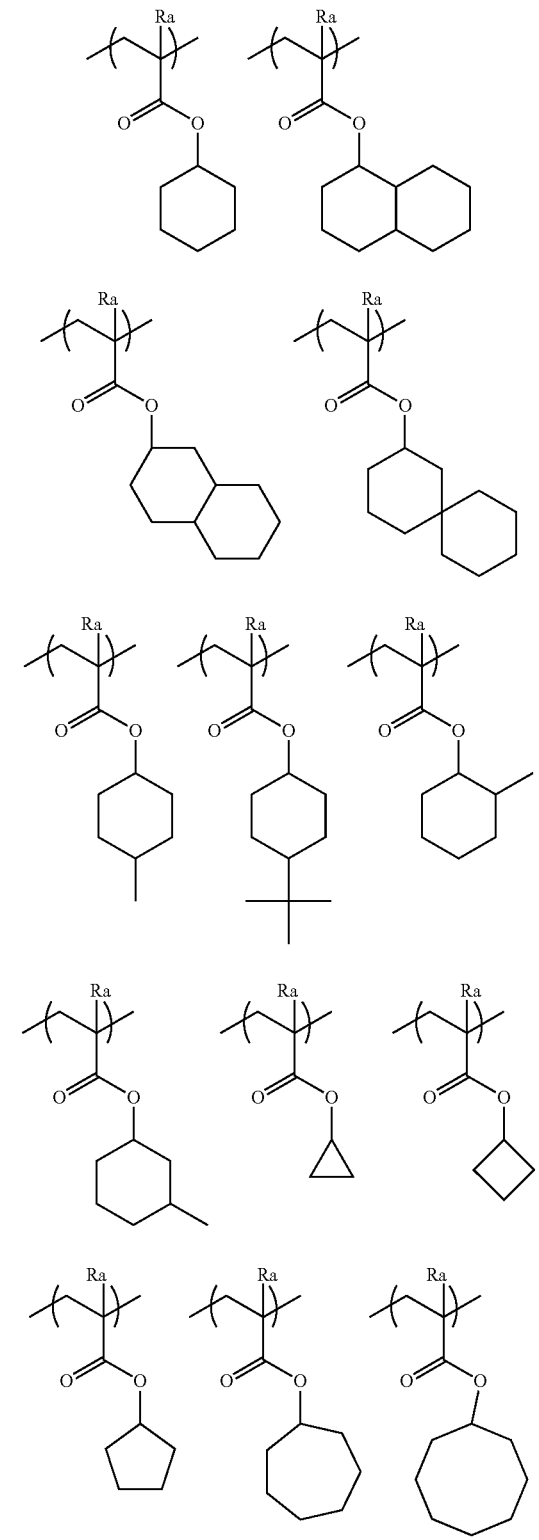

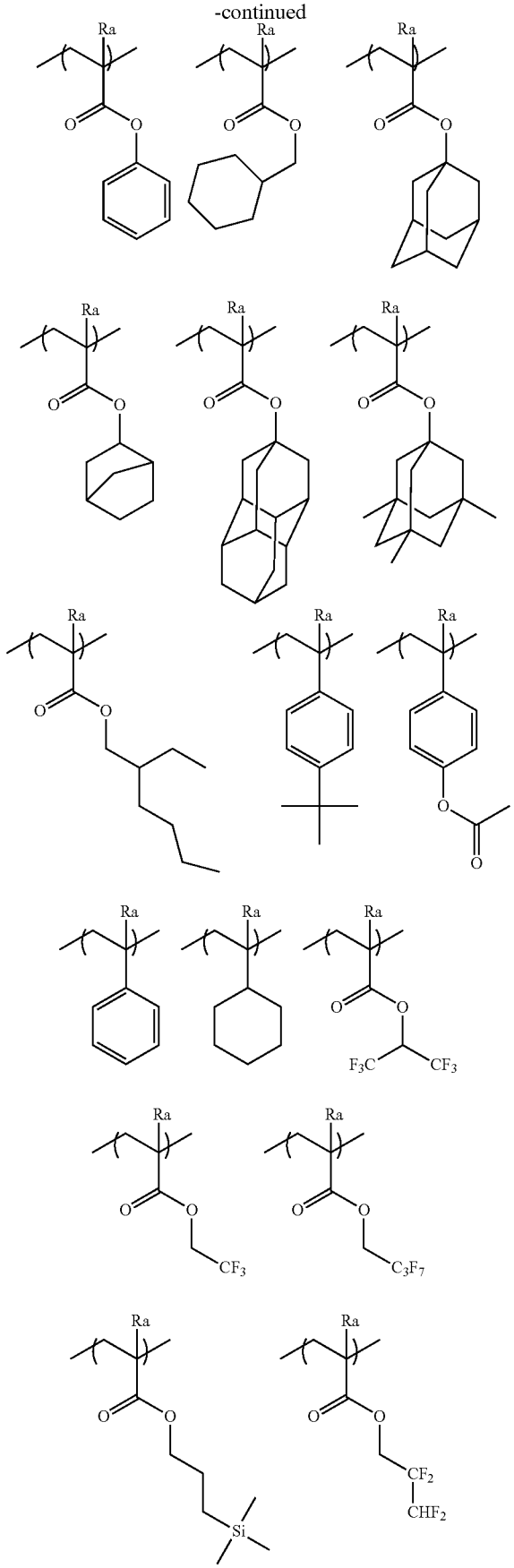
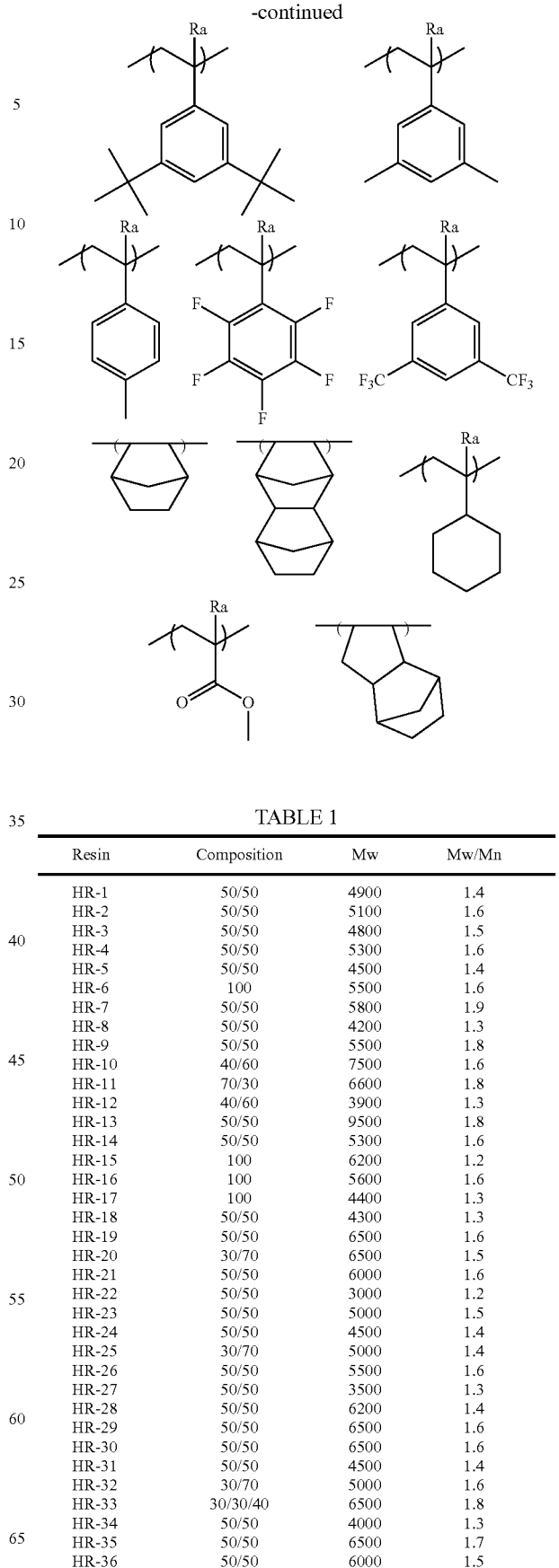
| Resin | Composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |

TABLE 1-continued
| | | | |
|---|---|---|---|
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |
| HR-64 | 100 | 5500 | 1.8 |
| HR-65 | 50/50 | 9500 | 1.9 |
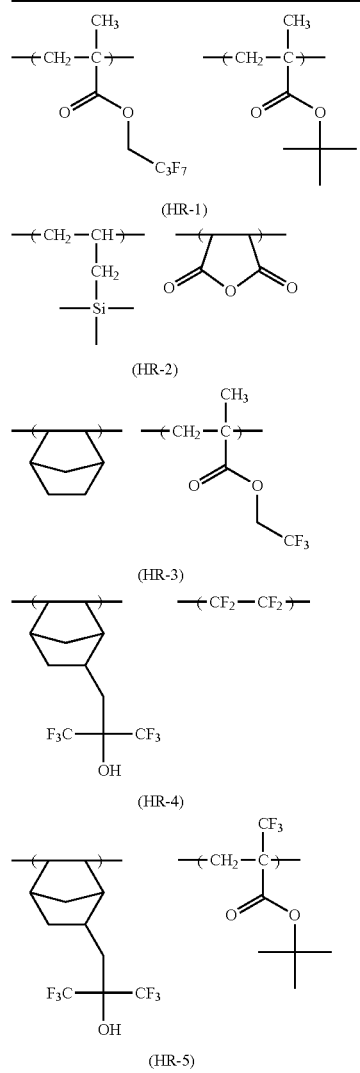
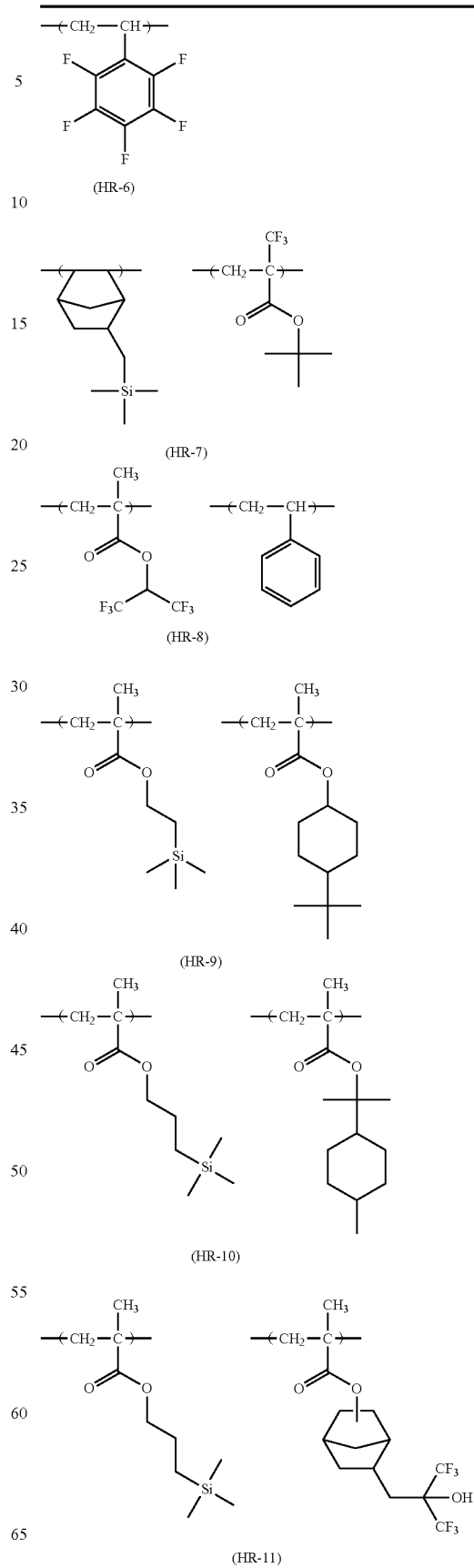

TABLE 1-continued
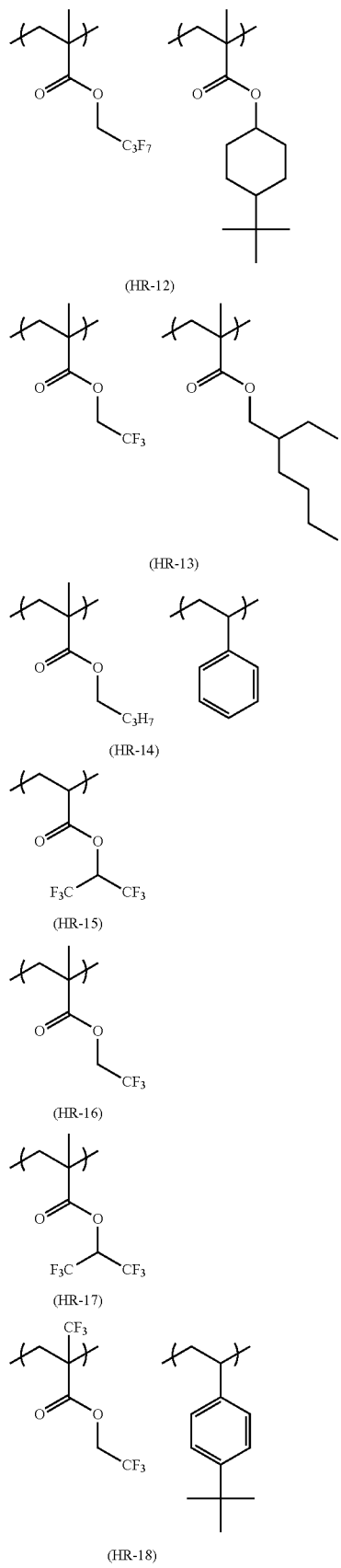
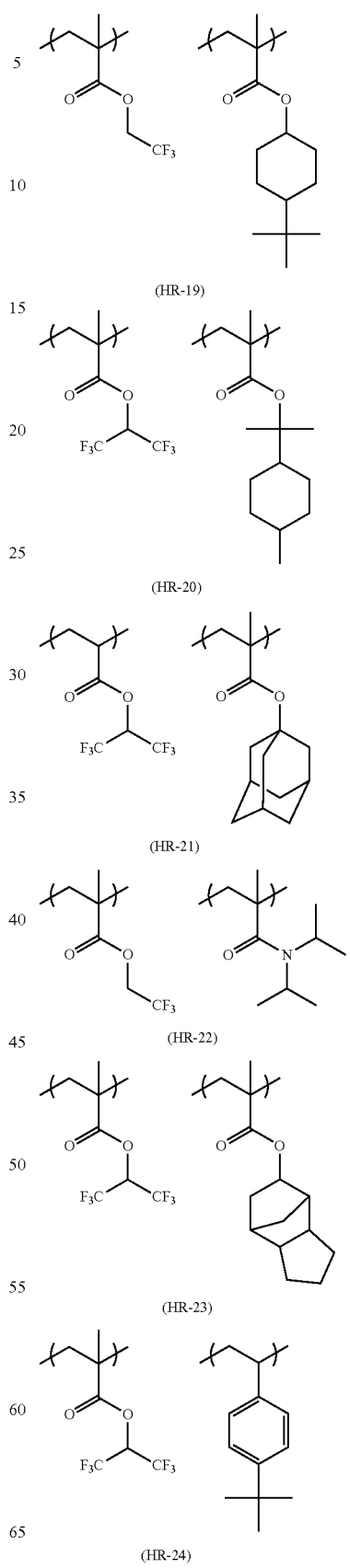

TABLE 1-continued
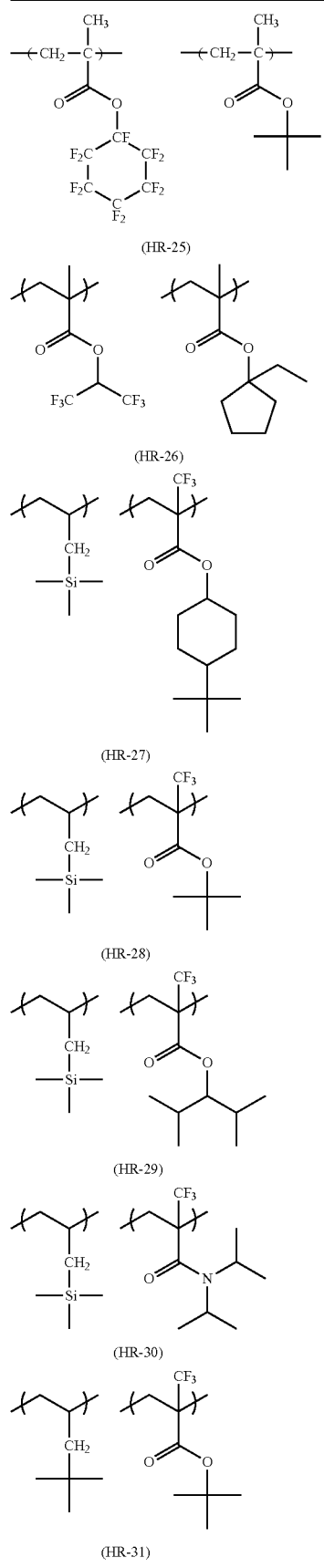
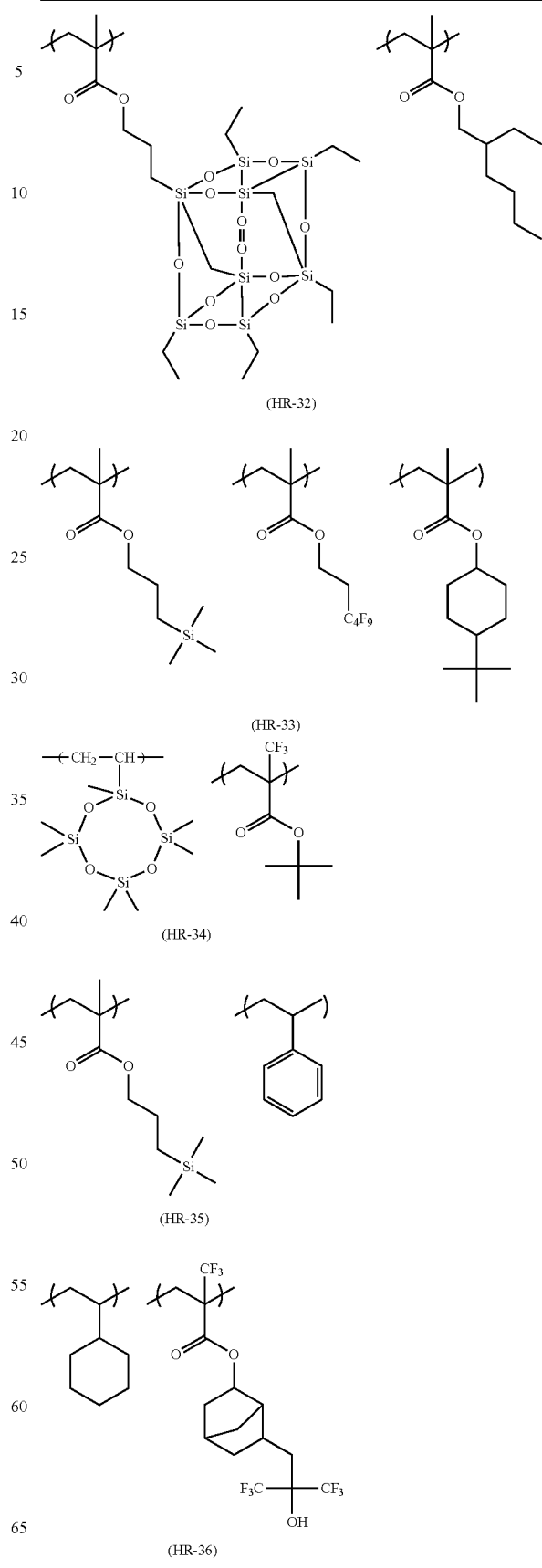

TABLE 1-continued
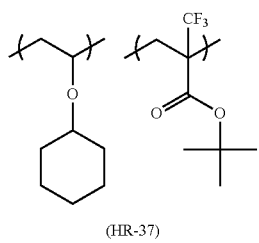
(HR-37)
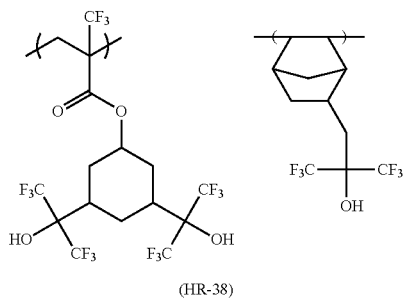
(HR-38)
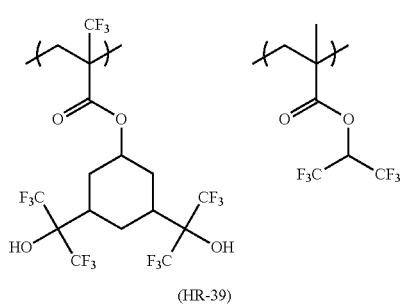
(HR-39)
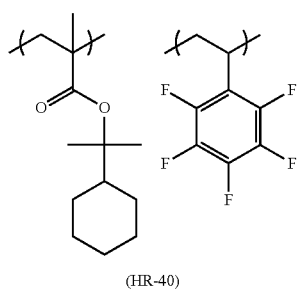
(HR-40)
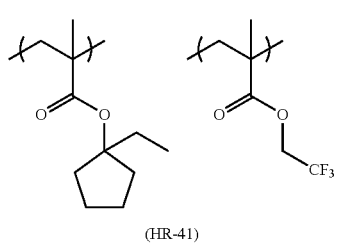
(HR-41)
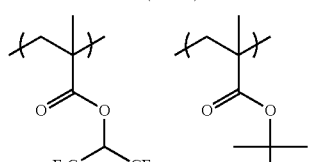
(HR-42)
TABLE 1-continued
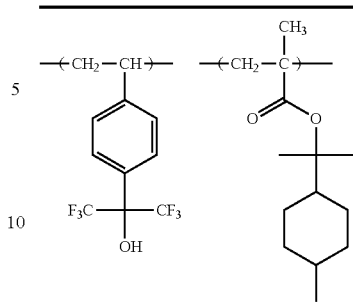
(HR-43)
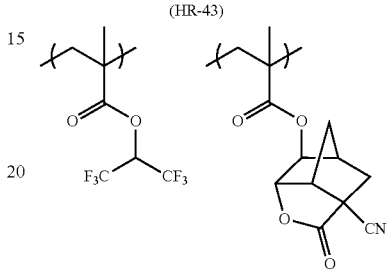
(HR-44)
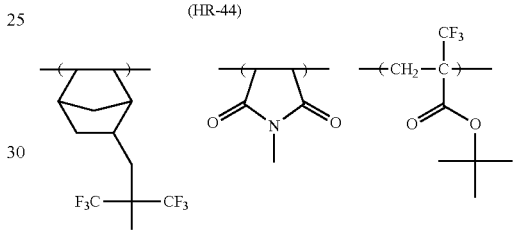
(HR-45)
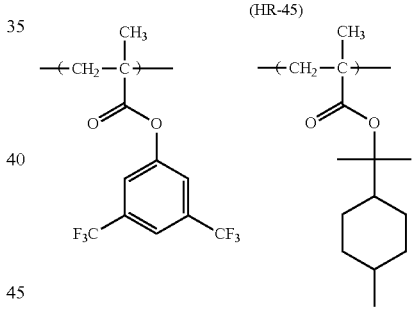
(HR-46)
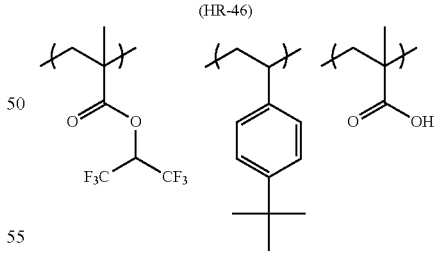
(HR-47)
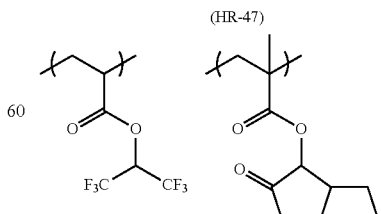
(HR-48)

TABLE 1-continued
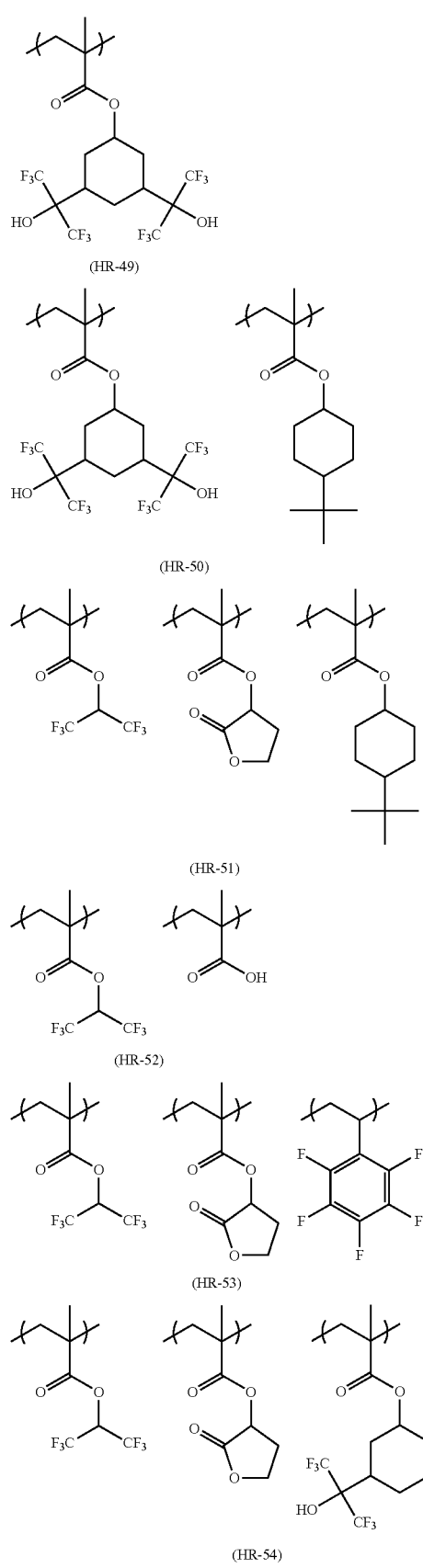
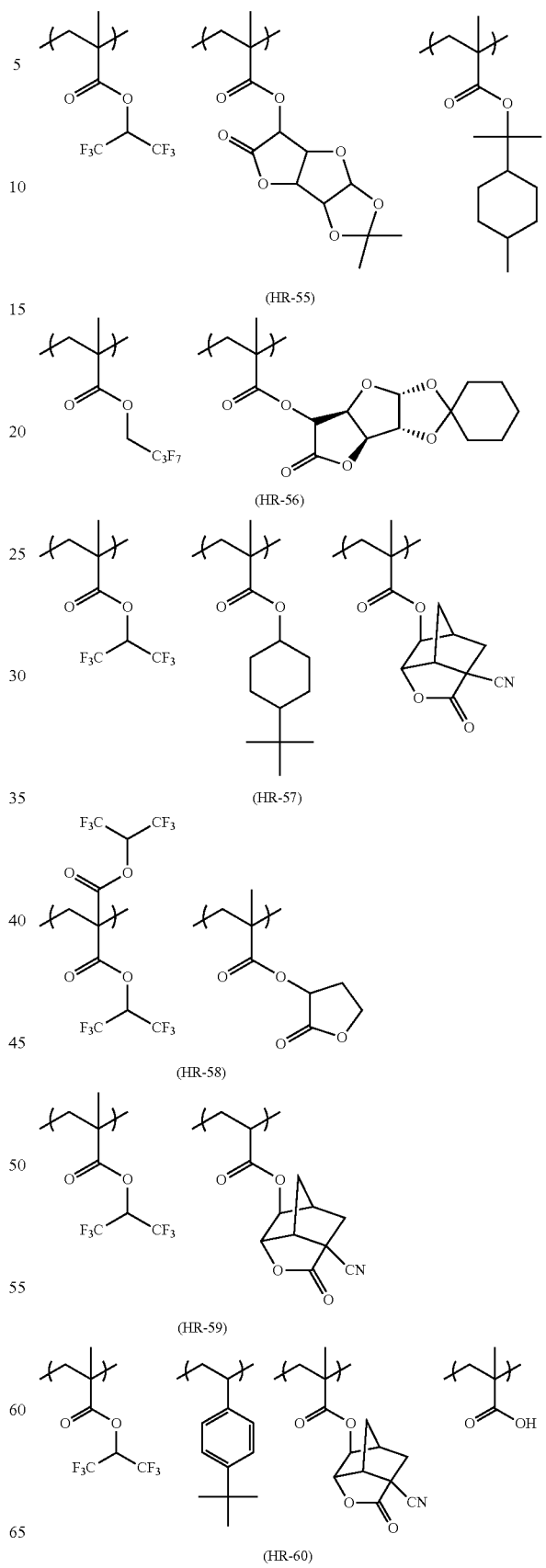

TABLE 1-continued

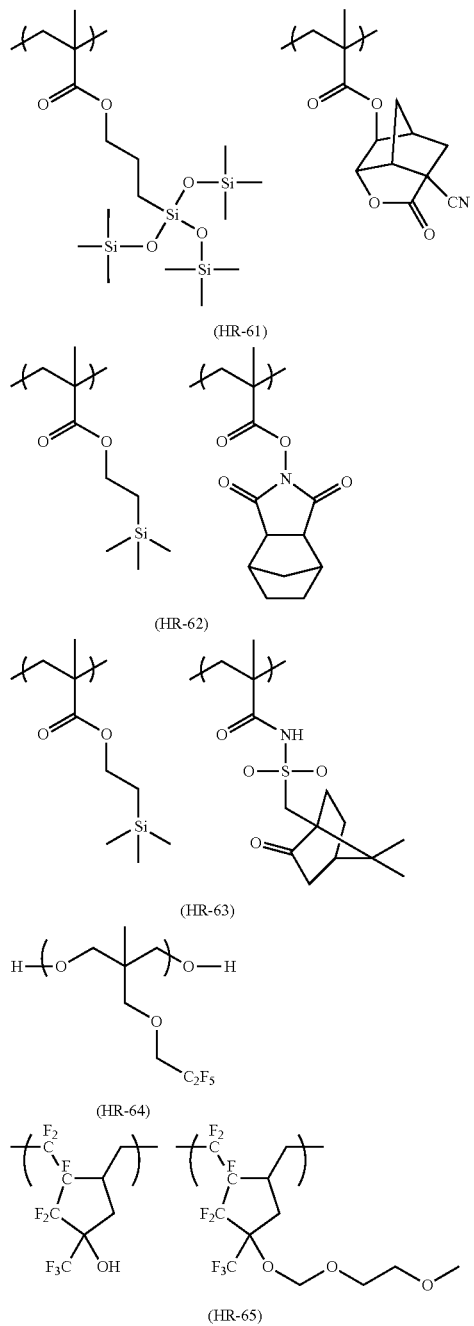

[A8] Organic Solvent

The composition according to the present invention in its typical form further contains a specified organic solvent capable of dissolving the above components.

As useful organic solvents, there can be mentioned, for example, ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone and tetrahydrofuran.

The solvents having a ketone structure include a linear ketone solvent and a cycloketone solvent. Compounds having 5 to 8 carbon atoms in total are preferred from the viewpoint of high coatability.

As the linear ketone solvent, there can be mentioned, for example, 2-heptanone, methyl ethyl ketone or methyl isobutyl ketone. Of these, 2-heptanone is most preferred.

As the cycloketone solvent, there can be mentioned, for example, cyclopentanone, 3-methyl-2-cyclopentanone, cyclohexanone, 2-methylcyclohexanone, 2,6-dimethylcyclohexanone, cycloheptanone, cyclooctanone or isophorone. Of these, cyclohexanone and cycloheptanone are most preferred.

As the organic solvent, it is preferred to use either a single solvent having a ketone structure alone or a mixed solvent consisting of a solvent having a ketone structure and another solvent.

As another solvent to be mixed with the solvent having a ketone structure (joint solvent), there can be mentioned, for example, a propylene glycol monoalkyl ether carboxylate, an alkyl lactate, a propylene glycol monoalkyl ether, an alkyl alkoxypropionate or a lactone compound.

As the propylene glycol monoalkyl ether carboxylate, there can be mentioned, for example, propylene glycol monomethyl ether acetate, propylene glycol monomethyl ether propionate or propylene glycol monoethyl ether acetate.

As the alkyl lactate, there can be mentioned, for example, methyl lactate or ethyl lactate.

As the propylene glycol monoalkyl ether, there can be mentioned, for example, propylene glycol monomethyl ether or propylene glycol monoethyl ether.

As the alkyl alkoxypropionate, there can be mentioned, for example, methyl methoxypropionate, ethyl methoxypropionate, methyl ethoxypropionate or ethyl ethoxypropionate.

As the lactone compound, there can be mentioned, for example, γ-butyrolactone.

As preferred joint solvents, there can be mentioned a propylene glycol monoalkyl ether carboxylate, an alkyl lactate and a propylene glycol monoalkyl ether. A more preferred joint solvent is propylene glycol monomethyl ether acetate.

A solvent with a boiling point as high as 200° C. or above, such as ethylene carbonate or propylene carbonate, may be mixed into the solvent for use from the viewpoint of film thickness uniformity and development defect performance.

The amount of high-boiling-point solvent added, based on the total mass of solvents, is generally in the range of 0.1 to 15 mass %, preferably 0.5 to 10 mass % and more preferably 1 to 5 mass %.

In the present invention, typically, an actinic-ray- or radiation-sensitive resin composition is prepared using an organic solvent, preferably a mixed solvent consisting of two or more types of solvents.

The solid content of the composition is generally in the range of 1 to 25 mass %, preferably 2 to 20 mass % and more preferably 2.5 to 10 mass %. In particular, when the pattern formation is carried out using electron beams, EUV light or ArF light, it is preferred for the solid content to fall within the range of 2.5 to 4.5 mass %.

[A9] Other Additives

The composition according to the present invention may further contain other additives, such as a dye, a plasticizer, a surfactant other than the above mentioned fluorized and/or siliconized surfactants, a photosensitizer, and a compound capable of increasing the solubility in a developer.

The compound capable of increasing the solubility in a developer (dissolution accelerating compound) is, for example, a low-molecular compound of 1000 or less molecular weight having two or more phenolic OH groups or one or more carboxyl groups. When a carboxyl group is contained, an alicyclic or aliphatic compound is preferred.

The amount of dissolution accelerating compound added, based on the mass of the resin, is preferably in the range of 2 to 50 mass %, more preferably 5 to 30 mass %. It is preferred for the amount to be up to 50 mass % from the viewpoint of suppression of any development residue and prevention of any pattern distortion at development.

The above phenolic compound of 1000 or less molecular weight can be easily synthesized by persons of ordinary skill in the art to which the present invention pertains while consulting the processes described in, for example, JP-A's 4-122938 and 2-28531, U.S. Pat. No. 4,916,210 and EP 219294.

As the carboxylated alicyclic or aliphatic compound, there can be mentioned, for example, a carboxylic acid derivative of steroid structure such as cholic acid, deoxycholic acid or lithocholic acid, an adamantanecarboxylic acid derivative, adamantanedicarboxylic acid, cyclohexanecarboxylic acid, cyclohexanedicarboxylic acid or the like. These are however nonlimiting.

Surfactants other than the above fluorinated and/or siliconized surfactants, there can be mentioned nonionic surfactants, such as a polyoxyethylene alkyl ether, a polyoxyethylene alkylallyl ether, a polyoxyethylene-polyoxypropylene block copolymer, a sorbitan aliphatic ester, a polyoxyethylene sorbitan aliphatic ester or the like. These surfactants may be added either individually or in combination.

[Method of Forming Pattern]

The method of forming a pattern using the composition according to the present invention will be described below.

The composition according to the present invention is typically used in such a manner that the components are dissolved in a given organic solvent, preferably the above mixed solvent, and applied onto a given support. For example, the composition is applied to a substrate (e.g., silicon, silicon/silicon dioxide coating, silicon nitride, quartz with a Cr layer, or the like) for use in the production of precision integrated circuit elements, imprint mold structures, etc. by appropriate application means, such as a spinner or a coater. The thus applied composition is dried, thereby obtain an actinic-ray- or radiation-sensitive film (hereinafter also referred to as a photosensitive film). The drying temperature is preferably in the range of 60 to 150° C., more preferably 80 to 130° C. In advance, the substrate may be provided with an antireflection film known in the art.

Subsequently, the photosensitive film is exposed to actinic rays or radiation, preferably baked (heated), and developed. It is preferred for the baking temperature to range from 80 to 150° C., especially from 90 to 130° C. from the viewpoint of sensitivity and stability. Accordingly, a desirable pattern can be obtained.

As the actinic rays or radiation, there can be mentioned, for example, infrared radiation, visible light, ultraviolet radiation, far ultraviolet radiation, X-rays or electron beams. As the actinic rays or radiation, preferred use is made of one with, for example, 250 nm or less, especially 220 nm or less wavelength. As the actinic rays or radiation, there can be mentioned, for example, a KrF excimer laser (248 nm), an ArF excimer laser (193 nm), an $F_2$ excimer laser (157 nm), X-rays or electron beams. As especially preferred actinic rays or radiation, there can be mentioned an ArF excimer laser, an $F_2$ excimer laser, EUV (13 nm) or electron beams.

In the stage of irradiation with actinic rays or radiation, exposure (liquid immersion exposure) may be carried out after filling the interstice between the photosensitive film and a lens with a liquid of refractive index higher than that of air. This would realize an enhancement of resolving power. For the prevention of direct contact of the resist film with the liquid for liquid immersion, a film that is highly insoluble in the liquid for liquid immersion (hereinafter also referred to as a "top coat") may be provided between the resist film formed by the composition of the present invention and the liquid for liquid immersion. As other means to prevent the contact between the resist film and the liquid for liquid immersion, a hydrophobic resin (HR) may be added to the composition. As the hydrophobic resin, in addition to those described above, the resins explained in paragraph 0172-0253 in US 2008/0305432 A1 can also be exemplified.

In the development step, an alkali developer is generally used.

As the alkali developer, use can be made of any of alkaline aqueous solutions containing, for example, an inorganic alkali compound such as sodium hydroxide, potassium hydroxide, sodium carbonate, sodium silicate, sodium metasilicate or aqueous ammonia; a primary amine such as ethylamine or n-propylamine; a secondary amine such as diethylamine or di-n-butylamine; a tertiary amine such as triethylamine or methyldiethylamine; an alcoholamine such as dimethylethanolamine or triethanolamine; a quaternary ammonium salt such as tetramethylammonium hydroxide or tetraethylammonium hydroxide; or a cycloamine such as pyrrole or piperidine.

Appropriate amounts of an alcohol and/or a surfactant may be added to the alkali developer.

The concentration of alkali developer is generally in the range of 0.1 to 20 mass %. The pH value of the alkali developer is generally in the range of 10.0 to 15.0.

With respect to the particulars of the process for fabricating an imprint mold using the composition according to the present invention, reference can be made to, for example, Japanese Patent No. 4109085, JP-A-2008-162101, "Fundamentals of nanoimprint and its technology development/application deployment—technology of nanoimprint substrate and its latest technology deployment" edited by Yoshihiko Hirai, published by Frontier Publishing, etc.

<Hardenable Composition>

The composition according to the present invention may be a hardenable composition. The hardenable composition may be sensitive to actinic rays or radiation or to heat. Namely, this hardenable composition may contain a photoacid generator [2], or may contain a thermal acid generator [3]. Alternatively, this hardenable composition may contain both of a photoacid generator [2] and a thermal acid generator [3].

If so, the composition according to the present invention in its typical form contains a cationically polymerizable compound [B1] or an acid crosslinking agent [B2]. This composition may further contain a sensitizer [B3], a radically polymerizable compound [B4], a colorant [B5], a cosensitizer [B6], a polymerization initiator [B7] and other components [B8].

The hardenable composition according to the present invention is used as, for example, an ink. Namely, this hardenable composition is, for example, an ink composition.

[B1] Cationically Polymerizable Compound

The cationically polymerizable compound is not particularly limited as long as it is a compound that initiates a polymerization reaction by virtue of a cationic polymerization initiating species generated from a cationic polymerization initiator and is cured. As such a compound, use can be made of, for example, any of heretofore known cationically polymerizable monomers known as photo-cationically polymerizable monomers. Examples of the cationically polymerizable monomers include the epoxy compounds, vinyl ether compounds, oxetane compounds described in JP-A's H6-9714, 2001-31892, 2001-40068, 2001-55507, 2001-310938, 2001-310937, 2001-220526, etc. As the cationically polymerizable compound, for example, a cationically polymerizable photohardenable resin is known. In recent years, cationically photopolymerizable photohardenable resins sensitized to a visible light wavelength region of 400 nm or longer have been disclosed in, for example, JP-A's H6-43633 and H8-324137.

Examples of the epoxy compounds include aromatic epoxides, alicyclic epoxides and aliphatic epoxides. As the aromatic epoxides, there can be mentioned a di- or polyglycidyl ether produced by the reaction of a polyhydric phenol having at least one aromatic nucleus or an alkylene oxide adduct thereof with epichlorohydrin. Examples of the di- or polyglycidyl ethers include a di- or polyglycidyl ether of bisphenol A or alkylene oxide adduct thereof, a di- or polyglycidyl ether of hydrogenated bisphenol A or alkylene oxide adduct thereof and a novolac epoxy resin. As the alkylene oxide, there can be mentioned, for example, ethylene oxide or propylene oxide.

The alicyclic epoxide is obtained by, for example, epoxidizing a compound having at least one cycloalkene ring with an oxidizing agent, such as hydrogen peroxide and peracid. As the cycloalkene ring, there can be mentioned, for example, a cyclohexene ring or a cyclopentene ring. Preferred alicyclic epoxides are, for example, compounds containing cyclohexene oxide or cyclopentene oxide.

As the aliphatic epoxide, there can be mentioned, for example, a di- or polyglycidyl ether of aliphatic polyhydric alcohol or alkylene oxide adduct thereof. Representative examples of the di- or polyglycidyl ethers include diglycidyl ethers of an alkylene glycol, such as a diglycidyl ether of ethylene glycol, a diglycidyl ether of propylene glycol and a diglycidyl ether of 1,6-hexanediol; polyglycidyl ethers of a polyhydric alcohol, such as a di- or triglyciyl ether of glycerol or alkylene oxide adduct thereof; and diglycidyl ethers of a polyalkylene glycol, such as a diglycidyl ether of polyethylene glycol or alkylene oxide adduct thereof and a diglycidyl ether of polypropylene glycol or alkylene oxide adduct thereof. As the alkylene oxide, there can be mentioned, for example, ethylene oxide or propylene oxide.

Particular examples of the monofunctional and polyfunctional epoxy compounds will be set forth below.

Examples of the monofunctional epoxy compounds include phenyl glycidyl ether, p-tert-butylphenyl glycidyl ether, butyl glycidyl ether, 2-ethylhexyl glycidyl ether, allyl glycidyl ether, 1,2-butylene oxide, 1,3-butadiene monoxide, 1,2-epoxydodecane, epichlorohydrin, 1,2-epoxydecane, styrene oxide, cyclohexene oxide, 3-methacryloyloxymethylcyclohexene oxide, 3-acryloyloxymethylcyclohexene oxide, 3-vinylcyclohexene oxide and 4-vinylcyclohexene oxide.

Examples of the polyfunctional epoxy compounds include bisphenol A diglycidyl ether, bisphenol F diglycidyl ether, bisphenol S diglycidyl ether, brominated bisphenol A diglycidyl ether, brominated bisphenol F diglycidyl ether, brominated bisphenol S diglycidyl ether, epoxynovolac resin, hydrogenated bisphenol A diglycidyl ether, hydrogenated bisphenol F diglycidyl ether, hydrogenated bisphenol S diglycidyl ether, 3,4-epoxycyclohexenylmethyl-3',4'-epoxycyclohexene carboxylate, 2-(3,4-epoxycyclohexyl-5,5-spiro-3,4-epoxy)cyclohexane-meta-dioxane, bis(3,4-epoxycyclohexylmethyl) adipate, bis(3,4-epoxy-6-methylcyclohexylmethyl) adipate, 3,4-epoxy-6-methylcyclohexenyl-3',4'-epoxy-6'-methylcyclohexene carboxylate, methylenebis(3,4-epoxycyclohexane), dicyclopentadiene diepoxide, di(3,4-epoxycyclohexylmethyl)ether of ethylene glycol, ethylene bis(3,4-epoxycyclohexane carboxylate), dioctyl epoxyhexahydrophthalate, di-2-ethylhexyl epoxyhexahydrophthalate, 1,4-butanediol diglycidyl ether, 1,6-hexanediol diglycidyl ether, glycerol triglycidyl ether, trimethylolpropane triglycidyl ether, polyethylene glycol diglycidyl ether, polypropylene glycol diglycidyl ethers, 1,13-tetradecadiene dioxide, limonene dioxide, 1,2,7,8-diepoxyoctane and 1,2,5,6-diepoxycyclooctane.

Among these epoxy compounds, aromatic epoxides and alicyclic epoxides are preferred from the viewpoint of high hardening rate. Alicyclic epoxides are most preferred.

Examples of the vinyl ether compounds include di- or trivinyl ether compounds, such as ethylene glycol divinyl ether, diethylene glycol divinyl ether, triethylene glycol divinyl ether, propylene glycol divinyl ether, dipropylene glycol divinyl ether, butanediol divinyl ether, hexanediol divinyl ether, cyclohexanedimethanol divinyl ether and trimethylolpropane trivinyl ether, and include monovinyl ether compounds, such as ethyl vinyl ether, n-butyl vinyl ether, isobutyl vinyl ether, octadecyl vinyl ether, cyclohexyl vinyl ether, hydroxybutyl vinyl ether, 2-ethylhexyl vinyl ether, cyclohexanedimethanol monovinyl ether, n-propyl vinyl ether, isopropyl vinyl ether, isopropenyl ether-O-propylene carbonate, dodecyl vinyl ether and diethylene glycol monovinyl ether.

Particular examples of the monofunctional and polyfunctional vinyl ethers will be set forth below.

As the monofunctional vinyl ethers, there can be mentioned, for example, methyl vinyl ether, ethyl vinyl ether, propyl vinyl ether, n-butyl vinyl ether, t-butyl vinyl ether, 2-ethylhexyl vinyl ether, n-nonyl vinyl ether, lauryl vinyl ether, cyclohexyl vinyl ether, cyclohexylmethyl vinyl ether, 4-methylcyclohexylmethyl vinyl ether, benzyl vinyl ether, dicyclopentenyl vinyl ether, 2-dicyclopentenoxyethyl vinyl ether, methoxyethyl vinyl ether, ethoxyethyl vinyl ether, butoxyethyl vinyl ether, methoxyethoxyethyl vinyl ether, ethoxyethoxyethyl vinyl ether, methoxypolyethylene glycol vinyl ether, tetrahydrofurfuryl vinyl ether, 2-hydroxyethyl vinyl ether, 2-hydroxypropyl vinyl ether, 4-hydroxybutyl vinyl ether, 4-hydroxymethylcyclohexylmethyl vinyl ether, diethylene glycol monovinyl ether, polyethylene glycol vinyl ether, chloroethyl vinyl ether, chlorobutyl vinyl ether, chloroethoxyethyl vinyl ether, phenylethyl vinyl ether and phenoxypolyethylene glycol vinyl ether.

As the polyfunctional vinyl ethers, there can be mentioned, for example, divinyl ethers, such as ethylene glycol divinyl ether, diethylene glycol divinyl ether, polyethylene glycol divinyl ether, propylene glycol divinyl ether, butylene glycol divinyl ether, hexanediol divinyl ether, bisphenol A alkylene oxide divinyl ether and bisphenol F alkylene oxide divinyl ether; and vinyl ethers of higher functionality, such as trimethylolethane trivinyl ether, trimethylolpropane trivinyl ether, ditrimethylolpropane tetravinyl ether, glycerol trivinyl ether, pentaerythritol tetravinyl ether, dipentaerythritol pentavinyl ether, dipentaerythritol hexavinyl ether, trimethylolpropane/ethylene oxide adduct trivinyl ether, trimethylolpropane/propylene oxide adduct trivinyl ether, ditrimethylolpropane/ethylene oxide adduct tetravinyl ether, ditrimethylolpropane/propylene oxide adduct tetravinyl ether, pentaerythritol/ethylene oxide adduct tetravinyl ether, pentaerythritol/propylene oxide adduct tetravinyl ether, dipentaerythritol/ethylene oxide adduct hexavinyl ether and dipentaerythritol/propylene oxide adduct hexavinyl ether.

Among these vinyl ether compounds, di- or trivinyl ether compounds are preferred from the viewpoint of hardenability. When a vinyl ether compound is used as a component of an ink composition, a di- or trivinyl ether compound is preferred from the viewpoint of the adhesion to a recording medium and the surface hardness of formed image. Divinyl ether compounds are especially preferred.

The oxetane compound refers to a compound containing at least one oxetane ring. The oxetane compound may be any of those described in JP-A's 2001-220526, 2001-310937 and 2003-341217.

The oxetane compound is preferably one having 1 to 4 oxetane rings in its structure. The use of such a compound makes it easy to keep the viscosity of the hardenable composition within a range such that the ink composition can be fairly handled. Further, in particular, the use in an ink composition makes it feasible to realize a high adhesion between the hardened ink and the recording medium.

As the compound having one or two oxetane rings in its molecule, there can be mentioned, for example, those of any of formulae (1) to (3) below:

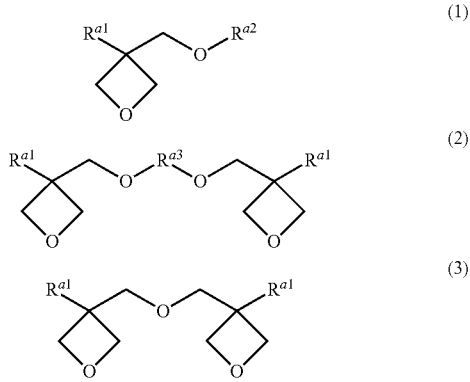

In the formulae, $R^{a1}$ represents a hydrogen atom, an alkyl group having 1 to 6 carbons, a fluoroalkyl group having 1 to 6 carbons, an allyl group, an aryl group, a furyl group or a thienyl group. When there are two $R^{a1}$s in the molecule, they may be identical to or different from each other.

Examples of the alkyl groups include a methyl group, an ethyl group, a propyl group and a butyl group. Examples of the fluoroalkyl groups include those obtained by substituting any of the hydrogen atoms of the above alkyl groups with a fluorine atom.

$R^{a2}$ represents a hydrogen atom, an alkyl group having 1 to 6 carbons, an alkenyl group having 2 to 6 carbons, a group having an aromatic ring, an alkylcarbonyl group having 2 to 6 carbons, an alkoxycarbonyl group having 2 to 6 carbons or an N-alkylcarbamoyl group having 2 to 6 carbons.

Examples of the alkyl groups include a methyl group, an ethyl group, a propyl group and a butyl group. Examples of the alkenyl groups include a 1-propenyl group, a 2-propenyl group, a 2-methyl-1-propenyl group, a 2-methyl-2-propenyl group, a 1-butenyl group, a 2-butenyl group and a 3-butenyl group. Examples of the groups each having an aromatic ring include a phenyl group, a benzyl group, a fluorobenzyl group, a methoxybenzyl group and a phenoxyethyl group. Examples of the alkylcarbonyl groups include an ethylcarbonyl group, a propylcarbonyl group and a butylcarbonyl group. Examples of the alkoxycarbonyl groups include an ethoxycarbonyl group, a propoxycarbonyl group and a butoxycarbonyl group. Examples of the N-alkylcarbamoyl groups include an ethylcarbamoyl group, a propylcarbamoyl group, a butylcarbamoyl group and a pentylcarbamoyl group.

One or more substituents may be introduced in $R^{a2}$. Examples of such substituents include an alkyl group having 1 to 6 carbon atoms and a fluorine atom.

$R^{a3}$ represents a linear or branched alkylene group, a linear or branched poly(alkyleneoxy) group, a linear or branched unsaturated hydrocarbon group, a carbonyl group, an alkylene group containing a carbonyl group, an alkylene group containing a carboxyl group, an alkylene group containing a carbamoyl group, or any of the below shown groups. Examples of the alkylene groups include an ethylene group, a propylene group and a butylene group. Examples of the poly(alkyleneoxy) groups include a poly(ethyleneoxy) group and a poly(propyleneoxy) group. Examples of the unsaturated hydrocarbon groups include a propenylene group, a methylpropenylene group and a butenylene group.

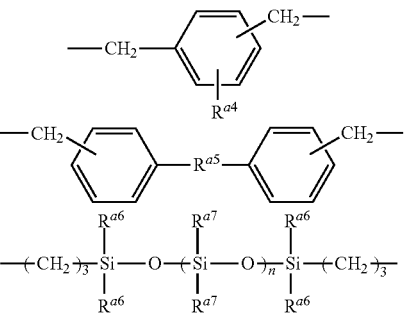

In the formulae, $R^{a4}$ represents a hydrogen atom, an alkyl group having 1 to 4 carbons, an alkoxy group having 1 to 4 carbons, a halogen atom, a nitro group, a cyano group, a mercapto group, an alkylcarboxyl group having 1 to 20 carbon atoms, a carboxyl group or a carbamoyl group.

$R^{a5}$ represents an oxygen atom, a sulfur atom, a methylene group, NH, SO, $SO_2$, $C(CF_3)_2$ or $C(CH_3)_2$.

$R^{a6}$ represents an alkyl group having 1 to 4 carbons or an aryl group.

In the formulae, n is an integer of 0 to 2,000.

$R^{a7}$ represents an alkyl group having 1 to 4 carbons, an aryl group, or a monovalent group with the structure below. In the formula, $R^{a8}$ represents an alkyl group having 1 to 4 carbons or an aryl group, and m is an integer of 0 to 100.

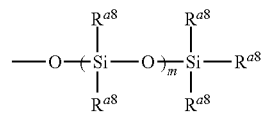

As the compounds of formula (1), there can be mentioned, for example, 3-ethyl-3-hydroxymethyloxetane (OXT101: produced by Toagosei Co., Ltd.), 3-ethyl-3-(2-ethylhexyloxymethyl)oxetane (OXT-212: produced by Toagosei Co., Ltd.) and 3-ethyl-3-phenoxymethyloxetane (OXT-211: produced by Toagosei Co., Ltd.). As the compounds of formula (2), there can be mentioned, for example, 1,4-bis[(3-ethyl-3-oxetanylmethoxy)methyl]benzene (OXT121: produced by Toagosei Co., Ltd.). As the compounds of formula (3), there can be mentioned, for example, bis(3-ethyl-3-oxetanylmethyl)ether (OXT-221: produced by Toagosei Co., Ltd.).

Examples of the compounds each having 3 or 4 oxetane rings in the molecule thereof include the compounds of formula (4) below.

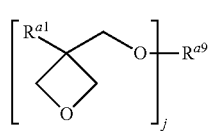
(4)

In formula (4), $R^{a1}$ is as defined above in connection with formula (1). Rag as a polyvalent connecting group represents, for example, a branched alkylene group having 1 to 12 carbon atoms, such as any of the groups of formulae A to C below; a branched poly(alkyleneoxy) group, such as any of the groups of formula D below; or a branched polysiloxy group, such as the group of formula E below, and j is 3 or 4.

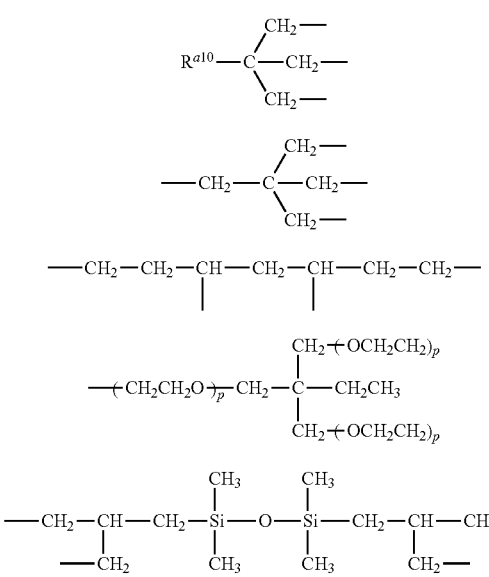

In the formulae, $R^{a10}$ represents a methyl group, an ethyl group or a propyl group, and p is an integer of 1 to 10.

As another form of appropriately usable oxetane compounds, there can be mentioned the compounds of formula (5) below in which an oxetane ring is introduced in the side chain thereof.

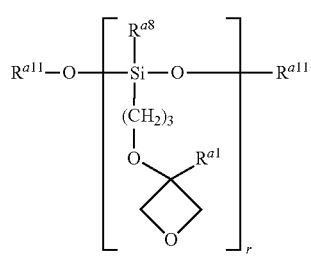
(5)

In formula (5), $R^{a1}$ and $R^{a8}$ are as defined above in connection with the above formulae. Rail represents an alkyl group having 1 to 4 carbons, such as a methyl group, an ethyl group, a propyl group or a butyl group, or a trialkylsilyl group, and r is an integer of 1 to 4.

For the details of the compounds with oxetane rings, reference can be made to, for example, Paragraph Nos. [0021] to [0084] of JP-A-2003-341217 mentioned above. The compounds described there can be suitably used in the composition according to the present invention.

The oxetane compounds described in JP-A-2004-91556 can also be jointly used in the composition according to the present invention. The compounds are described in detail in, for example, Paragraph Nos. [0022] to of the reference.

Among the other oxetane compounds jointly used in the present invention, using a compound having one oxetane ring is preferred from the viewpoint of composition viscosity and tackiness.

A single type of cationically polymerizable compound may be used alone, or two or more types thereof may be used in combination. It is preferred to use an oxetane compound and/or an epoxy compound in combination with a vinyl ether compound from the viewpoint of effective suppression of any shrinkage at the hardening of the hardenable composition.

The content of cationically polymerizable compound based on the total solids of the composition is preferably in the range of 30 to 100 mass %, more preferably 50 to 95 wt %.

[B2] Acid Crosslinking Agent

As the acid crosslinking agent that can be contained in the hardenable composition, there can be mentioned, for example, those described above in the section for acid crosslinking agent [A4].

[B3] Sensitizer

When the hardenable composition according to the present invention contains a photoacid generator, it is preferred for the composition to contain a sensitizer for the purpose of improving the acid generating efficiency of the photoacid generator and realizing a longer photosensitive wavelength. The sensitizer is preferably one capable of sensitizing the photoacid generator in accordance with an electron transfer mechanism or an energy transfer mechanism.

As preferred sensitizers, there can be mentioned, for example, those belonging to the following compound category and having an absorption wavelength in the region of 350 to 450 nm.

As such sensitizers, there can be mentioned, for example, polynuclear aromatic compounds, such as phenanthrene, anthracene, pyrene, perylene, triphenylene and 9,10-dialkoxyanthracenes; triphenylamines; xanthenes, such as fluorescein, eosine, erythirosine, rhodamine B and rosebengal; thioxanthones, such as isopropylthioxanthone, diethylthioxanthone and chlorothioxanthone; cyanines, such as thiacarbocyanine and oxacarbocyanine; merocyanines, such as merocyanine and carbomerocyanine; phthalocyanines; thiazines, such as thionine, methylene blue and toluidine blue; acridines, such as acridine orange, chloroflavin and acriflavine; anthraquinones, such as anthraquinone; squaliums, such as squalium; acridine orange; coumarins, such as 7-diethylamino-4-methylcoumarin; ketocoumarin;

phenothiazines; phenazines; styrylbenzenes; azo compounds; diphenylmethane; triphenylmethane; distyrylbenzenes; carbazoles; porphyrin; spiro compounds; quinacridone; indigo; styryl; pyrylium compounds; pyromethene compounds; pyrazolotriazole compounds; benzothiazole compounds; barbituric acid derivatives; and thiobarbituric acid derivatives. Further, there can be mentioned the compounds described in European Patent No. 568,993, U.S. Pat. Nos. 4,508,811 and 5,227,227 and JP-A's 2001-125255 and H11-271969.

Particular examples of the sensitizers will be shown below.
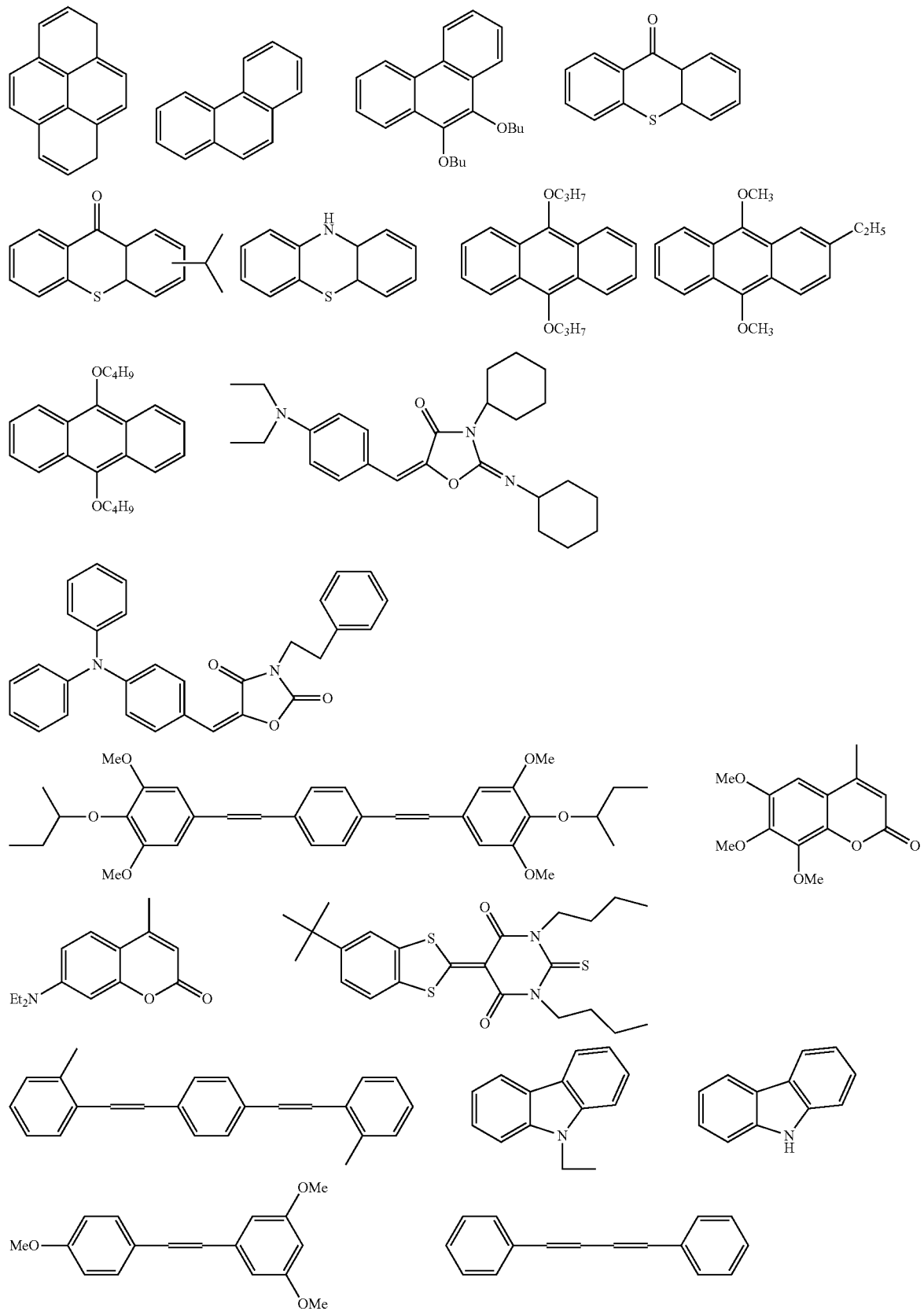

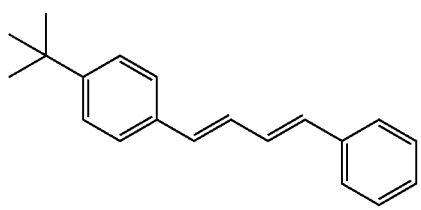

A single type of sensitizer may be used alone, or two or more types thereof may be used in combination.

It is preferred for the content of sensitizer in the hardenable composition to be in the range of 0.01 to 20 mass % based on the total mass thereof from the viewpoint of the colorability of the hardenable composition, etc. The content is more preferably in the range of 0.1 to 15 mass %, further more preferably 0.5 to 10 mass %.

[B4] Radically Polymerizable Compound

The hardenable composition according to the present invention may further contain a radically polymerizable compound. The radically polymerizable compound refers to a radically polymerizable organic compound that undergoes a polymerization or crosslinking reaction when irradiated typically with actinic rays or radiation in the presence of a radical polymerization initiator. The radically polymerizable compound is preferably a compound having at least one ethylenically unsaturated double bond per molecule.

For example, photohardenable materials employing a photopolymerizable composition described in JP-A-H7-159983, Jpn. Pat. Appln. KOKOKU Publication No. (hereinafter referred to as JP-B-) H7-31399, JP-A's H8-224982, H10-863 and H9-80675, etc. are known as the radically polymerizable compounds.

As such compounds, there can be mentioned, for example, an acrylate compound, a methacrylate compound, an allylurethane compound, an unsaturated polyester compound and a styrene-based compound.

Among these radically polymerizable compounds, a compound having a (meth)acrylic group is preferred since it is easy to synthesize and procure the same and the handling thereof is also easy. As such a compound, there can be mentioned, for example, an epoxy(meth)acrylate, a urethane (meth)acrylate, a polyester(meth)acrylate, a polyether(meth) acrylate or a (meth)acrylic ester of an alcohol.

Herein, "(meth)acrylic acid" refers to acrylic acid, methacrylic acid or a mixture thereof. "(Meth)acrylate" refers to an acrylate, a methacrylate or a mixture thereof.

The epoxy(meth)acrylate referred to herein is, for example, a (meth)acrylate obtained by reacting (meth)acrylic acid with a heretofore known aromatic epoxy resin, alicyclic epoxy resin, aliphatic epoxy resin, etc.

Among these epoxy acrylates, an acrylate of an aromatic epoxy resin is preferred. In particular, a (meth)acrylate obtained by reacting (meth)acrylic acid with a polyglycidyl ether of a polyhydric phenol having at least one aromatic nucleus or an alkylene oxide adduct thereof is especially preferred. Examples of such (meth)acrylates include a (meth) acrylate obtained by reacting (meth)acrylic acid with a glycidyl ether obtained by reacting bisphenol A or an alkylene oxide adduct thereof with epichlorohydrin, and a (meth)acrylate obtaining by reacting an epoxy novolac resin with (meth) acrylic acid.

The urethane(meth)acrylate is, for example, a (meth)acrylate obtained by reacting one or two or more types of hydroxylated polyesters and/or hydroxylated polyethers with a hydroxylated (meth)acrylic ester and an isocyanate, or a (meth)acrylate obtained by reacting a hydroxylated (meth) acrylic ester with an isocyanate.

As preferred hydroxylated polyesters, there can be mentioned, for example, those obtained by a reaction between one or two or more types of polyhydric alcohols and one or two or more types of polybasic acids. Examples of preferred aliphatic polyhydric alcohols include 1,3-butanediol, 1,4-butanediol, 1,6-hexanediol, diethylene glycol, triethylene glycol, neopentyl glycol, polyethylene glycol, polypropylene glycol, polybutylene glycol, trimethylolpropane, glycerol, pentaerythritol and dipentaerythritol. Examples of the polybasic acids include adipic acid, terephthalic acid, phthalic anhydride and trimellitic acid.

A preferred hydroxylated polyether is, for example, one obtained by adding one or two or more types of alkylene oxides to a polyhydric alcohol. Examples of preferred polyhydric alcohols are the same as set forth above. As the alkylene oxide, there can be mentioned, for example, ethylene oxide, propylene oxide or butylene oxide.

The hydroxylated (meth)acrylic ester is preferably, for example, one obtained by an esterification reaction between a polyhydric alcohol and (meth)acrylic acid. Examples of the polyhydric alcohols are the same as set forth above.

It is especially preferred for the hydroxylated (meth) acrylic ester to be one obtained by an esterification reaction between a divalent alcohol and (meth)acrylic acid. Examples of such hydroxylated (meth)acrylic esters include 2-hydroxyethyl(meth)acrylate.

The isocyanate is preferably a compound having at least one isocyanate group per molecule. In particular, divalent isocyanate compounds, such as tolylene diisocyanate, hexamethylene diisocyanate and isophorone diisocyanate, are preferred.

The polyester(meth)acrylate is preferably one obtained by a reaction between a hydroxylated polyester and (meth) acrylic acid.

The hydroxylated polyester is preferably, for example, one obtained by an esterification reaction between one or two or more types of polyhydric alcohols and one or two or more types of monobasic acids and/or polybasic acids. Examples of the polyhydric alcohols are the same as set forth above. As the monobasic acid, there can be mentioned, for example, formic acid, acetic acid, butyric acid or benzoic acid. As the polybasic acid, there can be mentioned, for example, adipic acid, terephthalic acid, phthalic anhydride or trimellitic acid.

The polyether(meth)acrylate is preferably, for example, one obtained by a reaction between a hydroxylated polyether and (meth)acrylic acid.

The hydroxylated polyether is preferably, for example, one obtained by adding one or two or more types of alkylene oxides to a polyhydric alcohol. Examples of the polyhydric alcohols are the same as set forth above. As the alkylene oxide, there can be mentioned, for example, ethylene oxide, propylene oxide or butylene oxide.

The (meth)acrylic ester of an alcohol is preferably one obtained by reacting an aromatic or aliphatic alcohol having at least one hydroxyl group per molecule or an alkylene oxide adduct thereof with (meth)acrylic acid. Examples of the (meth)acrylic esters include 2-ethylhexyl(meth)acrylate, 2-hydroxyethyl(meth)acrylate, 2-hydroxypropyl(meth)acrylate, isoamyl(meth)acrylate, lauryl(meth)acrylate, stearyl (meth)acrylate, isooctyl(meth)acrylate, tetrahydrofurfuryl (meth)acrylate, isobornyl(meth)acrylate, benzyl(meth) acrylate, 1,3-butanediol di(meth)acrylate, 1,4-butanediol di(meth)acrylate, 1,6-hexanediol di(meth)acrylate, diethylene glycol di(meth)acrylate, triethylene glycol di(meth)acrylate, neopentyl glycol di(meth)acrylate, polyethylene glycol di(meth)acrylate, polypropylene glycol di(meth)acrylate, trimethylolpropane tri(meth)acrylate, ethylene-oxide-modified trimethylolpropane tri(meth)acrylate, propylene-oxide-modified trimethylolpropane tri(meth)acrylate, pentaerythritol tetra(meth)acrylate, dipentaerythritol hexa(meth)acrylate and ε-caprolactone-modified dipentaerythritol hexa(meth) acrylate.

A single type of radically polymerizable compound may be used alone, or two or more types thereof may be used in combination depending on a desired performance.

It is preferred for at least 50 parts by mass out of 100 parts by mass of radically polymerizable compound to be a compound having a (meth)acrylic group in each molecule.

When the cationically polymerizable compound and the radically polymerizable compound are simultaneously used, the mass ratio between cationically polymerizable compound and radically polymerizable compound is preferably in the range of 10:90 to 90:10, more preferably 20:80 to 80:20.

[B5] Colorant

The hardenable composition according to the present invention may further contain a colorant, depending on the field of application thereof. The colorant is not particularly limited. However, generally, a pigment and an oil-soluble dye that ensure excellent weatherability and rich color reproduction are preferred. An appropriate colorant can be selected from among arbitrary heretofore known colorants, such as soluble dyes, and used. When the hardenable composition according to the present invention is used as an ink composition, a colored ink composition can be obtained by incorporating such a colorant in the composition.

As the colorant used in the hardenable composition according to the present invention, it is preferred to select one that does not act as a polymerization inhibitor in the hardening polymerization reaction. The reason therefor is to prevent any lowering of the sensitivity of the hardening reaction by actinic rays or radiation.

Various components usable as colorants will be described below. In particular, pigments and dyes will be described.

<Pigment>

The pigment is not particularly limited, and an appropriate pigment can be selected from among all commercially available organic and inorganic pigments and used. Further, use can be made of processed pigments, such as a surface-treated pigment.

For example, use can be made of a pigment-resin composite having a pigment dispersed in an insoluble resin or the like as a dispersion medium, or one having a pigment surface coated with a resin, or one having a resin introduced by grafting in the surface of a pigment. Also, colored resin particles consisting of resin particles dyed with a dyestuff can be used in the same manner as pigments.

These pigments include those described in, for example, Seijiro Itoh Ed., "Dictionary of Pigments" (2000); W. Herbst K. Hunger, "Industrial Organic Pigments"; and JP-A's 2002-12607, 2002-188025, 2003-26978 and 2003-342503.

Specific examples of the organic and inorganic pigments include the following.

For example, as pigments imparting a yellow color, there can be mentioned monoazo pigments such as C.I. Pigment Yellow 1 (Fast Yellow G, etc.) and C.I. Pigment Yellow 74; disazo pigments such as C.I. Pigment Yellow 155, C.I. Pigment Yellow 12 (Disazo Yellow AAA, etc.) and C.I. Pigment Yellow 17; non-benzidine azo pigments such as C.I. Pigment Yellow 180 and C.I. Pigment Yellow 120; azolake pigments such as C.I. Pigment Yellow 100 (tartrazine yellow lake, etc.); condensation azo pigments such as C.I. Pigment Yellow 95 (condensation azo yellow GR, etc.); acidic dye lake pigments such as C.I. Pigment Yellow 115 (quinoline yellow lake, etc.); basic dye lake pigments such as C.I. Pigment Yellow 18 (thioflavin lake, etc.); anthraquinone-based pigments such as fravantrone yellow (Y-24); isoindolinone pigments such as isoindolinone yellow 3RLT (Y-110); quinophtharone pigments such as quinophtharone yellow (Y-138); isoindoline pigments such as isoindoline yellow (Y-139); nitroso pigments such as C.I. Pigment Yellow 153 (nickel nitroso yellow, etc.); and metal complex salt azomethine pigments such as C.I. Pigment Yellow 117 (copper azomethine yellow, etc.).

As pigments imparting a red or magenta color, there can be mentioned, for example, monoazo-based pigments such as C.I. Pigment Red 3 (toluidine red, etc.); disazo pigments such as C.I. pigment red 38 (pyrazolone red B, etc.); azolake pigments such as C.I. Pigment Red 53:1 (lake red C, etc.) and C.I. Pigment Red 57:1 (Brilliant Carmine 6B); condensation azo pigments such as C.I. Pigment Red 144 (condensation azo red BR, etc.); acidic dye lake pigments such as C.I. Pigment Red 174 (phloxine B lake, etc.); basic dye lake pigments such as C.I. Pigment Red 81 (rhodamine 6G' lake, etc.); anthraquinone pigments such as C.I. Pigment Red 177 (dianthraquinonyl red, etc.); thioindigo pigments such as C.I. Pigment Red 88 (Thioindigo Bordeaux, etc.); perynone pigments such as C.I. Pigment Red 194 (perynone red, etc.); perylene pigments such as C.I. pigment red 149 (perylene scarlet, etc.); quinacridone pigments such as C.I. Pigment Violet 19 (unsubstituted quinacridone) and C.I. Pigment Red 122 (quinacridone magenta, etc.); isoindolinone pigments such as C.I. Pigment Red 180 (isoindolinone red 2BLT, etc.); and alizarin lake pigments such as C.I. Pigment Red 83 (madder lake, etc.).

As pigments imparting a blue or cyan color, there can be mentioned, for example, disazo-based pigments such as C.I. Pigment Blue 25 (dianisidine blue, etc.); phthalocyanine pigments such as C.I. Pigment Blue 15 (phthalocyanine blue, etc.); acidic dye lake pigments such as C.I. Pigment Blue 24 (peacock blue lake, etc.); basic dye lake pigments such as C.I. Pigment Blue 1 (Victria Pure Blue BO lake, etc.); anthraquinone-based pigments such as C.I. Pigment Blue 60 (indanthron blue, etc.); and alkali blue pigments such as C.I. Pigment Blue 18 (alkali Blue V-5:1).

As pigments imparting a green color, there can be mentioned, for example, phthalocyanine pigments such as C.I. Pigment green 7 (phthalocyanine green) and C.I. Pigment green 36 (phthalocyanine green); and azo metal complex pigments such as C.I. Pigment green 8 (nitroso green).

As pigments imparting an orange color, there can be mentioned, for example, isoindoline-based pigments such as C.I. Pigment orange 66 (isoindoline orange) and anthraquinone-based pigments such as C.I. Pigment orange 51 (dichloropyranthron orange).

As pigments imparting a black color, there can be mentioned, for example, carbon black, titanium black and aniline black.

As white pigments, use can be made of, for example, basic lead carbonate (2PbCO$_3$Pb(OH)$_2$, so-called silver white), zinc oxide (ZnO, so-called zinc white), titanium oxide (TiO$_2$, so-called titanium white) and strontium titanate (SrTiO$_3$, so-called titanium strontium white).

Titanium oxide has a specific gravity lower than and refractive index higher than those of other white pigments and is chemically and physically stabler, so that it has a greater covering power and coloring power as a pigment and has an excellent resistance to acid or alkali and other environmental factors. Therefore, using titanium oxide as a white pigment is preferred. Naturally, other white pigments may be used according to necessity. As the other white pigments, use may be made of the pigments other than set forth above.

In the dispersion of the pigments, use can be made of a dispersing machine, such as a ball mill, sand mill, attriter, roll mill, jet mill, homogenizer, paint shaker, kneader, agitator, Henschel mixer, colloid mill, ultrasonic wave homogenizer, pearl mill or wet jet mill.

In the dispersion of the pigments, a dispersant may be added. As the dispersant, there can be mentioned, for example, a hydroxylated carboxylic ester, a salt of long-chain polyaminoamide and high-molecular-weight acid ester, a salt of high-molecular-weight polycarboxylic acid, a high-molecular-weight unsaturated acid ester, a high-molecular copolymer, a modified polyacrylate, an aliphatic polycarboxylic acid, a naphthalenesulfonic acid formaldehyde condensate, a polyoxyethylene alkylphosphoric ester or a pigment derivative. Further, commercially available polymer dispersants, such as Solsperse series produced by Noveon Corp., can preferably be used.

Still further, as a dispersion aid, a synergist corresponding to each of the various pigments can be used. The dispersant and dispersion aid are preferably added in an amount of 1 to 50 parts by mass based on 100 parts by mass of pigment.

When the composition according to the present invention is used as an ink, a solvent may be added as the dispersant for pigment and other components. Alternatively, a cationically polymerizable compound being a low-molecular-weight component may be used in place of the solvent. The ink composition according to the present invention is a radiation-hardenable ink, and upon application to a recording medium, the ink composition must be quickly hardened. Therefore, a mode in which no solvent is used as the dispersant is preferred. The reason therefor is that when a solvent remains in hardened ink images, it is probable to encounter the problems of deterioration of image resistance to solvent, nonuniformity of image, surface tackiness, etc. From this viewpoint, using a cationically polymerizable compound as the dispersant is preferred. It is preferred to select and use a cationically polymerizable monomer with the lowest viscosity from the viewpoint of dispersion adaptability and improvement of the handling easiness of ink composition.

The average diameter of pigment particles is preferably in the range of 0.02 to 0.9 μm, more preferably 0.05 to 0.8 μm and further more preferably 0.06 to 0.6 μm.

In a typical manner, the pigment, the dispersant and the dispersion medium are selected and the dispersion and filtration conditions are determined so that the average diameter of pigment particles falls within the above range. When the composition according to the present invention is used as an ink composition, the ink storage stability, ink transparency and hardening sensitivity can be maintained by controlling the particle diameter as described above. Further, in the use as an ink for inkjet recording, any head nozzle clogging can be effectively inhibited by the control.

<Dye>

The dye used as a colorant is preferably an oil-soluble dye. In particular, the oil-soluble dye preferably exhibits a solubility in water at 25° C. (mass of the dye which is dissolved in 100 g of water) of not more than 1 g, more preferably not more than 0.5 g and further more preferably not more than 0.1 g. Accordingly, a water-insoluble and oil-soluble dye is preferably used.

This dye may be one in which an oil-solubilizing group is introduced into the mother nucleus of the foregoing dye for the purpose of dissolving a necessary amount of the dye in the composition.

Examples of the oil-solubilizing groups include a long-chain or branched alkyl group, a long-chain or branched alkoxy group, a long-chain or branched alkylthio group, a long-chain or branched alkylsulfonyl group, a long-chain or branched acyloxy group, a long-chain or branched alkoxycarbonyl group, a long-chain or branched acyl group, a long-chain or branched acylamino group, a long-chain or branched alkylsulfonylamino group and a long-chain or branched alkylaminosulfonyl group; and further includes an aryl group, an aryloxy group, an aryloxycarbonyl group, an arylcarbonyloxy group, an arylaminocarbonyl group, an arylaminosulfonyl group and an arylsulfonylamino group each containing these long-chain or branched substituents.

Furthermore, dyes may be obtained by converting a water-soluble dye containing a carboxyl acid or a sulfonic acid so as to have an oil-solubilizing group such as an alkoxycarbonyl group, an aryloxycarbonyl group, an alkylaminosulfonyl group or an arylaminosulfonyl group, using a long-chain or branched alcohol, amine, phenol or aniline derivative.

The oil-soluble dye is preferably one having a melting point of not higher than 200° C., more preferably not higher than 150° C., and further more preferably not higher than 100° C. By using an oil-soluble dye having a low melting point, the deposition of a crystal of the dye in the ink composition can be controlled, and the storage stability of the ink composition can be improved.

Furthermore, for the purpose of improving the fading, especially the resistance to oxidizers such as ozone and hardening characteristics, it is preferred for the oxidation potential to be noble (high). For that reason, an oil-soluble dye having an oxidation potential of 1.0 V (vs SCE) or higher is preferably employed as the oil-soluble dye to be used in the invention. Higher oxidation potentials are preferred. The oxidation potential is more preferably 1.1 V (vs SCE) or higher and most preferably 1.15 V (vs SCE) or higher.

As a dye having a yellow color, the compounds with the structures of general formula (Y-I) described in JP-A-2004-250483 are preferred.

Dyes of general formulae (Y-II) to (Y-IV) described in paragraph [0034] of JP-A-2004-250483 are especially preferred. Specific examples thereof include compounds described in paragraphs [0060] to [0071] of JP-A-2004-250483. Incidentally, the oil-soluble dyes of general formula (Y-I) described in the reference may be used for inks of any colors including not only yellow inks but also black inks and red inks.

As a dye having a magenta color, the compounds with the structures of general formulae (3) and (4) described in JP-A-2002-114930 are preferred. Specific examples thereof include the compounds described in paragraphs [0054] to [0073] of the reference.

The azo dyes of general formulae (M-1) to (M-2) described in paragraphs [0084] to [0122] of JP-A-2002-121414 are especially preferred. Specific examples thereof include the compounds described in paragraphs [0123] to [0132] of the reference. Incidentally, the oil-soluble dyes of general formulae (3), (4), (M-1) and (M-2) described in the reference may be used for inks of any colors including not only magenta inks but also black inks and red inks.

As dyes having a cyan color, there can be mentioned, for example, the dyes of formulae (1) to (IV) described in JP-A-2001-181547 and the dyes of general formulae (IV-1) to (IV-4) described in paragraphs [0063] to [0078] of JP-A-2002-121414. Specific examples thereof include the compounds described in paragraphs [0052] to [0066] of JP-A-2001-181547 and the compounds described in paragraphs [0079] to [0081] of JP-A-2002-121414.

Phthalocyanine dyes of general formulae (C-I) and (C-II) described in paragraphs [0133] to [0196] of JP-A-2002-121414 are especially preferred. The phthalocyanine dyes of general formula (C-II) are more preferred. Specific examples thereof include the compounds described in paragraphs [0198] to [0201] of JP-A-2002-121414. Incidentally, the oil-soluble dyes of formulae (1) to (IV), (IV-1) to (IV-4), (C-I) and (C-II) may be used for inks of any colors including not only cyan inks but also black inks and green inks.

—Oxidation Potential—

The value of oxidation potential (Eox) of dyes can be easily determined by persons skilled in the art to which the invention pertains. The measuring methods are described in, for example, P. Delahay et al.: New Instrumental Methods in Electrochemistry, Interscience Publishers, 1954; A. J. Bard et al.: Electrochemical Methods, John Wiley & Sons, 1980; and Akira Fujishima et al. Electrochemical Measuring Methods, Gihodo Shuppansha, 1984.

In particular, the oxidation potential is determined in the following manner. A test sample is dissolved in an amount of $1\times10^{-2}$ to $1\times10^{-6}$ mol/lit. in a solvent, such as dimethylformamide or acetonitrile, containing a supporting electrolyte, such as sodium perchlorate or tetrapropylammonium perchlorate. The oxidation potential is measured as a value relative to that of SCE (saturated calomel electrode) by cyclic voltammetry or direct current polarography. In the measurement, a carbon (GC) electrode is used as the acting electrode and a rotary platinum electrode is used as the counter electrode. The oxidation wave obtained by the sweep to the oxidation side (noble side) is approximated to a straight line. The midpoint potential value of the line segment created by the intersection of this straight line and a residual current/potential line and the intersection of this straight line and a saturation current line (or intersection of this straight line and a line parallel to the axis of ordinate which passes a peak potential value) is measured as a value relative to SCE (saturated calomel electrode). The oxidation potential value may possibly be deviated with about several tens of millivolts due to influences of liquid junction potential, liquid resistance of the sample solution, etc. However, by using a standard sample (for example, hydroquinone), the reproducibility of measured potential value can be guaranteed. The supporting electrolyte and solvent used can be appropriately selected depending on the oxidation potential and solubility of the test sample. The support electrolyte and solvent which can be used are described in, for example, pp. 101-118 in Electrochemical Measurement Methods authored by Akira Fujioka et al., Gihodo Shuppansha, 1984.

Any of these colorants is preferably added to the composition in an amount of 1 to 30 mass %, more preferably 2 to 25 mass %, in terms of solid content.

[B6] Co-Sensitizer

The hardenable composition according to the present invention may still further contain a co-sensitizer. The co-sensitizer can exert the action of enhancing the sensitivity of the sensitizer to actinic rays or radiation, and/or suppressing the inhibition of polymerization of polymerizable compounds by oxygen, etc.

Examples of such co-sensitizers include amines. As the amines employable as co-sensitizers, there can be mentioned, for example, the compounds described in M. R. Sander et al. "Journal of Polymer Society", Vol. 10, p. 3173 (1972), JP-B-44-20189, JP-A's S51-82102, S52-134692, S59-138205, S60-84305, S62-18537, S64-33104 and Research Disclosure, No. 33825. Specific examples thereof include triethanolamine, ethyl p-dimethylaminobenzoate, p-formyldimethylaniline and p-methylthiodimethylaniline.

Other examples of the co-sensitizers include thiols and sulfides. As the thiols and sulfides employable as co-sensitizers, there can be mentioned, for example, the thiol compounds described in JP-A-S53-702, JP-B-S55-500806 and JP-A-H5-142772 and disulfide compounds described in JP-A-S56-75643. Specific examples thereof include 2-mercaptobenzothiazole, 2-mercaptobenzoxazole, 2-mercaptobenzimidazole, 2-mercapto-4(3H)quinazoline and β-mercaptonaphthalene.

Still other examples of the co-sensitizers include amino acid compounds such as N-phenylglycine, organometallic compounds such as tributyltin acetate described in JP-B-S48-42965, hydrogen donors described in JP-B-S55-34414, sulfur compounds such as trithian described in JP-A-H6-308727, phosphorus compounds such as diethyl phosphite described in JP-A-H6-250387 and Si—H and Ge—H compounds described in Japanese Patent Application No. H6-191605.

When the composition according to the present invention contains a co-sensitizer, the content thereof is preferably in the range of 0.1 to 30 mass %, more preferably 1 to 20 mass %, based on the total solids of the composition.

[B7] Polymerization Initiator

The hardenable composition according to the present invention may still further contain a polymerization initiator. The polymerization initiator may be any of heretofore known radical polymerization initiators. A single type of polymerization initiator may be used alone, or two or more types thereof may be used in combination.

The radical polymerization initiator is a compound capable of absorbing external energy and producing polymerization initiating species. The external energy used for the initiation of polymerization is largely classified into heat and actinic rays or radiation, for which a thermal polymerization initiator and a photopolymerization initiator are used, respectively. Examples of the actinic rays or radiation include γ-rays, β-rays, electron beams, ultraviolet radiation, visible light and infrared radiation. It is preferred for the polymerization initiator to be a radiation-sensitive radical polymerization initiator that is sensitive to actinic rays or radiation, known as a photoradical polymerization initiator.

As preferred radical polymerization initiators, there can be mentioned (a) aromatic ketones, (b) organic peroxides, (c) thio compounds, (d) hexaarylbiimidazole compounds (e) ketoxime ester compounds, (f) borate compounds, (g) azinium compounds, (h) metallocene compounds, (i) active ester compounds, (j) compounds having a carbon-halogen bond and (k) alkylamine compounds. These radical polymerization initiators (a) to (k) may be used individually or in combination.

When the composition according to the present invention contains a polymerization initiator, the content thereof based on the total solids of the composition is preferably in the range of 0.1 to 30 mass %, more preferably 0.5 to 20 mass %.

[B8] Other Components

The hardenable composition according to the present invention may still further contain other components such as a basic compound, a polymerization inhibitor and a solvent.

<Basic Compound>

The addition of a basic compound is preferred from the viewpoint of enhancing the storage stability of the hardenable composition. For example, heretofore known basic compounds can be used as the same. For example, basic inorganic compounds, such as inorganic salts, and/or basic organic compounds, such as amines, can be preferably used.

When the composition according to the present invention contains a basic compound, the content thereof based on the total solids of the composition is preferably in the range of 0.1 to 30 mass %, more preferably 0.5 to 20 mass %.

<Polymerization Inhibitor>

The addition of a polymerization inhibitor is preferred from the viewpoint of improving the storage stability. When the composition according to the present invention is used as an ink composition for inkjet recording, it is preferred to heat the composition within the range of 40 to 80° C. to thereby lower the viscosity thereof before discharge. Accordingly, in order to inhibit the clogging of a head due to thermal polymerization as well, it is preferred to add a polymerization inhibitor. The polymerization inhibitor is preferably added in an amount of 200 to 20,000 ppm based on the total amount of the composition. As the polymerization inhibitor, there can be mentioned, for example, hydroquinone, benzoquinone, p-methoxyphenol, TEMPO, TEMPOL or cupferron Al.

When the ink composition or ink composition for inkjet recording is a radiation-hardenable ink composition, it is preferred for the ink composition to contain no solvent from the viewpoint of ensuring immediate reaction upon landing and hardening. However, the ink composition may contain a given solvent as long as it does not affect the hardening speed thereof, etc. As the solvent, use can be made of, for example, an organic solvent or water. In particular, an organic solvent can be added to improve the adherence to a recording medium (support such as paper). The addition of an organic solvent is effective for the avoidance of the problem of volatile organic compounds (VOC). The amount of organic solvent based on the mass of the whole composition is, for example, in the range of 0.1 to 5 mass %, preferably 0.1 to 3 mass %.

Means for preventing the lowering of sensitivity by the light shielding effect of colorants can be provided by not only a combination of cationically polymerizable compound and cationic polymerization initiator and a combination of radically polymerizable compound and radical polymerization initiator but also a radical/cation hybrid hardenable ink simultaneously using these polymerizable compounds and polymerization initiators.

In addition, the hardenable composition according to the present invention may further contain heretofore known compounds according to necessity. For example, this composition may contain a surfactant, a leveling additive, a matting agent, a resin for regulating film physical properties such as a polyester resin, a polyurethane resin, a vinyl resin, an acrylic resin or a rubber-based resin, and/or a wax. Furthermore, a tackifier that does not disturb a polymerization reaction is preferably contained so as to enhance the adherence to a recording medium, such as a polyolefin or PET. Specific examples thereof include high-molecular-weight adhesive polymers described in JP-A-2001-49200, pp. 5 to 6 (for example, copolymers made of an ester of (meth)acrylic acid and alcohol having an alkyl group having 1 to 20 carbon atoms, an ester of (meth)acrylic acid and alicyclic alcohol having 3 to 14 carbon atoms and as ester of (meth)acrylic acid and of aromatic alcohol having 6 to 14 carbon atoms), and low-molecular-weight tackifier resins having a polymerizable unsaturated bond.

When the composition according to the present invention is used as an ink composition for inkjet recording, from the viewpoint of dischargeability, the viscosity of the composition at a temperature during the discharge (for example, 40 to 80° C., preferably 25 to 30° C.) is preferably in the range of 35 to 500 mPa·s, more preferably 35 to 200 mPa·s. In the composition according to the present invention, it is preferred to appropriately regulate a component ratio so that the viscosity may fall in the above range. When the viscosity at room temperature is set high, even when a porous recording medium is used, ink permeation into the recording medium can be avoided, thereby realizing the reduction of uncured monomer and the reduction of odor. Further, ink bleeding at the landing of ink droplet can be suppressed with the result that an enhancement of image quality can be attained.

Recording media include common noncoated paper and coated paper as well as various non-absorptive plastics and films thereof, which are employed in so-called soft packaging. As plastic films, there can be mentioned, for example, a polyethylene terephthalate (PET) film, an oriented polystyrene (OPS) film, an oriented polypropylene (OPP) film, an oriented nylon (ONy) film, a polyvinyl chloride (PVC) film, a polyethylene (PE) film and a triacetyl cellulose (TAC) film. As other plastics, there can be mentioned, for example, a polycarbonate, an acrylic resin, ABS, a polyacetal, PVA and a rubber. Further, metals and glass are also usable.

The surface energies of these plastic films significantly differ from each other depending on the material characteristics, so that it has been a problem that the dot diameter after ink landing is changed depending on the recording material. However, by virtue of the constitution of the present invention, it is feasible to form desired highly detailed images on a wide range of recording materials whose surface energy ranges from 35 to 60 mN/m, including an OPP film and an OPS film which exhibit low surface energies and a PET which exhibits a relatively high surface energy.

The surface tension of the composition according to the present invention is preferably in the range of 20 to 30 mN/m, more preferably 23 to 28 mN/m. When recording is performed on various recording media such as a polyolefin, PET, coated paper and non-coated paper, from the viewpoint of bleeding and permeation, the surface tension is preferably 20 mN/m or higher. From the viewpoint of wettability, the surface tension is preferably 30 mN/m or below.

The ink composition according to the present invention can be appropriately used as an ink for inkjet recording. In the use as an ink for inkjet recording, recording is performed by injecting the ink composition onto a recording medium by means of an inkjet printer and exposing the injected ink composition to radiation to thereby harden the same.

The print obtained from this ink has its image areas hardened by exposure to radiation such as ultraviolet and excels in the strength of image areas. Therefore, the ink can find various applications other than image formation, for example, the formation of an ink receiving layer (image areas) of planographic printing plate and the like.

<Method of Inkjet Recording>

The method of inkjet recording in which the ink composition according to the present invention can be appropriately used (method of inkjet recording according to the present invention) will be described below.

The method of inkjet recording according to the present invention comprises discharging the above ink composition onto a recording medium and exposing the discharged composition to actinic rays or radiation to thereby harden the composition. The hardened ink composition forms an image on the recording medium.

As the recording medium, use is made of, for example, a support or a recording material. The recording medium is not particularly limited, and includes common paper, such as noncoated paper or coated paper, as well as various non-absorptive resin materials and resin films as obtained by molding the same, which are employed in so-called soft packaging. As plastic films, there can be mentioned, for example, a PET film, an OPS film, an OPP film, an ONy film, a PVC film, a PE film and a TAC film. As other plastics employable as the material of the recording medium, there can be mentioned, for example, a polycarbonate, an acrylic resin, ABS, a polyacetal, PVA and a rubber. Further, metals and glass are also usable as the recording medium.

The ink composition according to the present invention exhibits less thermal shrinkage at the hardening and excels in the adherence to recording media. Therefore, the composition is advantageous in that highly fine images can be formed on films tending to suffer film curling or other deformation by, for example, hardening shrinkage of ink or heat generated at hardening reaction, such as a thermally shrinkable PET film, OPS film, OPP film, ONy film and PVC film.

As the active rays or radiation used in the method of inkjet recording according to the present invention, there can be mentioned, for example, $\alpha$-rays, $\gamma$-rays, X-rays, ultraviolet radiation, visible light, infrared radiation or electron beams. The peak wavelength of the active rays or radiation is preferably in the range of 200 to 600 nm, more preferably 300 to 450 nm and further more preferably 350 to 420 nm. The output of the active rays or radiation is preferably 2,000 mJ/cm$^2$ or less, more preferably in the range of 10 to 2,000 mJ/cm$^2$, further more preferably 20 to 1,000 mJ/cm$^2$ and most preferably 50 to 800 mJ/cm$^2$.

In the method of inkjet recording according to the present invention, the active rays or radiation is preferably emitted from a light-emitting diode, fluorescent tube or mercury lamp capable of emitting ultraviolet having an emission wavelength peak of 350 to 420 nm and realizing a maximum illuminance on recording medium surface ranging from 10 to 1,000 mW/cm$^2$.

In the method of inkjet recording according to the present invention, the dot diameter of landed ink can be maintained constant on various recording media whose surface wettabilities are different from each other, thereby enhancing image quality. In order to obtain a color image by this method, it is preferred to superpose ink layers in sequence starting from that lowest in brightness. Superposing ink layers in sequence starting from that lowest in brightness may promise easy reaching of exposure radiation to lower ink and accordingly excellent hardening sensitivity, reduction of residual monomers, reduction of odor and improvement of adherence. Exposure can be performed in block after all colors are discharged. However, from the viewpoint of promotion of hardening, it is preferred to carry out exposure for every color.

The radiation-hardenable ink composition generally has a viscosity higher than that of ordinary ink compositions or aqueous ink used as an ink for inkjet recording, so that it suffers a high viscosity fluctuation depending on the temperature fluctuation at discharge. The viscosity fluctuation of the ink markedly influences changes of droplet size and droplet discharge rate, consequently inviting the deterioration of image quality. Therefore, the ink temperature at discharge must be kept constant as far as possible. Accordingly, the appropriate control range of temperature is set temperature±5° C., preferably set temperature±2° C. and more preferably set temperature±1° C.

[Inkjet Recording System]

The inkjet recording system for use in the present invention is not particularly limited, and any commercially available inkjet recording system can be used. That is, in the present invention, recording can be performed by means of any commercially available inkjet recording system.

The inkjet recording system, for example, comprises an ink supply system, a temperature sensor and an active rays or radiation source.

The ink supply system includes, for example, a tank for storing the ink composition, a supply piping, an ink supply tank disposed immediately before an inkjet head, a filter and a piezoelectric inkjet head. The piezoelectric inkjet head can be operated so that the discharge may be conducted at the resolution of, for example, 320×320 to 4,000×4,000 dpi, preferably 400×400 to 1,600×1,600 dpi and more preferably 720×720 dpi to form multi-sized dots of 1 to 100 pi, preferably 8 to 30 pi. The term "dpi" herein means the number of dots per 2.54 cm.

As described hereinbefore, when the radiation-hardenable ink is used, the ink temperature at the time of discharge is preferably maintained constant. Accordingly, the region from the ink supply tank to the inkjet head can be thermally insulated and heated. The method of controlling the temperature is not particularly limited. However, for example, it is preferred to dispose a plurality of temperature sensors at piping sites to thereby conduct heating control corresponding to the flow rate of ink and the ambient temperature. The temperature sensors can be disposed in the ink supply tank and near the nozzles of the inkjet head. Further, the heating head unit is preferably thermally shielded or insulated so as to minimize the influence of ambient air temperature on the system body. It is preferred to insulate the head unit from other units and reduce the thermal capacity of the entire heating unit in order to shorten the printer start-up time needed for heating or in order to reduce the loss of heat energy.

[Process Comprising Exposing Discharged Ink Composition to Actinic Rays or Radiation so as to Harden The Ink Composition, Thereby Forming Hydrophobic Image Consisting Of Hardened Ink Composition On Recording Medium]

The ink composition having been discharged on a support surface is typically hardened by exposing the same to actinic rays or radiation. In the stage of exposure, when a polymerization initiator (photoinitiator) and a sensitizing dye are simultaneously contained in the ink composition, the sensitizing dye in the system absorbs actinic rays or radiation to be raised to an excited state. The excited sensitizing dye, when coming into contact with the polymerization initiator, promotes the decomposition of the polymerization initiator to thereby realize an enhanced-sensitivity hardening reaction.

Herein, as the actinic rays or radiation, use is made of, for example, $\alpha$-rays, $\gamma$-rays, electron beams, X-rays, ultraviolet radiation, visible light or infrared radiation. It is appropriate for the peak wavelength of the actinic rays or radiation to, though depending on the absorption characteristics of the sensitizing dye, fall within the range of, for example, 200 to 600 nm, preferably 300 to 450 nm and more preferably 350 to 420 nm. In the present invention, the polymerization initiation system has satisfactory sensitivity to even low-output actinic rays or radiation. Accordingly, it is appropriate for the output of the actinic rays or radiation to be one capable of providing an exposure energy of, for example, 2,000 mJ/cm$^2$ or less, preferably 10 to 2,000 mJ/cm², more preferably 20 to 1,000 mJ/cm² and further more preferably 50 to 800 mJ/cm². Further, the actinic rays or radiation is appropriately irradiated so that the exposed surface illuminance falls within the range of, for example, 10 to 2,000 mW/cm², preferably 20 to 1,000 mW/cm².

A mercury lamp, a gaseous or solid state lasers and the like are mainly used as the actinic rays or radiation source. A mercury lamp and a metal halide lamp are widely known for ultraviolet-photohardenable inkjet recording inks. However, under the current strong demand for the elimination of the use of mercury from the viewpoint of environmental protection, it is industrially and environmentally very advantageous to replace mercury lamps with GaN-type semiconductor UV-emitting devices. Further, LED (UV-LED) and LD (UV-LD) are smaller in size, longer in lifetime, higher in efficiency and lower in cost, and thus, are attracting attention as photohardenable inkjet light sources.

In the present invention, a light-emitting diode (LED) and a laser diode (LD) can be used as the actinic rays or radiation source. In particular, when an ultraviolet radiation source is required, use can be made of an ultraviolet LED or an ultraviolet LD. For example, a purple LED having a main emission spectrum in the wavelength range of 365 to 420 nm is available from Nichia Corporation. When a further shorter wavelength is required, U.S. Pat. No. 6,084,250 discloses an LED capable of irradiating actinic rays or radiation having a main emission spectrum in the wavelength range of 300 to 370 nm. Other ultraviolet LED's are also commercially available, which are capable of emitting radiations of different UV ranges. The actinic rays or radiation source most preferred in the present invention is a UV-LED, especially a UV-LED having a peak wavelength in the range of 350 to 420 nm.

The maximum illuminance of LED light on a recording medium is preferably in the range of from 10 to 2,000 mW/cm², more preferably from 20 to 1,000 mW/cm², and most preferably from 50 to 800 mW/cm².

It is appropriate to expose the ink composition to such actinic rays or radiation in the period of, for example, 0.01 to 120 seconds, preferably 0.1 to 90 seconds.

With respect to the conditions of exposure to actinic rays or radiation and fundamental exposing method, reference can be made to, for example, the contents disclosed in JP-A-S60-132767. Specifically, light sources are disposed on both sides of a head unit including an ink discharger, and the head unit and the light sources are scanned in a so-called shuttle mode.

A given period of time (for example, 0.01 to 0.5 second, preferably 0.01 to 0.3 second and more preferably 0.01 to 0.15 second) is interposed between the ink landing and the exposure to actinic rays or radiation. By controlling the period from the ink landing to the exposure to an extremely short period, it becomes feasible to prevent the ink landed on a recording medium from bleeding before the landed ink is hardened. It also becomes feasible to expose the ink composition before it penetrates into a deep portion of a porous recording medium to which no light is penetrable, so that the remaining of unreacted monomer can be suppressed, resulting in odor reduction.

Moreover, the hardening can be completed by irradiation from another stationary light source. WO 99/54415 (pamphlet) discloses, as an irradiation method, a method of using an optical fiber and a method of irradiating UV light on a recording area by guiding a collimated light source to a mirror surface disposed on the sidewall of a head unit.

EXAMPLE

The present invention will be described in greater detail below by way of its examples. However, the gist of the present invention is in no way limited to these examples.

(Acid Amplifier)
[Synthesis]

As acid amplifiers, the compounds 1 to 17 of Table 2 below were synthesized in the following manner. Further, for control, the comparative compounds 1 to 5 of the table were synthesized in the following manner.

TABLE 2

| Compound | Structure |
| --- | --- |
| 1 | 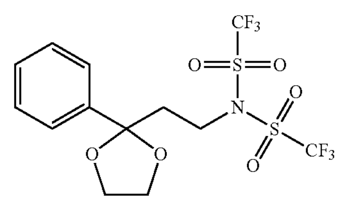 [SMILES: O=S(=O)(N(CCC1(c2ccccc2)OCCO1)S(=O)(=O)C(F)(F)F)C(F)(F)F] |
| 2 | 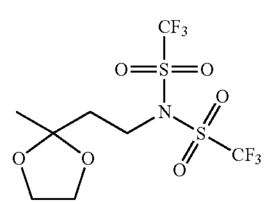 [SMILES: CC1(CCN(S(=O)(=O)C(F)(F)F)S(=O)(=O)C(F)(F)F)OCCO1] |
| 3 | 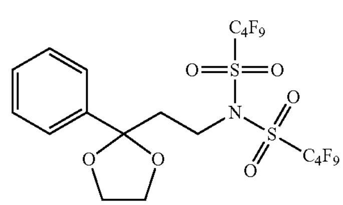 |

TABLE 2-continued

| Compound | Structure |
|---|---|
| 4 | 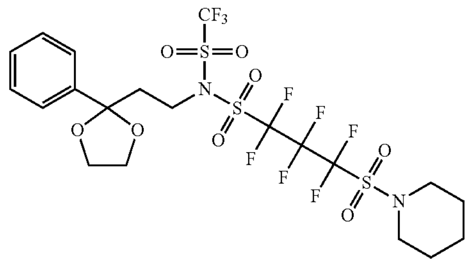 [SMILES: O=S(=O)(N(CCC1(c2ccccc2)OCCO1)S(=O)(=O)C(F)(F)C(F)(F)C(F)(F)S(=O)(=O)N1CCCCC1)C(F)(F)F] |
| 5 | 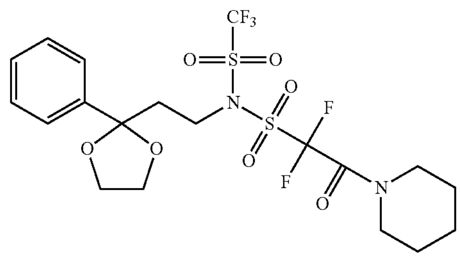 [SMILES: O=C(N1CCCCC1)C(F)(F)S(=O)(=O)N(CCC1(c2ccccc2)OCCO1)S(=O)(=O)C(F)(F)F] |
| 6 | 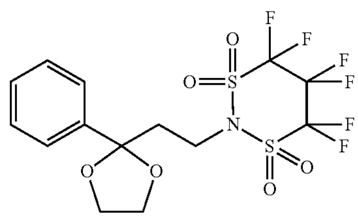 [SMILES: O=S1(=O)N(CCC2(c3ccccc3)OCCO2)S(=O)(=O)C(F)(F)C(F)(F)C1(F)F] |
| 7 | 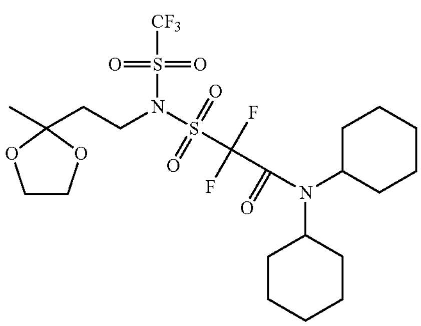 [SMILES: CC1(CCN(S(=O)(=O)C(F)(F)F)S(=O)(=O)C(F)(F)C(=O)N(C2CCCCC2)C2CCCCC2)OCCO1] |
| 8 | 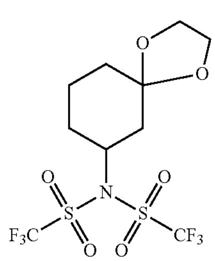 [SMILES: O=S(=O)(N(C1CCCC2(C1)OCCO2)S(=O)(=O)C(F)(F)F)C(F)(F)F] |
| 9 | 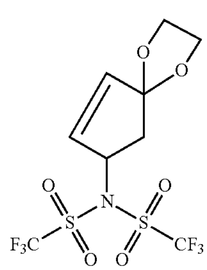 [SMILES: O=S(=O)(N(C1C=CC2(C1)OCCO2)S(=O)(=O)C(F)(F)F)C(F)(F)F] |

TABLE 2-continued
| Compound | Structure |
|---|---|
| 10 | 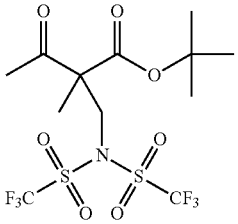 [SMILES: CC(=O)C(C)(CN(S(=O)(=O)C(F)(F)F)S(=O)(=O)C(F)(F)F)C(=O)OC(C)(C)C] |
| 11 | 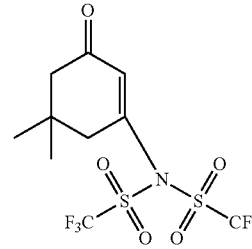 |
| 12 | 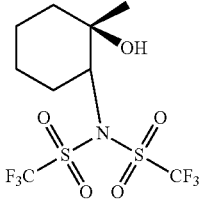 [SMILES: C[C@]1(O)CCCCC1N(S(=O)(=O)C(F)(F)F)S(=O)(=O)C(F)(F)F] |
| 13 | 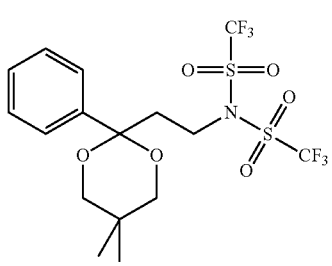 [SMILES: CC1(C)COC(CCN(S(=O)(=O)C(F)(F)F)S(=O)(=O)C(F)(F)F)(c2ccccc2)OC1] |
| 14 | 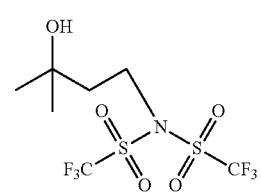 [SMILES: CC(C)(O)CCN(S(=O)(=O)C(F)(F)F)S(=O)(=O)C(F)(F)F] |
| 15 | 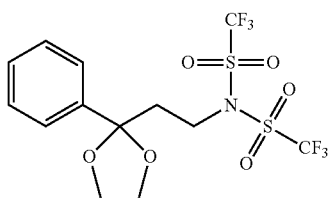 [SMILES: COC(CCN(S(=O)(=O)C(F)(F)F)S(=O)(=O)C(F)(F)F)(OC)c1ccccc1] |

TABLE 2-continued
| Compound | Structure |
|---|---|
| 16 | 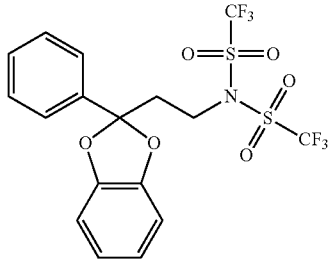 [SMILES: O=S(=O)(N(CCC1(c2ccccc2)Oc2ccccc2O1)S(=O)(=O)C(F)(F)F)C(F)(F)F] |
| 17 | 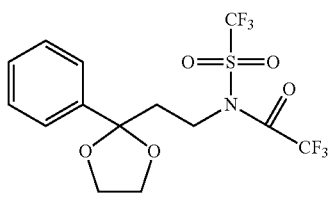 [SMILES: O=C(N(CCC1(c2ccccc2)OCCO1)S(=O)(=O)C(F)(F)F)C(F)(F)F] |
| Compar. 1 | 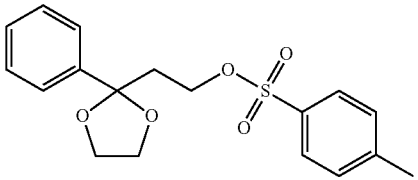 [SMILES: Cc1ccc(S(=O)(=O)OCCC2(c3ccccc3)OCCO2)cc1] |
| Compar. 2 | 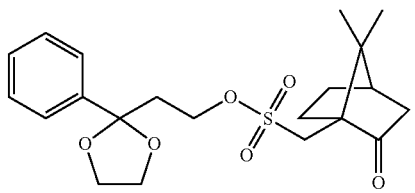 [SMILES: CC1(C)C2CCC1(CS(=O)(=O)OCCC1(c3ccccc3)OCCO1)C(=O)C2] |
| Compar. 3 | 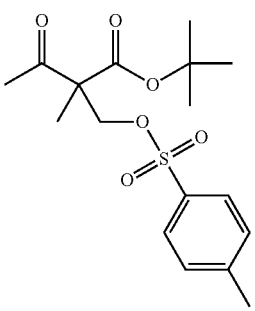 [SMILES: CC(=O)C(C)(COS(=O)(=O)c1ccc(C)cc1)C(=O)OC(C)(C)C] |
| Compar. 4 | 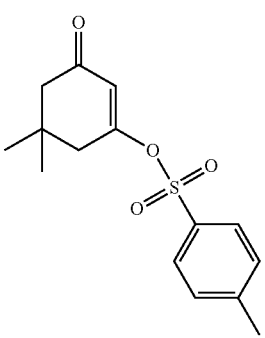 |

TABLE 2-continued

| Compound | Structure |
|---|---|
| Compar. 5 | ![structure] |

<Synthesis of Compound 1>

The amine X of the following formula (15.0 g, 77.6 mmol), 150 ml of chloroform and triethylamine (23.6 g, 233 mmol) were mixed together.

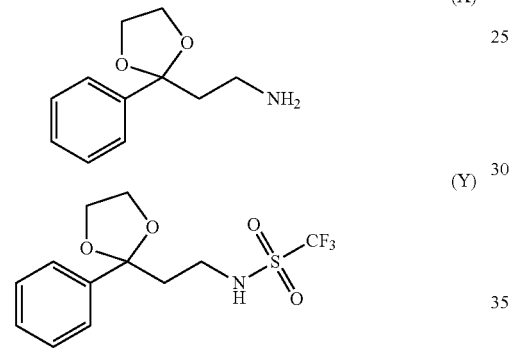

The thus obtained mixed solution was cooled with ice water, and trifluoromethanesulfonic anhydride (24.0 g, 85.1 mmol) was slowly dropped into the cooled solution. The mixture was heated to room temperature and agitated for two hours. Subsequently, 100 ml of saturated aqueous sodium hydrogen carbonate solution was added to the mixture, and an organic phase was extracted with 100 ml of chloroform. The organic phase was washed with 50 ml of water thrice. The organic phase was washed with 50 ml of saturated aqueous sodium chloride solution, and dried over magnesium sulfate. The solvent was distilled off in vacuum, thereby obtaining 9.5 g of compound Y.

The compound Y (9.5 g, 29.0 mmol) was dissolved in 50 ml of diethyl ether, and cooled with ice water. Sodium hydride (containing about 50 wt. % mineral oil) (2.1 g) was added to the mixed solution, and agitated in ice water for 30 minutes. Subsequently, trifluoromethanesulfonic anhydride (8.2 g, 29.2 mmol) was slowly dropped into the cooled mixture. The mixture was heated to room temperature and agitated for two hours. Thereafter, 50 ml of saturated aqueous sodium hydrogen carbonate solution was added to the mixture, and an organic phase was extracted with 100 ml of chloroform. The organic phase was washed with 50 ml of water thrice. The organic phase was washed with 50 ml of saturated aqueous sodium chloride solution, and dried over magnesium sulfate. The solvent was distilled off in vacuum. The product was purified by silica gel chromatography, thereby obtaining 4.81 g of target compound 1.

$^1$H-NMR (300 MHz, CDCl$_3$) δ=7.46-7.35 (m, 5H), 4.15 (t, J=7.8 Hz, 2H), 4.02 (t, J=3.3 Hz, 2H), 3.79 (t, J=3.3 Hz, 2H), 2.40 (t, J=7.8 Hz, 2H).

$^{19}$F-NMR (300 MHz, CDCl$_3$) δ=−102.6 (s, 6F).

<Synthesis of Compound 2>

The amine Z of the following formula (4.2 g, 32.2 mmol), 30 ml of chloroform and triethylamine (9.8 g, 96.8 mmol) were mixed together.

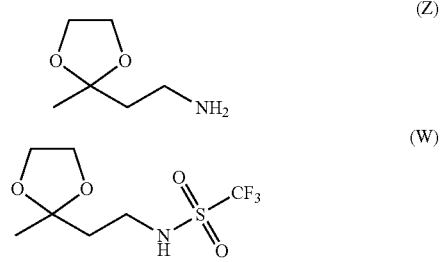

The thus obtained mixed solution was cooled with ice water, and trifluoromethanesulfonic anhydride (10.0 g, 35.4 mmol) was slowly dropped into the cooled solution. The mixture was heated to room temperature and agitated for two hours. Subsequently, 50 ml of saturated aqueous sodium hydrogen carbonate solution was added to the mixture, and an organic phase was extracted with 100 ml of chloroform. The organic phase was washed with 50 ml of water thrice. The organic phase was washed with 50 ml of saturated aqueous sodium chloride solution, and dried over magnesium sulfate. The solvent was distilled off in vacuum, thereby obtaining 4.1 g of compound W.

The compound W (4.1 g, 15.5 mmol) was dissolved in 50 ml of diethyl ether, and cooled with ice water. Sodium hydride (containing about 50 wt. % mineral oil) (1.48 g) was added to the mixed solution, and agitated in ice water for 30 minutes. Subsequently, trifluoromethanesulfonic anhydride (4.4 g, 15.5 mmol) was slowly dropped into the cooled mixture. The mixture was heated to room temperature and agitated for two hours. Thereafter, 50 ml of saturated aqueous sodium hydrogen carbonate solution was added to the mixture, and an organic phase was extracted with 100 ml of chloroform. The organic phase was washed with 50 ml of water thrice. The organic phase was washed with 50 ml of saturated aqueous sodium chloride solution, and dried over magnesium sulfate. The solvent was distilled off in vacuum. The product was purified by silica gel chromatography, thereby obtaining 3.0 g of target compound 2.

$^1$H-NMR (300 MHz, CDCl$_3$) δ=4.08 (t, J=8.4 Hz, 2H), 3.95 (m, 4H), 2.20 (t, J=8.4 Hz, 2H), 1.33 (s, 3H).
$^{19}$F-NMR (300 MHz, CDCl$_3$) δ=−102.6 (s, 6F).
<Synthesis of Compounds 3 to 17>

Compounds 3 to 17 were synthesized in the same manner as described above in connection with compound 1. Namely, these compounds were synthesized by reactions between the corresponding amines and sulfonic anhydride or sulfonic chloride in basic conditions.

(Photoacid Generator)

As the photoacid generator, use was made of at least one of the above-mentioned photoacid generators (z1) to (z102).

(Basic Compound)

As the basic compound, use was made of the following compounds C-1 to C-3.

C-1: 2,4,5-triphenylimidazole,
C-2: tetrabutylammonium hydroxide, and
C-3: 1,5-diazabicyclo[4.3.0]non-5-ene.

(Surfactant)

As the surfactant, use was made of the following products W-1 to W-4.

W-1: Megafac F176 (produced by Dainippon Ink & Chemicals, Inc.; fluorinated),
W-2: Megafac R08 (produced by Dainippon Ink & Chemicals, Inc.; fluorinated and siliconized),
W-3: polysiloxane polymer KP-341 (produced by Shin-Etsu Chemical Co., Ltd.; siliconized), and
W-4: Troy Sol S-366 (produced by Troy Chemical Co., Ltd.; fluorinated).

(Solvent)

As the solvent, use was made of the following solvents A1 to A4, B1 and B2. These solvents were appropriately mixed together before use.

A1: propylene glycol monomethyl ether acetate,
A2: 2-heptanone,
A3: cyclohexanone,
A4: γ-butyrolactone,
B1: propylene glycol monomethyl ether, and
B2: ethyl lactate.

Example A

Examples 1A to 13A and Comparative Examples 1A to 6A

Preparation of Resist

Referring to Table 3 below, with respect to each of the resists, the individual components were dissolved in the solvent, thereby obtaining a solution of 4.0 mass % solid content. This solution was passed through a polytetrafluoroethylene filter of 0.1 μm pore size, thereby obtaining a positive resist solution.

(Evaluation of Resist)

An antireflection film DUV-42 produced by Brewer Science Inc. was uniformly applied at a thickness of 60 nm onto a silicon substrate having undergone a hexamethyldisilazane treatment by use of a spin coater, and dried on a hot plate at 100° C. for 90 seconds. Further drying was carried out by heating at 190° C. for 240 seconds. Thereafter, each of the positive resist solutions was applied thereonto by use of a spin coater and dried at 120° C. for 90 seconds, thereby obtaining a 0.12 μm-thick resist film.

The obtained resist film was exposed through a mask by means of an ArF excimer laser stepper (manufactured by ASML, PAS5500/1100, NA0.75). Immediately after the exposure, the resist film was baked on a hot plate at 120° C. for 90 seconds. Thereafter, the resist film was developed with a 2.38 mass % aqueous tetramethylammonium hydroxide solution at 23° C. for 60 seconds, rinsed with pure water for 30 seconds and dried. Thus, an intended line pattern was obtained.

[Sensitivity, Resolution (γ)]

Surface exposure was carried out while changing the exposure amount by 0.5 mJ at a time within the range of 10 to 40 mJ/cm$^2$, and the exposed film was baked at 110° C. for 90 seconds. Thereafter, using a 2.38 mass % aqueous tetramethylammonium hydroxide (TMAH) solution, the dissolution rate at each of the exposure amounts was measured, thereby obtaining a sensitivity curve.

The sensitivity was defined as the exposure amount at which the dissolution rate of the resist was saturated on the dissolution rate curve. Resolution (γ value) was calculated from the gradient of the straight line portion of the dissolution rate curve. The larger the γ value, the greater the excellence in dissolution contrast.

[Line Edge Roughness (LER)]

A 150 nm line pattern (L/S=1/1) was formed at the exposure amount realizing the above sensitivity. At arbitrary 30 points in a 50 μm region in the longitudinal direction thereof, the distance of actual edges from a reference line on which edges were to be present was measured by means of a scanning electron microscope (model S-9220, manufactured by Hitachi, Ltd.). The standard deviation of measured distances was determined, and 3σ was computed.

[Configuration of Pattern]

The optimum exposure amount was defined as the exposure amount that reproduced a line-and-space (L/S=1/1) mask pattern of 150 nm line width. The profile at the optimum exposure amount was observed by means of a scanning electron microscope (SEM).

[Aging Stability]

Each of the compositions was stored at room temperature for a month. The degree of sensitivity change between before the storage and after the storage was evaluated. The evaluation was effected on the following judgment criteria.

(Judgment Criteria)

○ (Good): when the observed sensitivity change was less than 1 mJ/cm$^2$,

Δ (Fair): when the observed sensitivity change was in the range of 1 to 3 mJ/cm$^2$, and x (insufficient): when the observed sensitivity change was greater than 3 mJ/cm$^2$.

The obtained measurement results are given in Table 3 below.

TABLE 3

| | (ArF; positive) | | | | | |
|---|---|---|---|---|---|---|
| Ex. | Photoacid generator | Acid amplifier | Resin (9.6 g) | Basic compound (0.02 g) | Surfactant (0.1 mass %) | Solvent (mass ratio) |
| 1A | z63(0.4 g) | 1(0.4 g) | RA-20 | C-1 | W-1 | A1/B1(6/4) |
| 2A | z63(0.4 g) | 2(0.4 g) | RA-20 | C-1 | W-1 | A2/B2(6/4) |

TABLE 3-continued (ArF; positive)

| Ex. | | | | | | |
|---|---|---|---|---|---|---|
| 3A | z63(0.4 g) | 6(0.4 g) | RA-20 | C-1 | W-1 | A3/B1(6/4) |
| 4A | z63(0.4 g) | 7(0.4 g) | RA-20(4.0 g) RA-23(5.6 g) | C-1 | W-1 | A4/B1(6/4) |
| 5A | z89(0.4 g) | 2(0.4 g) | RA-20 | C-1 | W-1 | A1/B1(6/4) |
| 6A | z92(0.2 g) z63(0.2 g) | 2(0.4 g) | RA-20 | C-1 | W-1 | A1/B1(6/4) |
| 7A | z93(0.4 g) | 2(0.4 g) | RA-20 | C-3 | W-1 | A1/B1(6/4) |
| 8A | z79(0.4 g) | 2(0.4 g) | RA-23 | C-1 | W-2 | A1/B1(6/4) |
| 9A | z63(0.4 g) | 10(0.4 g) | RA-25 | C-1 | W-3 | A1/B1(6/4) |
| 10A | z63(0.4 g) | 12(0.4 g) | RA-20 | C-2 | W-1 | B1 |
| 11A | z63(0.6 g) | 14(0.2 g) | RA-1 | C-1 | W-4 | A1/B1(6/4) |
| 12A | z63(0.4 g) | 17(0.4 g) | RA-20 | C-1 | W-1 | A1/B1(6/4) |
| 13A | z63(0.4 g) | 2(0.2 g) 7(0.2 g) | RA-20 | C-1 | W-1 | A1/B1(6/4) |

| Ex. | Sensitivity (mJ/cm$^2$) | γ | LER (nm) | Pattern configuration | Aging stability |
|---|---|---|---|---|---|
| 1A | 26.0 | 6.2 | 4.3 | Rectangular | ○ |
| 2A | 24.1 | 6.2 | 4.0 | Rectangular | ○ |
| 3A | 24.2 | 6.3 | 4.2 | Rectangular | ○ |
| 4A | 24.0 | 6.2 | 4.3 | Rectangular | ○ |
| 5A | 24.0 | 6.1 | 4.2 | Rectangular | ○ |
| 6A | 24.2 | 6.3 | 4.3 | Rectangular | ○ |
| 7A | 24.2 | 6.2 | 4.4 | Rectangular | ○ |
| 8A | 24.0 | 6.0 | 4.3 | Rectangular | ○ |
| 9A | 28.0 | 6.0 | 5.0 | Rectangular | ○ |
| 10A | 29.0 | 6.5 | 4.8 | Rectangular | ○ |
| 11A | 28.0 | 6.5 | 5.2 | Rectangular | ○ |
| 12A | 29.0 | 6.2 | 5.0 | Rectangular | ○ |
| 13A | 29.1 | 6.5 | 5.1 | Rectangular | ○ |

| Ex. | Photoacid generator | Acid amplifier | Resin (9.6 g) | Basic compound (0.02 g) | Surfactant (0.1 mass %) | Solvent (mass ratio) |
|---|---|---|---|---|---|---|
| Compar. 1A | z63(0.4 g) | Compar. 1 (0.4 g) | RA-20 | C-1 | W-1 | A1/B1(6/4) |
| Compar. 2A | z63(0.4 g) | Compar. 2 (0.4 g) | RA-20 | C-1 | W-1 | A1/B1(6/4) |
| Compar. 3A | z63(0.4 g) | Compar. 3 (0.4 g) | RA-20 | C-1 | W-1 | A1/B1(6/4) |
| Compar. 4A | z63(0.4 g) | Compar. 4 (0.4 g) | RA-20 | C-1 | W-1 | A1/B1(6/4) |
| Compar. 5A | z63(0.4 g) | Compar. 5 (0.4 g) | RA-20 | C-1 | W-1 | A1/B1(6/4) |
| Compar. 6A | z63(0.4 g) | None | RA-20 | C-1 | W-1 | A1/B1(6/4) |

| Ex. | Sensitivity (mJ/cm$^2$) | γ | LER (nm) | Pattern configuration | Aging stability |
|---|---|---|---|---|---|
| Compar. 1A | 30.0 | 4.3 | 6.0 | Tapered | Δ |
| Compar. 2A | 30.0 | 5.2 | 5.5 | Tapered | Δ |
| Compar. 3A | 35.0 | 5.2 | 5.5 | Tapered | x |
| Compar. 4A | 35.0 | 5.2 | 5.5 | Tapered | x |
| Compar. 5A | 35.0 | 5.2 | 5.5 | Tapered | x |
| Compar. 6A | 40.0 | 5.2 | 5.5 | Tapered | ○ |

The photoacid generator, acid amplifier, basic compound, surfactant and solvent were appropriately selected from among those set forth hereinbefore and used.

The resin was selected from among the following resins (RA-1), (RA-20), (RA-23) and (RA-25) and used. In the following formulae, the numeral appearing on the right side of each repeating unit is a molar ratio. Mw represents a weight average molecular weight, and Mw/Mn represents a molecular weight dispersity.

invention can exhibit excellent performance as a positive resist composition exposed to an ArF excimer laser.

Example B

A resist solution was prepared according to the same procedure as in Example A except that 0.06 g of the polymer shown below was added to the composition of Example 1A. The resist solution was applied in the same manner, thereby

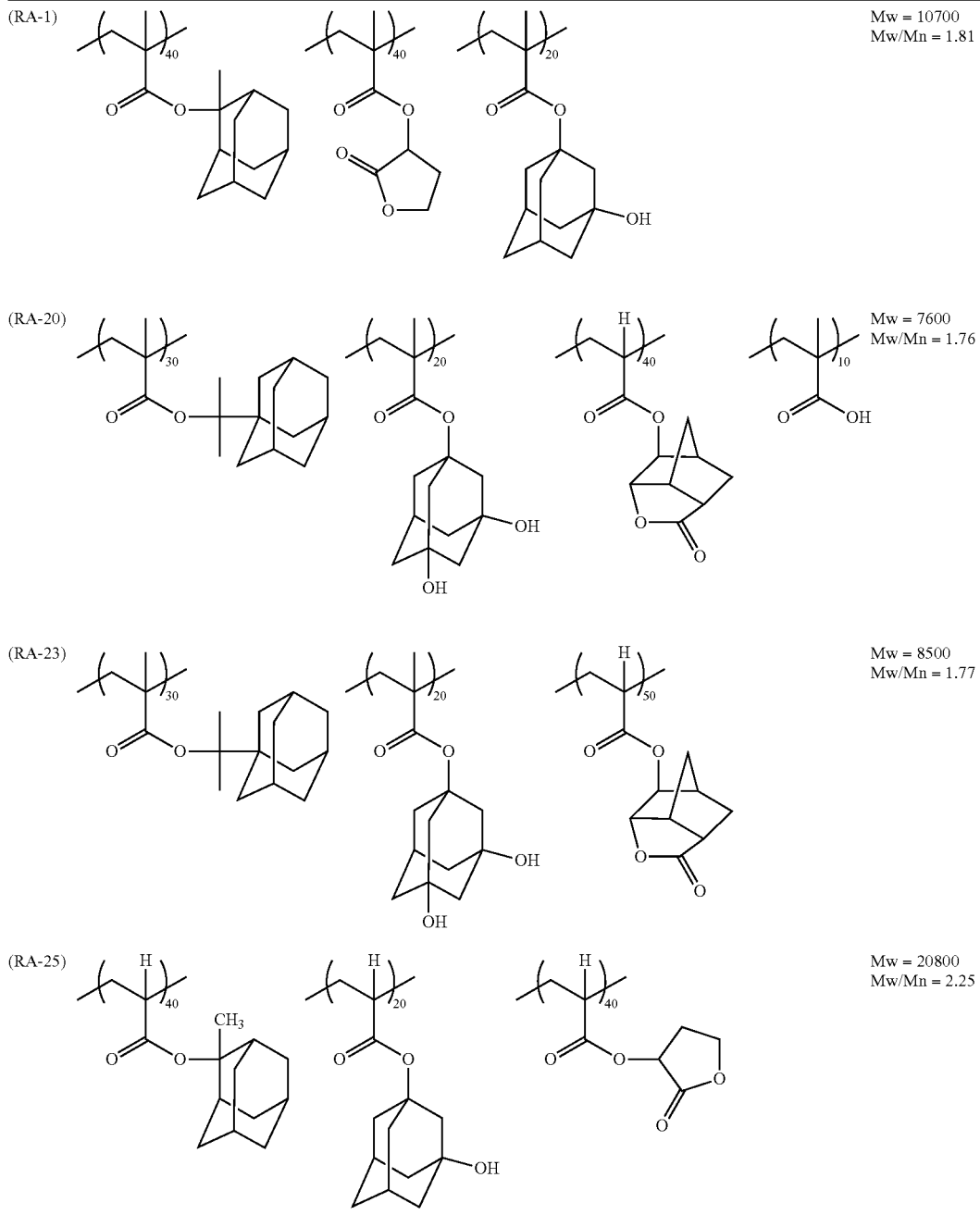

It is apparent from the results of Table 3 that in the application of ArF exposure, the composition according to the present invention excels in the sensitivity, resolution, LER, pattern configuration and aging stability. That is, it is apparent that the photosensitive composition according to the present obtaining a resist film. The obtained resist film was exposed through a 6% half-tone mask of 55 nm 1:1 line and space pattern by means of an ArF excimer laser liquid-immersion scanner (manufactured by ASML, XT1700i, NA 1.20, C-Quad, outer sigma 0.981, inner sigma 0.895, XY deflection). It was ascertained that in all of the sensitivity, resolution (γ), LER, pattern configuration and aging stability, the same evaluation results were obtained on the obtained pattern.

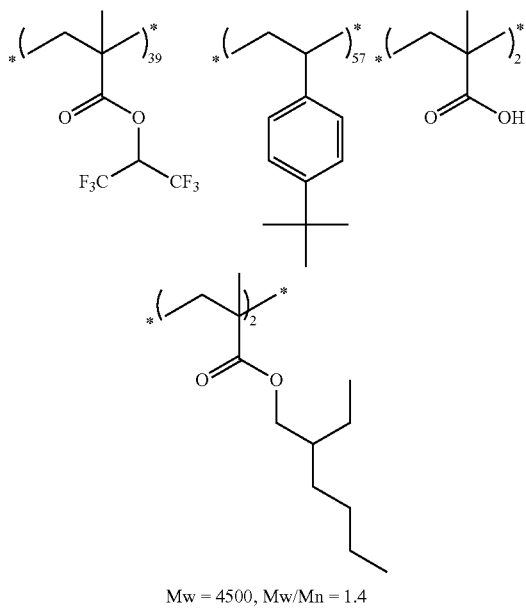

Mw = 4500, Mw/Mn = 1.4

Example C

Examples 10 to 20C and Comparative Examples 10 to 6C

Preparation of Resist

Referring to Table 4 below, with respect to each of the resists, the individual components were dissolved in the solvent and passed through a polytetrafluoroethylene filter of 0.1 μm pore size, thereby obtaining a positive resist solution of 4.5 mass % solid content.

<Evaluation of Resist>

Each of the obtained positive resist solutions was uniformly applied onto a silicon substrate having undergone a hexamethyldisilazane treatment by means of a spin coater, and heated and dried on a hot plate at 100° C. for 90 seconds, thereby obtaining a 0.4 μm resist film.

The obtained resist film was patternwise exposed through a line-and-space mask by means of a KrF excimer laser stepper (NA=0.63). Immediately after the exposure, the resist film was baked on a hot plate at 110° C. for 90 seconds. Thereafter, the resist film was developed with a 2.38 mass % aqueous tetramethylammonium hydroxide solution at 23° C. for 60 seconds, rinsed with pure water for 30 seconds and dried. Thus, an intended line pattern was obtained.

[Sensitivity, Resolution (γ)]

The sensitivity and resolution (γ) were determined in the same manner as in Example A.

[Line Edge Roughness (LER)]

A 180 nm line pattern (L/S=1/1) was formed at the exposure amount realizing the above sensitivity. At arbitrary 30 points in a 50 μm region in the longitudinal direction thereof, the distance of actual edges from a reference line on which edges were to be present was measured by means of a scanning electron microscope (model S-9220, manufactured by Hitachi, Ltd.). The standard deviation of measured distances was determined, and 3σ was computed.

[Configuration of Pattern]

The optimum exposure amount was defined as the exposure amount that reproduced a line-and-space (L/S=1/1) mask pattern of 180 nm line width. The profile at the optimum exposure amount was observed by means of a scanning electron microscope (SEM).

[Aging Stability]

The aging stability was evaluated in the same manner as in Example A.

The obtained evaluation results are given in Table 4 below.

TABLE 4

(KrF; positive)

| Ex. | Photoacid generator | Acid amplifier | Resin (9.7 g) | Basic compound (0.02 g) | Surfactant (0.1 mass %) | Solvent (mass ratio) | Sensitivity (mJ/cm$^2$) | γ | LER (nm) | Pattern configuration | Aging stability |
|---|---|---|---|---|---|---|---|---|---|---|---|
| 1C | z7 (0.3 g) | 1 (0.3 g) | R-18 | C-1 | W-1 | A1/B1 (6/4) | 18.0 | 6.3 | 4.3 | Rectangular | ○ |
| 2C | z7 (0.3 g) | 2 (0.3 g) | R-18 | C-1 | W-1 | A2/B2 (6/4) | 18.0 | 6.3 | 4.2 | Rectangular | ○ |
| 3C | z7 (0.3 g) | 3 (0.3 g) | R-18 | C-1 | W-2 | A3/B1 (6/4) | 20.0 | 6.1 | 4.2 | Rectangular | ○ |
| 4C | z7 (0.3 g) | 5 (0.3 g) | R-18 | C-1 | W-3 | A4/B1 (6/4) | 21.0 | 6.0 | 4.2 | Rectangular | ○ |
| 5C | z7 (0.3 g) | 6 (0.3 g) | R-18 | C-1 | W-1 | A1/B2 (6/4) | 21.0 | 6.0 | 4.2 | Rectangular | ○ |
| 6C | z7 (0.3 g) | 9 (0.3 g) | R-18 | C-1 | W-1 | A1/B1 (6/4) | 20.0 | 6.0 | 4.2 | Rectangular | ○ |
| 7C | z7 (0.3 g) | 10 (0.3 g) | R-18 | C-1 | W-4 | A1/B1 (6/4) | 25.0 | 5.5 | 4.9 | Rectangular | ○ |
| 8C | z7 (0.1 g) z35 (0.2 g) | 11 (0.3 g) | R-18 | C-1 | W-4 | A1/B1 (6/4) | 25.3 | 5.5 | 4.9 | Rectangular | ○ |
| 9C | z7 (0.3 g) | 12 (0.3 g) | R-18 (4.0 g) R-10 (5.6 g) | C-1 | W-1 | A1/B1 (6/4) | 25.0 | 5.2 | 4.8 | Rectangular | ○ |
| 10C | z7 (0.3 g) | 14 (0.3 g) | R-18 | C-1 | W-1 | A1/B1 (6/4) | 25.0 | 5.2 | 4.8 | Rectangular | ○ |
| 11C | z7 (0.3 g) | 1 (0.3 g) | R-17 | C-1 | W-2 | B1 | 20.0 | 6.0 | 4.5 | Rectangular | ○ |
| 12C | z7 (0.3 g) | 1 (0.3 g) | R-2 | C-1 | W-3 | A1/B1 (6/4) | 18.0 | 6.5 | 4.3 | Rectangular | ○ |
| 13C | z7 (0.3 g) | 1 (0.3 g) | R-10 | C-1 | W-1 | A1/B1 (6/4) | 20.4 | 6.5 | 4.0 | Rectangular | ○ |
| 14C | z83 (0.3 g) | 7 (0.3 g) | R-18 | C-1 | W-1 | A1/B1 (6/4) | 20.2 | 5.0 | 4.5 | Rectangular | ○ |
| 15C | z88 (0.5 g) | 1 (0.1 g) | R-18 | C-1 | W-1 | A1/B1 (6/4) | 20.2 | 5.0 | 4.5 | Rectangular | ○ |
| 16C | z2 (0.3 g) | 1 (0.3 g) | R-18 | C-1 | W-1 | A1/B1 (6/4) | 18.0 | 6.3 | 4.5 | Rectangular | ○ |
| 17C | z7 (0.3 g) | 4 (0.3 g) | R-18 | C-1 | W-1 | A1/B1 (6/4) | 20.0 | 6.0 | 4.2 | Rectangular | ○ |
| 18C | z7 (0.3 g) | 15 (0.3 g) | R-18 | C-1 | W-1 | A1/B1 (6/4) | 23.0 | 6.0 | 4.5 | Rectangular | ○ |
| 19C | z7 (0.3 g) | 16 (0.3 g) | R-18 | C-1 | W-1 | A1/B1 (6/4) | 23.0 | 6.0 | 4.5 | Rectangular | ○ |
| 20C | z44 (0.3 g) | 17 (0.3 g) | R-18 | C-1 | W-1 | A1/B1 (6/4) | 25.0 | 6.0 | 4.7 | Rectangular | ○ |
| Compar. 1C | z7 (0.3 g) | Compar. 1 (0.3 g) | R-2 | C-1 | W-1 | A1/B1 (6/4) | 30.5 | 4.5 | 6.5 | Tapered | Δ |

TABLE 4-continued (KrF; positive)

| Ex. | Photoacid generator | Acid amplifier | Resin (9.7 g) | Basic compound (0.02 g) | Surfactant (0.1 mass %) | Solvent (mass ratio) | Sensitivity (mJ/cm$^2$) | γ | LER (nm) | Pattern configuration | Aging stability |
|---|---|---|---|---|---|---|---|---|---|---|---|
| Compar. 2C | z7 (0.3 g) | Compar. 2 (0.3 g) | R-2 | C-1 | W-1 | A1/B1 (6/4) | 30.0 | 4.5 | 7.5 | Tapered | Δ |
| Compar. 3C | z7 (0.3 g) | Compar. 3 (0.4 g) | R-2 | C-1 | W-1 | A1/B1 (6/4) | 33.2 | 4.2 | 7.2 | Tapered | x |
| Compar. 4C | z7 (0.3 g) | Compar. 4 (0.4 g) | R-2 | C-1 | W-1 | A1/B1 (6/4) | 33.2 | 4.2 | 7.2 | Tapered | x |
| Compar. 5C | z7 (0.3 g) | Compar. 5 (0.4 g) | R-2 | C-1 | W-1 | A1/B1 (6/4) | 33.0 | 4.2 | 7.2 | Tapered | x |
| Compar. 6C | z7 (0.3 g) | None | R-2 | C-1 | W-1 | A1/B1 (6/4) | 35.0 | 4.2 | 7.2 | Tapered | ○ |

The photoacid generator, acid amplifier, basic compound, surfactant and solvent were appropriately selected from among those set forth hereinbefore and used.

The resin was appropriately selected from among the resins (R-1) to (R-27) set forth hereinbefore by way of example and used. With respect to each of the resins (R-2), (R-10), (R-14), (R-17), (R-18), (R-18(H)), (R-18(L)), (R-22), (R-23) and (R-27) appearing in Table 4 and the following tables, the molar ratio of individual repeating units and the weight average molecular weight (Mw), and the diversity (Mw/Mn) are given in Table 5 below.

TABLE 5

| Resin | Molar ratio | Mw | Mw/Mn |
|---|---|---|---|
| R-2 | 60/20/20 | 12000 | 1.7 |
| R-10 | 70/30 | 11000 | 1.6 |
| R-14 | 15/60/25 | 12000 | 1.5 |
| R-17 | 80/20 | 15000 | 1.8 |
| R-18 | 65/35 | 9000 | 1.7 |
| R-18(H) | 60/40 | 10000 | 1.9 |
| R-18(L) | 60/40 | 4000 | 1.2 |
| R-22 | 70/30 | 10000 | 1.9 |
| R-23 | 65/35 | 11000 | 1.6 |
| R-27 | 50/40/10 | 12000 | 1.8 |

It is apparent from the results of Table 4 that in the application of KrF exposure, the composition according to the present invention excels in the sensitivity, resolution, LER, pattern configuration and aging stability. That is, it is apparent that the photosensitive composition according to the present invention can also exhibit excellent performance as a positive resist composition exposed to an KrF excimer laser.

Example D

Examples 1D to 29D and Comparative Examples 1D to 6D

Preparation of Resist

Referring to Table 6 below, with respect to each of the resists, the individual components were dissolved in the solvent and passed through a polytetrafluoroethylene filter of 0.1 μm pore size, thereby obtaining a positive resist solution of 4.0 mass % solid content.

(Evaluation of Resist)

Each of the prepared positive resist solutions was uniformly applied onto a silicon substrate having undergone a hexamethyldisilazane treatment by means of a spin coater, and heated and dried on a hot plate at 100° C. for 60 seconds, thereby obtaining a 0.12 μm-thick resist film.

Each of the resist films was irradiated with electron beams by means of an electron beam projection lithography system (acceleration voltage 100 KeV) manufactured by Nikon Corporation. Immediately after the irradiation, the film was baked on a hot plate at 110° C. for 90 seconds. Thereafter, the baked film was developed with a 2.38 mass % aqueous tetramethylammonium hydroxide solution at 23° C. for 60 seconds. After the development, the film was rinsed with pure water for 30 seconds and dried. Thus, a line-and-space pattern was formed.

[Sensitivity]

Each of the obtained patterns was observed by means of a scanning electron microscope (model S-9220 manufactured by Hitachi, Ltd.). The sensitivity (Eo) was defined as the electron beam irradiation amount in which a line and space (L/S=1/1) of 0.10 μm line width was resolved.

[Resolving Power]

The resolving power (dense) was defined as the limiting resolving power (minimum line width at which the line and space were separated and resolved from each other) of 1:1 line space in the exposure amount exhibiting the above sensitivity (Eo).

[Line Edge Roughness (LER)]

LER was determined in the same manner as in Example A.

[Configuration of Pattern]

The optimum exposure amount was defined as the exposure amount that reproduced a line-and-space (L/S=1/1) mask pattern of 50 nm line width. The profile at the optimum exposure amount was observed by means of a scanning electron microscope (SEM).

[Outgas Performance: Ratio of Change in Film Thickness By Exposure]

Exposure to electron beams was carried out in the exposure amount equal to 2.0 times the exposure amount realizing the above sensitivity. The film thickness after the exposure but before postbake was measured, and the ratio of change from the film thickness before the exposure was calculated by the following formula.

Ratio of change in film thickness (%)=[(film thickness before exposure−film thickness after exposure)/ (film thickness before exposure)]×100.

[Aging Stability]

Each of the compositions was stored at room temperature for a month. The degree of sensitivity change between before the storage and after the storage was evaluated by visual inspection. The evaluation was effected on the following judgment criteria.

(Judgment Criteria)

○ (Good): when the sensitivity change was less than 1 μC/cm²,

Δ (Fair): when the sensitivity change was in the range of 1 to 3 μC/cm², and x (Insufficient): when the sensitivity change was greater than 3 μC/cm².

These evaluation results are given in Table 6 below.

TABLE 6

(EB; positive)

| Ex. | Photoacid generator | Acid amplifier | Resin (9.7 g) | Basic compound (0.02 g) | Surfactant (0.1 mass %) | Solvent (mass ratio) | Sensitivity (μC/cm²) | Pattern configuration | LER (nm) | Ratio of change in film thickness (%) | Aging stability |
|---|---|---|---|---|---|---|---|---|---|---|---|
| 1D | z7 (0.3 g) | 1 (0.3 g) | R-18 (H) | C-2 | W-1 | A1/B1 (6/4) | 10.3 | Rectangular | 4.3 | 1.8 | ○ |
| 2D | z94 (0.3 g) | 2 (0.3 g) | R-18 (H) | C-2 | W-1 | A1/B1 (6/4) | 10.5 | Rectangular | 4.1 | 1.3 | ○ |
| 3D | z95 (0.3 g) | 3 (0.3 g) | R-18 (H) | C-2 | W-1 | A1/B1 (6/4) | 10.5 | Rectangular | 4.2 | 1.5 | ○ |
| 4D | z96 (0.3 g) | 4 (0.3 g) | R-18 (H) | C-1 | W-1 | A1/B1 (6/4) | 10.0 | Rectangular | 4.4 | 1.7 | ○ |
| 5D | z97 (0.3 g) | 5 (0.3 g) | R-18 (H) | C-2 | W-1 | A1/B1 (6/4) | 10.1 | Rectangular | 4.3 | 1.5 | ○ |
| 6D | z7 (0.3 g) | 6 (0.3 g) | R-18 (H) | C-2 | W-1 | A1/B1 (6/4) | 10.2 | Rectangular | 4.5 | 1.5 | ○ |
| 7D | z95 (0.3 g) | 7 (0.3 g) | R-18 (H) | C-2 | W-1 | A1/B1 (6/4) | 10.1 | Rectangular | 4.5 | 1.5 | ○ |
| 8D | z7 (0.3 g) | 8 (0.3 g) | R-18 (H) | C-2 | W-1 | A1/B1 (6/4) | 10.3 | Rectangular | 4.4 | 1.4 | ○ |
| 9D | z96 (0.3 g) | 9 (0.3 g) | R-18 (H) | C-2 | W-1 | A1/B1 (6/4) | 10.2 | Rectangular | 4.3 | 1.6 | ○ |
| 10D | z97 (0.3 g) | 10 (0.3 g) | R-18 (H) | C-2 | W-1 | A1/B1 (6/4) | 15.3 | Rectangular | 5.0 | 1.7 | ○ |
| 11D | z7 (0.3 g) | 11 (0.3 g) | R-18 (H) | C-2 | W-1 | A1/B1 (6/4) | 15.5 | Rectangular | 4.8 | 1.8 | ○ |
| 12D | z97 (0.3 g) | 12 (0.3 g) | R-18 (H) | C-2 | W-1 | A1/B1 (6/4) | 15.2 | Rectangular | 4.9 | 1.6 | ○ |
| 13D | z94 (0.3 g) | 14 (0.3 g) | R-18 (H) | C-2 | W-1 | A1/B1 (6/4) | 15.5 | Rectangular | 4.9 | 1.0 | ○ |
| 14D | z94 (0.3 g) | 1 (0.3 g) | R-14 | C-2 | W-1 | A1/B1 (6/4) | 10.2 | Rectangular | 4.1 | 1.5 | ○ |
| 15D | z94 (0.3 g) | 1 (0.3 g) | R-17 | C-2 | W-1 | A1/B1 (6/4) | 10.5 | Rectangular | 4.2 | 1.7 | ○ |
| 16D | z7 (0.3 g) | 1 (0.3 g) | R-18 (L) | C-2 | W-1 | A1/B1 (6/4) | 10.4 | Rectangular | 3.5 | 1.6 | ○ |
| 17D | z7 (0.3 g) | 1 (0.3 g) | R-2 | C-2 | W-1 | A1/B1 (6/4) | 10.2 | Rectangular | 4.0 | 1.6 | ○ |
| 18D | z63 (0.3 g) | 1 (0.3 g) | R-22 | C-2 | W-1 | A1/B1 (6/4) | 10.5 | Rectangular | 4.2 | 1.6 | ○ |
| 19D | z56 (0.3 g) | 6 (0.3 g) | R-23 | C-2 | W-1 | A1/B1 (6/4) | 10.3 | Rectangular | 4.9 | 1.5 | ○ |
| 20D | z89 (0.3 g) | 6 (0.3 g) | R-27 | C-2 | W-1 | A1/B1 (6/4) | 10.2 | Rectangular | 4.9 | 1.5 | ○ |
| 21D | z63 (0.3 g) | 8 (0.3 g) | R-27 | C-2 | W-1 | A1/B1 (6/4) | 10.2 | Rectangular | 4.8 | 1.5 | ○ |
| 22D | z7 (0.5 g) | 1 (0.1 g) | R-18 (H) | C-2 | W-1 | A1/B1 (6/4) | 13.3 | Rectangular | 4.5 | 1.8 | ○ |
| 23D | z7 (0.3 g) | 14 (0.3 g) | R-18 (H) | C-2 | W-1 | A1/B1 (6/4) | 15.6 | Rectangular | 4.8 | 1.8 | Δ |
| 24D | z7 (0.3 g) | 15 (0.3 g) | R-18 (H) | C-2 | W-1 | A1/B1 (6/4) | 14.7 | Rectangular | 4.8 | 1.9 | ○ |
| 25D | z7 (0.3 g) | 16 (0.3 g) | R-18 (H) | C-2 | W-1 | A1/B1 (6/4) | 14.3 | Rectangular | 4.8 | 1.8 | ○ |
| 26D | z7 (0.3 g) | 17 (0.3 g) | R-18 (H) | C-2 | W-1 | A1/B1 (6/4) | 15.3 | Rectangular | 5.0 | 1.8 | ○ |
| 27D | z7 (0.1 g) z55 (0.2 g) | 1 (0.3 g) | R-18 (H) | C-2 | W-1 | A1/B1 (6/4) | 14.7 | Rectangular | 4.8 | 1.8 | ○ |
| 28D | z7 (0.3 g) | 1 (0.3 g) | R-22 (4.0 g) R-27 (5.7 g) | C-2 | W-1 | B1 | 14.9 | Rectangular | 4.8 | 1.8 | ○ |
| 29D | z7 (0.3 g) | 1 (0.1 g) 6 (0.2 g) | R-22 (4.0 g) R-27 (5.7 g) | C-2 | W-1 | B1 | 14.8 | Rectangular | 4.9 | 1.8 | ○ |
| Compar. 1D | z7 (0.3 g) | Compar. 1 (0.3 g) | R-2 | C-1 | W-1 | A1/B1 (6/4) | 20.8 | Tapered | 7.0 | 1.9 | Δ |
| Compar. 2D | z7 (0.3 g) | Compar. 2 (0.3 g) | R-2 | C-1 | W-1 | A1/B1 (6/4) | 20.9 | Tapered | 7.0 | 1.8 | Δ |
| Compar. 3D | z7 (0.3 g) | Compar. 3 (0.3 g) | R-2 | C-1 | W-1 | A1/B1 (6/4) | 25.2 | Tapered | 7.0 | 1.9 | x |
| Compar. 4D | z7 (0.3 g) | Compar. 4 (0.3 g) | R-2 | C-1 | W-1 | A1/B1 (6/4) | 25.1 | Tapered | 6.9 | 1.9 | x |
| Compar. 5D | z7 (0.3 g) | Compar. 5 (0.3 g) | R-2 | C-1 | W-1 | A1/B1 (6/4) | 26.0 | Tapered | 6.8 | 1.9 | x |
| Compar. 6D | z7 (0.3 g) | None | R-2 | C-1 | W-1 | A1/B1 (6/4) | 30.1 | Tapered | 7.2 | 1.9 | ○ |

It is apparent from the results of Table 6 that in the exposure to electron beams, the composition according to the present invention excels in the sensitivity, resolution, LER, outgas performance and aging stability. That is, it is apparent that the photosensitive composition according to the present invention can also exhibit excellent performance as a positive resist composition exposed to electron beams.

Example E

Examples 1E to 16E and Comparative Examples 1E to 6E

Preparation of Resist

Referring to Table 7 below, with respect to each of the resists, the individual components were dissolved in the solvent and passed through a polytetrafluoroethylene filter of 0.1 μm pore size, thereby obtaining a negative resist solution of 12 mass % solid content.

(Evaluation of Resist)

Each of the prepared negative resist solutions was uniformly applied onto a silicon substrate having undergone a hexamethyldisilazane treatment by means of a spin coater, and heated and dried on a hot plate at 120° C. for 60 seconds, thereby obtaining a 0.3 μm-thick resist film.

Each of the resist films was irradiated with electron beams by means of an electron beam projection lithography system (acceleration voltage 100 KeV) manufactured by Nikon Corporation. Immediately after the irradiation, the film was baked on a hot plate at 110° C. for 90 seconds. Thereafter, the baked film was developed with a 2.38 mass % aqueous tetramethylammonium hydroxide solution at 23° C. for 60 seconds. After the development, the film was rinsed with pure water for 30 seconds and dried. Thus, a line-and-space pattern was formed.

Evaluation was conducted in the same manner as in Example D. The evaluation results are given in Table 7.

TABLE 7

| | (EB; negative) | | | | | | | | | | | |
|---|---|---|---|---|---|---|---|---|---|---|---|---|
| Ex. | Photoacid generator | Acid amplifier | Resin (9.7 g) | Cross-linking agent (3.0 g) | Basic Compound (0.02 g) | Surfactant (0.1 mass %) | Solvent (mass ratio) | Sensitivity (μC/cm²) | Pattern configuration | LER (nm) | Ratio of change in film thickness (%) | Aging stability |
| 1E | z7 (0.3 g) | 1 (0.3 g) | P-3 | CL-1 | C-1 | W-1 | A1/B1 (6/4) | 13.8 | Rectangular | 4.5 | 1.8 | ○ |
| 2E | z7 (0.3 g) | 2 (0.3 g) | P-3 | CL-1 | C-1 | W-2 | A2/B2 (6/4) | 13.8 | Rectangular | 4.6 | 1.8 | ○ |
| 3E | z2 (0.3 g) | 3 (0.3 g) | P-3 | CL-1 | C-1 | W-3 | A3/B1 (6/4) | 13.7 | Rectangular | 4.4 | 1.5 | ○ |
| 4E | z55 (0.3 g) | 4 (0.3 g) | P-3 | CL-1 | C-1 | W-1 | A4/B1 (6/4) | 13.8 | Rectangular | 4.6 | 1.5 | ○ |
| 5E | z63 (0.3 g) | 9 (0.3 g) | P-3 | CL-1 | C-1 | W-3 | A1/B2 (6/4) | 13.9 | Rectangular | 4.2 | 1.7 | ○ |
| 6E | z70 (0.3 g) | 10 (0.3 g) | P-3 | CL-1 | C-1 | W-2 | A1/B1 (6/4) | 16.8 | Rectangular | 5.1 | 1.7 | ○ |
| 7E | z7 (0.3 g) | 11 (0.3 g) | P-3 | CL-1 | C-1 | W-4 | A1/B1 (6/4) | 17.8 | Rectangular | 5.0 | 1.5 | ○ |
| 8E | z94 (0.3 g) | 12 (0.3 g) | P-3 | CL-1 | C-1 | W-4 | A1/B1 (6/4) | 16.8 | Rectangular | 5.0 | 1.5 | ○ |
| 9E | z97 (0.3 g) | 14 (0.3 g) | P-2 | CL-1 | C-1 | W-1 | A1/B1 (6/4) | 17.3 | Rectangular | 5.0 | 1.8 | ○ |
| 10E | z7 (0.3 g) | 1 (0.3 g) | P-1 | CL-1 | C-1 | W-1 | A1/B1 (6/4) | 14.2 | Rectangular | 4.5 | 1.5 | ○ |
| 11E | z98 (0.3 g) | 1 (0.3 g) | P-3 | CL-2 | C-1 | W-1 | A1/B1 (6/4) | 13.5 | Rectangular | 4.4 | 1.5 | ○ |
| 12E | z95 (0.3 g) | 7 (0.3 g) | P-3 | CL-3 | C-1 | W-1 | A1/B1 (6/4) | 13.5 | Rectangular | 4.5 | 1.5 | ○ |
| 13E | z23 (0.3 g) | 1 (0.3 g) | P-3 | CL-1 | C-2 | W-1 | A1/B1 (6/4) | 13.0 | Rectangular | 4.4 | 1.5 | ○ |
| 14E | z23 (0.3 g) | 6 (0.15 g) | P-3 | CL-1 | C-2 | W-2 | A1/B1 (6/4) | 13.8 | Rectangular | 4.7 | 1.7 | ○ |
| 15E | z23 (0.3 g) | 17 (0.15 g) | P-3 | CL-1 | C-2 | W-2 | A1/B1 (6/4) | 13.7 | Rectangular | 4.7 | 1.7 | ○ |
| 16E | z23 (0.1 g) z95 (0.2 g) | 1 (0.15 g) | P-3 | CL-1 | C-2 | W-2 | A1/B1 (6/4) | 13.9 | Rectangular | 4.8 | 1.7 | ○ |
| Compar. 1E | z7 (0.3 g) | Compar. 1 (0.3 g) | P-1 | CL-1 | C-1 | W-1 | A1/B1 (6/4) | 29.8 | Tapered | 8.8 | 1.9 | Δ |
| Compar. 2E | z7 (0.3 g) | Compar. 2 (0.3 g) | P-1 | CL-1 | C-1 | W-1 | A1/B1 (6/4) | 29.8 | Tapered | 8.9 | 2.0 | Δ |
| Compar. 3E | z7 (0.3 g) | Compar. 3 (0.3 g) | P-1 | CL-1 | C-1 | W-1 | A1/B1 (6/4) | 30.2 | Tapered | 8.9 | 1.9 | x |
| Compar. 4E | z7 (0.3 g) | Compar. 4 (0.3 g) | P-1 | CL-1 | C-1 | W-1 | A1/B1 (6/4) | 29.8 | Tapered | 8.0 | 2.0 | x |
| Compar. 5E | z7 (0.3 g) | Compar. 5 (0.3 g) | P-1 | CL-1 | C-1 | W-1 | A1/B1 (6/4) | 29.8 | Tapered | 8.0 | 1.8 | x |
| Compar. 6E | z7 (0.3 g) | None | P-1 | CL-1 | C-1 | W-1 | A1/B1 (6/4) | 33.8 | Tapered | 8.1 | 1.9 | ○ |

The structures, molecular weights and molecular weight distributions of employed alkali-soluble resins are shown below. Also, the structures of employed acid crosslinking agents are shown below.

|  |  | Mw | Mw/Mn |
|---|---|---|---|
| P-1 | 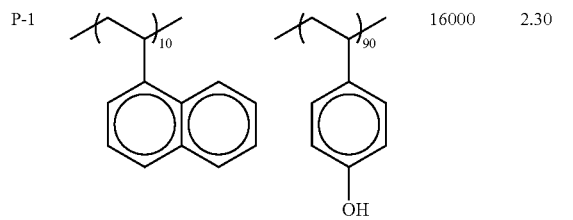 | 16000 | 2.30 |
| P-2 | 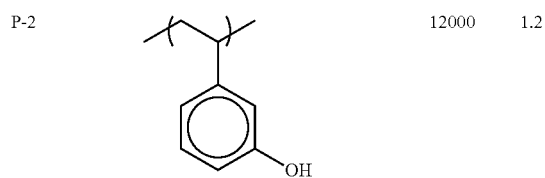 | 12000 | 1.2 |
| P-3 | 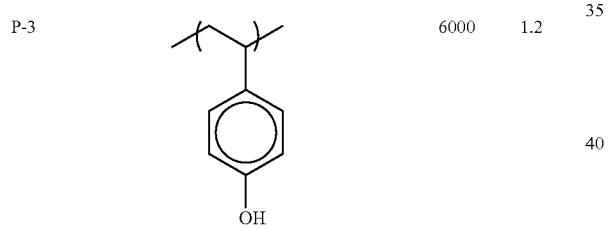 | 6000 | 1.2 |
|  | VP-5000, provided by Nihon-Sotatsu |  |  |

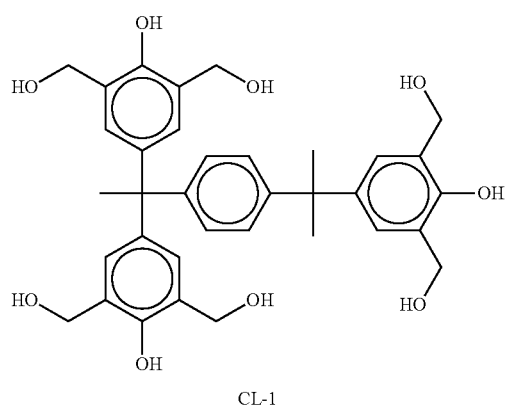

CL-1

-continued

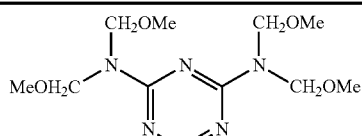

CL-2

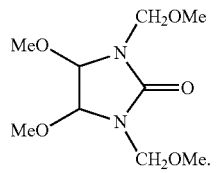

CL-3

It is apparent from the results of Table 7 that in the exposure to electron beams, the composition according to the present invention excels in the sensitivity, resolution, LER, outgas performance and aging stability. That is, it is apparent that the photosensitive composition according to the present invention can also exhibit excellent performance as a negative resist composition exposed to electron beams.

Example F

Examples 1F to 25F and Comparative Examples 1F to 6F

Preparation of Resist

Referring to Table 8 below, with respect to each of the resists, the individual components were dissolved in the solvent and passed through a polytetrafluoroethylene filter of 0.1 µm pore size, thereby obtaining a positive resist solution of 8 mass % solid content.

(Evaluation of Resist)

Each of the prepared positive resist solutions was uniformly applied onto a silicon substrate having undergone a hexamethyldisilazane treatment by means of a spin coater, and heated and dried on a hot plate at 100° C. for 60 seconds, thereby obtaining a 0.12 µm-thick resist film.

[Sensitivity]

The surface exposure of each of the obtained resist films was carried out using EUV light (wavelength 13 nm) while changing the exposure amount by 0.5 mJ/cm² at a time within the range of 0 to 10.0 mJ/cm². The exposed film was baked at 110° C. for 90 seconds. Thereafter, using a 2.38 mass % aqueous tetramethylammonium hydroxide (TMAH) solution, the dissolution rate at each exposure amount was measured, thereby obtaining a dissolution rate curve.

[Configuration of Pattern]

The optimum exposure amount was defined as the exposure amount that reproduced a line-and-space (L/S=1/1) mask pattern of 50 nm line width. The profile at the optimum exposure amount was observed by means of a scanning electron microscope (SEM).

[Line Edge Roughness (LER)]

A 50 nm line pattern (L/S=1/1) was formed at the exposure amount realizing the above sensitivity. At arbitrary 30 points in a 50 μm region in the longitudinal direction thereof, the distance of actual edges from a reference line on which edges were to be present was measured by means of a scanning electron microscope (model S-9220, manufactured by Hitachi, Ltd.). The standard deviation of measured distances was determined, and 3σ was computed.

[Outgas Performance: Ratio of Change in Film Thickness by Exposure]

The ratio of change in film thickness by exposure to EUV light was determined in the same manner as in Example D.

[Aging Stability]

The aging stability was evaluated in the same manner as in Example A.

The obtained evaluation results are given in Table 8 below.

exhibit excellent performance as a positive resist composition exposed to EUV.

Example G

Examples 1G to 8G and Comparative Examples 1G to 6G

Preparation of Resist

Referring to Table 9 below, with respect to each of the resists, the individual components were dissolved in the solvent and passed through a polytetrafluoroethylene filter of 0.1 μm pore size, thereby obtaining a negative resist solution of 8 mass % solid content. The negative resist solution was evaluated in the following manner.

(Evaluation of Resist)

Each of the prepared negative resist solutions was uniformly applied onto a silicon substrate having undergone a

TABLE 8

(EUV; positive)

| Ex. | Photoacid generator | Acid amplifier | Resin (9.7 g) | Basic compound (0.02 g) | Surfactant (0.1 mass %) | Solvent (mass ratio) | Sensitivity ($\mu C/cm^2$) | Pattern configuration | LER (nm) | Ratio of change in film thickness (%) | Aging stability |
|---|---|---|---|---|---|---|---|---|---|---|---|
| 1F | z7 (0.3 g) | 1 (0.3 g) | R-18 (H) | C-2 | W-1 | A1/B1 (6/4) | 12.3 | Rectangular | 5.0 | 1.8 | ○ |
| 2F | z94 (0.3 g) | 2 (0.3 g) | R-18 (H) | C-2 | W-1 | A1/B1 (6/4) | 12.5 | Rectangular | 4.8 | 1.3 | ○ |
| 3F | z95 (0.3 g) | 3 (0.3 g) | R-18 (H) | C-2 | W-1 | A1/B1 (6/4) | 12.5 | Rectangular | 5.0 | 1.5 | ○ |
| 4F | z96 (0.3 g) | 4 (0.3 g) | R-18 (H) | C-1 | W-1 | A1/B1 (6/4) | 12.0 | Rectangular | 5.1 | 1.5 | Δ |
| 5F | z97 (0.3 g) | 5 (0.3 g) | R-18 (H) | C-2 | W-1 | A1/B1 (6/4) | 13.1 | Rectangular | 5.1 | 3.5 | ○ |
| 6F | z7 (0.3 g) | 6 (0.3 g) | R-18 (H) | C-2 | W-1 | A1/B1 (6/4) | 12.2 | Rectangular | 5.1 | 1.5 | ○ |
| 7F | z7 (0.3 g) | 7 (0.3 g) | R-18 (H) | C-2 | W-1 | A1/B1 (6/4) | 12.1 | Rectangular | 5.2 | 1.5 | ○ |
| 8F | z94 (0.3 g) | 8 (0.3 g) | R-18 (H) | C-2 | W-1 | A1/B1 (6/4) | 12.3 | Rectangular | 5.1 | 1.4 | Δ |
| 9F | z94 (0.3 g) | 9 (0.3 g) | R-18 (H) | C-2 | W-1 | A1/B1 (6/4) | 12.2 | Rectangular | 5.0 | 1.6 | ○ |
| 10F | z94 (0.3 g) | 10 (0.3 g) | R-18 (H) | C-2 | W-1 | A1/B1 (6/4) | 15.3 | Rectangular | 5.6 | 1.5 | ○ |
| 11F | z94 (0.3 g) | 11 (0.3 g) | R-18 (H) | C-2 | W-1 | A1/B1 (6/4) | 15.5 | Rectangular | 5.7 | 1.8 | ○ |
| 12F | z94 (0.3 g) | 12 (0.3 g) | R-18 (H) | C-2 | W-1 | A1/B1 (6/4) | 15.2 | Rectangular | 5.6 | 1.5 | ○ |
| 13F | z94 (0.3 g) | 14 (0.3 g) | R-18 (H) | C-2 | W-1 | A1/B1 (6/4) | 15.2 | Rectangular | 5.9 | 1.5 | ○ |
| 14F | z94 (0.3 g) | 1 (0.3 g) | R-14 | C-2 | W-1 | A1/B1 (6/4) | 13.2 | Rectangular | 5.1 | 1.5 | ○ |
| 15F | z94 (0.3 g) | 1 (0.3 g) | R-17 | C-2 | W-1 | A1/B1 (6/4) | 13.4 | Rectangular | 5.2 | 1.5 | ○ |
| 16F | z7 (0.3 g) | 1 (0.3 g) | R-18 (L) | C-2 | W-1 | A1/B1 (6/4) | 11.4 | Rectangular | 4.5 | 1.6 | ○ |
| 17F | z94 (0.3 g) | 1 (0.3 g) | R-2 | C-2 | W-1 | A1/B1 (6/4) | 12.2 | Rectangular | 5.0 | 1.9 | ○ |
| 18F | z63 (0.3 g) | 1 (0.3 g) | R-22 | C-2 | W-1 | A1/B1 (6/4) | 13.2 | Rectangular | 6.2 | 1.9 | ○ |
| 19F | z73 (0.3 g) | 7 (0.3 g) | R-23 | C-2 | W-1 | A1/B1 (6/4) | 13.2 | Rectangular | 6.1 | 1.9 | ○ |
| 20F | z55 (0.3 g) | 7 (0.3 g) | R-27 | C-2 | W-1 | A1/B1 (6/4) | 13.2 | Rectangular | 6.0 | 1.5 | ○ |
| 21F | z89 (0.3 g) | 8 (0.3 g) | R-27 | C-2 | W-1 | A1/B1 (6/4) | 13.2 | Rectangular | 6.0 | 1.5 | ○ |
| 22F | z7 (0.5 g) | 1 (0.1 g) | R-18 (H) | C-2 | W-1 | A1/B1 (6/4) | 14.3 | Rectangular | 5.0 | 1.8 | ○ |
| 23F | z94 (0.3 g) | 13 (0.3 g) | R-18 (H) | C-2 | W-1 | A1/B1 (6/4) | 15.5 | Rectangular | 4.8 | 1.5 | ○ |
| 24F | z94 (0.3 g) | 15 (0.3 g) | R-18 (H) | C-2 | W-1 | A1/B1 (6/4) | 14.6 | Rectangular | 4.8 | 1.9 | ○ |
| 25F | z94 (0.3 g) | 16 (0.3 g) | R-18 (H) | C-2 | W-1 | A1/B1 (6/4) | 14.3 | Rectangular | 4.8 | 1.8 | ○ |
| Compar. 1F | z7 (0.3 g) | Compar. 1 (0.3 g) | R-2 | C-1 | W-1 | A1/B1 (6/4) | 22.0 | Tapered | 8.0 | 2.1 | Δ |
| Compar. 2F | z7 (0.3 g) | Compar. 2 (0.3 g) | R-2 | C-1 | W-1 | A1/B1 (6/4) | 22.0 | Tapered | 8.0 | 2.0 | Δ |
| Compar. 3F | z7 (0.3 g) | Compar. 3 (0.3 g) | R-2 | C-1 | W-1 | A1/B1 (6/4) | 24.0 | Tapered | 7.0 | 2.1 | x |
| Compar. 4F | z7 (0.3 g) | Compar. 4 (0.3 g) | R-2 | C-1 | W-1 | A1/B1 (6/4) | 24.0 | Tapered | 7.0 | 2.1 | x |
| Compar. 5F | z7 (0.3 g) | Compar. 5 (0.3 g) | R-2 | C-1 | W-1 | A1/B1 (6/4) | 24.0 | Tapered | 7.0 | 2.1 | x |
| Compar. 6F | z7 (0.3 g) | None | R-2 | C-1 | W-1 | A1/B1 (6/4) | 30.0 | Tapered | 7.5 | 2.0 | ○ |

It is apparent from the results of Table 8 that in the exposure to EUV, the composition according to the present invention excels in the sensitivity, resolution, LER, outgas performance and aging stability. That is, it is apparent that the photosensitive composition according to the present invention can also hexamethyldisilazane treatment by means of a spin coater, and heated and dried on a hot plate at 120° C. for 60 seconds, thereby obtaining a 0.15 μm-thick resist film.

The resist films were evaluated in the same manner as in Example F. The results are given in Table 9 below.

TABLE 9

(EUV; negative)

| Ex. | Photoacid generator | Acid amplifier | Resin (10 g) | Cross-linking agent (3.0 g) | Basic compound (0.02 g) | Surfactant (0.1 mass %) | Solvent (mass ratio) | Sensitivity (mJ/cm$^2$) | Pattern configuration | LER (nm) | Ratio of change in film thickness (%) | Aging stability |
|---|---|---|---|---|---|---|---|---|---|---|---|---|
| 1G | z7 (0.3 g) | 1 (0.3 g) | P-3 | CL-1 | C-2 | W-1 | A1/B1 (6/4) | 10.3 | Rectangular | 6.2 | 1.8 | ○ |
| 2G | z7 (0.3 g) | 2 (0.3 g) | P-3 | CL-1 | C-2 | W-2 | A1/B1 (6/4) | 10.8 | Rectangular | 6.0 | 1.5 | ○ |
| 3G | z94 (0.3 g) | 3 (0.3 g) | P-3 | CL-1 | C-2 | W-3 | A1/B1 (6/4) | 10.0 | Rectangular | 7.0 | 1.8 | ○ |
| 4G | z95 (0.3 g) | 4 (0.3 g) | P-3 | CL-2 | C-2 | W-1 | A1/B1 (6/4) | 12.3 | Rectangular | 6.5 | 1.9 | ○ |
| 5G | z55 (0.3 g) | 13 (0.3 g) | P-3 | CL-3 | C-2 | W-1 | A1/B1 (6/4) | 10.3 | Rectangular | 6.2 | 1.0 | ○ |
| 6G | z63 (0.3 g) | 10 (0.3 g) | P-3 | CL-3 | C-2 | W-1 | A1/B1 (6/4) | 15.3 | Rectangular | 6.5 | 1.9 | ○ |
| 7G | z89 (0.3 g) | 11 (0.3 g) | P-3 | CL-3 | C-2 | W-1 | A1/B1 (6/4) | 15.5 | Rectangular | 6.6 | 1.9 | ○ |
| 8G | z2 (0.3 g) | 12 (0.3 g) | P-3 | CL-3 | C-2 | W-1 | A1/B1 (6/4) | 15.3 | Rectangular | 6.7 | 1.9 | ○ |
| Compar. 1G | z7 (0.3 g) | Compar. 1 (0.3 g) | P-1 | CL-1 | C-1 | W-1 | A1/B1 (6/4) | 22.0 | Tapered | 10.1 | 1.9 | Δ |
| Compar. 2G | z7 (0.3 g) | Compar. 2 (0.3 g) | P-1 | CL-1 | C-1 | W-1 | A1/B1 (6/4) | 22.5 | Tapered | 11.3 | 2.0 | Δ |
| Compar. 3G | z7 (0.3 g) | Compar. 3 (0.3 g) | P-1 | CL-1 | C-1 | W-1 | A1/B1 (6/4) | 26.0 | Tapered | 11.1 | 2.0 | x |
| Compar. 4G | z7 (0.3 g) | Compar. 4 (0.3 g) | P-1 | CL-1 | C-1 | W-1 | A1/B1 (6/4) | 27.0 | Tapered | 11.1 | 2.0 | x |
| Compar. 5G | z7 (0.3 g) | Compar. 5 (0.3 g) | P-1 | CL-1 | C-1 | W-1 | A1/B1 (6/4) | 28.0 | Tapered | 10.0 | 1.9 | x |
| Compar. 6G | z7 (0.3 g) | None | P-1 | CL-1 | C-1 | W-1 | A1/B1 (6/4) | 35.0 | Tapered | 10.1 | 1.9 | ○ |

It is apparent from the results of Table 9 that in the exposure to EUV, the composition according to the present invention excels in the sensitivity, resolution, LER, outgas performance and aging stability. That is, it is apparent that the photosensitive composition according to the present invention can also exhibit excellent performance as a negative resist composition exposed to EUV.

<Evaluation of UV Ink>

[Preparation of Pigment Dispersion]

Yellow pigment dispersion 1 was prepared in the following manner. Dispersion was carried out using a heretofore known dispersing apparatus while appropriately regulating dispersing conditions so that the average diameter of individual pigment particles fell within the range of 0.2 to 0.3 μm. Subsequently, filtration was carried out while heating.

—Yellow pigment dispersion 1—

C.I. Pigment Yellow 13; 20 pts·mass

High-molecular dispersant (Solsperse series, produced by AstraZeneca K.K.); 20 pts·mass OXT-221 (produced by Toagosei Co. Ltd.); 60 pts·mass Example 1

Yellow ink 1

An ink of the following composition was prepared.
Yellow pigment dispersion 1; 5 pts·mass
UVI-6992 (produced by The Dow Chemical Company); 10 pts·mass
Sensitizer: 9,10-dibutoxyanthracene; 3 pts·mass
Acid amplifier: compound 1; 3 pts·mass
Polymerizable Compounds
Monomer: 3,4-epoxycyclohexylmethyl-3',4'-epoxycyclohexane carboxylate (Celoxide 2021A, produced by Daicel-UCB Co., Ltd.); 40 pts·mass
Monomer: 3,7-bis(3-oxetanyl)-5-oxanonane (OXT-221 produced by Toagosei Co. Ltd.); 37 pts·mass
Surfactant: BYK307 (produced by BYK Chemie GmbH); 1 pt·mass
Octylamine; 1 pt·mass Example 2

Yellow Ink 2

An ink of the following composition was prepared.
Yellow pigment dispersion 1; 5 pts·mass
UVI-6992 (produced by The Dow Chemical Company); 10 pts·mass
Sensitizer: 9,10-dibutoxyanthracene; 3 pts·mass
Acid amplifier: compound 2; 3 pts·mass
Polymerizable Compounds
Monomer: 3,4-epoxycyclohexylmethyl-3',4'-epoxycyclohexane carboxylate (Celoxide 2021A, produced by Daicel-UCB Co., Ltd.); 40 pts·mass
Monomer: 3,7-bis(3-oxetanyl)-5-oxanonane (OXT-221 produced by Toagosei Co. Ltd.); 37 pts·mass
Surfactant: BYK307 (produced by BYK Chemie GmbH); 1 pt·mass Octylamine; 1 pt·mass Comparative Example 1

Yellow Ink 3

An ink of the following composition was prepared.
Yellow pigment dispersion 1; 5 pts·mass
UVI-6992 (produced by The Dow Chemical Company); 10 pts·mass
Sensitizer: 9,10-dibutoxyanthracene; 3 pts·mass
Polymerizable Compounds
Monomer: 3,4-epoxycyclohexylmethyl-3',4'-epoxycyclohexane carboxylate (Celoxide 2021A, produced by Daicel-UCB Co., Ltd.); 40 pts·mass
Monomer: 3,7-bis(3-oxetanyl)-5-oxanonane (OXT-221 produced by Toagosei Co. Ltd.); 37 pts·mass
Surfactant: BYK307 (produced by BYK Chemie GmbH); 1 pt·mass
Octylamine; 1 pt·mass Comparative Example 2

Yellow Ink 4

An ink of the following composition was prepared.
Yellow pigment dispersion 1; 5 pts·mass
UVI-6992 (produced by The Dow Chemical Company); 10 pts·mass
  Sensitizer: 9,10-dibutoxyanthracene; 3 pts·mass
  Acid amplifier: comparative compound 1; 3 pts·mass
  Polymerizable Compounds
  Monomer: 3,4-epoxycyclohexylmethyl-3',4'-epoxycyclohexane carboxylate (Celoxide 2021A, produced by Daicel-UCB Co., Ltd.)) 40 pts·mass
  Monomer: 3,7-bis(3-oxetanyl)-5-oxanonane (OXT-221 produced by Toagosei Co. Ltd.); 37 pts·mass
  Surfactant: BYK307 (produced by BYK Chemie GmbH); 1 pt·mass
  Octylamine; 1 pt·mass
Each of the prepared inks was passed through a filter of 2 μm absolute filtration precision. Thus, yellow-colored ink compositions were obtained.

(Evaluation of Ink Composition)
Using each of the obtained yellow-colored ink compositions and an inkjet recording system equipped with a piezoelectric inkjet head (CA3 head manufactured by TOSHIBA TEC CORPORATION), recording was performed on a polyvinyl chloride sheet. The ink supply system included a tank, a supply piping, an ink supply tank disposed immediately before an inkjet head, a filter and a piezoelectric inkjet head. Temperature control was conducted so that the temperature of the nozzle part was maintained at 45±3° C. (100% covered image printed). Each of the ink compositions was discharged and exposed by passing the same under the radiation from an iron-doped ultraviolet lamp (power 120 W/cm$^2$) at a rate of 40 m/min. Thus, the ink was hardened, thereby obtaining a print.

The following evaluation was performed. The obtained evaluation results together with those of other Examples and Comparative Examples are summarized in Table 10 below.

<Hardening Sensitivity>
The exposure energy at hardening was measured by means of a light quantity integrating meter (UV Power MAP manufactured by BIT Inc.). The smaller this value, the higher the sensitivity at which hardening is effected. The ink composition of Example 1 exhibited an ultraviolet integrated exposure amount of 260 mJ/cm$^2$ on a sheet, so that the hardening thereof at high sensitivity was ascertained.

<Hardenability>
The hardenability was evaluated by performing hardening under an ultraviolet integrated exposure amount of about 600 mJ/cm$^2$ on a sheet and palpating hardened image areas. The hardenability was evaluated on the basis of the presence or absence of tackiness on the surface of the hardened film. Accordingly, with respect to the ink composition of Example 1, the tackiness after hardening was completely lost, so that an excellent hardenability was ascertained.

<Adherence to Recording Medium>
The adherence to recording medium was evaluated by cross hatch test (EN ISO2409). The results were expressed by notations 5B to 1B according to ASTM standards. In the evaluation, notation 5B denoted the highest adherence, and notations 3B and higher denoted a practically problem-free level. The ink composition of Example 1 exhibited high adherence, and the value thereof was notation 5B according to ASTM standards.

<Discharge Stability>
Each of the obtained ink compositions was stored at 60° C. for two weeks and further at −15° C. for two weeks. Thereafter, using an inkjet recording system equipped with a piezoelectric inkjet nozzle, recording was performed on a recording medium. Continuous printing was performed at ordinary temperature for an hour, during which the presence or absence of missing dot or ink scattering was visually inspected. This was carried out thrice, and the average of results was evaluated on the following criteria. The test results are given in Table 10 below. The marks "A" and "B" denote a practically problem-free level, and the marks "C" and "D" denote a level posing a practical problem.
  A: neither missing dot nor ink scattering was observed;
  B: missing dot or ink scattering was observed at one locality;
  C: missing dot or ink scattering was observed at two to five localities; and
  D: missing dot or ink scattering was observed at six or more localities.

TABLE 10

| Ex. | Sensitivity (integrated exposure amount) (mJ/cm$^2$) | Hardenability | Adherence | Discharge stability |
|---|---|---|---|---|
| Ex. 1 | 260 | Good | 5B | A |
| Ex. 2 | 260 | Good | 5B | A |
| Compar. Ex. 1 | 300 | Sticky | 3B | B |
| Compar. Ex. 2 | 400 | Sticky | 3B | C |

Thermal Hardening Test

Example 1

Three parts by mass of compound (1) shown below as a thermal acid generator, 3 parts by mass of acid amplifier (compound 1), and 100 parts by mass of 3,4-epoxycyclohexylmethyl-3',4'-epoxycyclohexane carboxylate (cationically polymerizable compound, alicyclic epoxy monomer, UVR-6110 (trade name) produced by Dow Chemical Japan Ltd.; hereinafter also referred to as compound (B)) were mixed together, thereby obtaining a thermally hardenable composition. This thermally hardenable composition was weighed in an amount of 0.5 g into a sample bottle, and was allowed to stand still in an oven at 150° C. for 30 minutes. Upon 30 minutes, the thermal hardenability was evaluated by inspecting whether or not the surface of the hardened film was tacky.

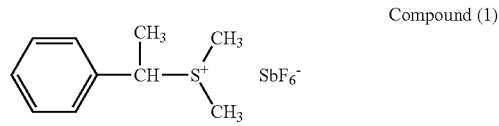

Compound (1)

Example 2 and Comparative Examples 1 and 2

The thermal hardening test was performed in the same manner as in Example 1 except that the compounds of Table 11 below were used as an acid amplifier in place of compound 1, or no acid amplifier was used. The results are given in Table 11. The evaluation criteria of this test were as follows.
  ○ (Good): hardening was observed,
  x and (Insufficient): no hardening was observed.

TABLE 11

| Ex. | Thermal acid generator | Cationically polymerizable compound | Acid amplifier | Results |
|---|---|---|---|---|
| Ex. 1 | Compound (1) | (B) | 1 | ○ |
| Ex. 2 | Compound (1) | (B) | 2 | ○ |
| Compar. Ex. 1 | Compound (1) | (B) | None | x |
| Compar. Ex. 2 | Compound (1) | (B) | Compar. 1 | x |

As apparent from Table 11, the thermally hardenable compositions of Examples 1 and 2 were satisfactorily hardened by given heating. In contrast, the thermally hardenable compositions of Comparative Examples 1 and 2 were not hardened by given heating.

What is claimed is:

1. A composition comprising:
any of compounds of the formula A-LG in which A represents any of residues of general formula (A-1) below and LG represents any of groups that are cleaved to generate acids of the formula A-H when acted on by an acid; and
at least one of a compound that generates an acid when exposed to actinic rays or radiation and a compound that generates an acid when heated,

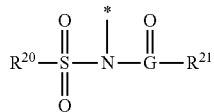
(A-1)

in which
each of $R^{20}$ and $R^{21}$ independently represents an organic group, provided that $R^{20}$ and $R^{21}$ may be bonded to each other to form a ring, and
G represents a carbon atom, a sulfur atom or S=O,
wherein the formula A-LG is represented by any of general formulae (1) (2), (3) and (5) below,

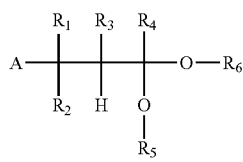
(1)

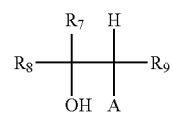
(2)

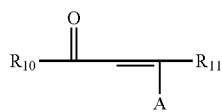
(3)

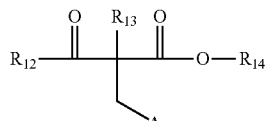
(4)

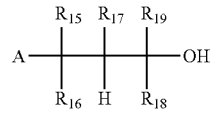
(5)

in the formulae,
each of $R_1$ to $R_4$, $R_7$ to $R_{11}$ and $R_{15}$ to $R_{19}$ independently represents a hydrogen atom or a monovalent substituent,
each of $R_5$ and $R_6$ independently represents a monovalent substituent, and
A represents any of residues of the general formula (A-1).

2. The composition according to claim 1, wherein A is any of residues of general formula (A-2) below,

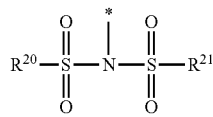
(A-2)

in which
each of $R^{20}$ and $R^{21}$ independently represents an organic group, provided that $R^{20}$ and $R^{21}$ may be bonded to each other to thereby form a ring.

3. The composition according to claim 2, wherein A is any of residues of general formula (A-3) below,

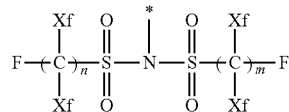
(A-3)

in which
each of Xf's independently represents a fluorine atom or an alkyl group having at least one hydrogen atom thereof substituted with a fluorine atom, and
each of m and n independently is an integer of 1 to 20.

4. The composition according to claim 1, wherein the formula A-LG is represented by the general formula (1).

5. The composition according to claim 1, which contains the compound that generates an acid when exposed to actinic rays or radiation, and further contains a resin that is decomposed to thereby increase its solubility in an alkali developer when acted on by an acid.

6. The composition according to claim 5 to be exposed to electron beams, X-rays or EUV light.

7. A resist film formed by the composition according to claim 5.

8. A method of forming a pattern, comprising:
forming the composition of claim 5 into a film,
exposing the film, and
developing the exposed film.

9. The composition according to claim 1, further comprising at least one of an acid crosslinking agent and a cationically polymerizable compound.

10. The composition according to claim 9, which contains the compound that generates an acid when exposed to actinic rays or radiation.

11. A method of inkjet recording, comprising:
discharging the composition of claim 10 onto a recording medium, and
exposing the discharged composition to actinic rays or radiation to harden the composition.

12. Compounds of general formula (A1-1) below,

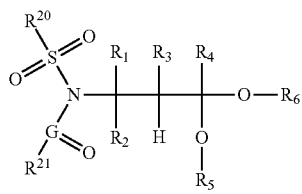
(A1-1)

in which
each of $R^{20}$ and $R^{21}$ independently represents an organic group, provided that $R^{20}$ and $R^{21}$ may be bonded to each other to thereby form a ring,
G represents a carbon atom, a sulfur atom or S=O,
each of $R_1$ to $R_4$ independently represents a hydrogen atom or a monovalent substituent, and
each of $R_5$ and $R_6$ independently represents a monovalent substituent.

13. A composition comprising:
any of compounds of the formula A-LG in which A represents any of residues of general formula (A-4) below and LG represents any of groups that are cleaved to generate acids of the formula A-H when acted on by an acid; and
at least one of a compound that generates an acid when exposed to actinic rays or radiation and a compound that generates an acid when heated,

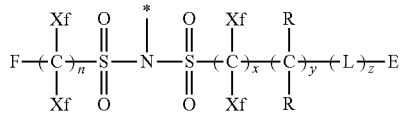
(A-4)

in which
each of Xf's independently represents a fluorine atom or an alkyl group having at least one hydrogen atom thereof substituted with a fluorine atom,
each of R's independently represents a hydrogen atom, a fluorine atom, an alkyl group, or an alkyl group having at least one hydrogen atom thereof substituted with a fluorine atom,
L, or when z≥2 each of L's independently, represents a single bond or a bivalent connecting group,
E represents a group with a cyclic structure,
each of n and x independently is an integer of 1 to 20,
y is an integer of 0 to 10, and
z is an integer of 0 to 10.

14. The composition according to claim 13, which contains the compound that generates an acid when exposed to actinic rays or radiation, and further contains a resin that is decomposed to thereby increase its solubility in an alkali developer when acted on by an acid.

15. The composition according to claim 13, wherein the formula A-LG is represented by any of general formulae (1) (2), (3) and (5) below,

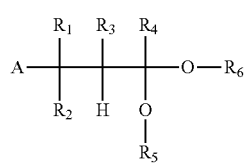
(1)

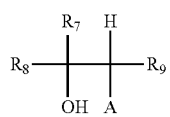
(2)

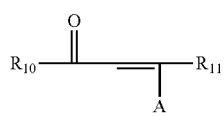
(3)

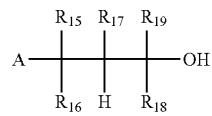
(5)

in the formulae,
each of $R_1$ to $R_4$, $R_7$ to $R_{11}$ and $R_{15}$ to $R_{19}$ independently represents a hydrogen atom or a monovalent substituent,
each of $R_5$ and $R_6$ independently represents a monovalent substituent, and
A represents any of residues of the general formula (A-1).

* * * * *